US012565527B1

(12) United States Patent
Choi et al.

(10) Patent No.: US 12,565,527 B1
(45) Date of Patent: Mar. 3, 2026

(54) IL13 AND IL31 BISPECIFIC POLYPEPTIDES AND USES THEREOF

(71) Applicant: Attovia Therapeutics, Inc., San Carlos, CA (US)

(72) Inventors: Jin Wook Choi, Pleasanton, CA (US); Lam Nguyen, Union City, CA (US); Shyr Jiann Li, Millbrae, CA (US); Jing Zhang, San Jose, CA (US); David Bellovin, San Jose, CA (US); Ole Petter Veiby, Redwood City, CA (US); Hangjun Zhan, Foster City, CA (US); Lequn Zhao, San Mateo, CA (US)

(73) Assignee: Attovia Therapeutics, Inc., San Carlos, CA (US)

( * ) Notice: Subject to any disclaimer, the term of this patent is extended or adjusted under 35 U.S.C. 154(b) by 0 days.

(21) Appl. No.: 19/316,633

(22) Filed: Sep. 2, 2025

Related U.S. Application Data

(60) Provisional application No. 63/863,120, filed on Aug. 13, 2025, provisional application No. 63/849,609, filed on Jul. 23, 2025, provisional application No. 63/814,997, filed on May 30, 2025, provisional application No. 63/690,296, filed on Sep. 3, 2024.

(51) Int. Cl.

| | |
|---|---|
| ***A61K 39/395*** | (2006.01) |
| ***A61P 17/04*** | (2006.01) |
| ***C07K 16/24*** | (2006.01) |
| *A61K 39/00* | (2006.01) |

(52) U.S. Cl.
CPC ............ *C07K 16/244* (2013.01); *A61P 17/04* (2018.01); *A61K 2039/505* (2013.01); *C07K 2317/31* (2013.01); *C07K 2317/52* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,648,237 | A | 7/1997 | Carter |
| 5,789,199 | A | 8/1998 | Joly et al. |
| 5,821,337 | A | 10/1998 | Carter et al. |
| 5,840,523 | A | 11/1998 | Simmons et al. |
| 5,959,177 | A | 9/1999 | Hein et al. |
| 6,040,498 | A | 3/2000 | Stomp et al. |
| 6,417,429 | B1 | 7/2002 | Hein et al. |
| 6,420,548 | B1 | 7/2002 | Vezina et al. |
| 6,982,321 | B2 | 1/2006 | Winter |
| 7,087,409 | B2 | 8/2006 | Barbas, III et al. |
| 7,125,978 | B1 | 10/2006 | Vezina et al. |
| 7,527,791 | B2 | 5/2009 | Adams et al. |
| 2006/0270045 | A1 | 11/2006 | Cregg et al. |

FOREIGN PATENT DOCUMENTS

| | | | |
|---|---|---|---|
| WO | WO-0075314 | A1 | 12/2000 |
| WO | WO-03060090 | A2 | 7/2003 |
| WO | WO-2004003140 | A2 | 1/2004 |
| WO | WO-2006122079 | A1 | 11/2006 |
| WO | WO-2007143231 | A1 | 12/2007 |
| WO | WO-2008028192 | A2 | 3/2008 |
| WO | WO-2009071696 | A2 | 6/2009 |
| WO | WO-2022136669 | A1 | 6/2022 |
| WO | WO-2022136672 | A1 | 6/2022 |
| WO | WO-2022147463 | A2 | 7/2022 |

OTHER PUBLICATIONS

Almagro, J.C., and Fransson, J., "Humanization of Antibodies," Frontiers in Bioscience 13:1619-1633, Frontiers In Bioscience Publications, United States (Jan. 2008).
Baca, M., et al., "Antibody Humanization Using Monovalent Phage Display," The Journal of Biological Chemistry 272(16):10678-10684, American Society for Biochemistry and Molecular Biology, United States (1997).
Benatuil, L., et al., "An Improved Yeast Transformation Method for the Generation of Very Large Human Antibody Libraries," Protein Engineering Design Selection 23(4):155-159, Oxford University Press, United Kingdom (Apr. 2010).
Carter, P., et al., "Humanization of an Anti-p185HER2 Antibody for Human Cancer Therapy," Proceedings of the National Academy of Sciences USA 89(10):4285-4289, National Academy of Sciences, United States (May 1992).
Charlton, K.A., "Expression and Isolation of Recombinant Antibody Fragments in *E. coli*," Methods in Molecular Biology 248:245-254, Humana Press, United States (2004).
Dall'Acqua, W.F., et al., "Antibody Humanization by Framework Shuffling," Methods 36(1):43-60, Academic Press, United States (2005).
Deer, J.R., and Allison, D.S., "High-level Expression of Proteins in Mammalian Cells Using Transcription Regulatory Sequences From the Chinese Hamster Ef-1alpha Gene," Biotechnology Progress 20(3):880-889, Wiley-Blackwell, United States (May-Jun. 2004).
Endo, Y., and Sawasaki, T., "High-throughput, Genome-scale Protein Production Method Based on the Wheat Germ Cell-free Expression System," Biotechnology Advances 21(8):695-713, Elsevier Science, United Kingdom (Nov. 2003).
Graham, F.L., et al., "Characteristics of a Human Cell Line Transformed by DNA from Human Adenovirus Type 5," The Journal of General Virology 36(1):59-72, Society For General Microbiology, United Kingdom (Jul. 1977).

(Continued)

*Primary Examiner* — Meera Natarajan
(74) *Attorney, Agent, or Firm* — Sterne, Kessler, Goldstein & Fox P.L.L.C.

(57) ABSTRACT

Provided herein are bispecific polypeptides that bind IL13 and IL31 and methods of using IL13 and IL31 bispecific polypeptides to modulate the biological activity of IL13 and/or IL31. Also provided herein are nucleic acids, host cells, and methods of preparing polypeptides that bind IL13 and IL31. Uses and methods provided herein include, but are not limited to, methods of treating an IL13-associated condition and/or an IL31-associated condition, such as a pruritic condition, atopic dermatitis, prurigo nodularis, and chronic spontaneous urticaria.

30 Claims, 16 Drawing Sheets

Specification includes a Sequence Listing.

(56) References Cited

OTHER PUBLICATIONS

Jain, T., et al., "Biophysical Properties of the Clinical-stage Antibody Landscape," Proceedings of the National Academy of Sciences of the United States of America 114(5):944-949, National Academy of Sciences, United States (Jan. 2017).
Jonsson, U., et al., "Introducing a Biosensor Based Technology for Real-time Biospecific Interaction Analysis," Annales De Biologie Clinique 51(1):19-26, John Libbey Eurotext, France (1993).
Kashmiri, S.V., et al., "SDR Grafting—a New Approach to Antibody Humanization," Methods 36(1):25-34, Academic Press, United States (May 2005).
Klimka, A., et al., "Human Anti-CD30 Recombinant Antibodies by Guided Phage Antibody Selection Using Cell Panning," British Journal of Cancer 83(2):252-260, Nature Publishing Group, United Kingdom (Jul. 2000).
Kraft, T.E., et al., "Heparin Chromatography as an in Vitro Predictor for Antibody Clearance Rate Through Pinocytosis," mAbs 12(1):1683432, Taylor & Francis, United States (Jan.-Dec. 2020), 10 pages.
Mather, J.P., "Establishment and Characterization of Two Distinct Mouse Testicular Epithelial Cell Lines," Biology of Reproduction 23(1):243-252, Oxford University Press, United States (Aug. 1980).
Mather, J.P., et al., "Culture of Testicular Cells in Hormone-Supplemented Serum- Free Medium," Annals New York Academy of Sciences 383(1):44-68, United States (1982).
Osbourn, J., et al., "From Rodent Reagents to Human Therapeutics using Antibody Guided Selection," Methods 36(1):61-68, Academic Press, United States (2005).
Padlan, E.A., "A Possible Procedure for Reducing the Immunogenicity of Antibody Variable Domains While Preserving their Ligand-binding Properties, " Molecular Immunology 28(4-5):489-498, Pergamon Press, United Kingdom (Apr. 1991).
Presta, L.G., et al., "Humanization of an Antibody Directed Against IgE," Journal of Immunology 151(5):2623-2632, Oxford University Press, United Kingdom (Sep. 1993).
Queen, C., et al., "A Humanized Antibody that Binds to the Interleukin 2 Receptor," Proceedings of the National Academy of Sciences of the United States of America 86(24):10029-10033, National Academy of Sciences, United States (Dec. 1989).
Riechmann, L., et al., "Reshaping Human Antibodies for Therapy," Nature 332(6162):323-327, Nature Publishing Group, United Kingdom (Mar. 1988).
Rosok, M.J., et al., "A Combinatorial Library Strategy for the Rapid Humanization of Anticarcinoma BR96 Fab," The Journal of Biological Chemistry 271(37):22611- 22618, Elsevier Inc, United States (Sep. 1996).
Sims, M.J., et al., "A Humanized CD18 Antibody can Block Function without Cell Destruction," The Journal of Immunology 151(4):2296-2308, The American Association of Immunologists, United States (Aug. 1993).
Sitaraman, K., and Chatterjee, D.K., "High-throughput Protein Expression Using Cell-free System," Methods in Molecular Biology 498:229-244, Humana Press, United States (2009).
Spirin, A.S., "High-throughput Cell-free Systems for Synthesis of Functionally Active Proteins, " Trends in Biotechnology 22(10):538-545, Elsevier Science Publishers, United Kingdom (Oct. 2004).
UniProtKB/Swiss-Prot, "IL31_Human," Accession No. Q6EBC2, accessed at https://www.uniprot.org/uniprotkb/Q6EBC2, accessed on Apr. 17, 2025, 6 pages.
UniProtKB/Swiss-Prot, "RecName: Full=Interleukin-13; Short=IL-13; Flags: Precursor," Accession No. P35225.3, accessed at https://www.ncbi.nlm.nih.gov/protein/P35225, accessed on Sep. 3, 2025, 7 pages.
Urlaub, G., and Chasin, L.A., "Isolation of Chinese Hamster Cell Mutants Deficient in Dihydrofolate Reductase Activity," Proceedings of the National Academy of Sciences of the United States of America 77(7):4216-4220, National Academy of Sciences, United States (Jul. 1980).
Wang, Z., et al., "A New Yeast Display Vector Permitting Free Scfv Amino Termini Can Augment Ligand Binding Affinities," Protein Engineering Design Selection 18(7):337-343, Oxford University Press, United Kingdom (Jul. 2005).
Xu, Y., et al., "Addressing Polyspecificity of Antibodies Selected From an in Vitro Yeast Presentation System: a Facs-based, High-throughput Selection and Analytical Tool," Protein Engineering, Design and Selection 26(10):663-670, Oxford University Press, United Kingdom (Oct. 2013).
Yazaki, P.J., and Wu, A.M., "Expression of Recombinant Antibodies in Mammalian Cell Lines," Methods in Molecular Biology 248:255-268, Humana Press, United States (2004).
Ghilardi, N., et al., "A Novel Type I Cytokine Receptor Is Expressed on Monocytes, Signals Proliferation, and Activates STAT-3 and STAT-5," The Journal of Biological Chemistry 277(19):16831-16836, American Society for Biochemistry and Molecular Biology, United States (May 2002).
Rudikoff, S., et al., "Single amino acid substitution altering antigen-binding specificity," PNAS 79:1979-1983, National Academy of Sciences, United States (Mar. 1982).
Attovia Therapeutics, "Attovia Announces Second Tranche Closing of $60 Million," news release on Feb. 8, 2024, retrieved at https://www.globenewsire.com/news-release/2024/02/08/2825910/0/en/Attovia-Announces-Second-Tranche-Closing-of-60-Million-Series-A-Financing-and -Highlights-Progress-Building-a-Best-in-Class-Pipeline-Leveraging-the-Attobody-Platform.html, 4 pages.
Anonymous, "ATTOBODY (TM) Platform: Improving on Nature's Selection," retrieved at https://alamarbio.com/technology/attobody_platform/, published Apr. 13, 2023, 4 pages.
International Search Report and Written Opinion for International Application No. PCT/US2025/026000, European Patent Office, Netherlands, mailed on Sep. 9, 2025, 20 pages.
Co-pending Application, U.S. Appl. No. 19/187,342, inventors Choi, J.W., et al., filed on Apr. 23, 2025 (Not yet Published).

SEQ ID NO:55

SEQUENCE LISTING

```
Sequence total quantity: 69
SEQ ID NO: 1            moltype = AA  length = 164
FEATURE                 Location/Qualifiers
source                  1..164
                        mol_type = protein
                        organism = Homo sapiens
SEQUENCE: 1
MASHSGPSTS VLFLFCCLGG WLASHTLPVR LLRPSDDVQK IVEELQSLSK MLLKDVEEEK  60
GVLVSQNYTL PCLSPDAQPP NNIHSPAIRA YLKTIRQLDN KSVIDEIIEH LDKLIFQDAP  120
ETNISVPTDT HECKRFILTI SQQFSECMDL ALKSLTSGAQ QATT                  164

SEQ ID NO: 2            moltype = AA  length = 141
FEATURE                 Location/Qualifiers
source                  1..141
                        mol_type = protein
                        organism = Homo sapiens
SEQUENCE: 2
SHTLPVRLLR PSDDVQKIVE ELQSLSKMLL KDVEEEKGVL VSQNYTLPCL SPDAQPPNNI  60
HSPAIRAYLK TIRQLDNKSV IDEIIEHLDK LIFQDAPETN ISVPTDTHEC KRFILTISQQ  120
FSECMDLALK SLTSGAQQAT T                                           141

SEQ ID NO: 3            moltype = AA  length = 118
FEATURE                 Location/Qualifiers
source                  1..118
                        mol_type = protein
                        organism = Synthetic construct
SEQUENCE: 3
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSS    118

SEQ ID NO: 4            moltype = AA  length = 118
FEATURE                 Location/Qualifiers
source                  1..118
                        mol_type = protein
                        organism = Synthetic construct
```

```
SEQUENCE: 4
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSS    118

SEQ ID NO: 5            moltype = AA  length = 5
FEATURE                 Location/Qualifiers
source                  1..5
                        mol_type = protein
                        organism = Synthetic construct
SEQUENCE: 5
SYTMG                                                              5

SEQ ID NO: 6            moltype = AA  length = 17
FEATURE                 Location/Qualifiers
source                  1..17
                        mol_type = protein
                        organism = Synthetic construct
SEQUENCE: 6
GISSSGYVMY NSESMKG                                                 17

SEQ ID NO: 7            moltype = AA  length = 9
FEATURE                 Location/Qualifiers
source                  1..9
                        mol_type = protein
                        organism = Synthetic construct
SEQUENCE: 7
GTIGRPYDY                                                          9

SEQ ID NO: 8            moltype = AA  length = 8
FEATURE                 Location/Qualifiers
source                  1..8
                        mol_type = protein
                        organism = Synthetic construct
SEQUENCE: 8
GGTFSSYT                                                           8

SEQ ID NO: 9            moltype = AA  length = 8
FEATURE                 Location/Qualifiers
source                  1..8
                        mol_type = protein
                        organism = Synthetic construct
SEQUENCE: 9
ISSSGYVM                                                           8

SEQ ID NO: 10           moltype = AA  length = 11
FEATURE                 Location/Qualifiers
source                  1..11
                        mol_type = protein
                        organism = Synthetic construct
SEQUENCE: 10
AAGTIGRPYD Y                                                       11

SEQ ID NO: 11           moltype = AA  length = 7
FEATURE                 Location/Qualifiers
source                  1..7
                        mol_type = protein
                        organism = Synthetic construct
SEQUENCE: 11
GGTFSSY                                                            7

SEQ ID NO: 12           moltype = AA  length = 6
FEATURE                 Location/Qualifiers
source                  1..6
                        mol_type = protein
                        organism = Synthetic construct
SEQUENCE: 12
SSSGYV                                                             6

SEQ ID NO: 13           moltype = AA  length = 9
FEATURE                 Location/Qualifiers
source                  1..9
                        mol_type = protein
                        organism = Synthetic construct
SEQUENCE: 13
GTIGRPYDY                                                          9

SEQ ID NO: 14           moltype = AA  length = 119
FEATURE                 Location/Qualifiers
source                  1..119
```

```
                        mol_type = protein
                        organism = Synthetic construct
SEQUENCE: 14
VKLEESGGGL VQPGGSLILS CAASGDISSI VAMGWYRQAP GKQRELVAAI TSGGRTHYRD  60
SVKGRFTISG NNDNSALYLH MNSLKPEDTA VYYCAADRGW TSVGEYDYWG KGTLVTVSS   119

SEQ ID NO: 15           moltype = AA  length = 119
FEATURE                 Location/Qualifiers
source                  1..119
                        mol_type = protein
                        organism = Synthetic construct
SEQUENCE: 15
VQLVESGGGL VQPGGSLRLS CAASGDISSI VAMGWYRQAP GKQRELVSAI TSGGRTHYRD  60
SVKGRFTISR DNAKNTLYLQ MNSLRAEDTA VYYCAADRGW TSVGEYDYWG QGTQVTVSS   119

SEQ ID NO: 16           moltype = AA  length = 5
FEATURE                 Location/Qualifiers
source                  1..5
                        mol_type = protein
                        organism = Synthetic construct
SEQUENCE: 16
IVAMG                                                              5

SEQ ID NO: 17           moltype = AA  length = 16
FEATURE                 Location/Qualifiers
source                  1..16
                        mol_type = protein
                        organism = Synthetic construct
SEQUENCE: 17
AITSGGRTHY RDSVKG                                                  16

SEQ ID NO: 18           moltype = AA  length = 12
FEATURE                 Location/Qualifiers
source                  1..12
                        mol_type = protein
                        organism = Synthetic construct
SEQUENCE: 18
DRGWTSVGEY DY                                                      12

SEQ ID NO: 19           moltype = AA  length = 8
FEATURE                 Location/Qualifiers
source                  1..8
                        mol_type = protein
                        organism = Synthetic construct
SEQUENCE: 19
GDISSIVA                                                           8

SEQ ID NO: 20           moltype = AA  length = 7
FEATURE                 Location/Qualifiers
source                  1..7
                        mol_type = protein
                        organism = Synthetic construct
SEQUENCE: 20
ITSGGRT                                                            7

SEQ ID NO: 21           moltype = AA  length = 14
FEATURE                 Location/Qualifiers
source                  1..14
                        mol_type = protein
                        organism = Synthetic construct
SEQUENCE: 21
AADRGWTSVG EYDY                                                    14

SEQ ID NO: 22           moltype = AA  length = 7
FEATURE                 Location/Qualifiers
source                  1..7
                        mol_type = protein
                        organism = Synthetic construct
SEQUENCE: 22
GDISSIV                                                            7

SEQ ID NO: 23           moltype = AA  length = 5
FEATURE                 Location/Qualifiers
source                  1..5
                        mol_type = protein
                        organism = Synthetic construct
SEQUENCE: 23
TSGGR                                                              5
```

-continued

```
SEQ ID NO: 24           moltype = AA  length = 12
FEATURE                 Location/Qualifiers
source                  1..12
                        mol_type = protein
                        organism = Synthetic construct
SEQUENCE: 24
DRGWTSVGEY DY                                                   12

SEQ ID NO: 25           moltype = AA  length = 275
FEATURE                 Location/Qualifiers
source                  1..275
                        mol_type = protein
                        organism = Synthetic construct
SEQUENCE: 25
EVQLVESGGG LVQAGGSLRL SCAASGGTFS SYTMGWFRQA PGKEREYVGG ISSSGYVMYN  60
SESMKGRFTI SRENAKNMVY LQMNSLKPED TAVYYCAAGT IGRPYDYWGQ GTQVTVSSGG  120
GSGGGGSGGG GSGGGGSGGG GSGGGGSGGG GSGMTGVKLE ESGGGLVQPG GSLILSCAAS  180
GDISSIVAMG WYRQAPGKQR ELVAAITSGG RTHYRDSVKG RFTISGNNDN SALYLHMNSL  240
KPEDTAVYYC AADRGWTSVG EYDYWGKGTL VTVSS                          275

SEQ ID NO: 26           moltype = AA  length = 275
FEATURE                 Location/Qualifiers
source                  1..275
                        mol_type = protein
                        organism = Synthetic construct
SEQUENCE: 26
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSS                          275

SEQ ID NO: 27           moltype = AA  length = 132
FEATURE                 Location/Qualifiers
source                  1..132
                        mol_type = protein
                        organism = Synthetic construct
SEQUENCE: 27
MALLLTTVIA LTCLGGFASP GPVPPSTALR ELIEELVNIT QNQKAPLCNG SMVWSINLTA  60
GMYCAALESL INVSGCSAIE KTQRMLSGFC PHKVSAGQFS SLHVRDTKIE VAQFVKDLLL  120
HLKKLFREGR FN                                                   132

SEQ ID NO: 28           moltype = AA  length = 132
FEATURE                 Location/Qualifiers
source                  1..132
                        mol_type = protein
                        organism = Synthetic construct
SEQUENCE: 28
MALLLTTVIA LTCLGGFASP GPVPPSTALR ELIEELVNIT QNQKAPLCNG SMVWSINLTA  60
GMYCAALESL INVSGCSAIE KTQRMLSGFC PHKVSAGQFS SLHVRDTKIE VAQFVKDLLL  120
HLKKLFREGQ FN                                                   132

SEQ ID NO: 29           moltype = AA  length = 115
FEATURE                 Location/Qualifiers
source                  1..115
                        mol_type = protein
                        organism = Synthetic construct
SEQUENCE: 29
EVQLVESGGD LVQAGGSLLL SCTASESISS INYIGWYRQA PGKGRELIAH FTDGTVTNYA  60
DSVKGRFTIS RDNGKNTLYL QMNSLKPEDT AVYYCAATDW RGDHWGQGTL VTVSS       115

SEQ ID NO: 30           moltype = AA  length = 115
FEATURE                 Location/Qualifiers
source                  1..115
                        mol_type = protein
                        organism = Synthetic construct
SEQUENCE: 30
EVQLVESGGG LVQPGGSLRL SCTASESISS INYIGWYRQA PGKGRELIAH FTDGTVTNYA  60
DSVKGRFTIS RDNAKNTLYL QMNSLRAEDT AVYYCAATDW EGDHWGQGTL VTVSS       115

SEQ ID NO: 31           moltype = AA  length = 5
FEATURE                 Location/Qualifiers
source                  1..5
                        mol_type = protein
                        organism = Synthetic construct
SEQUENCE: 31
INYIG                                                           5

SEQ ID NO: 32           moltype = AA  length = 16
```

-continued

```
FEATURE                Location/Qualifiers
source                 1..16
                       mol_type = protein
                       organism = Synthetic construct
SEQUENCE: 32
HFTDGTVTNY ADSVKG                                             16

SEQ ID NO: 33          moltype = AA  length = 7
FEATURE                Location/Qualifiers
source                 1..7
                       mol_type = protein
                       organism = Synthetic construct
SEQUENCE: 33
TDWRGDH                                                       7

SEQ ID NO: 34          moltype = AA  length = 8
FEATURE                Location/Qualifiers
source                 1..8
                       mol_type = protein
                       organism = Synthetic construct
SEQUENCE: 34
ESISSINY                                                      8

SEQ ID NO: 35          moltype = AA  length = 7
FEATURE                Location/Qualifiers
source                 1..7
                       mol_type = protein
                       organism = Synthetic construct
SEQUENCE: 35
FTDGTVT                                                       7

SEQ ID NO: 36          moltype = AA  length = 9
FEATURE                Location/Qualifiers
source                 1..9
                       mol_type = protein
                       organism = Synthetic construct
SEQUENCE: 36
AATDWRGDH                                                     9

SEQ ID NO: 37          moltype = AA  length = 7
FEATURE                Location/Qualifiers
source                 1..7
                       mol_type = protein
                       organism = Synthetic construct
SEQUENCE: 37
ESISSIN                                                       7

SEQ ID NO: 38          moltype = AA  length = 5
FEATURE                Location/Qualifiers
source                 1..5
                       mol_type = protein
                       organism = Synthetic construct
SEQUENCE: 38
TDGTV                                                         5

SEQ ID NO: 39          moltype = AA  length = 7
FEATURE                Location/Qualifiers
source                 1..7
                       mol_type = protein
                       organism = Synthetic construct
SEQUENCE: 39
TDWRGDH                                                       7

SEQ ID NO: 40          moltype = AA  length = 127
FEATURE                Location/Qualifiers
source                 1..127
                       mol_type = protein
                       organism = Synthetic construct
SEQUENCE: 40
QLVESGGGSV QPGGSLRLSC AAPRFTLGSY AIAWFRQSPG KEREWVSCIS RSGGDTIYSD  60
SVKGRFTISR DNTKNMVYLQ MNSLNPEDTA VYYCATDKRS FCYAPNGLGK GWTYDYWGQG  120
TQVTVSS                                                       127

SEQ ID NO: 41          moltype = AA  length = 127
FEATURE                Location/Qualifiers
source                 1..127
                       mol_type = protein
                       organism = Synthetic construct
SEQUENCE: 41
```

-continued

```
QLVESGGGVV QPGGSLRLSC AAPRFTLGSY AIAWFRQSPG KEREWVSCIS RSGGDTIYSD  60
SVKGRFTISR DNAKNTLYLQ MNSLRAEDTA VYYCATDKRS FCYAPEGLGK GWTYDYWGQG  120
TQVTVSS                                                            127

SEQ ID NO: 42          moltype = AA  length = 5
FEATURE                Location/Qualifiers
source                 1..5
                       mol_type = protein
                       organism = Synthetic construct
SEQUENCE: 42
SYAIA                                                              5

SEQ ID NO: 43          moltype = AA  length = 17
FEATURE                Location/Qualifiers
source                 1..17
                       mol_type = protein
                       organism = Synthetic construct
SEQUENCE: 43
CISRSGGDTI YSDSVKG                                                 17

SEQ ID NO: 44          moltype = AA  length = 20
FEATURE                Location/Qualifiers
source                 1..20
                       mol_type = protein
                       organism = Synthetic construct
SEQUENCE: 44
DKRSFCYAPN GLGKGWTYDY                                              20

SEQ ID NO: 45          moltype = AA  length = 8
FEATURE                Location/Qualifiers
source                 1..8
                       mol_type = protein
                       organism = Synthetic construct
SEQUENCE: 45
RFTLGSYA                                                           8

SEQ ID NO: 46          moltype = AA  length = 8
FEATURE                Location/Qualifiers
source                 1..8
                       mol_type = protein
                       organism = Synthetic construct
SEQUENCE: 46
ISRSGGDT                                                           8

SEQ ID NO: 47          moltype = AA  length = 22
FEATURE                Location/Qualifiers
source                 1..22
                       mol_type = protein
                       organism = Synthetic construct
SEQUENCE: 47
ATDKRSFCYA PNGLGKGWTY DY                                           22

SEQ ID NO: 48          moltype = AA  length = 7
FEATURE                Location/Qualifiers
source                 1..7
                       mol_type = protein
                       organism = Synthetic construct
SEQUENCE: 48
RFTLGSY                                                            7

SEQ ID NO: 49          moltype = AA  length = 6
FEATURE                Location/Qualifiers
source                 1..6
                       mol_type = protein
                       organism = Synthetic construct
SEQUENCE: 49
SRSGGD                                                             6

SEQ ID NO: 50          moltype = AA  length = 20
FEATURE                Location/Qualifiers
source                 1..20
                       mol_type = protein
                       organism = Synthetic construct
SEQUENCE: 50
DKRSFCYAPN GLGKGWTYDY                                              20

SEQ ID NO: 51          moltype = AA  length = 280
FEATURE                Location/Qualifiers
source                 1..280
```

```
                        mol_type = protein
                        organism = Synthetic construct
SEQUENCE: 51
EVQLVESGGD LVQAGGSLLL SCTASESISS INYIGWYRQA PGKGRELIAH FTDGTVTNYA  60
DSVKGRFTIS RDNGKNTLYL QMNSLKPEDT AVYYCAATDW RGDHWGQGTL VTVSSGGGSG  120
GGGSGGGGSG GGGSGGGGSG GGGSGGGGSL GVGQLVESGG GSVQPGGSLR LSCAAPRFTL  180
GSYAIAWFRQ SPGKEREWVS CISRSGGDTI YSDSVKGRFT ISRDNTKNMV YLQMNSLNPE  240
DTAVYYCATD KRSFCYAPNG LGKGWTYDYW GQGTQVTVSS                        280

SEQ ID NO: 52           moltype = AA  length = 280
FEATURE                 Location/Qualifiers
source                  1..280
                        mol_type = protein
                        organism = Synthetic construct
SEQUENCE: 52
EVQLVESGGG LVQPGGSLRL SCTASESISS INYIGWYRQA PGKGRELIAH FTDGTVTNYA  60
DSVKGRFTIS RDNAKNTLYL QMNSLRAEDT AVYYCAATDW EGDHWGQGTL VTVSSGGGSG  120
GGGSGGGGSG GGGSGGGGSG GGGSGGGGSL GVGQLVESGG GVVQPGGSLR LSCAAPRFTL  180
GSYAIAWFRQ SPGKEREWVS CISRSGGDTI YSDSVKGRFT ISRDNAKNTL YLQMNSLRAE  240
DTAVYYCATD KRSFCYAPEG LGKGWTYDYW GQGTQVTVSS                        280

SEQ ID NO: 53           moltype = AA  length = 512
FEATURE                 Location/Qualifiers
source                  1..512
                        mol_type = protein
                        organism = Synthetic construct
SEQUENCE: 53
EVQLVESGGD LVQAGGSLLL SCTASESISS INYIGWYRQA PGKGRELIAH FTDGTVTNYA  60
DSVKGRFTIS RDNGKNTLYL QMNSLKPEDT AVYYCAATDW RGDHWGQGTL VTVSSGGGSG  120
GGGSGGGGSG GGGSGGGGSG GGGSGGGGSL GVGQLVESGG GSVQPGGSLR LSCAAPRFTL  180
GSYAIAWFRQ SPGKEREWVS CISRSGGDTI YSDSVKGRFT ISRDNTKNMV YLQMNSLNPE  240
DTAVYYCATD KRSFCYAPNG LGKGWTYDYW GQGTQVTVSS EPKSSDKTHT CPPCPAPEAA  300
GGPSVFLFPP KPKDTLYITR EPEVTCVVVD VSHEDPEVKF NWYVDGVEVH NAKTKPREEQ  360
YNSTYRVVSV LTVLHQDWLN GKEYKCKVSN KALPAPIEKT ISKAKGQPRE PQVYTLPPSR  420
DELTKNQVSL TCLVKGFYPS DIAVEWESNG QPENNYKTTP PVLDSDGSFF LYSKLTVDKS  480
RWQQGNVFSC SVMHEALHNH YTQKSLSLSP GK                                512

SEQ ID NO: 54           moltype = AA  length = 512
FEATURE                 Location/Qualifiers
source                  1..512
                        mol_type = protein
                        organism = Synthetic construct
SEQUENCE: 54
EVQLVESGGG LVQPGGSLRL SCTASESISS INYIGWYRQA PGKGRELIAH FTDGTVTNYA  60
DSVKGRFTIS RDNAKNTLYL QMNSLRAEDT AVYYCAATDW EGDHWGQGTL VTVSSGGGSG  120
GGGSGGGGSG GGGSGGGGSG GGGSGGGGSL GVGQLVESGG GLVQPGGSLR LSCAAPRFTL  180
GSYAIAWFRQ SPGKEREWVS CISRSGGDTI YSDSVKGRFT ISRDNAKNTL YLQMNSLRAE  240
DTAVYYCATD KRSFCYAPEG LGKGWTYDYW GQGTQVTVSS EPKSSDKTHT CPPCPAPEAA  300
GGPSVFLFPP KPKDTLYITR EPEVTCVVVD VSHEDPEVKF NWYVDGVEVH NAKTKPREEQ  360
YNSTYRVVSV LTVLHQDWLN GKEYKCKVSN KALPAPIEKT ISKAKGQPRE PQVYTLPPSR  420
DELTKNQVSL TCLVKGFYPS DIAVEWESNG QPENNYKTTP PVLDSDGSFF LYSKLTVDKS  480
RWQQGNVFSC SVMHEALHNH YTQKSLSLSP GK                                512

SEQ ID NO: 55           moltype = AA  length = 798
FEATURE                 Location/Qualifiers
source                  1..798
                        mol_type = protein
                        organism = Synthetic construct
SEQUENCE: 55
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSSEPKSS DKTHTCPPCP APEAAGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGKGGG GSGGGGSGGGV QLVESGGGLV QPGGSLRLSC  540
TASESISSIN YIGWYRQAPG KGRELIAHFT DGTVTNYADS VKGRFTISRD NAKNTLYLQM  600
NSLRAEDTAV YYCAATDWEG DHWGQGTLVT VSSGGGSGGG GSGGGGSGGG GSGGGGSGGG  660
GSGGGGSLGV GQLVESGGGV VQPGGSLRLS CAAPRFTLGS YAIAWFRQSP GKEREWVSCI  720
SRSGGDTIYS DSVKGRFTIS RDNAKNTLYL QMNSLRAEDT AVYYCATDKR SFCYAPEGLG  780
KGWTYDYWGQ GTQVTVSS                                                798

SEQ ID NO: 56           moltype = AA  length = 798
FEATURE                 Location/Qualifiers
source                  1..798
                        mol_type = protein
                        organism = Synthetic construct
```

```
SEQUENCE: 56
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSSGGGGS GGGSGGGVQL VESGGGLVQP  300
GGSLRLSCTA SESISSINYI GWYRQAPGKG RELIAHFTDG TVTNYADSVK GRFTISRDNA  360
KNTLYLQMNS LRAEDTAVYY CAATDWEGDH WGQGTLVTVS SGGGSGGGGS GGGGSGGGGS  420
GGGGSGGGGS GGGGSLGVGQ LVESGGGLVQ PGGSLRLSCA APRFTLGSYA IAWFRQSPGK  480
EREWVSCISR SGGDTIYSDS VKGRFTISRD NAKNTLYLQM NSLRAEDTAV YYCATDKRSF  540
CYAPEGLGKG WTYDYWGQGT QVTVSSEPKS SDKTHTCPPC PAPEAAGGPS VFLFPPKPKD  600
TLYITREPEV TCVVVDVSHE DPEVKFNWYV DGVEVHNAKT KPREEQYNST YRVVSVLTVL  660
HQDWLNGKEY KCKVSNKALP APIEKTISKA KGQPREPQVY TLPPSRDELT KNQVSLTCLV  720
KGFYPSDIAV EWESNGQPEN NYKTTPPVLD SDGSFFLYSK LTVDKSRWQQ GNVFSCSVMH  780
EALHNHYTQK SLSLSPGK                                                798

SEQ ID NO: 57           moltype = AA  length = 797
FEATURE                 Location/Qualifiers
source                  1..797
                        mol_type = protein
                        organism = Synthetic construct
SEQUENCE: 57
EVQLVESGGG LVQPGGSLRL SCTASESISS INYIGWYRQA PGKGRELIAH FTDGTVTNYA  60
DSVKGRFTIS RDNAKNTLYL QMNSLRAEDT AVYYCAATDW EGDHWGQGTL VTVSSGGGSG  120
GGGSGGGGSG GGGSGGGGSG GGGSGGGGSL GVGQLVESGG GLVQPGGSLR LSCAAPRFTL  180
GSYAIAWFRQ SPGKEREWVS CISRSGGDTI YSDSVKGRFT ISRDNAKNTL YLQMNSLRAE  240
DTAVYYCATD KRSFCYAPEG LGKGWTYDYW GQGTQVTVSS EPKSSDKTHT CPPCPAPEAA  300
GGPSVFLFPP KPKDTLYITR EPEVTCVVVD VSHEDPEVKF NWYVDGVEVH NAKTKPREEQ  360
YNSTYRVVSV LTVLHQDWLN GKEYKCKVSN KALPAPIEKT ISKAKGQPRE PQVYTLPPSR  420
DELTKNQVSL TCLVKGFYPS DIAVEWESNG QPENNYKTTP PVLDSDGSFF LYSKLTVDKS  480
RWQQGNVFSC SVMHEALHNH YTQKSLSLSP GGGGGSGGGS GGGVQLVESG GGLVQPGGSL  540
RLSCAASGGT FSSYTMGWFR QAPGKEREYV GGISSSGYVM YNSESMKGRF TISRDNAKNT  600
LYLQMNSLRA EDTAVYYCAA GTIGRPYDYW GQGTQVTVSS GGGSGGGGSG GGGSGGGGSG  660
GGGSGGGGSG GGGSGMTGVQ LVESGGGVVQ PGGSLRLSCA ASGDISSIVA MGWYRQAPGK  720
QRELVSAITS GGRTHYRDSV KGRFTISRDN AKNTLYLQMN SLRAEDTAVY YCAADRGWTS  780
VGEYDYWGQG TQVTVSS                                                 797

SEQ ID NO: 58           moltype = AA  length = 798
FEATURE                 Location/Qualifiers
source                  1..798
                        mol_type = protein
                        organism = Synthetic construct
SEQUENCE: 58
EVQLVESGGG LVQPGGSLRL SCTASESISS INYIGWYRQA PGKGRELIAH FTDGTVTNYA  60
DSVKGRFTIS RDNAKNTLYL QMNSLRAEDT AVYYCAATDW EGDHWGQGTL VTVSSGGGSG  120
GGGSGGGGSG GGGSGGGGSG GGGSGGGGSL GVGQLVESGG GLVQPGGSLR LSCAAPRFTL  180
GSYAIAWFRQ SPGKEREWVS CISRSGGDTI YSDSVKGRFT ISRDNAKNTL YLQMNSLRAE  240
DTAVYYCATD KRSFCYAPEG LGKGWTYDYW GQGTQVTVSS GGGGSGGGSG GGVQLVESGG  300
GLVQPGGSLR LSCAASGGTF SSYTMGWFRQ APGKEREYVG GISSSGYVMY NSESMKGRFT  360
ISRDNAKNTL YLQMNSLRAE DTAVYYCAAG TIGRPYDYWG QGTQVTVSSG GGSGGGGSGG  420
GGSGGGGSGG GGSGGGGSGG GGSGMTGVQL VESGGGLVQP GGSLRLSCAA SGDISSIVAM  480
GWYRQAPGKQ RELVSAITSG GRTHYRDSVK GRFTISRDNA KNTLYLQMNS LRAEDTAVYY  540
CAADRGWTSV GEYDYWGQGT QVTVSSEPKS SDKTHTCPPC PAPEAAGGPS VFLFPPKPKD  600
TLYITREPEV TCVVVDVSHE DPEVKFNWYV DGVEVHNAKT KPREEQYNST YRVVSVLTVL  660
HQDWLNGKEY KCKVSNKALP APIEKTISKA KGQPREPQVY TLPPSRDELT KNQVSLTCLV  720
KGFYPSDIAV EWESNGQPEN NYKTTPPVLD SDGSFFLYSK LTVDKSRWQQ GNVFSCSVMH  780
EALHNHYTQK SLSLSPGK                                                798

SEQ ID NO: 59           moltype = AA  length = 232
FEATURE                 Location/Qualifiers
source                  1..232
                        mol_type = protein
                        organism = Synthetic construct
SEQUENCE: 59
EPKSSDKTHT CPPCPAPEAA GGPSVFLFPP KPKDTLYITR EPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 60           moltype = AA  length = 7
FEATURE                 Location/Qualifiers
source                  1..7
                        mol_type = protein
                        organism = Synthetic construct
SEQUENCE: 60
TDWEGDH                                                            7

SEQ ID NO: 61           moltype = AA  length = 9
FEATURE                 Location/Qualifiers
```

-continued

```
source                  1..9
                        mol_type = protein
                        organism = Synthetic construct
SEQUENCE: 61
AATDWEGDH                                                       9

SEQ ID NO: 62           moltype = AA  length = 7
FEATURE                 Location/Qualifiers
source                  1..7
                        mol_type = protein
                        organism = Synthetic construct
SEQUENCE: 62
TDWEGDH                                                         7

SEQ ID NO: 63           moltype = AA  length = 20
FEATURE                 Location/Qualifiers
source                  1..20
                        mol_type = protein
                        organism = Synthetic construct
SEQUENCE: 63
DKRSFCYAPE GLGKGWTYDY                                           20

SEQ ID NO: 64           moltype = AA  length = 22
FEATURE                 Location/Qualifiers
source                  1..22
                        mol_type = protein
                        organism = Synthetic construct
SEQUENCE: 64
ATDKRSFCYA PEGLGKGWTY DY                                        22

SEQ ID NO: 65           moltype = AA  length = 20
FEATURE                 Location/Qualifiers
source                  1..20
                        mol_type = protein
                        organism = Synthetic construct
SEQUENCE: 65
DKRSFCYAPE GLGKGWTYDY                                           20

SEQ ID NO: 66           moltype = AA  length = 38
FEATURE                 Location/Qualifiers
source                  1..38
                        mol_type = protein
                        organism = Synthetic construct
SEQUENCE: 66
GGGSGGGGSG GGGSGGGGSG GGGSGGGGSG GGGSGMTG                       38

SEQ ID NO: 67           moltype = AA  length = 38
FEATURE                 Location/Qualifiers
source                  1..38
                        mol_type = protein
                        organism = Synthetic construct
SEQUENCE: 67
GGGSGGGGSG GGGSGGGGSG GGGSGGGGSG GGGSLGVG                       38

SEQ ID NO: 68           moltype = AA  length = 12
FEATURE                 Location/Qualifiers
source                  1..12
                        mol_type = protein
                        organism = Synthetic construct
SEQUENCE: 68
GGGGSGGGSG GG                                                   12

SEQ ID NO: 69           moltype = AA  length = 507
FEATURE                 Location/Qualifiers
source                  1..507
                        mol_type = protein
                        organism = synthetic construct
SEQUENCE: 69
EVQLVESGGG LVQPGGSLRL SCAASGGTFS SYTMGWFRQA PGKEREYVGG ISSSGYVMYN  60
SESMKGRFTI SRDNAKNTLY LQMNSLRAED TAVYYCAAGT IGRPYDYWGQ GTQVTVSSGG  120
GSGGGGSGGG GSGGGGSGGG GSGGGGSGGG GSGMTGVQLV ESGGGLVQPG GSLRLSCAAS  180
GDISSIVAMG WYRQAPGKQR ELVSAITSGG RTHYRDSVKG RFTISRDNAK NTLYLQMNSL  240
RAEDTAVYYC AADRGWTSVG EYDYWGQGTQ VTVSSEPKSS DKTHTCPPCP APELLGGPSV  300
FLFPPKPKDT LYITREPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSRDELTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                   507
```

IL13 AND IL31 BISPECIFIC POLYPEPTIDES AND USES THEREOF

CROSS-REFERENCE TO RELATED APPLICATIONS

This application claims the benefit of U.S. provisional patent application Ser. No. 63/690,296, filed Sep. 3, 2024, U.S. provisional patent application Ser. No. 63/814,997, filed May 30, 2025, U.S. provisional patent application Ser. No. 63/849,609, filed Jul. 23, 2025, and U.S. provisional patent application Ser. No. 63/863,120, filed Aug. 13, 2025, each of which is incorporated herein by reference in its entirety.

REFERENCE TO SEQUENCE LISTING SUBMITTED ELECTRONICALLY

The content of the electronically submitted sequence listing (Name: 5614_0030005_SequenceListing_ST26.xml; Size: 68,312 bytes; and Date of Creation: Sep. 2, 2025) filed with the application is incorporated herein by reference in its entirety.

FIELD

The present disclosure relates to IL13 and IL31 bispecific polypeptides, and methods of using IL13 and IL31 bispecific polypeptides to modulate the biological activity of IL13 and/or IL31. Such methods include, but are not limited to, methods of treating pruritic conditions, atopic dermatitis, prurigo nodularis, and chronic spontaneous urticaria.

BACKGROUND

Interleukin 13 (IL13) and interleukin 31 (IL31) are cytokines produced by T helper type 2 (Th2) cells and have been implicated in the pathophysiology of several skin disorders, such as pruritic conditions, allergic diseases, and other inflammatory conditions. IL13 signals through a shared receptor with IL4 via a heterodimer receptor complex comprising IL4 receptor alpha (IL4Rα) and IL13 receptor alpha 1 (IL13Rα1), and it is implicated as a central regulator in IgE synthesis, mucus hypersecretion, airway hyperresponsiveness (AHR), and fibrosis. IL31 functions by binding IL31 receptor A (IL31RA)/oncostatin M receptor beta (OSMRB) and activation of downstream JAK/STAT and PI3K/AKT pathways, which mediates inflammatory responses, initiating immunoregulatory circuits, stimulating itch, and neuronal outgrowth. Many of the clinical problems associated with dermatitis and other skin disorders are thought to be associated with IL13 and/or IL31 activity.

Chronic inflammatory skin diseases such as atopic dermatitis (AD), prurigo nodularis (PN), and chronic spontaneous urticaria (CSU) lead to intensely pruritic skin lesions resulting in severe scratching. Topical steroids and calcineurin inhibitors are not sufficient to manage symptoms in AD, PN, or CSU patients. Existing therapies include dupilumab (targeting IL4Ra) and tralokinumab and lebrikizumab (both targeting IL13), establishing a new standard of care in AD, CSU, and other inflammatory skin diseases. Existing therapies also include nemolizumab, an antibody that targets IL31RA and that has shown promising anti-pruritic efficacy, validating the IL31-IL31RA pathway in providing symptom relief in AD and PN patients. Overall, however, there remains a strong need for improved therapies for treating IL13-associated conditions and IL31-associated conditions, including therapies that have the potential to induce fast and prolonged control of symptoms in patients with chronic inflammatory skin disease.

SUMMARY

Provided herein are bispecific polypeptides that bind IL31 and IL 13, comprising a high affinity and potent biparatopic polypeptide that binds to the IL31 ligand and a high affinity and potent biparatopic polypeptide that binds to the IL13 ligand, thereby having the potential to induce fast and prolonged control of pruritus in patients with chronic inflammatory skin disease.

The bispecific polypeptides that bind IL31 and IL13 disclosed herein provide for multiple advantages and improvements over standard-of-care treatments and/or treatments still in development. Such advantages and improvements include, but are not limited to, greater efficacy against lesions and itches, greater safety (e.g., less conjunctivitis), rapid itch relief (days to weeks), extended half-life, avoidance of target-mediated drug disposition (TMDD), and more convenient and/or less frequent dosing (e.g., subcutaneous dosing and/or Q8W to Q12W or Q3M dosing), which leads to reduced injection burden. Such advantages and improvements allow the bispecific polypeptides that bind IL31 and IL13 disclosed herein to be used as treatment options for nonresponding and/or relapsed patients who received standard-of-care treatments and/or treatments still in development.

In some aspects, polypeptides that bind IL31 and IL 13 provided herein comprise i) a first co-binder that binds IL31 comprising a first Variable Heavy domain of Heavy chain 1 (VHH1) and a second VHH (VHH2) and ii) a second co-binder that binds IL 13 comprising a third VHH (VHH3) and a fourth VHH (VHH4), wherein:

a) the VHH1 comprises a CDR1 comprising the amino acid sequence of SEQ ID NO:8; a CDR2 comprising the amino acid sequence of SEQ ID NO:9; and a CDR3 comprising the amino acid sequence of SEQ ID NO:10; the VHH2 comprises a CDR1 comprising the amino acid sequence of SEQ ID NO: 19; a CDR2 comprising the amino acid sequence of SEQ ID NO:20; and a CDR3 comprising the amino acid sequence of SEQ ID NO:21; the VHH3 comprises a CDR1 comprising the amino acid sequence of SEQ ID NO:34; a CDR2 comprising the amino acid sequence of SEQ ID NO:35; and a CDR3 comprising the amino acid sequence of SEQ ID NO: 61; and the VHH4 comprises a CDR1 comprising the amino acid sequence of SEQ ID NO: 45; a CDR2 comprising the amino acid sequence of SEQ ID NO:46; and a CDR3 comprising the amino acid sequence of SEQ ID NO:64; or b) the VHH1 comprising a CDR1 comprises the amino acid sequence of SEQ ID NO:5; a CDR2 comprising the amino acid sequence of SEQ ID NO:6; and a CDR3 comprising the amino acid sequence of SEQ ID NO:7; the VHH2 comprises a CDR1 comprising the amino acid sequence of SEQ ID NO:16; a CDR2 comprising the amino acid sequence of SEQ ID NO: 17; and a CDR3 comprising the amino acid sequence of SEQ ID NO: 18; the VHH3 comprises a CDR1 comprising the amino acid sequence of SEQ ID NO:31; a CDR2 comprising the amino acid sequence of SEQ ID NO:32; and a CDR3 comprising the amino acid sequence of SEQ ID NO: 60; and the VHH4 comprises a CDR1 comprising the amino acid sequence of SEQ ID NO: 42; a CDR2 comprising the amino acid sequence of SEQ ID NO:43; and a CDR3 comprising the amino acid sequence of SEQ ID NO:63; or c) the VHH1 comprises a CDR1 comprising the amino acid sequence of SEQ ID NO:11; a CDR2 comprising the amino acid sequence of SEQ ID NO:12; and a CDR3 comprising the amino acid sequence of SEQ ID NO:13; the VHH2 comprises a CDR1 comprising the amino acid sequence of SEQ ID NO:22; a CDR2 comprising the amino acid sequence of SEQ ID NO:23; and a CDR3 comprising the amino acid sequence of SEQ ID NO:24; the VHH3 comprises a CDR1 comprising the amino acid sequence of SEQ ID NO:37; a CDR2 comprising the amino acid sequence of SEQ ID NO:38; and a CDR3 comprising the amino acid sequence of SEQ ID NO: 62; and the VHH4 comprises a CDR1 comprising the amino acid sequence of SEQ ID NO: 48; a CDR2 comprising the amino acid sequence of SEQ ID NO:49; and a CDR3 comprising the amino acid sequence of SEQ ID NO:65.

In some aspects, the bispecific polypeptides that bind IL31 and IL 13 provided herein comprise i) a first co-binder that binds IL31 comprising a VHH1 and a VHH2 and ii) a second co-binder that binds IL 13 comprising a VHH3 and a VHH4, wherein:

a) the VHH1 comprises a CDR1 comprising the amino acid sequence of SEQ ID NO:8; a CDR2 comprising the amino acid sequence of SEQ ID NO:9; and a CDR3 comprising the amino acid sequence of SEQ ID NO:10; the VHH2 comprises a CDR1 comprising the amino acid sequence of SEQ ID NO: 19; a CDR2 comprising the amino acid sequence of SEQ ID NO:20; and a CDR3 comprising the amino acid sequence of SEQ ID NO:21; the VHH3 comprises a CDR1 comprising the amino acid sequence of SEQ ID NO:34; a CDR2 comprising the amino acid sequence of SEQ ID NO:35; and a CDR3 comprising the amino acid sequence of SEQ ID NO:36 or 61; and the VHH4 comprises a CDR1 comprising the amino acid sequence of SEQ ID NO:45; a CDR2 comprising the amino acid sequence of SEQ ID NO:46; and a CDR3 comprising the amino acid sequence of SEQ ID NO:47 or 64; or b) the VHH1 comprises a CDR1 comprising the amino acid sequence of SEQ ID NO:5; a CDR2 comprising the amino acid sequence of SEQ ID NO:6; and a CDR3 comprising the amino acid sequence of SEQ ID NO:7; the VHH2 comprises a CDR1 comprising the amino acid sequence of SEQ ID NO:16; a CDR2 comprising the amino acid sequence of SEQ ID NO:17; and a CDR3 comprising the amino acid sequence of SEQ ID NO: 18; the VHH3 comprises a CDR1 comprising the amino acid sequence of SEQ ID NO:31; a CDR2 comprising the amino acid sequence of SEQ ID NO:32; and a CDR3 comprising the amino acid sequence of SEQ ID NO:33 or 60; and the VHH4 comprises a CDR1 comprising the amino acid sequence of SEQ ID NO:42; a CDR2 comprising the amino acid sequence of SEQ ID NO:43; and a CDR3 comprising the amino acid sequence of SEQ ID NO:44 or 63; or c) the VHH1 comprises a CDR1 comprising the amino acid sequence of SEQ ID NO:11; a CDR2 comprising the amino acid sequence of SEQ ID NO: 12; and a CDR3 comprising the amino acid sequence of SEQ ID NO: 13; the VHH2 comprises a CDR1 comprising the amino acid sequence of SEQ ID NO:22; a CDR2 comprising the amino acid sequence of SEQ ID NO:23; and a CDR3 comprising the amino acid sequence of SEQ ID NO:24; the VHH3 comprises a CDR1 comprising the amino acid sequence of SEQ ID NO:37; a CDR2 comprising the amino acid sequence of SEQ ID NO:38; and a CDR3 comprising the amino acid sequence of SEQ ID NO:39 or 62; and the VHH4 comprises a CDR1 comprising the amino acid sequence of SEQ ID NO:48; a CDR2 comprising the amino acid sequence of SEQ ID NO:49; and a CDR3 comprising the amino acid sequence of SEQ ID NO:50 or 65.

In some aspects, the VHH3 useful for the second co-binder comprises a CDR1 comprising the amino acid sequence of SEQ ID NO:34; a CDR2 comprising the amino acid sequence of SEQ ID NO:35; and a CDR3 comprising the amino acid sequence of SEQ ID NO:36 or 61; the VHH4 comprises a CDR1 comprising the amino acid sequence of SEQ ID NO:45; a CDR2 comprising the amino acid sequence of SEQ ID NO:46; and a CDR3 comprising the amino acid sequence of SEQ ID NO:47 or 64.

In some aspects, the VHH3 for the second co-binder comprising a CDR1 comprising the amino acid sequence of SEQ ID NO:31; a CDR2 comprising the amino acid sequence of SEQ ID NO: 32; and a CDR3 comprising the amino acid sequence of SEQ ID NO:33 or 60; the VHH4 for the second co-binder comprises a CDR1 comprising the amino acid sequence of SEQ ID NO: 42; a CDR2 comprising the amino acid sequence of SEQ ID NO:43; and a CDR3 comprising the amino acid sequence of SEQ ID NO:44 or 63.

In some aspects, the VHH3 for the second co-binder comprises a CDR1 comprising the amino acid sequence of SEQ ID NO:37; a CDR2 comprising the amino acid sequence of SEQ ID NO: 38; and a CDR3 comprising the amino acid sequence of SEQ ID NO:39 or 62; the VHH4 for the second co-binder comprises a CDR1 comprising the amino acid sequence of SEQ ID NO:48; a CDR2 comprising the amino acidsequence of SEQ ID NO:49; and a CDR3 comprising the amino acidsequence of SEQ ID NO:50 or 65.

In some aspects, the VHH3 for the second co-binder comprises a CDR1 comprising the amino acid sequence of SEQ ID NO:34; a CDR2 comprising the amino acid sequence of SEQ ID NO: 35; and a CDR3 comprising the amino acid sequence of SEQ ID NO:61; the VHH4 comprising a CDR1 comprises the amino acid sequence of SEQ ID NO:45; a CDR2 comprising the amino acid sequence of SEQ ID NO:46; and a CDR3 comprising the amino acid sequence of SEQ ID NO:64.

In some aspects, the VHH3 for the second co-binder comprising a CDR1 comprising the amino acid sequence of SEQ ID NO:31; a CDR2 comprising the amino acid sequence of SEQ ID NO: 32; and a CDR3 comprising the amino acid sequence of SEQ ID NO:60; the VHH4 for the second co-binder comprises a CDR1 comprising the amino acid sequence of SEQ ID NO:42; a CDR2 comprising the amino acid sequence of SEQ ID NO:43; and a CDR3 comprising the amino acid sequence of SEQ ID NO: 63.

In some aspects, the VHH3 for the second co-binder comprises a CDR1 comprising the amino acid sequence of SEQ ID NO:37; a CDR2 comprising the amino acid sequence of SEQ ID NO: 38; and a CDR3 comprising the amino acid sequence of SEQ ID NO:62; the VHH4 for the second co-binder comprises a CDR1 comprising the amino acid sequence of SEQ ID NO:48; a CDR2 comprising the amino acid sequence of SEQ ID NO:49; and a CDR3 comprising the amino acid sequence of SEQ ID NO:65.

In some aspects, the bispecific polypeptides that bind IL31, as parts of polypeptides that bind IL13 and IL31 and comprising one or more VHH1 and VHH2, are provided herein.

In some aspects, the VHH1 for the first co-binder comprises a CDR1 comprising the amino acidsequence of SEQ ID NO:8; a CDR2 comprising the amino acidsequence of SEQ ID NO: 9; and a CDR3 comprising the amino acid sequence of SEQ ID NO:10; and the VHH2 for the first co-binder comprises a CDR1 comprising the amino acid sequence of SEQ ID NO: 19; a CDR2 comprising the amino acid sequence of SEQ ID NO:20; and a CDR3 comprising the amino acid sequence of SEQ ID NO:21.

In some aspects, the VHH1 comprises a CDR1 comprising the amino acid sequence of SEQ ID NO:5; a CDR2 comprising the amino acid sequence of SEQ ID NO:6; and a CDR3 comprising the amino acid sequence of SEQ ID NO:7; and the VHH2 comprises a CDR1 comprising the amino acid sequence of SEQ ID NO: 16; a CDR2 comprising the amino acid sequence of SEQ ID NO:17; and a CDR3 comprising the amino acid sequence of SEQ ID NO: 18.

In some aspects, the VHH1 comprises a CDR1 comprising the amino acid sequence of SEQ ID NO:11; a CDR2 comprising the amino acid sequence of SEQ ID NO:12; and a CDR3 comprising the amino acid sequence of SEQ ID NO: 13; and the VHH2 comprising a CDR1 comprising the amino acid sequence of SEQ ID NO:22; a CDR2 comprising the amino acid sequence of SEQ ID NO:23; and a CDR3 comprising the amino acid sequence of SEQ ID NO: 24.

In some aspects, the first VHH (VHH1) and/or the second VHH (VHH2) of the polypeptide that binds IL31 are humanized. In some aspects, the first VHH and/or the second VHH of the polypeptide that binds IL13 are humanized.

In some aspects, the third VHH (VHH3) of the second co-binder that binds IL13 comprises an amino acid sequence having at least 85%, at least 90%, at least 95%, at least 96%, at least 97%, at least 98%, or at least 99% sequence identity to the amino acid sequence of SEQ ID NO: 29 or 30, or amino acid residues 2-115 of SEQ ID NO:29 or 30. In some aspects, the VHH3 of the second co-binder that binds IL 13 comprises the amino acid sequence of SEQ ID NO: 29 or 30, or amino acid residues 2-115 of SEQ ID NO:29 or 30.

In some aspects, the fourth VHH (VHH4) of the second co-binder that binds IL 13 comprises an amino acid sequence having at least 85%, at least 90%, at least 95%, at least 96%, at least 97%, at least 98%, or at least 99% sequence identity to the amino acid sequence of SEQ ID NO: 40 or 41, or amino acid residues 2-127 of SEQ ID NO:40 or 41. In some aspects, the VHH4 of the polypeptide that binds IL 13 comprises the amino acid sequence of SEQ ID NO:40 or 41, or amino acid residues 2-127 of SEQ ID NO:40 or 41.

In some aspects, the VHH4 of the polypeptide that binds IL13 comprises an amino acid sequence having at least 85%, at least 90%, at least 95%, at least 96%, at least 97%, at least 98%, or at least 99% sequence identity to the amino acid residues 154-280 of SEQ ID NO:51 or 52, optionally wherein residue 162 is valine according to SEQ ID NO:51 or 52. In some aspects, the VHH4 of the polypeptide that binds IL 13 comprises the amino acid residues 154-280 of SEQ ID NO: 51 or 52, optionally wherein residue 162 is valine according to SEQ ID NO:51 or 52.

In some aspects, the VHH3 of the bispecific polypeptide that binds IL13 comprises the amino acid residues 1-115 or 2-115 of SEQ ID NO:51 or 52, and the VHH4 of the bispecific polypeptide that binds IL13 comprises the amino acid residues 154-280 of SEQ ID NO:51 or 52, optionally wherein residue 162 is valine according to SEQ ID NO:51 or 52.

In some aspects, the VHH1 of the polypeptide that binds IL31 comprises an amino acid sequence having at least 85%, at least 90%, at least 95%, at least 96%, at least 97%, at least 98%, or at least 99% sequence identity to the amino acid residues 1-118 or 2-118 of SEQ ID NO:25 or 26, or the amino acid sequence of SEQ ID NO:3 or 4, or amino acid residues 2-118 of SEQ ID NO: 3 or 4. In some aspects, the VHH1 of the polypeptide that binds IL31 comprises amino acid residues 2-118 of SEQ ID NO: 25 or 26, or amino acid sequence of SEQ ID NO:3 or 4, or amino acid residues 2-118 of SEQ ID NO:3 or 4.

In some aspects, the VHH2 of the polypeptide that binds IL31 comprises an amino acid sequence having at least 85%, at least 90%, at least 95%, at least 96%, at least 97%, at least 98%, or at least 99% sequence identity to the amino acid residues 157-275 of SEQ ID NO:25 or 26, optionally wherein residue 166 is valine according to SEQ ID NO:25 or 26. In some aspects, the VHH2 of the bispecific polypeptide that binds IL31 comprises amino acid residues 157-275 of SEQ ID NO:25 or 26, optionally wherein residue 166 is valine according to SEQ ID NO:25 or 26.

In some aspects, the VHH2 of the bispecific polypeptide that binds IL31 comprises an amino acid sequence having at least 85%, at least 90%, at least 95%, at least 96%, at least 97%, at least 98%, or at least 99% sequence identity to the amino acid sequence of SEQ ID NO:14 or 15, or amino acid residues 2-119 of SEQ ID NO: 14 or 15, optionally wherein residue 10 is valine according to SEQ ID NO:14 or 15. In some aspects, the VHH2 of the bispecific polypeptide that binds IL31 comprises the amino acid sequence of SEQ ID NO:14 or 15, or amino acid residues 2-119 of SEQ ID NO: 14 or 15, optionally wherein residue 10 is valine according to SEQ ID NO: 14 or 15.

In some aspects, the VHH1 of the bispecific polypeptide that binds IL31 comprises amino acid residues 1-118 or 2-118 of SEQ ID NO:25 or 26, and the VHH2 of the bispecific polypeptide that binds IL31 comprises amino acid residues 157-275 of SEQ ID NO: 25 or 26, optionally wherein residue 166 is valine according to SEQ ID NO: 25 or 26.

In some aspects, the VHH1 of the bispecific polypeptide that binds IL31 comprises the amino acid sequence of SEQ ID NO:3 or 4, or amino acid residues 2-118 of SEQ ID NO:3 or 4, and the VHH2 of the bispecific polypeptide that binds IL31 comprises the amino acid sequence of SEQ ID NO: 14 or 15, or amino acid residues 2-119 of SEQ ID NO:14 or 15.

In some aspects, the VHH1 of the bispecific polypeptide that binds IL31 is connected to the VHH2 of the bispecific polypeptide that binds IL31 by a first linker. In some aspects, the first linker comprises 33-43 amino acids in length. In some aspects, the first linker is 37-39 amino acids in length. In some aspects, the first linker is 38 amino acids in length. In some aspects, the VHH1 and VHH2 of the co-binder that binds IL31 are connected by a peptide linker comprising the amino acid sequence of SEQ ID NO:66. In some aspects, the VHH3 of the polypeptide that binds IL13 is connected to the VHH4 of the co-binder that binds IL 13 by a second linker. In some aspects, the first linker and the second linker are different. In some aspects, the second linker comprises 33-43 amino acids in length. In some aspects, the second linker is 37-39 amino acids in length. In some aspects, the second linker is 38 amino acids in length. In some aspects, the VHH3 and VHH4 of the co-binder that binds IL 13 are connected by a peptide linker comprising the amino acid sequence of SEQ ID NO:67. In some aspects, the co-binder that binds IL31 has the structure: [VHH1]-linker-[VHH2]. In some aspects, the co-binder that binds IL 13 has the structure: [VHH3]-linker-[VHH4].

In some aspects, the co-binder that binds IL13 comprises an amino acid sequence having at least 85%, at least 90%, at least 95%, at least 96%, at least 97%, at least 98%, or at least 99% sequence identity to the amino acid sequence of SEQ ID NO:51 or 52 or to the amino acid residues 2-280 of SEQ ID NO:51 or 52, optionally wherein residue 162 is valine according to SEQ ID NO:51 or 52. In some aspects, the co-binder that binds IL 13 comprises the amino acid sequence of SEQ ID NO:51 or 52 or the amino acid residues 2-280 of SEQ ID NO:51 or 52, optionally wherein residue 162 is valine according to SEQ ID NO:51 or 52.

In some aspects, the co-binder that binds IL13 comprises an amino acid sequence having at least 85%, at least 90%, at least 95%, at least 96%, at least 97%, at least 98%, or at least 99% sequence identity to the amino acid sequence of SEQ ID NO:52 or to the amino acid residues 2-280 of SEQ ID NO:52. In some aspects, the co-binder that binds IL 13 comprises the amino acid sequence of SEQ ID NO:52 or the amino acid residues 2-280 of SEQ ID NO:52.

In some aspects, the co-binder that binds IL31 comprises an amino acid sequence having at least 85%, at least 90%, at least 95%, at least 96%, at least 97%, at least 98%, or at least 99% sequence identity to the amino acid sequence of SEQ ID NO:25 or 26 or to the amino acid residues 2-275 of SEQ ID NO:25 or 26, optionally wherein residue 166 is valine according to SEQ ID NO:25 or 26. In some aspects, the co-binder that binds IL31 comprises the amino acid sequence of SEQ ID NO:25 or 26 or the amino acid residues 2-275 of SEQ ID NO:25 or 26, optionally wherein residue 166 is valine according to SEQ ID NO:25 or 26.

In some aspects, the co-binder that binds IL31 comprises an amino acid sequence having at least 85%, at least 90%, at least 95%, at least 96%, at least 97%, at least 98%, or at least 99% sequence identity to the amino acid sequence of SEQ ID NO:26 or to amino acid residues 2-275 of SEQ ID NO:26, optionally wherein residue 166 is valine according to SEQ ID NO: 26. In some aspects, the co-binder that binds IL31 comprises the amino acid sequence of SEQ ID NO:26 or the amino acid residues 2-275 of SEQ ID NO:26, optionally wherein residue 166 is valine according to SEQ ID NO:26.

In some aspects, the bispecific polypeptide that binds IL31 and IL13 comprises an Fc region. In some aspects, the bispecific polypeptide that binds IL31 and IL13 comprises an IgG1, IgG2, IgG3, or IgG4 Fc region. In some aspects, the bispecific polypeptide that binds IL31 and IL13 comprises a human Fc region. In some aspects, the Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the C-terminal amino acid residue of the Fc region is Lysine. In some aspects, the C-terminal amino acid residue of the Fc region is not Lysine. In some aspects, the bispecific polypeptide that binds IL13 and IL31 comprises an Fc region with a modified effector function. In some aspects, the bispecific polypeptide that binds IL 13 and IL31 comprises an effector null Fc region. In some aspects, the bispecific polypeptide comprises an Fc region comprising a full or partial hinge region. In some aspects, the full or partial hinge region comprises a cysteine (C) to serine(S) mutation. In some aspects, the Fc region comprises an amino acid sequence having at least 85%, at least 90%, at least 95%, at least 96%, at least 97%, at least 98%, or at least 99% sequence identity to SEQ ID NO:59 or to the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO: 59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises the amino acid sequence of SEQ ID NO:59 or the amino acid residues 1-231 of SEQ ID NO:59.

In some aspects, the co-binder that binds IL 13 is connected to the co-binder that binds IL31 by a third linker. In some aspects, the first linker, the second linker, and/or the third linker are different. In some aspects, the bispecific polypeptide that binds IL 13 and IL31 has the structure: [co-binder that binds IL 13]-linker-[co-binder that binds IL31]-Fc region, [co-binder that binds IL31]-linker-[co-binder that binds IL13]-Fc region, [co-binder that binds IL13]-Fc region-linker-[co-binder that binds IL31], or [co-binder that binds IL31]-Fc region-linker-[co-binder that binds IL 13]. In some aspects, the bispecific polypeptide that binds IL13 and IL31 has the structure: [co-binder that binds IL31]-Fc region-linker-[co-binder that binds IL 13].

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR 1 comprising the amino acid sequence of SEQ ID NO:8, a CDR2 comprising the amino acid sequence of SEQ ID NO:9, and a CDR3 comprising the amino acid sequence of SEQ ID NO: 10; and the VHH2 comprises a CDR1 comprising the amino acid sequence of SEQ ID NO: 19, a CDR2 comprising the amino acid sequence of SEQ ID NO:20, and a CDR3 comprising the amino acid sequence of SEQ ID NO:21; wherein the VHH1 and VHH2 are joined by a first linker; wherein the VHH3 comprises a CDR1 comprising the amino acid sequence of SEQ ID NO: 34, a CDR2 comprising the amino acid sequence of SEQ ID NO:35, and a CDR3 comprising the amino acid sequence of SEQ ID NO:36 or 61; and the VHH4 comprises a CDR1 comprising the amino acid sequence of SEQ ID NO:45, a CDR2 comprising the amino acid sequence of SEQ ID NO: 46, and a CDR3 comprising the amino acid sequence of SEQ ID NO:47 or 64; wherein the VHH3 and VHH4 are joined by a second linker; wherein the C-terminus of first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO:67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR 1 comprising the amino acid sequence of SEQ ID NO:8, a CDR2 comprising the amino acid sequence of SEQ ID NO:9, and a CDR3 comprising the amino acid sequence of SEQ ID NO: 10; and the VHH2 comprises a CDR1 comprising the amino acid sequence of SEQ ID NO: 19, a CDR2 comprising the amino acid sequence of SEQ ID NO:20, and a CDR3 comprising the amino acid sequence of SEQ ID NO:21; wherein the VHH1 and VHH2 are joined by a first linker; wherein the VHH3 comprises a CDR1 comprising the amino acid sequence of SEQ ID NO: 34, a CDR2 comprising the amino acid sequence of SEQ ID NO:35, and a CDR3 comprising the amino acid sequence of SEQ ID NO:61; and the VHH4 comprises a CDR1 comprising the amino acid sequence of SEQ ID NO:45, a CDR2 comprising the amino acid sequence of SEQ ID NO: 46, and a CDR3 comprising the amino acid sequence of SEQ ID NO:64; wherein the VHH3 and VHH4 are joined by a second linker; wherein the C-terminus of first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO: 67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7; and the VHH2 comprises a CDR1 comprising the amino acid sequence of SEQ ID NO: 16, a CDR2 comprising the amino acid sequence of SEQ ID NO: 17, and a CDR3 comprising the amino acid sequence of SEQ ID NO: 18; wherein the VHH1 and VHH2 are joined by a first linker; wherein the VHH3 comprises a CDR1 comprising the amino acid sequence of SEQ ID NO: 31, a CDR2 comprising the amino acid sequence of SEQ ID NO:32, and a CDR3 comprising the amino acid sequence of SEQ ID NO:33 or 60; and the VHH4 comprises a CDR1 comprising the amino acid sequence of SEQ ID NO:42, a CDR2 comprising the amino acid sequence of SEQ ID NO: 43, and a CDR3 comprising the amino acid sequence of SEQ ID NO:44 or 63; wherein the VHH3 and VHH4 are joined by a second linker; wherein the C-terminus of first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO:67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7; and the VHH2 comprises a CDR1 comprising the amino acid sequence of SEQ ID NO:16, a CDR2 comprising the amino acid sequence of SEQ ID NO:17, and a CDR3 comprising the amino acid sequence of SEQ ID NO: 18; wherein the VHH1 and VHH2 are joined by a first linker; wherein the VHH3 comprises a CDR1 comprising the amino acid sequence of SEQ ID NO: 31, a CDR2 comprising the amino acid sequence of SEQ ID NO:32, and a CDR3 comprising the amino acid sequence of SEQ ID NO:60; and the VHH4 comprises a CDR1 comprising the amino acid sequence of SEQ ID NO:42, a CDR2 comprising the amino acid sequence of SEQ ID NO: 43, and a CDR3 comprising the amino acid sequence of SEQ ID NO:63; wherein the VHH3 and VHH4 are joined by a second linker; wherein the C-terminus of first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO: 67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR 1 comprising the amino acid sequence of SEQ ID NO: 11, a CDR2 comprising the amino acid sequence of SEQ ID NO: 12, and a CDR3 comprising the amino acid sequence of SEQ ID NO: 13; and the VHH2 comprises a CDR1 comprising the amino acid sequence of SEQ ID NO: 22, a CDR2 comprising the amino acid sequence of SEQ ID NO:23, and a CDR3 comprising the amino acid sequence of SEQ ID NO:24; wherein the VHH1 and VHH2 are joined by a first linker; wherein the VHH3 comprises a CDR1 comprising the amino acid sequence of SEQ ID NO: 37, a CDR2 comprising the amino acid sequence of SEQ ID NO:38, and a CDR3 comprising the amino acid sequence of SEQ ID NO:39 or 62; and the VHH4 comprises a CDR1 comprising the amino acid sequence of SEQ ID NO:48, a CDR2 comprising the amino acid sequence of SEQ ID NO: 49, and a CDR3 comprising the amino acid sequence of SEQ ID NO:50 or 65; wherein the VHH3 and VHH4 are joined by a second linker; wherein the C-terminus of first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO:67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, the bispecific polypeptide that binds IL31 and IL13 comprises a first co-binder that specifically binds IL31 comprising a VHH1 and a VHH2, and a second co-binder that specifically binds IL 13 comprising a VHH3 and a VHH4, wherein the VHH1 comprises a CDR1 comprising the amino acid sequence of SEQ ID NO:11, a CDR2 comprising the amino acid sequence of SEQ ID NO: 12, and a CDR3 comprising the amino acid sequence of SEQ ID NO: 13; and the VHH2 comprises a CDR1 comprising the amino acid sequence of SEQ ID NO: 22, a CDR2 comprising the amino acid sequence of SEQ ID NO:23, and a CDR3 comprising the amino acid sequence of SEQ ID NO:24; wherein the VHH1 and VHH2 are joined by a first linker; wherein the VHH3 comprises a CDR1 comprising the amino acid sequence of SEQ ID NO: 37, a CDR2 comprising the amino acid sequence of SEQ ID NO:38, and a CDR3 comprising the amino acid sequence of SEQ ID NO:62; and the VHH4 comprises a CDR1 comprising the amino acid sequence of SEQ ID NO:48, a CDR2 comprising the amino acid sequence of SEQ ID NO: 49, and a CDR3 comprising the amino acid sequence of SEQ ID NO:65; wherein the VHH3 and VHH4 are joined by a second linker; wherein the C-terminus of the first co-binder is joined to an Fc region; wherein the C-terminus of the Fc region is joined to a third linker; and wherein the C-terminus of the third linker is joined to the N-terminus of the second co-binder. In some aspects, the first linker comprises 33-43 amino acids in length. In some aspects, the first linker comprises 37-39 amino acids in length. In some aspects, the first linker is 38 amino acids in length. In some aspects, the first linker comprises the amino acid sequence of SEQ ID NO:66. In some aspects, the second linker comprises 33-43 amino acids in length. In some aspects, the second linker comprises 37-39 amino acids in length. In some aspects, the second linker is 38 amino acids in length. In some aspects, the second linker comprises the amino acid sequence of SEQ ID NO:67. In some aspects, the third linker comprises 8-16 amino acids in length. In some aspects, the third linker comprises $10^{-14}$ amino acids in length. In some aspects, the third linker comprises 11-13 amino acids in length. In some aspects, the third linker is 12 amino acids in length. In some aspects, the third linker comprises the amino acid sequence of SEQ ID NO:68. In some aspects, the Fc region comprises an IgG1, IgG2, IgG3, or IgG4 Fc region. In some aspects, the Fc region is a human Fc region. In some aspects, Fc region comprises one or more substitutions, deletions, insertions, or any combination thereof. In some aspects, the one or more substitutions comprise C220S, M252Y, S254T, T256E, L234A, L235A, L309Y, Q311M, M428L, N434S, or any combination thereof, according to the EU numbering system. In some aspects, the one or more substitutions comprise C220S, M252Y, S254T, T256E, L234A, L235A, or any combination thereof, according to the EU numbering system. In some aspects, the one or more substitutions comprise C220S, M252Y, S254T, T256E, L234A, and L235A according to the EU numbering system. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59, or amino acid residues 1-231 of SEQ ID NO:59.

In some aspects, any one of the linkers is from about 5 to about 50 amino acids in length. In some aspects, any one of the linkers is from about 8 to about 40 amino acids in length. In some aspects, any one of the linkers is from about 12 to about 37 amino acids in length. In some aspects, any one of the linkers is a flexible linker.

In some aspects, the bispecific polypeptide that binds IL 13 and IL31 comprises the amino acid sequence of any one of SEQ ID NOs: 55-58 or the amino acid residues 1-797 of SEQ ID NO: 56 or 58. In some aspects, the bispecific polypeptide that binds IL13 and IL31 comprises the amino acid sequence of SEQ ID NO:55. In some aspects, the bispecific polypeptide that binds IL13 and IL31 comprises the amino acid sequence of SEQ ID NO:56 or the amino acid residues 1-797 of SEQ ID NO:56. In some aspects, the bispecific polypeptide that binds IL13 and IL31 comprises the amino acid sequence of SEQ ID NO:57. In some aspects, the bispecific polypeptide that binds IL13 and IL31 comprises the amino acid sequence of SEQ ID NO:58 or the amino acid residues 1-797 of SEQ ID NO:58.

In some aspects, the bispecific polypeptide that binds IL 13 and IL31 binds to human IL13 and/or human IL31. In some aspects, the human IL 13 comprises the amino acid sequence of SEQ ID NO:27 or SEQ ID NO:28. In some aspects, the human IL31 comprises the amino acid sequence of SEQ ID NO: 1 or SEQ ID NO:2.

In some aspects, the bispecific polypeptide that binds IL 13 and IL31 binds to human IL13 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the bispecific polypeptide that binds IL 13 and IL31 binds to human IL31 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the bispecific polypeptide that binds IL13 and IL31 binds to human IL13 with a koff rate of less than or equal to $5\times10^{-4}$ M per second, less than or equal to $1\times10^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance. In some aspects, the bispecific polypeptide that binds IL13 and IL31 binds to human IL31 with a koff rate of less than or equal to $5\times10^{-4}$ M per second, less than or equal to $1\times10^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance.

Also provided herein are multimeric polypeptides, each comprising two of the any one of the polypeptides that bind IL 13 and IL31 provided herein. Also provided herein are multimeric polypeptides, each comprising two polypeptides that bind IL13 and IL31, wherein each of the polypeptides that bind IL13 and IL31 comprises the amino acid sequence of SEQ ID NO: 55.

Also provided herein are pharmaceutical compositions comprising any one or more of the polypeptides that bind IL 13 and IL31 or any one or more of the multimeric polypeptides described herein and a pharmaceutically acceptable carrier.

Also provided herein are isolated nucleic acids encoding any one or more of the polypeptides that bind IL13 and IL31 or any one or more of the multimeric polypeptides described herein. Further provided herein are vectors comprising any one or more of the nucleic acids described herein. Further provided herein are host cells comprising any one or more of the nucleic acids described herein. Further provided herein are host cells comprising any one or more of the vectors described herein.

Also provided herein are methods of producing any one or more of the polypeptides that bind IL13 and IL31 or any one or more of the multimeric polypeptides described herein. In some aspects, the method comprises culturing a host cell comprising any one or more of the nucleic acids described herein under conditions suitable for expression of the polypeptide(s) or multimeric polypeptide(s). In some aspects, the method comprises culturing a host cell comprising any one or more of the vectors described herein under conditions suitable for expression of the polypeptide(s) or multimeric polypeptide(s). In some aspects, the method further comprises isolating the polypeptide(s) or multimeric polypeptide(s).

Also provided herein are methods for treating a subject having an IL13-associated condition and/or an IL31-associated condition comprising administering to the subject a pharmaceutically effective amount of any one or more the polypeptides that bind IL13 and IL31 or any one or more of the multimeric polypeptides described herein or a pharmaceutical composition thereof.

In some aspects, the subject is a human subject.

In some aspects, the IL 13-associated condition and/or IL31-associated condition is a pruritic condition. In some aspects, the IL 13-associated condition and/or IL31-associated condition is atopic dermatitis, prurigo nodularis, or chronic spontaneous urticaria.

In some aspects, the IL13-associated condition is airway hyperresponsiveness, allergic asthma, allergic conjunctivitis, allergic contact dermatitis, allergic lung disease, allergic rhinitis, alopecia areata, Alzheimer's disease, aspirin-exacerbated respiratory disease, asthma, atopic dermatitis, atopic keratoconjunctivitis, bronchial asthma, bullous pemphigoid, chronic hand eczema, chronic inducible urticaria, chronic obstructive pulmonary disease, chronic pruritus of unknown origin, chronic Rhinosinusitis with nasal polyposis, chronic spontaneous urticaria, colitis, dermatitis, eczema, eosinophilic chronic obstructive pulmonary disease (COPD), eosinophilic esophagitis, eosinophilic gastritis, eosinophilic duodenitis, epidermolysis bullosa, food allergy, goblet cell metaplasia, hepatic fibrosis, Hodgkin's disease, idiopathic pulmonary fibrosis, Netherton syndrome, progressive systemic sclerosis, prurigo nodularis, rheumatoid arthritis, sinusitis, Sjogren's syndrome, systemic lupus erythematosus, systemic sclerosis, type 1 diabetes, or ulcerative colitis.

In some aspects, the IL31-associated condition is acne rosacea, acne vulgaris, allergic asthma, allergic contact dermatitis, allergic rhinitis, alopecia areata, arthritis, atopic dermatitis, bile acid induced urticaria, bullous pemphigoid, checkpoint inhibitor induced pruritus, cholestatic pruritus, chronic hand eczema, chronic inducible urticaria, chronic kidney disease associated pruritus, chronic pruritus of unknown origin, chronic spontaneous urticaria, chronic urticaria, contact dermatitis, contact hypersensitivity, Crohn's disease, cutaneous (lichen) amyloidosis, cutaneous T cell lymphoma, dermatomyositis, a drug-induced allergic reaction, eczema, epidermolysis bullosa, folliculitis, inflammatory bowel disease, intrahepatic cholestasis of pregnancy, itch associated with wound healing, lichen planus, metabolic dysfunction-associated (non-alcoholic) steatohepatitis, neurodermatitis, osteoarthritis, osteoporosis, pemphigus, pemphigus herpetiformis, porokeratosis, primary biliary cholangitis, primary sclerosing cholangitis, prurigo nodularis, pruritus, pruritus associated with cutaneous T-cell lymphoma, psoriasis, psoriatic arthritis, rheumatoid arthritis, scleroderma, skin-tropic viruses and viral associated pruritus, spondyloarthritis, stasis dermatitis, systemic lupus erythematosus, systemic sclerosis, toxic epidermal necrolysis, ulcerative colitis, uremic pruritus, or wound healing pruritus.

In some aspects, the polypeptide that binds IL 13 and IL31, the multimeric polypeptide, or the pharmaceutical composition is administered parenterally. In some aspects, the polypeptide that binds IL13 and IL31, the multimeric polypeptide, or the pharmaceutical composition is administered by an intravenous route, a subcutaneous route, an intramuscular route, or an intraperitoneal route. In some aspects, the polypeptide that binds IL13 and IL31, the multimeric polypeptide, or the pharmaceutical composition is administered by intravenous route. In some aspects, the polypeptide that binds IL13 and IL31, the multimeric polypeptide, or the pharmaceutical composition is administered by subcutaneous route.

In some aspects, the method comprises administering one or more therapeutic agent in combination with the polypeptide that binds IL 13 and IL31, the multimeric polypeptide, or the pharmaceutical composition. In some aspects, the one or more therapeutic agent is an antibody, a topical steroid, a small molecule inhibitor, and/or a systemic immunosuppressant agent. In some aspects, the one or more therapeutic agent is a topical corticosteroid, a calcineurin inhibitor, an anti-IL4RA antibody, an anti-IL13RA antibody, an anti-OSMR antibody, an anti-Ox40 antibody, an anti-Ox40L antibody, an anti-TSLP antibody an anti-IL 17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, anti-IL23p19 antibody, an anti-IL31 antibody, an anti-IgE antibody, an anti-CD11α antibody, anti-IL6R antibody, anti-α4-Intergrin antibody, an anti-IL12 antibody, an anti-IL1β antibody, an anti-BlyS antibody, an anti-CKIT antibody, an anti-SIGLEC-6 antibody, and/or an anti-SIGLEC-8 antibody. In some aspects, the one or more therapeutic agent is a small molecule inhibitor of calcineurin, IL4RA, IL13RA, IL13, IL31, OSMR, Ox40, Ox40L, TSLP, IL17, TNFα, CD20, CD19, CD25, IL4, IL23, IgE, CD11α, IL6R, α4-Intergrin, IL12, IL1β, BlyS, CKIT, and/or SIGLEC-6. In some aspects, the one or more therapeutic agent is a calcineurin inhibitor, a STAT inhibitor, a JAK inhibitor, a PI3K inhibitor, an AKT inhibitor, a MAPK inhibitor, a MRGPRX2 inhibitor, a topical corticosteroid, a calcineurin inhibitor, and/or a fusion protein comprising a portion of CTLA-4 and an Fc region of an immunoglobulin, optionally wherein the fusion protein is abatacept or belatacept.

BRIEF DESCRIPTION OF THE DRAWINGS

FIG. 1A shows round 1 (R1) MACS flow plot images taken from flow cytometry analysis of R1 MACS eluates for 0 nM IL13 and 10 nM IL13 stained samples. FIG. 1B and FIG. 1C show round 2 (R2)

FACS and round (R3) FACS images, respectively, representing flow plots for sorting human anti-IL 13 single binder displaying yeast cells at 0 and 10 nM human IL13 concentration.

Figure 2:
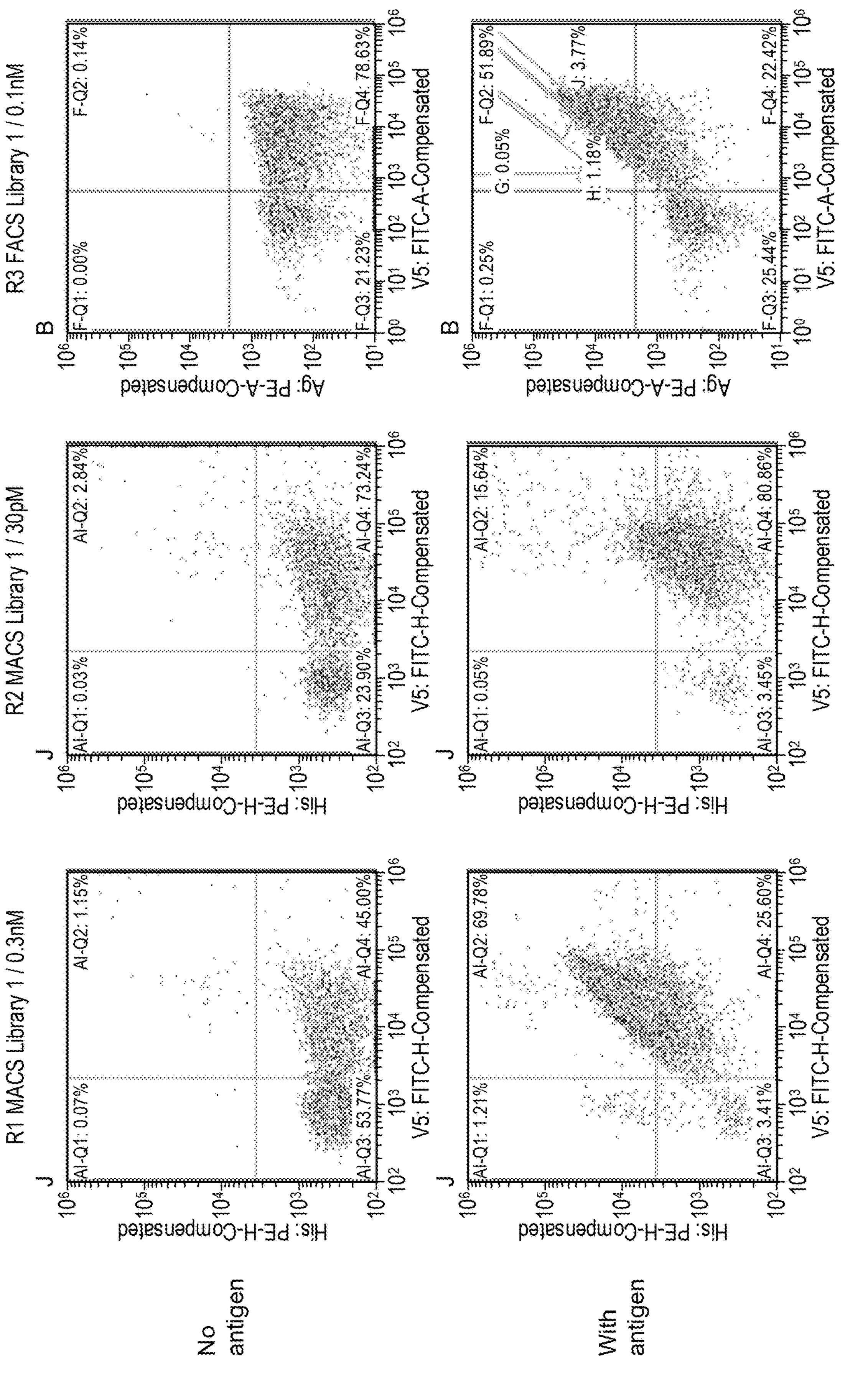

FIG. 2 shows anti-IL13 co-binder selection flow cytometry plots. Round 1 (R1) and round 2 (R2) MACS flow plot images were taken from flow cytometry analysis of R1 and R2 MACS eluates for 0 nM and 0.3 nM IL 13 stained samples for R1 and 0 nM and 30 PM IL13 stained samples for R2. R3 FACS was performed for sorting human anti-IL 13 single binder displaying yeast cells at 0 and 0.1 nM human IL13 concentration.

Figure 3:
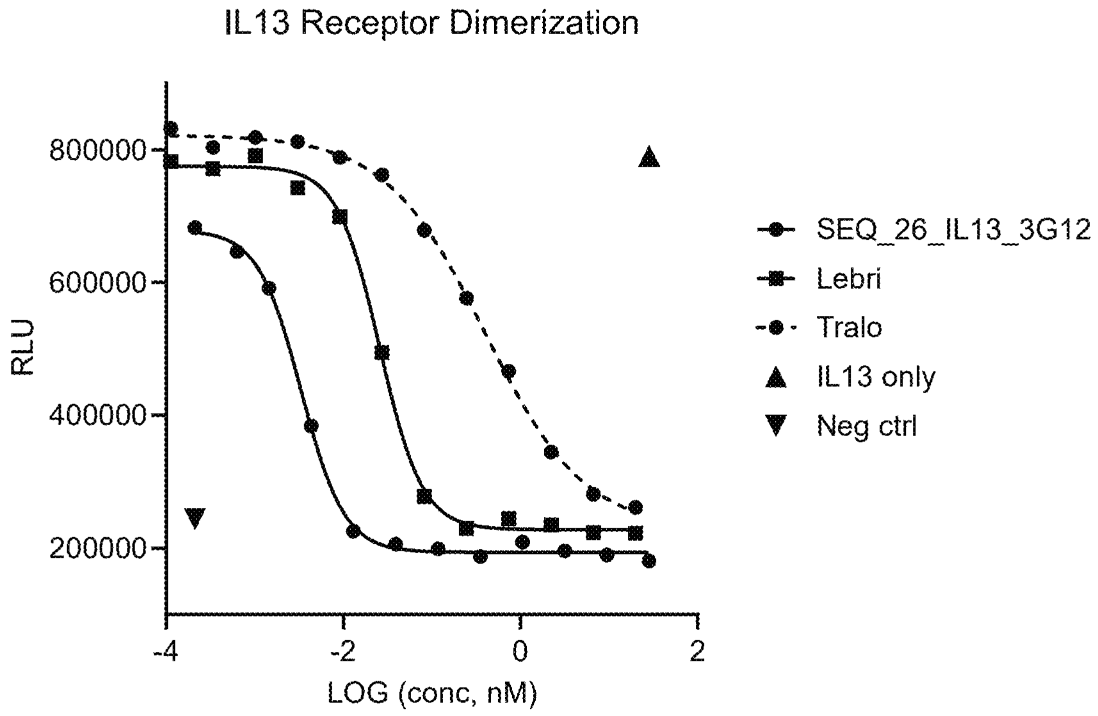

FIG. 3 is a plot showing dose-dependent inhibition activity of 3G12 co-binder using IL13 dimerization assays. 3G12-YTE-Fc was diluted from 30 μg/ml with 3× dilution for 12 points and incubated with equal volume of 10 ng/ml IL13/IL31 in AssayComplete™ Cell Plating 0 Reagent (Eurofins DiscoverX) for 1 hour at room temperature. 3G12 was then added to IL 13 receptor dimerization reporter cells. RLU was read and normalized to IL13 activity without IL13 only control and presented as percentage. For comparison, 3G12-YTE-Fc, lebrikizumab (anti-IL13 hIgG4 monoclonal), or tralokinumab were diluted and incubated with IL 13 and assessed for IL13 receptor dimerization, respectively.

Figure 4:
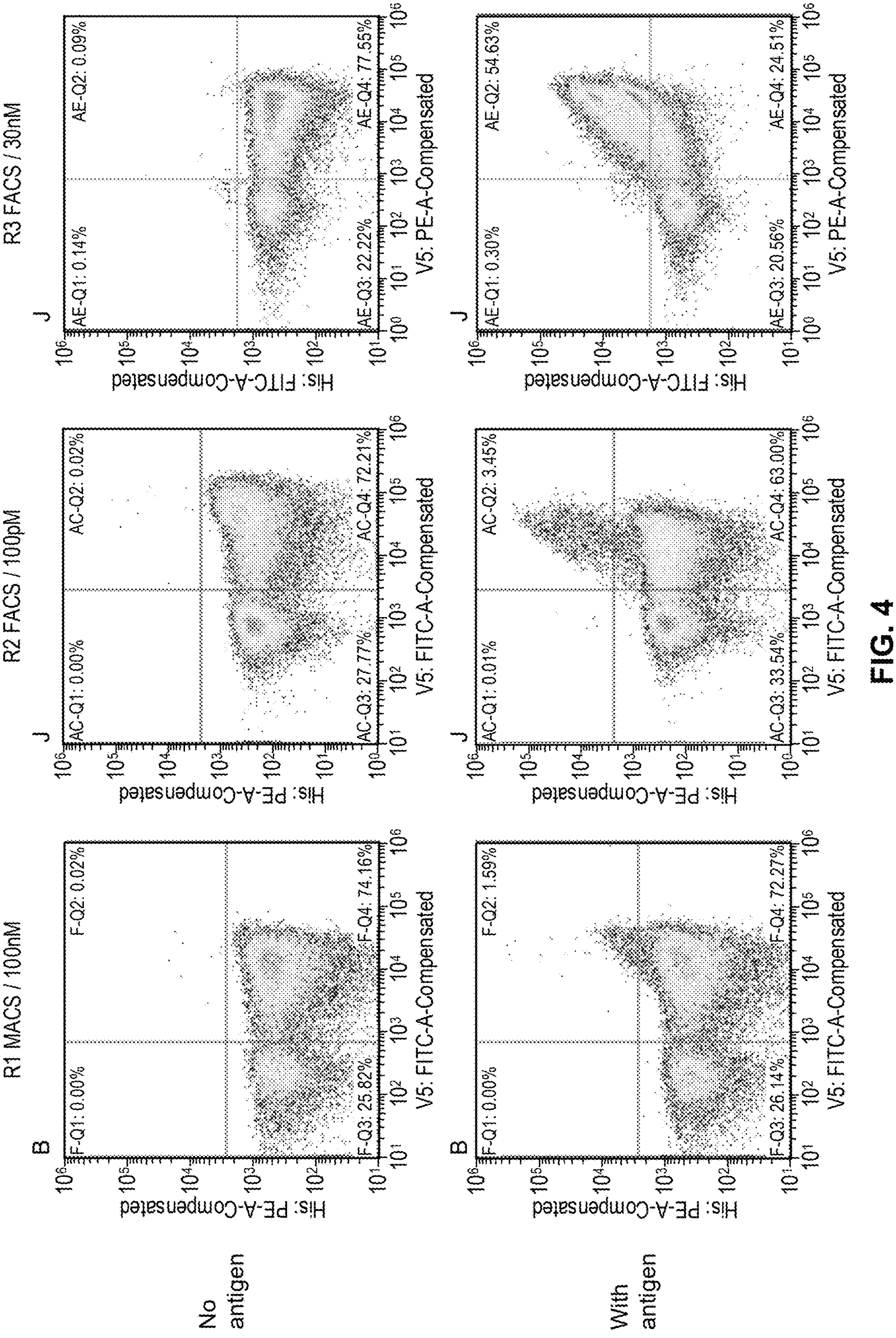

FIG. 4 shows flow cytometry plots for Campaign 1 anti-IL31 single binder selection. Round 1 (R1) MACS flow plot images were taken from flow cytometry analysis of R1 MACS eluates for 0 nM IL31 and 100 nM IL31 stained samples. Round 2 (R2) FACS and round 3 (R3) FACS images represent flow plots for sorting human IL31 specific single binder displaying yeast cells at 100 nM and 30 nM human IL31 concentrations, respectively.

Figure 5:
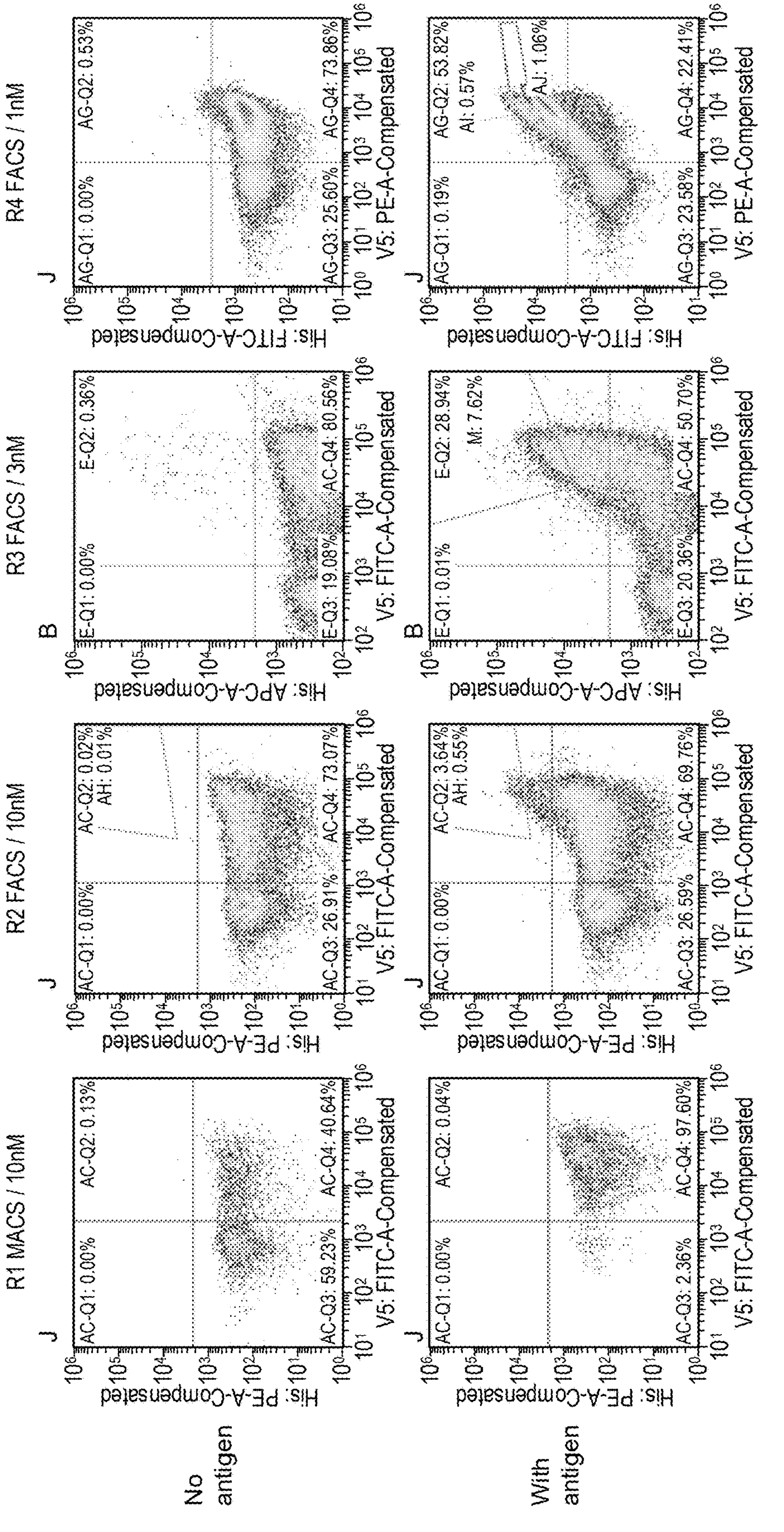

FIG. 5 shows flow cytometry plots for Campaign 1 anti-IL31 co-binder selection. Round 1 (R1) MACS flow plot images were taken from flow cytometry analysis of R1 MACS eluates for 0 nM IL31 and 10 nM IL31 stained samples. Round 2 (R2) FACS, round 3 (R3) FACS, and round 4 (R4) FACS images represent flow plots for sorting human IL31 specific co-binder displaying yeast cells at 10 nM, 3 nM, and 1 nM human IL31 concentrations, respectively. In R4 FACS plot, AI gate represents populations with higher affinity to human IL31 than AJ gate.

Figure 6A:
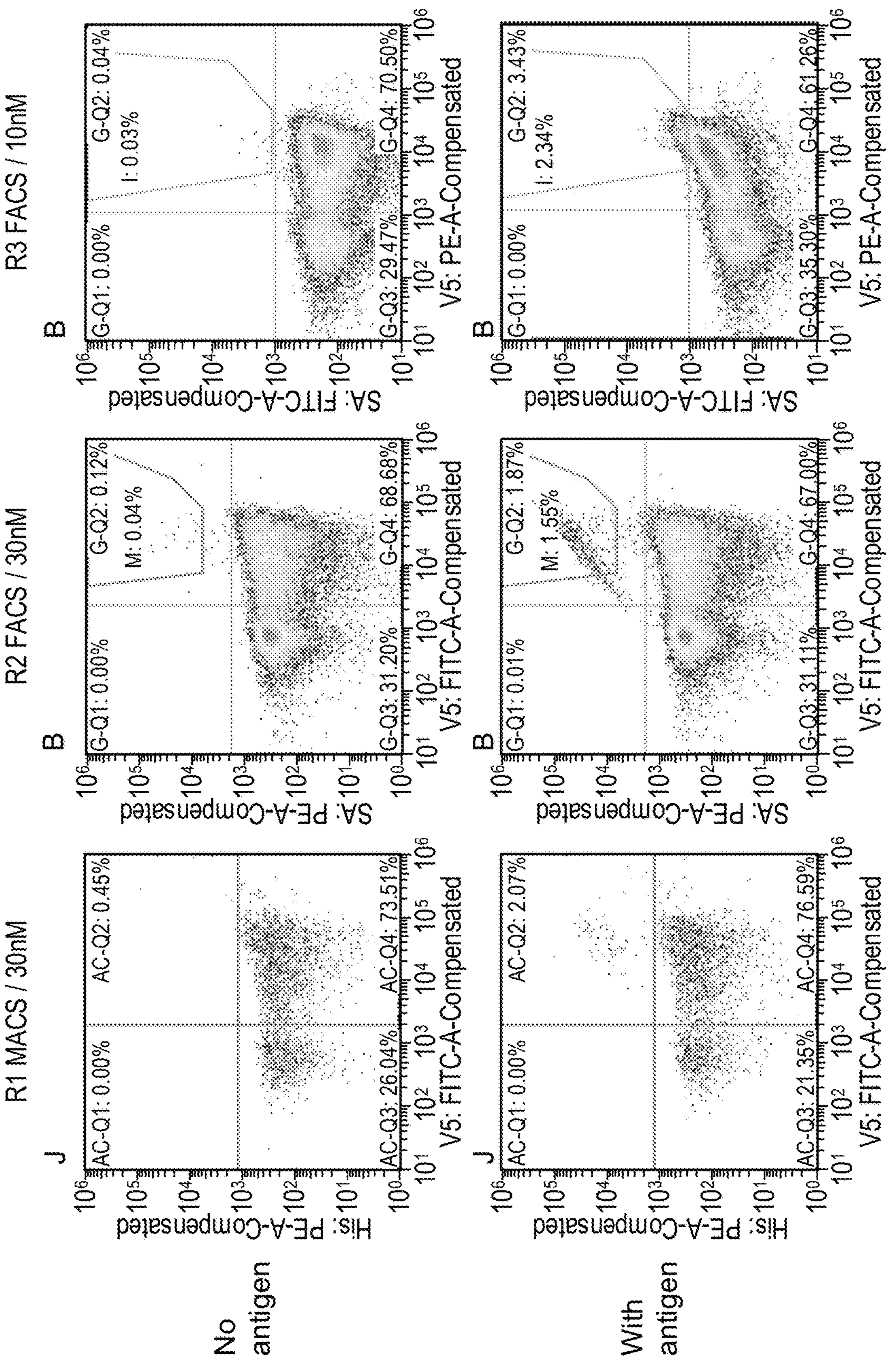
Figure 6B:
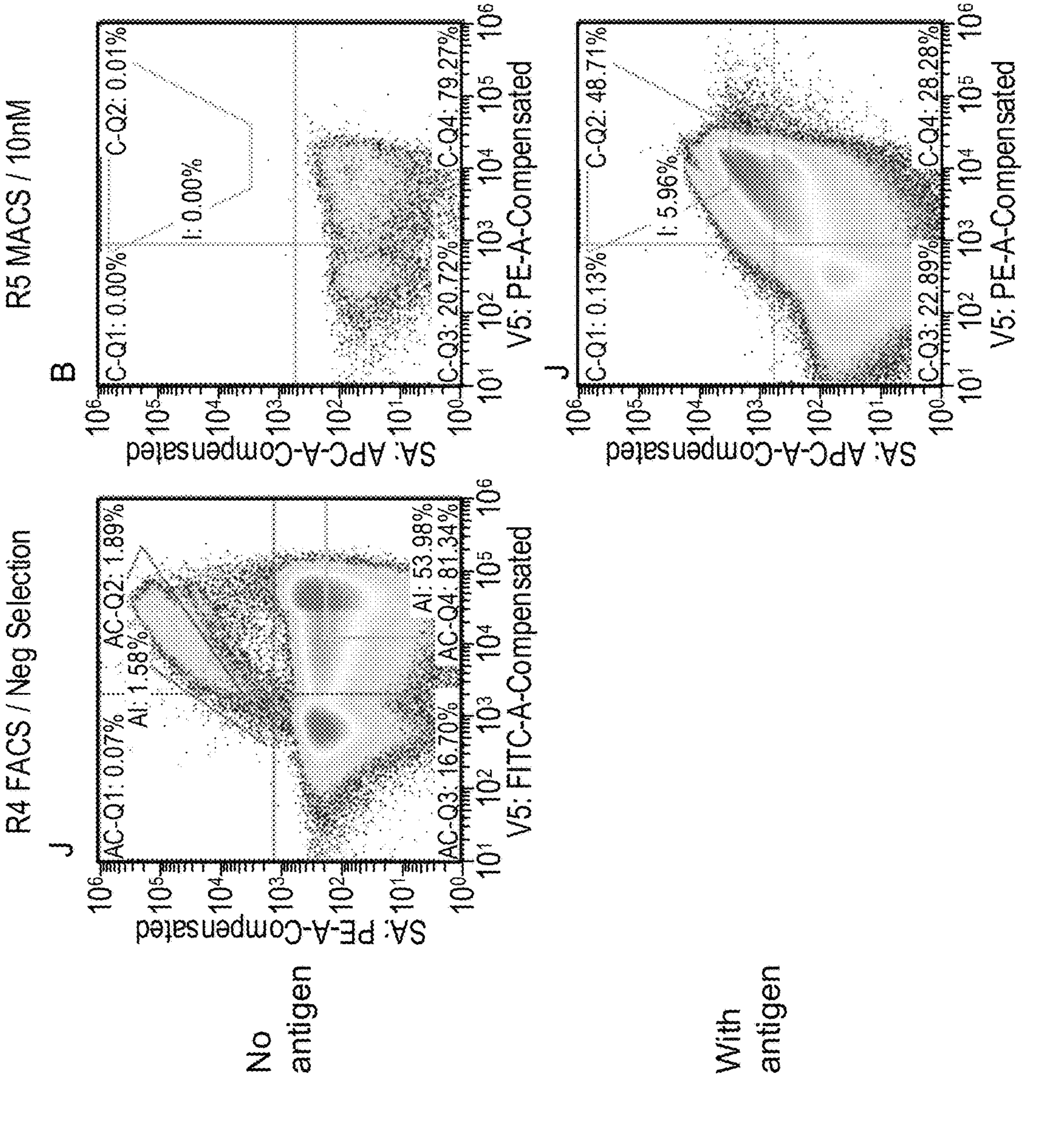

FIGS. 6A-6B show flow cytometry plots for Campaign 2 anti-IL31 single-binder selection. Round 1 (R1) MACS flow plot images were taken from flow cytometry analysis of R1 MACS eluates for 0 nM IL31 and 30 nM IL31 stained samples. Round 2 (R2) FACS and round 3 (R3) FACS images represent flow plots for sorting human anti-IL31 VHH displaying yeast cells at 30 nM and 10 nM human IL31 concentrations, respectively. R1 to R3 are shown in FIG. 6A. A negative selection was performed in round 4 (R4) FACS to avoid potential non-specific binding. Round 5 (R5) FACS was performed for positive selection of anti-IL31 VHH displaying cells with 10 nM IL31 concentration. R4 and R5 are shown in FIG. 6B.

Figure 7A:
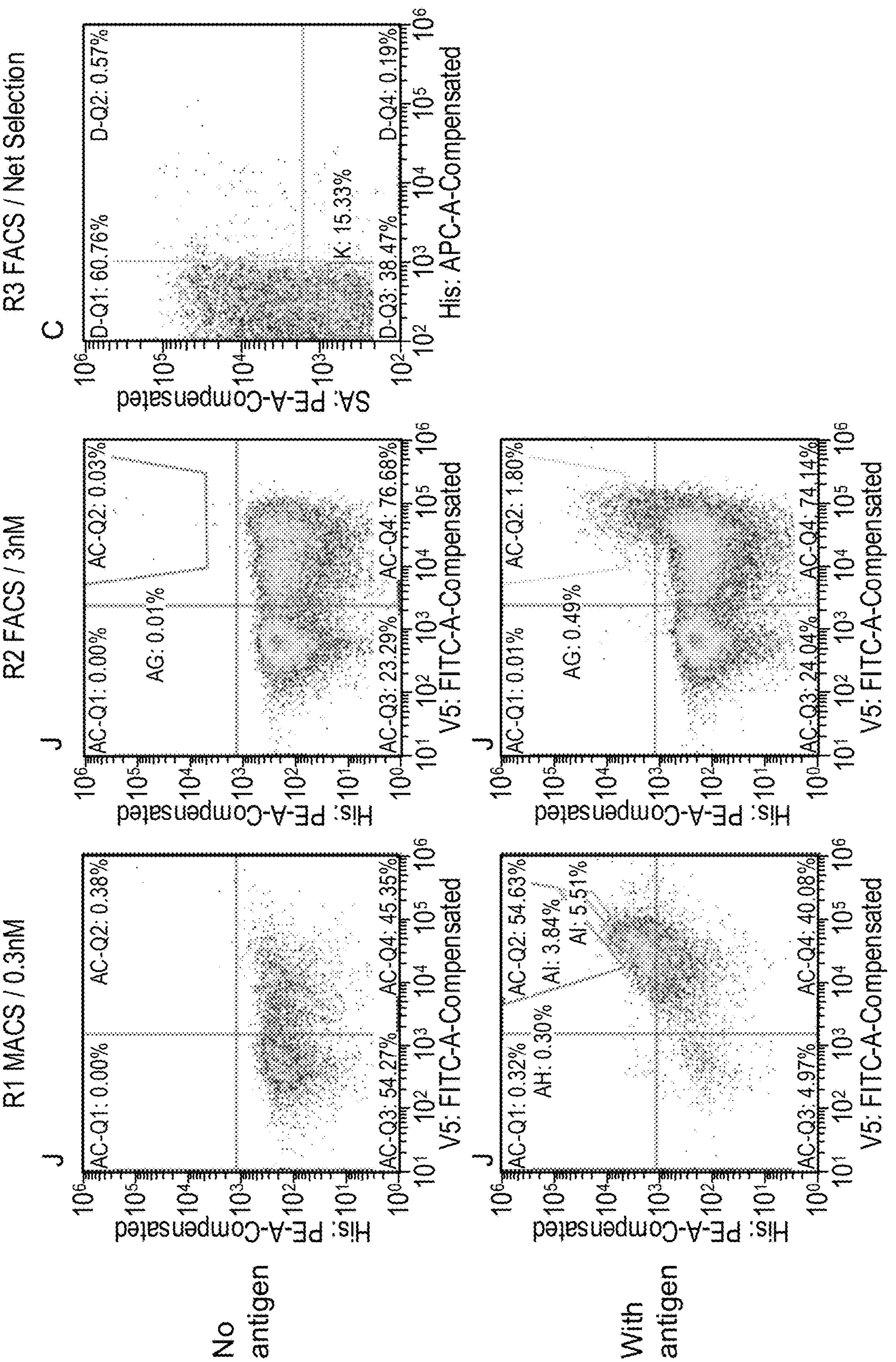
Figure 7B:
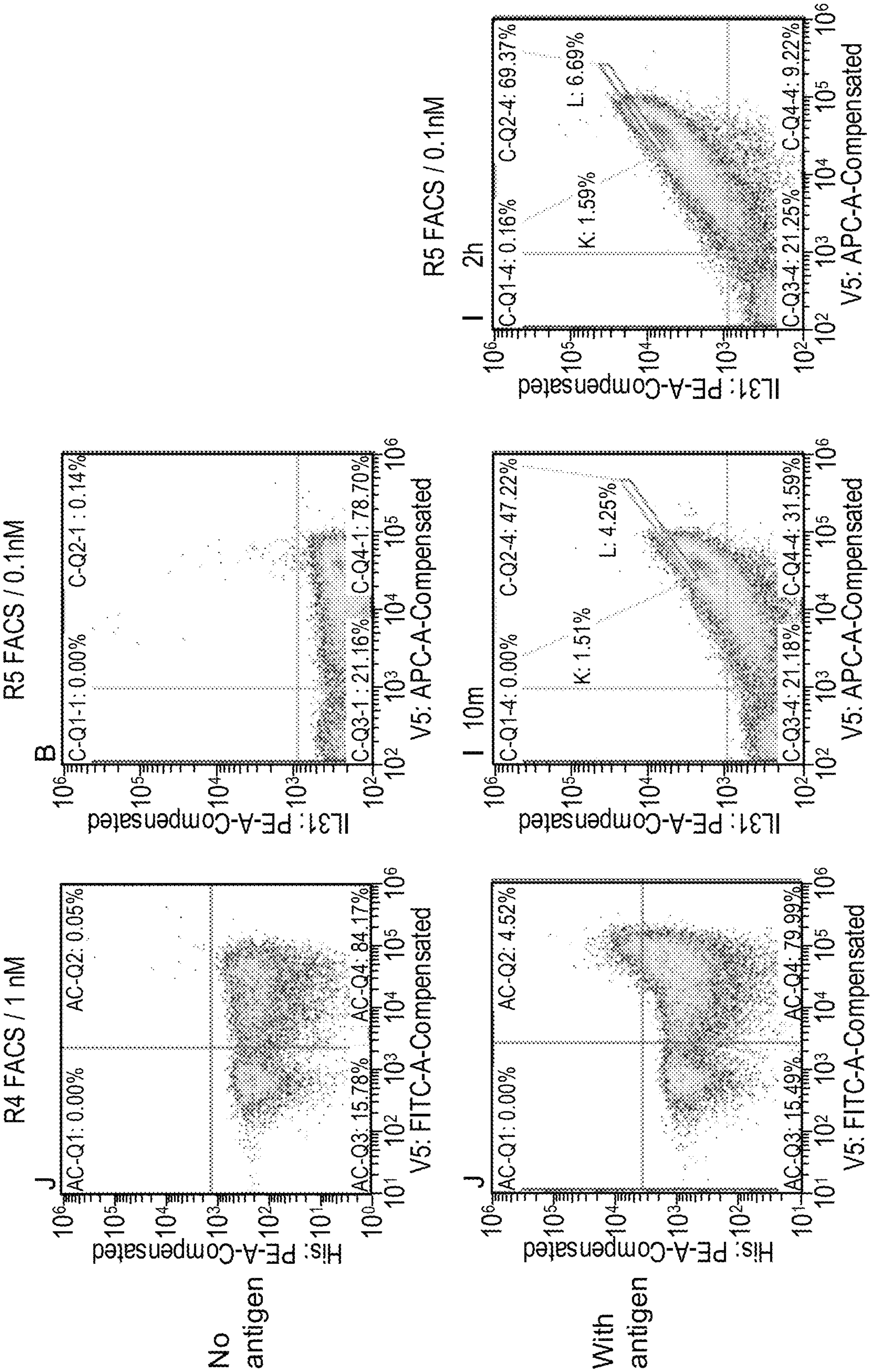

FIGS. 7A-7B show flow cytometry plots for Campaign 2 anti-IL31 co-binder selection. Round 1 (R1) MACS flow plot images were taken from flow cytometry analysis of R1 MACS eluates for 0 nM IL31 and 0.3 nM IL31 stained samples. Round 2 (R2) FACS was performed for sorting human anti-IL31 single-binder displaying yeast cells at 3 nM human IL31 concentrations. A negative selection was performed in round 3 (R3) FACS to avoid potential non-specific binding. R1 to R3 are shown in FIG. 7A. Round 4 (R4) and round 5 (R5) FACS were performed for positive selection of anti-IL31 VHH displaying cells with 1 nM and 0.1 nM human IL31 concentrations, respectively (FIG. 7B).

Figure 8A:
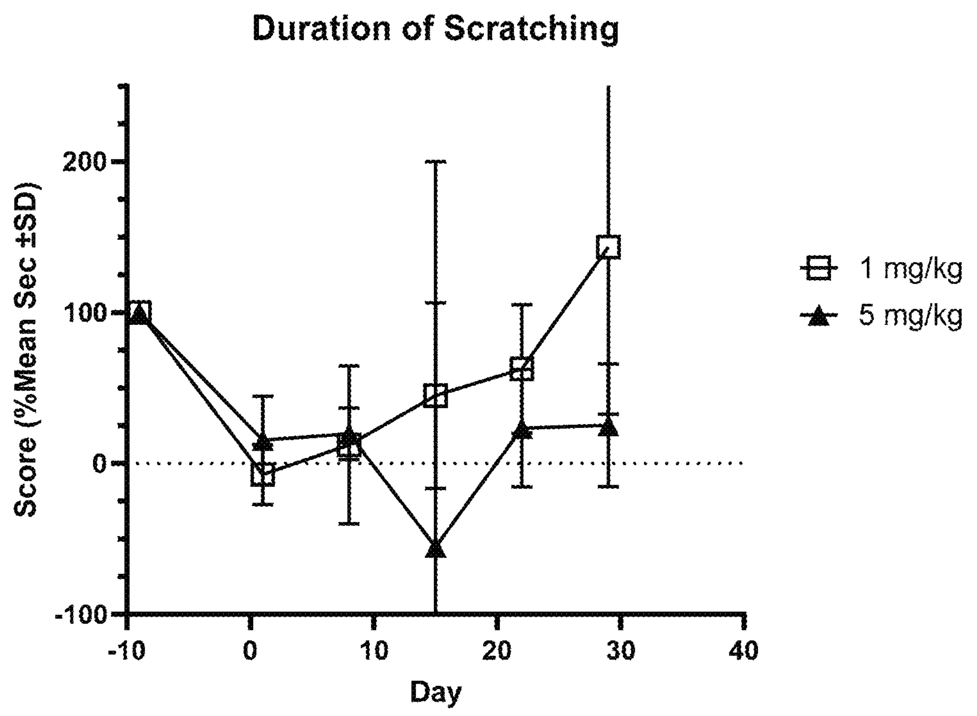
Figure 8B:
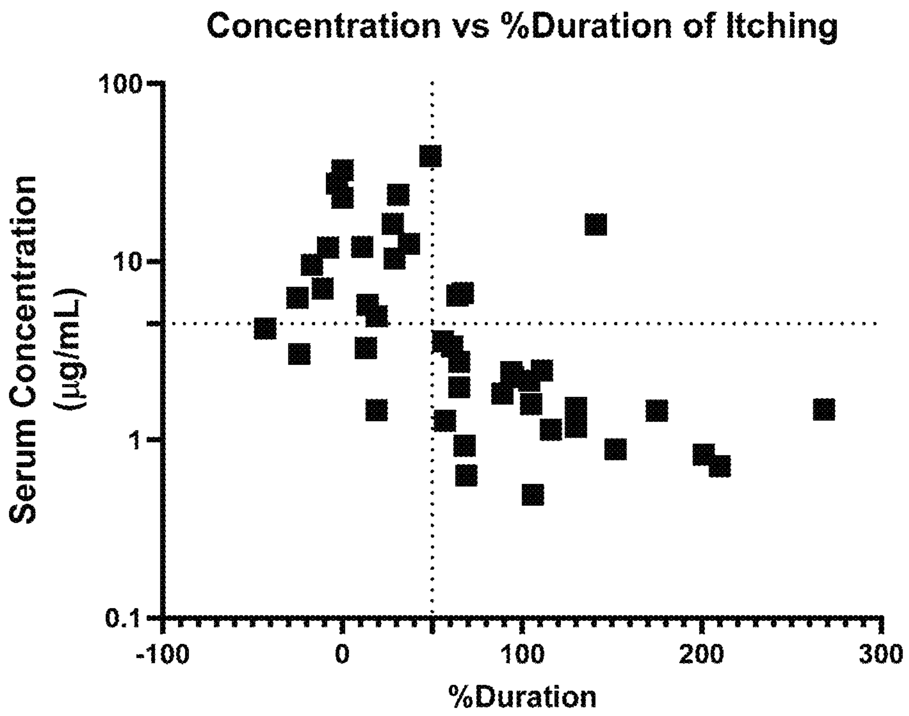

FIGS. 8A-8B are plots showing anti-pruritic activity in non-human primates. Healthy male cynomolgus monkeys were administered anti-IL31 co-binder 1C10 at either 1 or 5 mg/kg. Animals were then treated intravenously with cynomolgus IL31 after 24 hours. FIG. 8A is a plot showing pruritic activity as percent duration of scratching relative to pre-study treatment with IL31. FIG. 8B is a plot showing the relative duration of pruritic activity to the calculated serum drug concentration.

Figure 9:
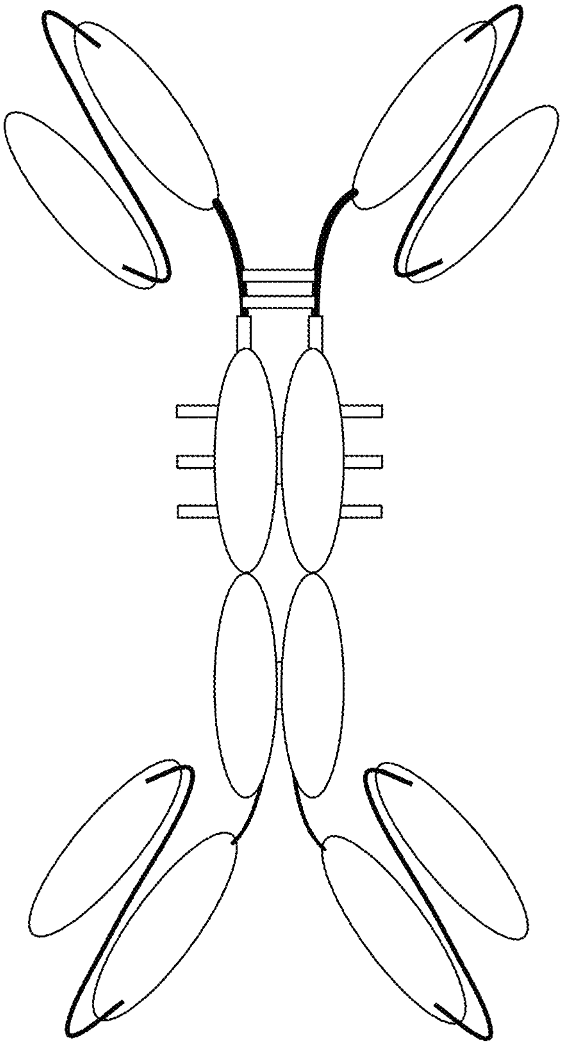

FIG. 9 is a schematic exemplifying a bi-specific format of anti-IL31 and anti-IL13 bispecific polypeptide (SEQ ID NO:55).

Figure 10A:
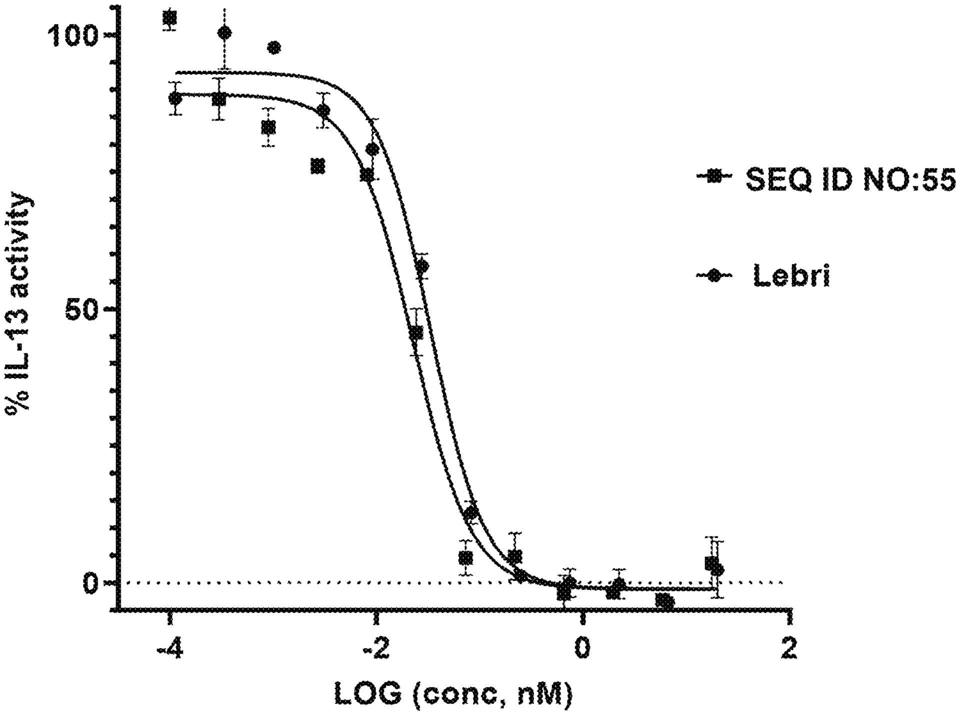
Figure 10B:
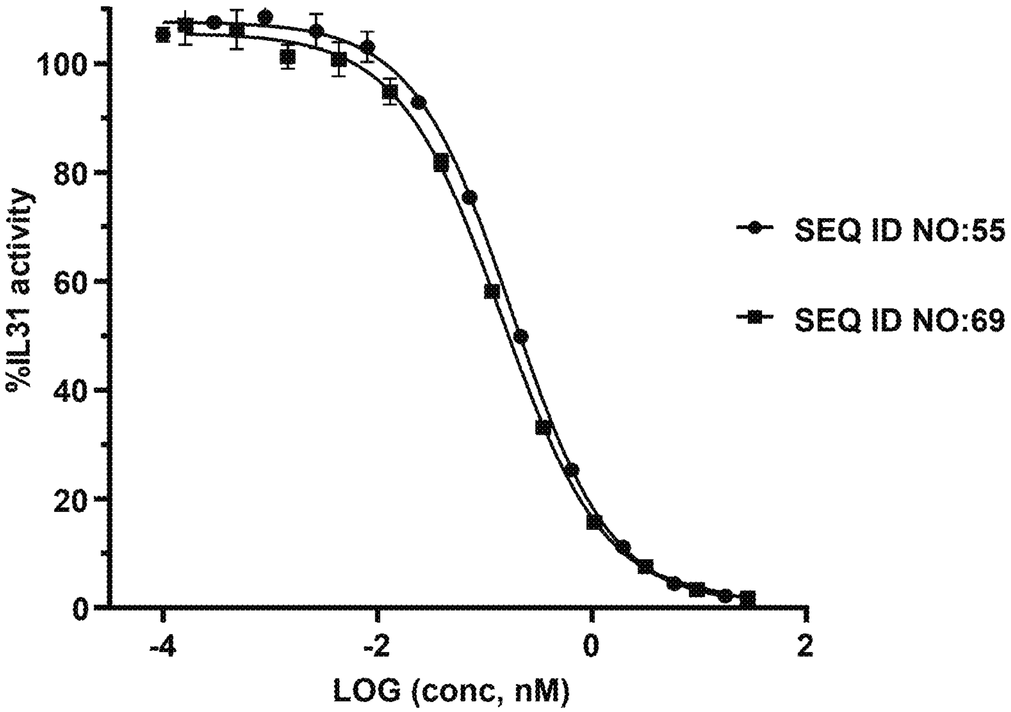

FIGS. 10A-10B are plots showing dose-dependent inhibition activity of anti-IL31 and anti-IL 13 bispecific polypeptide (SEQ ID NO:55) using IL 13 and IL31 dimerization assays. Anti-IL31 and anti-IL 13 bispecific polypeptide was diluted from 30 μg/ml with 3× dilution for 12 points and incubated with equal volume of 10 ng/ml IL13/IL31 in AssayComplete™ Cell Plating 0 Reagent (Eurofins DiscoverX) for 1 hr at room temperature. The complex was then added to IL 13 receptor dimerization reporter cells (FIG. 10A) and IL31 receptor dimerization reporter cells (FIG. 10B). RLU was read and normalized to IL13/IL31 activity with and without cytokines and presented as 100 and 0 percent activity, respectively. For comparison, lebrikizumab (anti-IL 13 hIgG4 monoclonal) or IL31 co-binder 1C10-Fc (SEQ ID NO:69) was diluted and incubated with IL13/IL31 and assessed for IL13 and IL31 receptor dimerization, respectively.

Figure 11A:
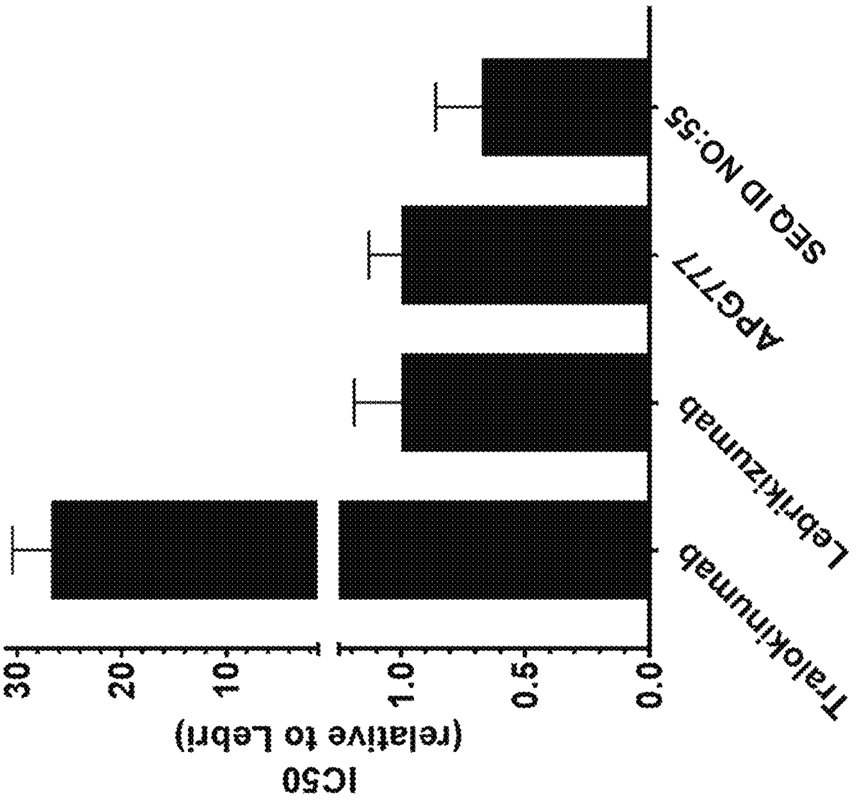
Figure 11B:
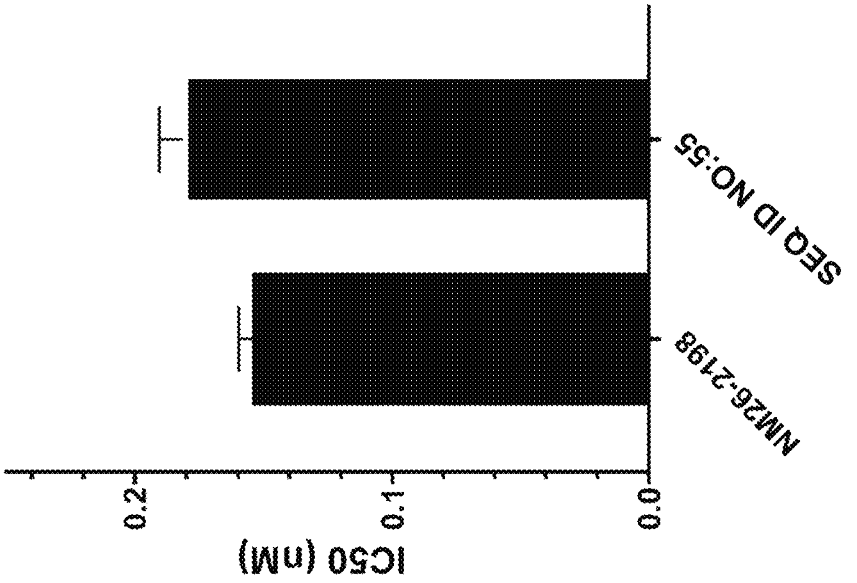

FIGS. 11A-11B are plots showing inhibition activity of anti-IL31 and anti-IL 13 bispecific polypeptide (SEQ ID NO:55) using IL13 and IL31 dimerization assays, as described for FIGS. 10A-10B, comparing the bispecific polpeptide, lebrikizumab, tralokinumab, and APG777 for IL 13 inhibition activity (FIG. 11A), and the bispecific polypeptide and NM26-2198 for IL31 inhibition activity (FIG. 11B).

Figure 12:
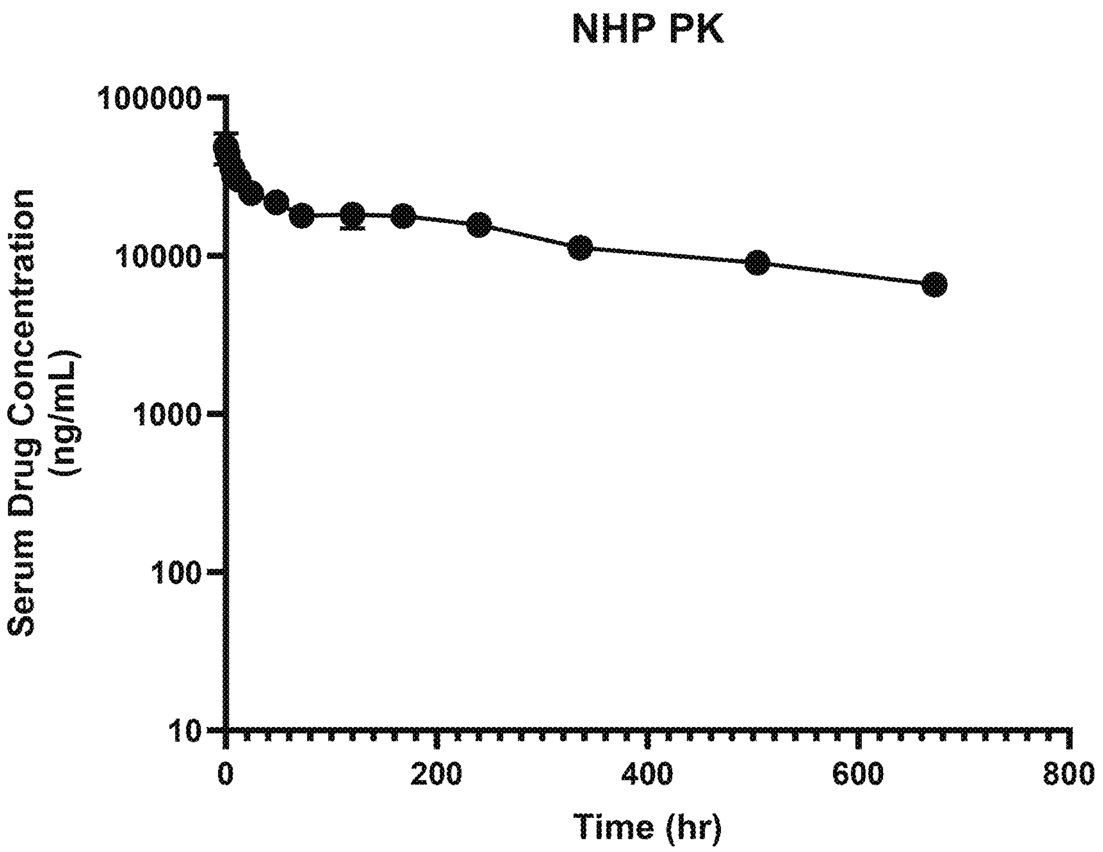

FIG. 12 is a plot showing the pharmacokinetic (PK) profiles of anti-IL31 and anti-IL13 bispecific polypeptide (SEQ ID NO:55) in non-human primates (NHP). Naive, female cynomolgus monkeys were administered the test article (n=2) at 2 mg/kg intravenously, and serum dug concentrations were assessed over 672 hours (28 days).

DESCRIPTION OF THE SEQUENCES

Table I provides a listing of certain sequences referenced herein.

TABLE 1

Description of Certain Sequences
Table 1: Description of Certain Sequences

| SEQ ID NO | Sequence | Description |
|---|---|---|
| 1 | MASHSGPSTSVLFLFCCLGGWLASHTLPVRLLRPS DDVQKIVEELQSLSKMLLKDVEEEKGVLVSQNYTL | Human IL31 with signal sequence |

TABLE 1-continued

Description of Certain Sequences
Table 1: Description of Certain Sequences

| SEQ ID NO | Sequence | Description |
|---|---|---|
| | PCLSPDAQPPNNIHSPAIRAYLKTIRQLDNKSVID EIIEHLDKLIFQDAPETNISVPTDTHECKRFILTI SQQFSECMDLALKSLTSGAQQATT | |
| 2 | SHTLPVRLLRPSDDVQKIVEELQSLSKMLLKDVEE EKGVLVSQNYTLPCLSPDAQPPNNIHSPAIRAYLK TIRQLDNKSVIDEIIEHLDKLIFQDAPETNISVPT DTHECKRFILTISQQFSECMDLALKSLTSGAQQAT T | Human IL31 without signal sequence |
| 3 | EVQLVESGGGLVQAGGSLRLSCAASGGTFSSYTMG WFRQAPGKEREYVGGISSSGYVMYNSESMKGRFTI SRENAKNMVYLQMNSLKPEDTAVYYCAAGTIGRPY DYWGQGTQVTVSS | 1C10 VHH1 single binder |
| 4 | EVQLVESGGGLVQPGGSLRLSCAASGGTFSSYTMG WFRQAPGKEREYVGGISSSGYVMYNSESMKGRFTI SRDNAKNTLYLQMNSLRAEDTAVYYCAAGTIGRPY DYWGQGTQVTVSS | Humanized 1C10 VHH1 single binder |
| 5 | SYTMG | 1C10 VHH1 CDR1 (Kabat numbering) |
| 6 | GISSSGYVMYNSESMKG | 1C10 VHH1 CDR2 (Kabat numbering) |
| 7 | GTIGRPYDY | 1C10 VHH1 CDR3 (Kabat numbering) |
| 8 | GGTFSSYT | 1C10 VHH1 CDR1 (IMGT numbering) |
| 9 | ISSSGYVM | 1C10 VHH1 CDR2 (IMGT numbering) |
| 10 | AAGTIGRPYDY | 1C10 VHH1 CDR3 (IMGT numbering) |
| 11 | GGTFSSY | 1C10 VHH1 CDR1 (Clothia numbering) |
| 12 | SSSGYV | 1C10 VHH1 CDR2 (Clothia numbering) |
| 13 | GTIGRPYDY | 1C10 VHH1 CDR3 (Clothia numbering) |
| 14 | VKLEESGGGLVQPGGSLILSCAASGDISSIVAMGW YRQAPGKQRELVAAITSGGRTHYRDSVKGRFTISG NNDNSALYLHMNSLKPEDTAVYYCAADRGWTSVGE YDYWGKGTLVTVSS | 1C10 VHH2 single binder |
| 15 | VQLVESGGGLVQPGGSLRLSCAASGDISSIVAMGW YRQAPGKQRELVSAITSGGRTHYRDSVKGRFTISR DNAKNTLYLQMNSLRAEDTAVYYCAADRGWTSVGE YDYWGQGTQVTVSS | Humanized 1C10 VHH2 single binder |
| 16 | IVAMG | 1C10 VHH2 CDR1 (Kabat numbering) |
| 17 | AITSGGRTHYRDSVKG | 1C10 VHH2 CDR2 (Kabat numbering) |
| 18 | DRGWTSVGEYDY | 1C10 VHH2 CDR3 (Kabat numbering) |
| 19 | GDISSIVA | 1C10 VHH2 CDR1 (IMGT numbering) |
| 20 | ITSGGRT | 1C10 VHH2 CDR2 (IMGT numbering) |
| 21 | AADRGWTSVGEYDY | 1C10 VHH2 CDR3 (IMGT numbering) |

TABLE 1-continued

Description of Certain Sequences
Table 1: Description of Certain Sequences

| SEQ ID NO | Sequence | Description |
|---|---|---|
| 22 | GDISSIV | 1C10 VHH2 CDR1 (Clothia numbering) |
| 23 | TSGGR | 1C10 VHH2 CDR2 (Clothia numbering) |
| 24 | DRGWTSVGEYDY | 1C10 VHH2 CDR3 (Clothia numbering) |
| 25 | EVQLVESGGGLVQAGGSLRLSCAASGGTFSSYTMG WFRQAPGKEREYVGGISSSGYVMYNSESMKGRFTI SRENAKNMVYLQMNSLKPEDTAVYYCAAGTIGRPY DYWGQGTQVTVSSGGGSGGGGGGGGSGGGGSGGG GSGGGGSGGGGSGMTGVKLEESGGGLVQPGGSLIL SCAASGDISSIVAMGWYRQAPGKQRELVAAITSGG RTHYRDSVKGRFTISGNNDNSALYLHMNSLKPEDT AVYYCAADRGWTSVGEYDYWGKGTLVTVSS | 1C10 co-binder |
| 26 | EVQLVESGGGLVQPGGSLRLSCAASGGTFSSYTMG WFRQAPGKEREYVGGISSSGYVMYNSESMKGRFTI SRDNAKNTLYLQMNSLRAEDTAVYYCAAGTIGRPY DYWGQGTQVTVSSGGGSGGGGSGGGGSGGGGSGGG GSGGGGSGGGGSGMTGVQLVESGGGLVQPGGSLRL SCAASGDISSIVAMGWYRQAPGKQRELVSAITSGG RTHYRDSVKGRFTISRDNAKNTLYLQMNSLRAEDT AVYYCAADRGWTSVGEYDYWGQGTQVTVSS | Humanized 1C10 co-binder |
| 27 | MALLLTTVIALTCLGGFASPGPVPPSTALRELIEE LVNITQNQKAPLCNGSMVWSINLTAGMYCAALESL INVSGCSAIEKTQRMLSGFCPHKVSAGQFSSLHVR DTKIEVAQFVKDLLLHLKKLFREGREN | Interleukin 13 [Homo sapiens] GenBank: AAK53823.1 |
| 28 | MALLLTTVIALTCLGGFASPGPVPPSTALRELIEE LVNITQNQKAPLCNGSMVWSINLTAGMYCAALESL INVSGCSAIEKTQRMLSGFCPHKVSAGQFSSLHVR DTKIEVAQFVKDLLLHLKKLFREGQFN | IL 13 clinical variant R130Q |
| 29 | EVQLVESGGDLVQAGGSLLLSCTASESISSINYIG WYRQAPGKGRELIAHFTDGTVTNYADSVKGRFTIS RDNGKNTLYLQMNSLKPEDTAVYYCAATDWRGDHW GQGTLVTVSS | 3G12 VHH1 single binder |
| 30 | EVQLVESGGGLVQPGGSLRLSCTASESISSINYIG WYRQAPGKGRELIAHFTDGTVTNYADSVKGRFTIS RDNAKNTLYLQMNSLRAEDTAVYYCAATDWEGDHW GQGTLVTVSS | Humanized 3G12 VHH1 single binder |
| 31 | INYIG | 3G12 VHH1 CDR1 (Kabat numbering) |
| 32 | HFTDGTVTNYADSVKG | 3G12 VHH1 CDR2 (Kabat numbering) |
| 33 | TDWRGDH | 3G12 VHH1 CDR3 (Kabat numbering) |
| 34 | ESISSINY | 3G12 VHH1 CDR1 (IMGT numbering) |
| 35 | FTDGTVT | 3G12 VHH1 CDR2 (IMGT numbering) |
| 36 | AATDWRGDH | 3G12 VHH1 CDR3 (IMGT numbering) |
| 37 | ESISSIN | 3G12 VHH1 CDR1 (Clothia numbering) |
| 38 | TDGTV | 3G12 VHH1 CDR2 (Clothia numbering) |
| 39 | TDWRGDH | 3G12 VHH1 CDR3 (Clothia numbering) |

TABLE 1-continued

Description of Certain Sequences
Table 1: Description of Certain Sequences

| SEQ ID NO | Sequence | Description |
|---|---|---|
| 40 | QLVESGGGSVQPGGSLRLSCAAPRFTLGSYAIAWFRQSPGKEREWVSCISRSGGDTIYSDSVKGRFTISRDNTKNMVYLQMNSLNPEDTAVYYCATDKRSFCYAPNGLGKGWTYDYWGQGTQVTVSS | 3G12 VHH2 single binder |
| 41 | QLVESGGGVVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSS | Humanized 3G12 VHH2 single binder |
| 42 | SYAIA | 3G12 VHH2 CDR1 (Kabat numbering) |
| 43 | CISRSGGDTIYSDSVKG | 3G12 VHH2 CDR2 (Kabat numbering) |
| 44 | DKRSFCYAPNGLGKGWTYDY | 3G12 VHH2 CDR3 (Kabat numbering) |
| 45 | RFTLGSYA | 3G12 VHH2 CDR1 (IMGT numbering) |
| 46 | ISRSGGDT | 3G12 VHH2 CDR2 (IMGT numbering) |
| 47 | ATDKRSFCYAPNGLGKGWTYDY | 3G12 VHH2 CDR3 (IMGT numbering) |
| 48 | RFTLGSY | 3G12 VHH2 CDR1 (Clothia numbering) |
| 49 | SRSGGD | 3G12 VHH2 CDR2 (Clothia numbering) |
| 50 | DKRSFCYAPNGLGKGWTYDY | 3G12 VHH2 CDR3 (Clothia numbering) |
| 51 | EVQLVESGGDLVQAGGSLLLSCTASESISSINYIGWYRQAPGKGRELIAHFTDGTVTNYADSVKGRFTISRDNGKNTLYLQMNSLKPEDTAVYYCAATDWRGDHWGQGTLVTVSSGGGSGGGGGGGGSGGGGSGGGGSGGGGSGGGGSLGVGQLVESGGGSVQPGGSLRLSCAAPRFTLGSYAIAWFRQSPGKEREWVSCISRSGGDTIYSDSVKGRFTISRDNTKNMVYLQMNSLNPEDTAVYYCATDKRSFCYAPNGLGKGWTYDYWGQGTQVTVSS | 3G12 co-binder |
| 52 | EVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGSGGGGSGGGGSGGGGSGGGGSGGGGSLGVGQLVESGGGVVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSS | Humanized 3G12 co-binder |
| 53 | EVQLVESGGDLVQAGGSLLLSCTASESISSINYIGWYRQAPGKGRELIAHFTDGTVTNYADSVKGRFTISRDNGKNTLYLQMNSLKPEDTAVYYCAATDWRGDHWGQGTLVTVSSGGGSGGGGSGGGGSGGGGSGGGGSGGGGSGGGGSLGVGQLVESGGGSVQPGGSLRLSCAAPRFTLGSYAIAWFRQSPGKEREWVSCISRSGGDTIYSDSVKGRFTISRDNTKNMVYLQMNSLNPEDTAVYYCATDKRSFCYAPNGLGKGWTYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 3G12_YTE-Fc |
| 54 | EVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGGGGGSGGGGSGGGGSG | 3G12_Mlm0mlm0-mlm0mlm0_EE_YTE-Fc |

TABLE 1-continued

Description of Certain Sequences
Table 1: Description of Certain Sequences

| SEQ ID NO | Sequence | Description |
|---|---|---|
| | GGGSGGGGSLGVGQLVESGGGLVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | |
| 55 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKGGGGSGGGSGGGVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGSGGGGSGGGGSGGGGSGGGGSGGGGSLGVGQLVESGGGVVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSS | Hz_1C10_MIM1M1_Fc-YTE_LALA_3G12_M1m0m1m0-m1m0m1m0_EE_L11V-Pr(L234A,L235A,M252Y,S254T,T256E) |
| 56 | EVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSSGGGGSGGGSGGGVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGSGGGGSGGGGSGGGGGGGGSGGGGSLGVGQLVESGGGLVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | Hz_1C10_MIM1M1_3G12_M1m0m1m0-m1m0m1m0_EE_Fc-YTE_LALA-Pr(L234A,L235A,M252Y,S254T,T256E) |
| 57 | EVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGSGGGGSGGGGSGGGGSGGGGSGGGGSLGVGQLVESGGGLVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGGGGGSGGGSGGGVQ | 3G12 M1m0m1m0-m1m0m1m0_EE_Fc-YTE_LALA_Hz_1C10_MIMIMIM1_L11V-Pr(L234A,L235A,M252Y,S254T,T256E) |

TABLE 1-continued

Description of Certain Sequences
Table 1: Description of Certain Sequences

| SEQ ID NO | Sequence | Description |
|---|---|---|
| | LVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGVVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSS | |
| 58 | EVQLVESGGGLVQPGGSLRLSCTASESISSINYIGWYRQAPGKGRELIAHFTDGTVTNYADSVKGRFTISRDNAKNTLYLQMNSLRAEDTAVYYCAATDWEGDHWGQGTLVTVSSGGGSGGGGSGGGGSGGGGSGGGGSGGGGSGGGGSLGVGQLVESGGGLVQPGGSLRLSCAAPRFTLGSYAIAWFRQSPGKEREWVSCISRSGGDTIYSDSVKGRFTISRDNAKNTLYLQMNSLRAEDTAVYYCATDKRSFCYAPEGLGKGWTYDYWGQGTQVTVSSGGGGSGGGSGGGVQLVESGGGLVQPGGSLRLSCAASGGTFSSYTMGWFRQAPGKEREYVGGISSSGYVMYNSESMKGRFTISRDNAKNTLYLQMNSLRAEDTAVYYCAAGTIGRPYDYWGQGTQVTVSSGGGSGGGGSGGGGSGGGGSGGGGSGGGGSGGGGSGMTGVQLVESGGGLVQPGGSLRLSCAASGDISSIVAMGWYRQAPGKQRELVSAITSGGRTHYRDSVKGRFTISRDNAKNTLYLQMNSLRAEDTAVYYCAADRGWTSVGEYDYWGQGTQVTVSSEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 3G12_M1m0mlm0-mlm0mlm0_EE_Hz_1C10_M1M1MIM1_Fc-YTE-LALA-Pr(L234A,L235A,M252Y,S254T,T256E) |
| 59 | EPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | hulgG1Fc_YTE_LALA_C→S |
| 60 | TDWEGDH | Humanized 3G12 VHH1 CDR3 (Kabat numbering) |
| 61 | AATDWEGDH | Humanized 3G12 VHH1 CDR3 (IMGT numbering) |
| 62 | TDWEGDH | Humanized 3G12 VHH1 CDR3 (Clothia numbering) |
| 63 | DKRSFCYAPEGLGKGWTYDY | Humanized 3G12 VHH2 CDR3 (Kabat numbering) |
| 64 | ATDKRSFCYAPEGLGKGWTYDY | Humanized 3G12 VHH2 CDR3 (IMGT numbering) |
| 65 | DKRSFCYAPEGLGKGWTYDY | Humanized 3G12 VHH2 CDR3 (Clothia numbering) |
| 66 | GGGSGGGGSG GGGSGGGGSG GGGSGGGGSG GGGSGMTG | 1C10 VHH1/VHH2 peptide linker |
| 67 | GGGSGGGGSG GGGSGGGGSG GGGSGGGGSG GGGSLGVG | 3G12 VHH1/VHH2 peptide linker |
| 68 | GGGGSGGGSG GG | Fc region C-terminus to 3G12 VHH1 N-terminus peptide linker |

TABLE 1-continued

Description of Certain Sequences
Table 1: Description of Certain Sequences

| SEQ ID NO | Sequence | | | Description |
|---|---|---|---|---|
| 69 | EVQLVESGGG | LVQPGGSLRL | SCAASGGTFS | Humanized (21) 1C10 |
| | SYTMGWFRQA | PGKEREYVGG | ISSSGYVMYN | co binder + |
| | SESMKGRFTI | SRDNAKNTLY | LQMNSLRAED | huIgG1Fc_YTE_C→S |
| | TAVYYCAAGT | IGRPYDYWGQ | GTQVTVSSGG | M252Y, S254T and |
| | GSGGGGSGGG | GSGGGGSGGG | GSGGGGSGGG | T256E (YTE mutation |
| | GSGMTGVQLV | ESGGGLVQPG | GSLRLSCAAS | for extending half- |
| | GDISSIVAMG | WYRQAPGKQR | ELVSAITSGG | life)(EU numbering) |
| | RTHYRDSVKG | RFTISRDNAK | NTLYLQMNSL | |
| | RAEDTAVYYC | AADRGWTSVG | EYDYWGQGTQ | |
| | VTVSSEPKSS | DKTHTCPPCP | APELLGGPSV | |
| | FLFPPKPKDT | LYITREPEVT | CVVVDVSHED | |
| | PEVKFNWYVD | GVEVHNAKTK | PREEQYNSTY | |
| | RVVSVLTVLH | QDWLNGKEYK | CKVSNKALPA | |
| | PIEKTISKAK | GQPREPQVYT | LPPSRDELTK | |
| | NQVSLTCLVK | GFYPSDIAVE | WESNGQPENN | |
| | YKTTPPVLDS | DGSFFLYSKL | TVDKSRWQQG | |
| | NVFSCSVMHE | ALHNHYTQKS | LSLSPGK | |

DESCRIPTION

I. Definitions

The section headings used herein are for organizational purposes only and are not to be construed as limiting the subject matter described.

The complete disclosures of all publications cited herein are incorporated herein by reference in their entireties as if each were individually set forth in full herein and incorporated.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in an antibody heavy chain is that of the EU index as in Kabat et al., Sequences of Proteins of Immunological Interest, 5th Ed. Public Health Service, National Institutes of Health, Bethesda, Md. (1991). Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The terms "multimer" and "multimeric" refer to a complex of two or more component molecules, such as two or more polypeptides. A multimer includes, but is not limited to, a dimer or a trimer. Within a multimer, the two or more component molecules may be the same (i.e., the multimer is a homomultimer), or one or more of the two or more component molecules may be different from the other component molecules (i.e., the multimer is a heteromultimer).

The terms "IL13," and "interleukin-13" as used herein refer to any native, mature IL13 that results from processing of an IL13 precursor in a cell. The term includes IL 13 from any vertebrate source, including mammals such as primates (e.g., humans and cynomolgus or rhesus monkeys) and rodents (e.g., mice and rats), unless otherwise indicated. The term also includes naturally occurring variants of IL13, such as splice variants or allelic variants. Nonlimiting exemplary human IL 13 amino acid sequences are shown in Table 1 (see SEQ ID NOs: 27 and 28). See also UniProtKB/Swiss-Prot Accession: P35225.

The terms "IL31," and "interleukin-31" as used herein refer to any native, mature IL31 that results from processing of an IL31 precursor in a cell. The term includes IL31 from any vertebrate source, including mammals such as primates (e.g., humans and cynomolgus or rhesus monkeys) and rodents (e.g., mice and rats), unless otherwise indicated. The term also includes naturally occurring variants of IL31, such as splice variants or allelic variants. Nonlimiting exemplary human IL31 amino acid sequences are shown in Table 1 (see SEQ ID NOs: 1 and 2; signal sequence is underlined). See also UniProtKB/Swiss-Prot Accession: Q6EBC2.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a IL13 or IL31 epitope is a sdAb or VHH-containing polypeptide that binds this epitope with greater affinity, avidity, more readily, and/or with greater duration than it binds to other IL13 or IL31 epitopes or non-IL 13 or non-IL31 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some aspects, by "reduce" or "inhibit" is meant the ability to cause an overall decrease of 10% or greater. In some aspects, by "reduce" or "inhibit" is meant the ability to cause an overall decrease of 50% or greater. In some aspects, by "reduce" or "inhibit" is meant the ability to cause an overall decrease of 75%, 85%, 90%, 95%, or greater. In some aspects, the amount noted above is inhibited or decreased over a period of time, relative to a control over the same period of time.

The term "antibody" is used in the broadest sense and encompasses various polypeptides that comprise antibody-like antigen-binding domains, including but not limited to conventional antibodies (typically comprising at least one heavy chain and at least one light chain), single-domain antibodies (sdAbs, comprising at least one variable heavy domain of heavy chain or "VHH" domain and an Fc region), VHH-containing polypeptides (polypeptides comprising at least one VHH domain), and fragments or multimers of any of the foregoing so long as they exhibit the desired antigen-binding activity. In some aspects, an antibody comprises a dimerization domain. Such dimerization domains include, but are not limited to, heavy chain constant domains (comprising CH1, hinge, CH2, and CH3 domains, where CH1 typically pairs with a light chain constant domain, CL, and where the hinge mediates dimerization) and Fc regions (comprising hinge, CH2, and CH3, where the hinge mediates dimerization).

As used herein, the term "binder" refers to a molecule or a portion of a molecule which binds a specific target molecule. A binder can comprise a protein, peptide, nucleic acid, carbohydrate, lipid, or small molecular weight compound. In some aspects, a binder comprises an antibody. In some aspects, a binder comprises an antigen-binding domain of an antibody. In some aspects, a binder comprises an antibody or an antigen-binding domain. In some aspects, a binder comprises a heavy chain variable region of an antibody. In some aspects, a binder comprises a light chain variable region of an antibody. In some aspects, a binder comprises a variable region of an antibody. In some aspects, a binder comprises an antibody mimetic. In some aspects, a binder comprises a small molecular weight component. In some aspects, a binding molecule (e.g., a polypeptide) has only one binding moiety. In some aspects, a binding molecule (e.g., a polypeptide) has two binding moieties. In some aspects, a binding molecule (e.g., a polypeptide) has three or more binding moieties. In some aspects, the two or more binding moieties on one binding molecule (e.g., a polypeptide) are the same. In some aspects, the two or more binding moieties on one binding molecule (e.g., a polypeptide) are different. For example, a binding molecule (e.g., a polypeptide) can have two binding moieties, both being antigen binding domains, such as VHHs. For another example, a binding molecule (e.g., a polypeptide) can also have two binding moieties, one being a variable heavy domain of heavy chain "VHH", and the other being scFv.

The term "antigen-binding domain" as used herein refers to a portion of an antibody sufficient to bind an antigen. In some aspects, an antigen binding domain of a conventional antibody comprises three heavy chain CDRs and three light chain CDRs. Thus, in some aspects, an antigen binding domain comprises a heavy chain variable region comprising CDR1-FR2-CDR2-FR3-CDR3, and any portions of FR1 and/or FR4 required to maintain binding to antigen, and a light chain variable region comprising CDR1-FR2-CDR2-FR3-CDR3, and any portions of FR1 and/or FR4 required to maintain binding to antigen. In some aspects, an antigen-binding domain of an sdAb or VHH-containing polypeptide comprises three CDRs of a VHH domain (e.g., CDR1, CDR2, and CDR3). Thus, in some aspects, an antigen binding domain of an sdAb or VHH-containing polypeptide comprises a VHH domain comprising CDR1-FR2-CDR2-FR3-CDR3, and any portions of FR1 and/or FR4 required to maintain binding to antigen.

The term "VHH" or "VHH domain" or "VHH antigen-binding domain" as used herein refers to the Variable Heavy domain of a Heavy chain, or the antigen-binding portion of a single-domain antibody, such as a camelid antibody, llama antibody, alpaca antibody, or shark antibody. In some aspects, a VHH comprises three CDRs and four framework regions, designated FR1, CDR1, FR2, CDR2, FR3, CDR3, and FR4. In some aspects, a VHH may be truncated at the N-terminus or C-terminus such that it comprises only a partial FR1 and/or FR4, or lacks one or both of those framework regions, so long as the VHH substantially maintains antigen binding and specificity.

The terms "single domain antibody" and "sdAb" are used interchangeably herein to refer to an antibody comprising at least one monomeric domain, such as a VHH domain, without a light chain, and an Fc region. In some aspects, an sdAb is a dimer of two polypeptides wherein each polypeptide comprises at least one VHH domain and an Fc region. As used herein, the terms "single domain antibody" and "sdAb" encompass polypeptides that comprise multiple VHH domains, such as a polypeptide having the structure VHH1-VHH2-Fc, wherein VHH1 and VHH2 may be the same or different.

The term "VHH-containing polypeptide" refers to a polypeptide that comprises at least one VHH domain. In some aspects, a VHH polypeptide comprises two, three, or four or more VHH domains, wherein each VHH domain may be the same or different. In some aspects, a VHH-containing polypeptide comprises an Fc region. In some such aspects, the VHH-containing polypeptide may be referred to as an sdAb. Further, in some such aspects, the VHH polypeptide may form a dimer. Nonlimiting structures of VHH-containing polypeptides, which are also sdAbs, include VHH1-VHH2-Fc, VHH1-linker-VHH2-Fc, wherein VHH1 and VHH2 may be the same or different. In some aspects of such structures, one VHH may be connected to another VHH by a linker, or one VHH may be connected to the Fc by a linker. In some such aspects, the linker comprises 5-50 amino acids.

In some such aspects, the linker comprises 8 to 40 amino acids. In some aspects, the linker comprises 12 to 37 amino acids. In some aspects, the linker is composed of glycine and serine. In some aspects, the linker is composed of glycine, serine, and other amino acids. Some examples of polypeptide linkers are described in WO2022147463, which is incorporated herein by reference in its entirety. In some aspects, when a VHH-containing polypeptide comprises an Fc, it forms a dimer. Thus, the structure VHH1-VHH2-Fc, if it forms a dimer, is considered to be tetravalent (i.e., the dimer has four VHH domains).

The term "single binder(s)" refers to a single domain binder, e.g., VHH, capable of specifically binding a target antigen. A general structure, for example, of a single binder is as follows: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3, respectively.

The term "co-binder" refers to two "single binders" or single domain binding moieties, e.g., VHHs, optionally joined together by a linker peptide, in which each single binder is capable of simultaneously binding the same target antigen, e.g., IL31 or IL13, as the other single binder. A co-binder may comprise two biparatopic single binders. For example, each single binder is capable of specifically binding to the same target antigen (e.g., bind at a non-overlapping epitope) allowing each single binder to simultaneously bind the target. A general structure, for example, of a co-binder is as follows: 1st Single Binder-Linker-2nd Single Binder or VHH1-linker-VHH2, wherein the N-terminal region of the 2nd single binder or VHH2 may be truncated, see WO 2022/147463. In some aspects, a IL31 co-binder, for example, is capable of binding to IL31 at a binding affinity at least about 2 folds, 3 folds, 4 folds, 5 folds, 6 folds, 7 folds, 8 folds, 9 folds, 10 folds, 11 folds, 12 folds, 13 folds, 14 folds, 15 folds 16 folds, 17 folds, 18 folds, 19 folds, or 20 folds stronger than each of the first IL31 and the second IL31 binders.

The term "biparatopic" refers to two or more antibodies, two or more "single binders", one or more "co-binder(s)" that recognize and bind two different epitopes of the same target antigen. For example, each single binder, such as a VHH, of a co-binder binds to the same target antigen at nonoverlapping epitopes, which allows both single binders to bind the same target antigen simultaneously.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts.

The term "CDR" denotes a complementarity determining region as defined by at least one manner of identification to one of skill in the art. In some aspects, CDRs can be defined in accordance with any of the IMGT numbering scheme, the Chothia numbering scheme, the Kabat numbering scheme, a combination of Kabat and Chothia, the AbM definition, and/or the contact definition. A VHH comprises three CDRs, designated CDR1, CDR2, and CDR3.

The term "heavy chain constant region" as used herein refers to a region comprising at least three heavy chain constant domains, CH1, hinge, CH2, and CH3. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an a constant region is an IgA antibody. Further, an antibody comprising a μ constant region is an IgM antibody, and an antibody comprising an & constant region is an IgE antibody. Certain isotypes can be further subdivided into subclasses. For example, IgG antibodies include, but are not limited to, IgG1 (comprising a γ1 constant region), IgG2 (comprising a γ2 constant region), IgG3 (comprising a γ3 constant region), and IgG4 (comprising a γ4 constant region) antibodies; IgA antibodies include, but are not limited to, IgA1 (comprising an al constant region) and IgA2 (comprising an α2 constant region) antibodies; and IgM antibodies include, but are not limited to, IgM1 and IgM2.

A "Fc region" as used herein refers to a portion of a heavy chain constant region comprising CH2 and CH3. In some aspects, an Fc region comprises a hinge, CH2, and CH3. In various aspects, when an Fc region comprises a hinge, wherein the hinge mediates dimerization between two Fc-containing polypeptides. In some aspects, the Fc region further comprises a full or partial hinge region. In some aspects, the full or partial hinge region comprises a cysteine (C) to serine(S) mutation at position 220 as determined by EU numbering. An Fc region may be of any antibody heavy chain constant region isotype discussed herein. In some aspects, an Fc region is an IgG1, IgG2, IgG3, or IgG4.

An "acceptor human framework" as used herein is a framework comprising the amino acid sequence of a heavy chain variable domain (VH) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some aspects, the number of amino acid changes are fewer than 10, or fewer than 9, or fewer than 8, or fewer than 7, or fewer than 6, or fewer than 5, or fewer than 4, or fewer than 3, across all the human frameworks in a single antigen binding domain, such as a VHH.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to remove any potential liabilities (e.g., immunogenicity or safety concerns in administering the polypeptide to a subject, or polypeptide stability), or further refine and optimize sdAb VHH-containing polypeptide performance. In some aspects, a humanized sdAb or VHH-containing polypeptide comprises a human Fc region. As will be appreciated, a humanized sequence can be identified by its primary sequence and does not necessarily denote the process by which the antibody was created.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some aspects, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

"Affinity" refers to the strength of the sum total of noncovalent interactions between a single binding site of a molecule (for example, an antibody, such as an sdAb, or VHH-containing polypeptide) and its binding partner (for example, an antigen). The affinity or the apparent affinity of a molecule X for its partner Y can generally be represented by the dissociation constant (kD) or the kD-apparent, respectively. Affinity can be measured by common methods known in the art (such as, for example, ELISA KD, KinExA, flow cytometry, and/or surface plasmon resonance (SPR) devices), including those described herein. Such methods include, but are not limited to, methods involving BIAcore®, Octet®, or flow cytometry.

The terms "kD," "$K_D$," "$K_d$," "Kd" or "Kd value" as used interchangeably to refer to the equilibrium dissociation constant of an antigen-binding molecule (e.g., an antibody or VHH) and antigen interaction. When the term "kD" is used herein, it includes kD and kD-apparent. The equilibrium dissociation constant ($K_d$) is calculated as the ratio of $k_{off}/k_{on}$. The term "kon" refers to the rate constant for association of an antibody to an antigen and the term "koff" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, surface plasmon resonance devices, or biolayer interferometry (BLI).

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51:19-26.

An "effector-positive Fc region" possesses an effector function of a native sequence Fc region.

An "effector null Fc region" lacks one or more effector function(s) of a native sequence Fc region.

Exemplary "effector functions" include Fc receptor binding; Clq binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "variant Fc region" comprises an amino acid sequence which differs from that of a native sequence Fc region by virtue of at least one amino acid modification. In some aspects, a "variant Fc region" comprises an amino acid sequence which differs from that of a native sequence Fc region by virtue of at least one amino acid modification, yet retains at least one effector function of the native sequence Fc region. In some aspects, a "variant Fc region" comprises an amino acid sequence which differs from that of a native sequence Fc region by virtue of at least one amino acid modification, and the variant Fc region has a modified effector function. In some aspects, a "variant Fc region" comprises an amino acid sequence which differs from that of a native sequence Fc region by virtue of at least one amino acid modification, and the variant Fc region is an effector null Fc region. In some aspects, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some aspects, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2. Amino acid substitutions may be introduced into a polypeptide of interest and the products screened for a desired activity, for example, retained/improved antigen binding, decreased immunogenicity, or improved ADCC or CDC.

TABLE 2

| Amino acid residues | |
|---|---|
| Original Residue | Exemplary Substitutions |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) as provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example, a mammal. In some aspects, methods of treating mammals, including, but not limited to, humans, rodents, and simians, are provided. In some examples, an "individual" or "subject" refers to an individual or subject in need of treatment for a disease or disorder. In some aspects, the subject to receive the treatment can be a patient, designating the fact that the subject has been identified as having a disease or disorder of relevance to the treatment, or being at adequate risk of contracting the disease or disorder.

A "disease" or "disorder" as used herein refers to a condition where treatment is needed and/or desired.

As used herein, "IL13-associated condition" refers to any condition, disorder, or disease that involves aberrant expression, activity, or function of the IL13 protein within a biological context, such as in vivo in a subject. For example, an IL13-associated condition may involve increased IL13 expression, excessive IL13 activity, and/or any IL 13 dysfunction that results in a condition where treatment is needed and/or desired.

As used herein, "IL31-associated condition" refers to any condition, disorder, or disease that involves aberrant expression, activity, or function of the IL31 protein within a biological context, such as in vivo in a subject. For example, an IL31-associated condition may involve increased IL31 expression, excessive IL31 activity, and/or any IL31 dysfunction that results in a condition where treatment is needed and/or desired.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms “pharmaceutical formulation” and “pharmaceutical composition” are used interchangeably and refer to a preparation which is in such form as to permit the biological activity of the active ingredient(s) to be effective, and which contains no additional components which are unacceptably toxic to a subject to which the formulation would be administered. Such formulations may be sterile.

A “pharmaceutically acceptable carrier” refers to a non-toxic solid, semisolid, or liquid filler, diluent, encapsulating material, formulation auxiliary, or carrier conventional in the art for use with a therapeutic agent that together comprise a “pharmaceutical composition” for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

II. Exemplary IL13 Binding and IL31 Co-Binders

Provided herein are bispecific polypeptides that bind IL13 and IL31. In some aspects, the bispecific polypeptide that binds IL 13 and IL31 comprises a first co-binder that binds IL 13 and a second co-binder that binds IL31.

In some aspects, the first co-binder that specifically binds IL13 comprises one or more IL13 VHHs, such as a first VHH (VHH1) and a second VHH (VHH2). In some aspects, the second co-binder that specifically binds IL31, for example, comprises a first IL31 VHH (IL31 VHH1 or VHH3) and a second IL31 VHH (IL31 VHH2 or VHH4). In one aspect are various single binders (e.g., VHH1 or VHH2 disclosed herein) or co-binders (VHH1 and VHH2 in combination, optionally joined by a peptide linker). The VHH1 and VHH2 may optionally be joined by a peptide linker.

In some aspects, the VHH1 for the IL 13 co-binder comprises a CDR1 comprising the amino acid sequence of SEQ ID NO:34, a CDR2 comprising the amino acid sequence of SEQ ID NO: 35, and a CDR3 comprising the amino acid sequence of SEQ ID NO:36 or 61; the VHH2 for the IL 13 co-binder comprises a CDR1 comprising the amino acid sequence of SEQ ID NO:45, a CDR2 comprising the amino acid sequence of SEQ ID NO:46, and a CDR3 comprising the amino acid sequence of SEQ ID NO:47 or 64; the VHH3 for the IL31 co-binder comprises a CDR 1 comprising the amino acid sequence of SEQ ID NO:8, a CDR2 comprising the amino acid sequence of SEQ ID NO:9, and a CDR3 comprising the amino acid sequence of SEQ ID NO: 10; and the VHH4 for the IL31 co-binder comprises a CDR1 comprising the amino acid sequence of SEQ ID NO:19, a CDR2 comprising the amino acid sequence of SEQ ID NO:20, and a CDR3 comprising the amino acid sequence of SEQ ID NO:21.

In some aspects, the VHH1 for the IL 13 co-binder comprises a CDR1 comprising the amino acid sequence of SEQ ID NO:34, a CDR2 comprising the amino acid sequence of SEQ ID NO: 35, and a CDR3 comprising the amino acid sequence of SEQ ID NO:61; the VHH2 for the IL13 co-binder comprises a CDR1 comprising the amino acid sequence of SEQ ID NO:45, a CDR2 comprising the amino acid sequence of SEQ ID NO:46, and a CDR3 comprising the amino acid sequence of SEQ ID NO:64; the VHH3 for the IL31 co-binder comprises a CDR1 comprising the amino acid sequence of SEQ ID NO:8, a CDR2 comprising the amino acid sequence of SEQ ID NO:9, and a CDR3 comprising the amino acid sequence of SEQ ID NO: 10; and the VHH4 for the IL31 co-binder comprises a CDR1 comprising the amino acid sequence of SEQ ID NO:19, a CDR2 comprising the amino acid sequence of SEQ ID NO:20, and a CDR3 comprising the amino acid sequence of SEQ ID NO:21.

In some aspects, the VHH1 for the IL 13 co-binder comprises a CDR1 comprising the amino acid sequence of SEQ ID NO:31, a CDR2 comprising the amino acid sequence of SEQ ID NO: 32, and a CDR3 comprising the amino acid sequence of SEQ ID NO:33 or 60; the VHH2 for the IL 13 co-binder comprises a CDR1 comprising the amino acid sequence of SEQ ID NO:42, a CDR2 comprising the amino acid sequence of SEQ ID NO:43, and a CDR3 comprising the amino acid sequence of SEQ ID NO:44 or 63; the VHH3 for the IL31 co-binder comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7; and the VHH4 for the IL31 co-binder comprises a CDR1 comprising the amino acid sequence of SEQ ID NO:16, a CDR2 comprising the amino acid sequence of SEQ ID NO:17, and a CDR3 comprising the amino acid sequence of SEQ ID NO:18.

In some aspects, the VHH1 for the IL13 co-binder comprises a CDR1 comprising the amino acid sequence of SEQ ID NO:31, a CDR2 comprising the amino acid sequence of SEQ ID NO: 32, and a CDR3 comprising the amino acid sequence of SEQ ID NO:60; the VHH2 for the IL13 co-binder comprises a CDR1 comprising the amino acid sequence of SEQ ID NO:42, a CDR2 comprising the amino acid sequence of SEQ ID NO:43, and a CDR3 comprising the amino acid sequence of SEQ ID NO:63; the VHH3 for the IL31 co-binder comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7; and the VHH4 for the IL31 co-binder comprises a CDR1 comprising the amino acid sequence of SEQ ID NO:16, a CDR2 comprising the amino acid sequence of SEQ ID NO:17, and a CDR3 comprising the amino acid sequence of SEQ ID NO:18.

In some aspects, the VHH1 for the IL13 co-binder comprises a CDR1 comprising the amino acid sequence of SEQ ID NO:37, a CDR2 comprising the amino acid sequence of SEQ ID NO: 38, and a CDR3 comprising the amino acid sequence of SEQ ID NO:39 or 62; the VHH2 for the IL 13 co-binder comprises a CDR1 comprising the amino acid sequence of SEQ ID NO:48, a CDR2 comprising the amino acid sequence of SEQ ID NO:49, and a CDR3 comprising the amino acid sequence of SEQ ID NO:50 or 65; the VHH3 for the IL31 co-binder comprises a CDR 1 comprising the amino acid sequence of SEQ ID NO:11, a CDR2 comprising the amino acid sequence of SEQ ID NO: 12, and a CDR3 comprising the amino acid sequence of SEQ ID NO: 13; and the VHH4 for the IL31 co-binder comprises a CDR1 comprising the amino acid sequence of SEQ ID NO:22, a CDR2 comprising the amino acid sequence of SEQ ID NO:23, and a CDR3 comprising the amino acid sequence of SEQ ID NO:24.

In some aspects, the VHH1 for the IL 13 co-binder comprises a CDR1 comprising the amino acid sequence of SEQ ID NO:37, a CDR2 comprising the amino acid sequence of SEQ ID NO: 38, and a CDR3 comprising the amino acid sequence of SEQ ID NO:62; the VHH2 for the IL13 co-binder comprises a CDR1 comprising the amino acid sequence of SEQ ID NO:48, a CDR2 comprising the amino acid sequence of SEQ ID NO:49, and a CDR3 comprising the amino acid sequence of SEQ ID NO:65; the VHH3 for the IL31 co-binder comprises a CDR1 comprising the amino acid sequence of SEQ ID NO:11, a CDR2 comprising the amino acid sequence of SEQ ID NO: 12, and a CDR3 comprising the amino acid sequence of SEQ ID NO: 13; and the VHH4 for the IL31 co-binder comprises a CDR1 comprising the amino acid sequence of SEQ ID NO:22, a CDR2 comprising the amino acid sequence of SEQ ID NO:23, and a CDR3 comprising the amino acid sequence of SEQ ID NO:24.

In some aspects, co-binders that bind IL 13, as parts of bispecific polypeptides that bind IL13 and IL31 and comprising one or more IL13 VHHs, are provided herein.

In some aspects, the co-binder that binds IL13 comprises a first IL13 VHH (VHH1) and a second IL13 VHH (VHH2).

In some aspects, the IL13 co-binder comprises (i) a VHH1 comprising a CDR1 comprising the amino acid sequence of SEQ ID NO:31, a CDR2 comprising the amino acid sequence of SEQ ID NO:32, and a CDR3 comprising the amino acid sequence of SEQ ID NO:33 or 60 and (ii) a VHH2 comprising a CDR1 comprising the amino acid sequence of SEQ ID NO: 42, a CDR2 comprising the amino acid sequence of SEQ ID NO:43, and a CDR3 comprising the amino acid sequence of SEQ ID NO:44 or 63.

In some aspects, the IL13 co-binder comprises (i) a VHH1 comprising a CDR1 comprising the amino acid sequence of SEQ ID NO:31, a CDR2 comprising the amino acid sequence of SEQ ID NO:32, and a CDR3 comprising the amino acid sequence of SEQ ID NO:60 and (ii) a VHH2 comprising a CDR1 comprising the amino acid sequence of SEQ ID NO:42, a CDR2 comprising the amino acid sequence of SEQ ID NO:43, and a CDR3 comprising the amino acid sequence of SEQ ID NO:63.

In some aspects, the IL 13 co-binder comprises (i) a VHH1 comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36 or 61 and (ii) a VHH2 comprising a CDR1 comprising the amino acid sequence of SEQ ID NO: 45, a CDR2 comprising the amino acid sequence of SEQ ID NO:46, and a CDR3 comprising the amino acid sequence of SEQ ID NO:47 or 64.

In some aspects, the IL 13 co-binder comprises (i) a VHH1 comprising a CDR1 comprising the amino acid sequence of SEQ ID NO:34, a CDR2 comprising the amino acid sequence of SEQ ID NO:35, and a CDR3 comprising the amino acid sequence of SEQ ID NO:61 and (ii) a VHH2 comprising a CDR1 comprising the amino acid sequence of SEQ ID NO:45, a CDR2 comprising the amino acid sequence of SEQ ID NO:46, and a CDR3 comprising the amino acid sequence of SEQ ID NO:64.

In some aspects, the IL 13 co-binder comprises (i) a VHH1 comprising a CDR1 comprising the amino acid sequence of SEQ ID NO:37, a CDR2 comprising the amino acid sequence of SEQ ID NO:38, and a CDR3 comprising the amino acid sequence of SEQ ID NO:39 or 62 and (ii) a VHH2 comprising a CDR1 comprising the amino acid sequence of SEQ ID NO: 48, a CDR2 comprising the amino acid sequence of SEQ ID NO:49, and a CDR3 comprising the amino acid sequence of SEQ ID NO:50 or 65.

In some aspects, the IL 13 co-binder comprises (i) a VHH1 comprising a CDR1 comprising the amino acid sequence of SEQ ID NO:37, a CDR2 comprising the amino acid sequence of SEQ ID NO:38, and a CDR3 comprising the amino acid sequence of SEQ ID NO:62 and (ii) a VHH2 comprising a CDR1 comprising the amino acid sequence of SEQ ID NO:48, a CDR2 comprising the amino acid sequence of SEQ ID NO:49, and a CDR3 comprising the amino acid sequence of SEQ ID NO:65.

In some aspects, co-binders that bind IL31, as parts of bispecific polypeptides that bind IL13 and IL31 and comprising one or more IL31 VHHs, are provided herein.

In some aspects, the co-binder that binds IL31 comprises a first IL31 VHH (IL31 VHH1 or VHH3) and a second IL31 VHH (IL31 VHH2 or VHH4).

In some aspects, the IL31 co-binder comprises (i) a IL31 VHH1 or VHH3 comprising a CDR 1 comprising the amino acid sequence of SEQ ID NO:8, a CDR2 comprising the amino acid sequence of SEQ ID NO:9, and a CDR3 comprising the amino acid sequence of SEQ ID NO:10; and (ii) a IL31 VHH2 or VHH4 comprising a CDR1 comprising the amino acid sequence of SEQ ID NO: 19, a CDR2 comprising the amino acid sequence of SEQ ID NO:20, and a CDR3 comprising the amino acid sequence of SEQ ID NO:21.

In some aspects, the IL31 co-binder comprises (i) a IL31 VHH1 or VHH3 comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; and (ii) a IL31 VHH2 or VHH4 comprising a CDR1 comprising the amino acid sequence of SEQ ID NO: 16, a CDR2 comprising the amino acid sequence of SEQ ID NO:17, and a CDR3 comprising the amino acid sequence of SEQ ID NO:18.

In some aspects, the IL31 co-binder comprises (i) a IL31 VHH1 or VHH3 comprising a CDR 1 comprising the amino acid sequence of SEQ ID NO: 11, a CDR2 comprising the amino acid sequence of SEQ ID NO: 12, and a CDR3 comprising the amino acid sequence of SEQ ID NO: 13; and (ii) a IL31 VHH2 or VHH4 comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24.

In some aspects, the single or co-binder that binds IL13 (e.g., VHH domain) may be humanized. In some aspects, the single or co-binder that binds IL31 (e.g., VHH domain) may be humanized. Humanized binding molecules (such as sdAbs or VHH-containing polypeptides) are useful as therapeutic molecules because they reduce or eliminate the human immune response to non-human binding molecules. For example, a humanized antibody can comprise one or more variable domains in which CDRs, (or portions thereof) are derived from a non-human antibody, and FRs (or portions thereof) are derived from human antibody sequences. A humanized antibody optionally may also comprise at least a portion of a human constant region. In some aspects, some FR residues in a humanized binding molecule are substituted with corresponding residues from a non-human binding molecule (for example, the antibody from which the CDR residues are derived), for example, to restore or improve antibody specificity or affinity.

Humanized binding molecules and methods of making them are reviewed, for example, in Almagro and Fransson, (2008) Front. Biosci. 13:1619-1633, and are further described, for example, in Riechmann et al., (1988) Nature 332:323-329; Queen et al., (1989) Proc. Natl Acad. Sci. USA 86:10029-10033 or 60; US Patent Nos. 5, 821,337, 7,527,791, 6,982,321, and 7,087,409; Kashmiri et al., (2005) Methods 36:25-34; Padlan, (1991) Mol. Immunol. 28:489-498 (describing "resurfacing"); Dall'Acqua et al., (2005) Methods 36:43-60 (describing "FR shuffling"); and Osbourn et al., (2005) Methods 36:61-68 and Klimka et al., (2000) Br. J. Cancer, 83:252-280 (describing the "guided selection" approach to FR shuffling).

Human framework regions that can be used for humanization include but are not limited to: framework regions selected using the "best-fit" method (see, for example, Sims et al. (1993) J. Immunol. 151:2296); framework regions derived from the consensus sequence of human antibodies of a particular subgroup of heavy chain variable regions (see, for example, Carter et al. (1992) Proc. Natl. Acad. Sci. USA, 89:4285; and Presta et al. (1993) J. Immunol, 151:2623); human mature (somatically mutated) framework regions or human germline framework regions (see, for example, Almagro and Fransson, (2008) Front. Biosci. 13:1619-1633); and framework regions derived from screening FR libraries (see, for example, Baca et al., (1997) J. Biol. Chem. 272:10678-10684 and Rosok et al., (1996) J. Biol. Chem. 271:22611-22618). Typically, the FR regions of a VHH are replaced with human FR regions to make a humanized VHH. In some aspects, certain FR residues of the human FR are replaced in order to improve one or more properties of the humanized VHH. VHH domains with such replaced residues are still referred to herein as "humanized."

In some aspects, the VHH1 of the co-binder that binds IL 13 (IL13 co-binder) comprises an amino acid sequence at least 85%, at least 90%, at least 95%, at least 96%, at least 97%, at least 98%, or at least 99% identical to the amino acid residues 1-115 or 2-115 of SEQ ID NO:51 or 52.

In some aspects, the VHH1 of the IL13 co-binder comprises an amino acid sequence at least 85%, at least 90%, at least 95%, at least 96%, at least 97%, at least 98%, or at least 99% identical to the amino acid residues 1-115 or 2-115 of SEQ ID NO:52.

In some aspects, the VHH1 of the IL13 co-binder comprises an amino acid sequence at least 85%, at least 90%, at least 95%, at least 96%, at least 97%, at least 98%, or at least 99% identical to the amino acid sequence of SEQ ID NO:29 or 30, or amino acid residues 2-115 of SEQ ID NO:29 or 30.

In some aspects, the VHH1 of the IL13 co-binder comprises an amino acid sequence at least 85%, at least 90%, at least 95%, at least 96%, at least 97%, at least 98%, or at least 99% identical to the amino acid sequence of SEQ ID NO:30, or amino acid residues 2-115 of SEQ ID NO: 30.

In some aspects, the VHH1 of the IL13 co-binder comprises an amino acid sequence at least 85%, at least 90%, at least 95%, at least 96%, at least 97%, at least 98%, or at least 99% identical to amino acid residues 1-115 of SEQ ID NO:51, or amino acid residues or 2-115 of SEQ ID NO:51. In some aspects, the VHH1 of the IL13 co-binder comprises an amino acid sequence at least 85% identical to amino acid residues 1-115 of SEQ ID NO:51, or amino acid residues 2-115 of SEQ ID NO:51. In some aspects, the VHH1 of the IL13 co-binder comprises an amino acid sequence at least 90% identical to amino acid residues 1-115 of SEQ ID NO:51, or amino acid residues 2-115 of SEQ ID NO:51. In some aspects, the VHH1 of IL 13 co-binder comprises an amino acid sequence at least 95% identical to amino acid residues 1-115 of SEQ ID NO: 51, or amino acid residues 2-115 of SEQ ID NO: 51. In some aspects, the VHH1 of the IL13 co-binder comprises an amino acid sequence at least 96% identical to amino acid residues 1-115 of SEQ ID NO:51, or amino acid residues 2-115 of SEQ ID NO:51. In some aspects, the VHH1 of the IL 13 co-binder comprises an amino acid sequence at least 97% identical to amino acid residues 1-115 of SEQ ID NO:51, or amino acid residues 2-115 of SEQ ID NO:51. In some aspects, the VHH1 of the IL13 co-binder comprises an amino acid sequence at least 98% identical to amino acid residues 1-115 or 2-115 of SEQ ID NO:51. In some aspects, the VHH1 of the IL13 co-binder comprises an amino acid sequence at least 99% identical to amino acid residues 1-115 of SEQ ID NO:51, or amino acid residues 2-115 of SEQ ID NO:51. In some aspects, the VHH1 of the IL13 co-binder comprises amino acid residues 1-115 of SEQ ID NO: 51, or amino acid residues 2-115 of SEQ ID NO:51.

In some aspects, the VHH1 of the IL13 co-binder comprises an amino acid sequence at least 85%, at least 90%, at least 95%, at least 96%, at least 97%, at least 98%, or at least 99% identical to amino acid residues 1-115 of SEQ ID NO:52, or amino acid residues 2-115 of SEQ ID NO: 52. In some aspects, the VHH1 of the IL13 co-binder comprises an amino acid sequence at least 85% identical to amino acid residues 1-115 of SEQ ID NO:52, or amino acid residues or 2-115 of SEQ ID NO:52. In some aspects, the VHH1 of the IL 13 co-binder comprises an amino acid sequence at least 90% identical to amino acid residues 1-115 of SEQ ID NO:52, or amino acid residues 2-115 of SEQ ID NO:52. In some aspects, the VHH1 of the IL 13 co-binder comprises an amino acid sequence at least 95% identical to amino acid residues 1-115 of SEQ ID NO: 52, or amino acid residues 2-115 of SEQ ID NO:52. In some aspects, the VHH1 of the IL 13 co-binder comprises an amino acid sequence at least 96% identical to amino acid residues 1-115 of SEQ ID NO:52, or amino acid residues 2-115 of SEQ ID NO:52. In some aspects, the VHH1 of the IL 13 co-binder comprises an amino acid sequence at least 97% identical to amino acid residues 1-115 of SEQ ID NO:52, or amino acid residues 2-115 of SEQ ID NO:52. In some aspects, the VHH1 of the IL 13 co-binder comprises an amino acid sequence at least 98% identical to amino acid residues 1-115 of SEQ ID NO:52, or amino acid residues 2-115 of SEQ ID NO: 52. In some aspects, the VHH1 of the IL 13 co-binder comprises an amino acid sequence at least 99% identical to amino acid residues 1-115 of SEQ ID NO:52, or amino acid residues 2-115 of SEQ ID NO:52. In some aspects, the VHH1 of the IL 13 co-binder comprises amino acid residues 1-115 of SEQ ID NO:52, or amino acid residues 2-115 of SEQ ID NO:52.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:51 or 52, optionally wherein residue 162 is valine according to SEQ ID NO: 51 or 52.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:52.

In some aspects, the VHH2 of the IL13 co-binder comprises an amino acid sequence at least 85%, at least 90%, at least 95%, at least 96%, at least 97%, at least 98%, or at least 99% identical to the amino acid sequence of SEQ ID NO:40 or 41, or amino acid residues 2-127 of SEQ ID NO:40 or 41, optionally wherein residue 9 is valine according to SEQ ID NO:40 or 41.

In some aspects, the VHH2 of the IL13 co-binder comprises an amino acid sequence at least 85%, at least 90%, at least 95%, at least 96%, at least 97%, at least 98%, or at least 99% identical to the amino acid sequence of SEQ ID NO:41, or amino acid residues 2-127 of SEQ ID NO: 41.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:51, optionally wherein residue 162 is valine according to SEQ ID NO:51. In some aspects, the VHH2 of the IL31 co-binder comprises an amino acid sequence at least 85% identical to the amino acid residues 154-280 of SEQ ID NO: 51, optionally wherein residue 162 is valine according to SEQ ID NO:51. In some aspects, the VHH2 of the IL13 co-binder comprises an amino acid sequence at least 90% identical to the amino acid residues 154-280 of SEQ ID NO:51, optionally wherein residue 162 is valine according to SEQ ID NO:51. In some aspects, the VHH2 of the IL13 co-binder comprises an amino acid sequence at least 95% identical to the amino acid residues 154-280 of SEQ ID NO: 51, optionally wherein residue 162 is valine according to SEQ ID NO:51. In some aspects, the VHH2 of the IL13 co-binder comprises an amino acid sequence at least 96% identical to the amino acid residues 154-280 of SEQ ID NO:51, optionally wherein residue 162 is valine according to SEQ ID NO:51. In some aspects, the VHH2 of the IL13 co-binder comprises an amino acid sequence at least 97% identical to the amino acid residues 154-280 of SEQ ID NO: 51, optionally wherein residue 162 is valine according to SEQ ID NO:51. In some aspects, the VHH2 of the IL13 co-binder comprises an amino acid sequence at least 98% identical to the amino acid residues 154-280 of SEQ ID NO:51, optionally wherein residue 162 is valine according to SEQ ID NO:51. In some aspects, the VHH2 of the IL 13 co-binder comprises an amino acid sequence at least 99% identical to the amino acid residues 154-280 of SEQ ID NO: 51, optionally wherein residue 162 is valine according to SEQ ID NO:51. In some aspects, the VHH2 of the IL 13 co-binder comprises the amino acid residues 154-280 of SEQ ID NO:51, optionally wherein residue 162 is valine according to SEQ ID NO:51. In some aspects, the VHH2 of the IL 13 co-binder comprises the amino acid residues 154-280 of SEQ ID NO:51, wherein residue 162 is valine according to SEQ ID NO:51.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:52. In some aspects, the VHH2 of the IL 13 co-binder comprises an amino acid sequence at least 85% identical to the amino acid residues 154-280 of SEQ ID NO:52. In some aspects, the VHH2 of the IL 13 co-binder comprises an amino acid sequence at least 90% identical to the amino acid residues 154-280 of SEQ ID NO: 52. In some aspects, the VHH2 of the IL13 co-binder comprises an amino acid sequence at least 95% identical to the amino acid residues 154-280 of SEQ ID NO:52. In some aspects, the VHH2 of the IL 13 co-binder comprises an amino acid sequence at least 96% identical to the amino acid residues 154-280 of SEQ ID NO:52. In some aspects, the VHH2 of the IL13 co-binder comprises an amino acid sequence at least 97% identical to the amino acid residues 154-280 of SEQ ID NO:52. In some aspects, the VHH2 of the IL13 co-binder comprises an amino acid sequence at least 98% identical to the amino acid residues 154-280 of SEQ ID NO:52. In some aspects, the VHH2 of the IL 13 co-binder comprises an amino acid sequence at least 99% identical to the amino acid residues 154-280 of SEQ ID NO:52. In some aspects, the VHH2 of the IL 13 co-binder comprises the amino acid residues 154-280 of SEQ ID NO:52. In some aspects, the second antibody variable domain of the IL 13 co-binder comprises the amino acid residues 154-280 of SEQ ID NO:52.

In some aspects, the VHH1 of the IL13 co-binder comprises the amino acid residues 1-115 or 2-115 of SEQ ID NO:51 or 52, and the VHH2 of the IL 13 co-binder comprises the amino acid residues 154-280 of SEQ ID NO:51 or 52, optionally wherein residue 162 is valine according to SEQ ID NO:51 or 52. In some aspects, the VHH1 of the IL 13 co-binder comprises the amino acid residues 1-115 or 2-115 of SEQ ID NO:51, and the VHH2 of the IL13 co-binder comprises the amino acid residues 154-280 of SEQ ID NO:51, optionally wherein residue 162 is valine according to SEQ ID NO:51. In some aspects, the VHH1 of the IL13 co-binder comprises the amino acid residues 1-115 or 2-115 of SEQ ID NO:51, and the VHH2 of the IL13 co-binder comprises the amino acid residues 154-280 of SEQ ID NO:51, wherein residue 162 is valine according to SEQ ID NO:51. In some aspects, the VHH1 of the IL13 co-binder comprises the amino acid residues 1-115 or 2-115 of SEQ ID NO:52, and the VHH2 of the IL 13 co-binder comprises the amino acid residues 154-280 of SEQ ID NO:52. In some aspects, the VHH1 of the IL13 co-binder comprises the amino acid residues 1-115 or 2-115 of SEQ ID NO:52, and the VHH2 of the IL 13 co-binder comprises the amino acid residues 154-280 of SEQ ID NO:52.

In some aspects, the VHH1 of the IL13 co-binder comprises the amino acid sequence of SEQ ID NO:29 or 30, or amino acid residues 2-115 of SEQ ID NO:29 or 30, and the VHH2 of the IL 13 co-binder comprises the amino acid sequence of SEQ ID NO:40 or 41, or amino acid residues 2-127 of SEQ ID NO:40 or 41, optionally wherein residue 9 is valine according to SEQ ID NO: 40 or 41. In some aspects, the VHH1 of the IL13 co-binder comprises the amino acid sequence of SEQ ID NO:29 or amino acid residues 2-115 of SEQ ID NO:29, and the VHH2 of the IL 13 co-binder comprises the amino acid sequence of SEQ ID NO:40, optionally wherein residue 9 is valine according to SEQ ID NO:40. In some aspects, the VHH1 of the IL13 co-binder comprises the amino acid sequence of SEQ ID NO:30 or amino acid residues 2-115 of SEQ ID NO:30, and the VHH2 of the IL13 co-binder comprises the amino acid sequence of SEQ ID NO: 41.

In some aspects, the VHH1 of the IL31 co-binder comprises an amino acid sequence at least 85%, at least 90%, at least 95%, at least 96%, at least 97%, at least 98%, or at least 99% identical to the amino acid residues 1-118 or 2-118 of SEQ ID NO:25 or 26.

In some aspects, the VHH1 of the IL31 co-binder comprises an amino acid sequence at least 85%, at least 90%, at least 95%, at least 96%, at least 97%, at least 98%, or at least 99% identical to the amino acid residues 1-118 or 2-118 of SEQ ID NO:25. In some aspects, the VHH1 of the IL31 co-binder comprises an amino acid sequence at least 85% identical to the amino acid residues 1-118 or 2-118 of SEQ ID NO:25. In some aspects, the VHH1 of the IL31 co-binder comprises an amino acid sequence at least 90% identical to the amino acid residues 1-118 or 2-118 of SEQ ID NO:25. In some aspects, the VHH1 of the IL31 co-binder comprises an amino acid sequence at least 95% identical to the amino acid residues 1-118 or 2-118 of SEQ ID NO: 25. In some aspects, the VHH1 of the IL31 co-binder comprises an amino acid sequence at least 96% identical to the amino acid residues 1-118 or 2-118 of SEQ ID NO:25. In some aspects, the VHH1 of the IL31 co-binder comprises an amino acid sequence at least 97% identical to the amino acid residues 1-118 or 2-118 of SEQ ID NO:25. In some aspects, the VHH1 of the IL31 co-binder comprises an amino acid sequence at least 98% identical to the amino acid residues 1-118 or 2-118 of SEQ ID NO:25. In some aspects, the VHH1 of the IL31 co-binder comprises an amino acid sequence at least 99% identical to the amino acid residues 1-118 or 2-118 of SEQ ID NO:25. In some aspects, the VHH1 of the IL31 co-binder comprises the amino acid residues 1-118 or 2-118 of SEQ ID NO:25.

In some aspects, the VHH1 of the IL31 co-binder comprises an amino acid sequence at least 85%, at least 90%, at least 95%, at least 96%, at least 97%, at least 98%, or at least 99% identical to the amino acid residues 1-118 or 2-118 of SEQ ID NO:26. In some aspects, the VHH1 of the IL31 co-binder comprises an amino acid sequence at least 85% identical to the amino acid residues 1-118 or 2-118 of SEQ ID NO:26. In some aspects, the VHH1 of the IL31 co-binder comprises an amino acid sequence at least 90% identical to the amino acid residues 1-118 or 2-118 of SEQ ID NO:26. In some aspects, the VHH1 of the IL31 co-binder comprises an amino acid sequence at least 95% identical to the amino acid residues 1-118 or 2-118 of SEQ ID NO: 26. In some aspects, the VHH1 of the IL31 co-binder comprises an amino acid sequence at least 96% identical to the amino acid residues 1-118 or 2-118 of SEQ ID NO:26. In some aspects, the VHH1 of the IL31 co-binder comprises an amino acid sequence at least 97% identical to the amino acid residues 1-118 or 2-118 of SEQ ID NO:26. In some aspects, the VHH1 of the IL31 co-binder comprises an amino acid sequence at least 98% identical to the amino acid residues 1-118 or 2-118 of SEQ ID NO:26. In some aspects, the VHH1 of the IL31 co-binder comprises an amino acid sequence at least 99% identical to the amino acid residues 1-118 or 2-118 of SEQ ID NO:26. In some aspects, the VHH1 of the IL31 co-binder comprises the amino acid residues 1-118 or 2-118 of SEQ ID NO:26.

In some aspects, the VHH1 of the IL31 co-binder comprises an amino acid sequence at least 85%, at least 90%, at least 95%, at least 96%, at least 97%, at least 98%, or at least 99% identical to the amino acid sequence of SEQ ID NO:3 or 4, or amino acid residues 2-118 of SEQ ID NO: 3 or 4. In some aspects, the VHH1 of the IL31 co-binder comprises an amino acid sequence at least 85%, at least 90%, at least 95%, at least 96%, at least 97%, at least 98%, or at least 99% identical to the amino acid sequence of SEQ ID NO:3, or amino acid residues 2-118 of SEQ ID NO:3. In some aspects, the VHH1 of the IL31 co-binder comprises an amino acid sequence at least 85%, at least 90%, at least 95%, at least 96%, at least 97%, at least 98%, or at least 99% identical to the amino acid sequence of SEQ ID NO:4, or amino acid residues 2-118 of SEQ ID NO:4. In some aspects, the VHH1 of the IL31 co-binder comprises the amino acid sequence of SEQ ID NO:3 or 4, or amino acid residues 2-118 of SEQ ID NO:3 or 4. In some aspects, the VHH1 of the IL31 co-binder comprises the amino acid sequence of SEQ ID NO:3, or amino acid residues 2-118 of SEQ ID NO:3. In some aspects, the VHH1 of the IL31 co-binder comprises the amino acid sequence of SEQ ID NO:4, or amino acid residues 2-118 of SEQ ID NO: 4.

In some aspects, the VHH2 of the IL31 co-binder comprises an amino acid sequence at least 85%, at least 90%, at least 95%, at least 96%, at least 97%, at least 98%, or at least 99% identical to the amino acid residues 157-275 of SEQ ID NO:25 or 26, optionally wherein residue 166 is valine according to SEQ ID NO:25 or 26.

In some aspects, the VHH2 of the IL31 co-binder comprises an amino acid sequence at least 85%, at least 90%, at least 95%, at least 96%, at least 97%, at least 98%, or at least 99% identical to the amino acid residues 157-275 of SEQ ID NO:25, optionally wherein residue 166 is valine according to SEQ ID NO:25. In some aspects, the VHH2 of the comprises an amino acid sequence at least 85% identical to the amino acid residues 157-275 of SEQ ID NO:25, optionally wherein residue 166 is valine according to SEQ ID NO:25. In some aspects, the VHH2 of the IL31 co-binder comprises an amino acid sequence at least 90% identical to the amino acid residues 157-275 of SEQ ID NO:25, optionally wherein residue 166 is valine according to SEQ ID NO: 25. In some aspects, the VHH2 of the IL31 co-binder comprises an amino acid sequence at least 95% identical to the amino acid residues 157-275 of SEQ ID NO:25, optionally wherein residue 166 is valine according to SEQ ID NO:25. In some aspects, the VHH2 of the IL31 co-binder comprises an amino acid sequence at least 96% identical to the amino acid residues 157-275 of SEQ ID NO:25, optionally wherein residue 166 is valine according to SEQ ID NO:25. In some aspects, the VHH2 of the IL31 co-binder comprises an amino acid sequence at least 97% identical to the amino acid residues 157-275 of SEQ ID NO:25, optionally wherein residue 166 is valine according to SEQ ID NO:25. In some aspects, the VHH2 of the IL31 co-binder comprises an amino acid sequence at least 98% identical to the amino acid residues 157-275 of SEQ ID NO: 25, optionally wherein residue 166 is valine according to SEQ ID NO:25. In some aspects, the VHH2 of the IL31 co-binder comprises an amino acid sequence at least 99% identical to the amino acid residues 157-275 of SEQ ID NO:25, optionally wherein residue 166 is valine according to SEQ ID NO:25. In some aspects, the VHH2 of the IL31 co-binder comprises the amino acid residues 157-275 of SEQ ID NO:25, optionally wherein residue 166 is valine according to SEQ ID NO:25. In some aspects, the VHH2 of the IL31 co-binder comprises the amino acid residues 157-275 of SEQ ID NO:25, wherein residue 166 is valine according to SEQ ID NO: 25.

In some aspects, the VHH2 of the IL31 co-binder comprises an amino acid sequence at least 85%, at least 90%, at least 95%, at least 96%, at least 97%, at least 98%, or at least 99% identical to the amino acid residues 157-275 of SEQ ID NO:26, optionally wherein residue 166 is valine according to SEQ ID NO:26. In some aspects, the VHH2 of the IL31 co-binder comprises an amino acid sequence at least 85% identical to the amino acid residues 157-275 of SEQ ID NO: 26, optionally wherein residue 166 is valine according to SEQ ID NO:26. In some aspects, the VHH2 of the IL31 co-binder comprises an amino acid sequence at least 90% identical to the amino acid residues 157-275 of SEQ ID NO:26, optionally wherein residue 166 is valine according to SEQ ID NO:26. In some aspects, the VHH2 of the IL31 co-binder comprises an amino acid sequence at least 95% identical to the amino acid residues 157-275 of SEQ ID NO: 26, optionally wherein residue 166 is valine according to SEQ ID NO:26. In some aspects, the VHH2 of the IL31 co-binder comprises an amino acid sequence at least 96% identical to the amino acid residues 157-275 of SEQ ID NO:26, optionally wherein residue 166 is valine according to SEQ ID NO:26. In some aspects, the VHH2 of the IL31 co-binder comprises an amino acid sequence at least 97% identical to the amino acid residues 157-275 of SEQ ID NO: 26, optionally wherein residue 166 is valine according to SEQ ID NO:26. In some aspects, the VHH2 of the IL31 co-binder comprises an amino acid sequence at least 98% identical to the amino acid residues 157-275 of SEQ ID NO:26, optionally wherein residue 166 is valine according to SEQ ID NO:26. In some aspects, the VHH2 of the IL31 co-binder comprises an amino acid sequence at least 99% identical to the amino acid residues 157-275 of SEQ ID NO: 26, optionally wherein residue 166 is valine according to SEQ ID NO:26. In some aspects, the VHH2 of the IL31 co-binder comprises the amino acid residues 157-275 of SEQ ID NO:26, optionally wherein residue 166 is valine according to SEQ ID NO:26. In some aspects, the VHH2 of the IL31 co-binder comprises the amino acid residues 157-275 of SEQ ID NO:26, wherein residue 166 is valine according to SEQ ID NO:26.

In some aspects, the VHH2 of the IL31 co-binder comprises an amino acid sequence at least 85%, at least 90%, at least 95%, at least 96%, at least 97%, at least 98%, or at least 99% identical to the amino acid sequence of SEQ ID NO: 14 or 15, or amino acid residues 2-119 of SEQ ID NO: 14 or 15, optionally wherein residue 10 is valine according to SEQ ID NO: 14 or 15. In some aspects, the VHH2 of the IL31 co-binder comprises an amino acid sequence at least 85%, at least 90%, at least 95%, at least 96%, at least 97%, at least 98%, or at least 99% identical to the amino acid sequence of SEQ ID NO: 14, or amino acid residues 2-119 of SEQ ID NO: 14, optionally wherein residue 10 is valine according to SEQ ID NO:14. In some aspects, the VHH2 of the IL31 co-binder comprises an amino acid sequence at least 85%, at least 90%, at least 95%, at least 96%, at least 97%, at least 98%, or at least 99% identical to the amino acid sequence of SEQ ID NO: 15, or amino acid residues 2-119 of SEQ ID NO:15, optionally wherein residue 10 is valine according to SEQ ID NO:15. In some aspects, the VHH2 of the IL31 co-binder comprises the amino acid sequence of SEQ ID NO: 14 or 15, or amino acid residues 2-119 of SEQ ID NO: 14 or 15, optionally wherein residue 10 is valine according to SEQ ID NO: 14 or 15. In some aspects, the VHH2 of the IL31 co-binder comprises the amino acid sequence of SEQ ID NO:14, or amino acid residues 2-119 of SEQ ID NO:14, optionally wherein residue 10 is valine according to SEQ ID NO: 14. In some aspects, the VHH2 of the IL31 co-binder comprises the amino acid sequence of SEQ ID NO:15, or amino acid residues 2-119 of SEQ ID NO: 15, optionally wherein residue 10 is valine according to SEQ ID NO:15.

In some aspects, the VHH1 of the IL31 co-binder comprises the amino acid residues 1-118 or 2-118 of SEQ ID NO:25 or 26 and the VHH2 of the IL31 co-binder comprises the amino acid residues 157-275 of SEQ ID NO:25 or 26, optionally wherein residue 166 is valine according to SEQ ID NO:25 or 26. In some aspects, the VHH1 of the IL31 co-binder comprises the amino acid residues 1-118 or 2-118 of SEQ ID NO:25 and the VHH2 of the IL31 co-binder comprises the amino acid residues 157-275 of SEQ ID NO:25, optionally wherein residue 166 is valine according to SEQ ID NO:25. In some aspects, the VHH1 of the IL31 co-binder comprises the amino acid residues 1-118 or 2-118 of SEQ ID NO:25 and the VHH2 of the IL31 co-binder comprises the amino acid residues 157-275 of SEQ ID NO:25, wherein residue 166 is valine according to SEQ ID NO:25. In some aspects, the VHH1 of the IL31 co-binder comprises the amino acid residues 1-118 or 2-118 of SEQ ID NO:26 and the VHH2 of the IL31 co-binder comprises the amino acid residues 157-275 of SEQ ID NO:26, optionally wherein residue 166 is valine according to SEQ ID NO:26. In some aspects, the VHH1 of the IL31 co-binder comprises the amino acid residues 1-118 or 2-118 of SEQ ID NO:26 and the VHH2 of the IL31 co-binder comprises the amino acid residues 157-275 of SEQ ID NO:26, wherein residue 166 is valine according to SEQ ID NO:26.

In some aspects, the VHH1 of the IL31 co-binder comprises the amino acid sequence of SEQ ID NO:3 or 4, or amino acid residues 2-118 of SEQ ID NO:3 or 4, and the VHH2 of the IL31 co-binder comprises the amino acid sequence of SEQ ID NO: 14 or 15, or amino acid residues 2-119 of SEQ ID NO: 14 or 15, optionally wherein residue 10 is valine according to SEQ ID NO: 14 or 15. In some aspects, the VHH1 of the IL31 co-binder comprises the amino acid sequence of SEQ ID NO:3, or amino acid residues 2-118 of SEQ ID NO:3, and the VHH2 of the IL31 co-binder comprises the amino acid sequence of SEQ ID NO:14 or amino acid residues 2-119 of SEQ ID NO: 14, optionally wherein residue 10 is valine according to SEQ ID NO:14. In some aspects, the VHH1 of the IL31 co-binder comprises the amino acid sequence of SEQ ID NO: 4, or amino acid residues 2-118 of SEQ ID NO:4, and the VHH2 of the IL31 co-binder comprises the amino acid sequence of SEQ ID NO: 15 or amino acid residues 2-119 of SEQ ID NO: 15, wherein residue 10 is valine according to SEQ ID NO:15.

In some aspects, the VHH1 of the IL13 co-binder comprises a CDR1 comprising the amino acid sequence of SEQ ID NO:31, a CDR2 comprising the amino acid sequence of SEQ ID NO: 32, and a CDR3 comprising the amino acid sequence of SEQ ID NO:33 or 60, wherein the VHH1 comprises an amino acid sequence at least 85%, at least 90%, at least 95%, at least 96%, at least 97%, at least 98%, or at least 99% identical to the amino acid sequence of SEQ ID NO: 29, or amino acid residues 2-115 of SEQ ID NO:29. In some aspects, the VHH1 of the IL 13 co-binder comprises a CDR1 comprising the amino acid sequence of SEQ ID NO:31, a CDR2 comprising the amino acid sequence of SEQ ID NO:32, and a CDR3 comprising the amino acid sequence of SEQ ID NO:33 or 60, wherein the VHH1 comprises an amino acid sequence at least 85%, at least 90%, at least 95%, at least 96%, at least 97%, at least 98%, or at least 99% identical to the amino acid sequence of SEQ ID NO:30, or amino acid residues 2-115 of SEQ ID NO:30.

In some aspects, the VHH1 of the IL13 co-binder comprises a CDR1 comprising the amino acid sequence of SEQ ID NO:34, a CDR2 comprising the amino acid sequence of SEQ ID NO: 35, and a CDR3 comprising the amino acid sequence of SEQ ID NO:36 or 61, wherein the VHH1 comprises an amino acid sequence at least 85%, at least 90%, at least 95%, at least 96%, at least 97%, at least 98%, or at least 99% identical to the amino acid sequence of SEQ ID NO: 29, or amino acid residues 2-115 of SEQ ID NO:29. In some aspects, the VHH1 comprises a CDR1 comprising the amino acid sequence of SEQ ID NO:34, a CDR2 comprising the amino acid sequence of SEQ ID NO:35, and a CDR3 comprising the amino acid sequence of SEQ ID NO: 36 or 61, wherein the VHH1 comprises an amino acid sequence at least 85%, at least 90%, at least 95%, at least 96%, at least 97%, at least 98%, or at least 99% identical to the amino acid sequence of SEQ ID NO:30, or amino acid residues 2-115 of SEQ ID NO:30.

In some aspects, the VHH1 of the IL13 co-binder comprises a CDR1 comprising the amino acid sequence of SEQ ID NO:37, a CDR2 comprising the amino acid sequence of SEQ ID NO: 38, and a CDR3 comprising the amino acid sequence of SEQ ID NO:39 or 62, wherein the VHH1 comprises an amino acid sequence at least 85%, at least 90%, at least 95%, at least 96%, at least 97%, at least 98%, or at least 99% identical to the amino acid sequence of SEQ ID NO: 29, or amino acid residues 2-115 of SEQ ID NO:29. In some aspects, the VHH1 comprises a CDR1 comprising the amino acid sequence of SEQ ID NO:37, a CDR2 comprising the amino acid sequence of SEQ ID NO:38, and a CDR3 comprising the amino acid sequence of SEQ ID NO: 39 or 62, wherein the VHH1 comprises an amino acid sequence at least 85%, at least 90%, at least 95%, at least 96%, at least 97%, at least 98%, or at least 99% identical to the amino acid sequence of SEQ ID NO:30, or amino acid residues 2-115 of SEQ ID NO:30.

In some aspects, the VHH2 of the IL13 co-binder comprises a CDR1 comprising the amino acid sequence of SEQ ID NO:42, a CDR2 comprising the amino acid sequence of SEQ ID NO: 43, and a CDR3 comprising the amino acid sequence of SEQ ID NO:44 or 63, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40, optionally wherein residue 9 is valine according to SEQ ID NO:40. In some aspects, the VHH2 comprises a CDR1 comprising the amino acid sequence of SEQ ID NO:42, a CDR2 comprising the amino acid sequence of SEQ ID NO:43, and a CDR3 comprising the amino acid sequence of SEQ ID NO:44 or 63, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, the VHH2 of the IL13 co-binder comprises a CDR1 comprising the amino acid sequence of SEQ ID NO:45, a CDR2 comprising the amino acid sequence of SEQ ID NO: 46, and a CDR3 comprising the amino acid sequence of SEQ ID NO:47 or 64, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40, optionally wherein residue 9 is valine according to SEQ ID NO:40. In some aspects, the VHH2 comprises a CDR1 comprising the amino acid sequence of SEQ ID NO:45, a CDR2 comprising the amino acid sequence of SEQ ID NO:46, and a CDR3 comprising the amino acid sequence of SEQ ID NO:47 or 64, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, the VHH2 of the IL13 co-binder comprises a CDR1 comprising the amino acid sequence of SEQ ID NO:48, a CDR2 comprising the amino acid sequence of SEQ ID NO: 49, and a CDR3 comprising the amino acid sequence of SEQ ID NO:50 or 65, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40, optionally wherein residue 9 is valine according to SEQ ID NO:40. In some aspects, the VHH2 comprises a CDR1 comprising the amino acid sequence of SEQ ID NO:48, a CDR2 comprising the amino acid sequence of SEQ ID NO:49, and a CDR3 comprising the amino acid sequence of SEQ ID NO:50 or 65, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, the VHH1 of the IL31 co-binder comprises a CDR1 comprising the amino acid sequence of SEQ ID NO:5, a CDR2 comprising the amino acid sequence of SEQ ID NO: 6, and a CDR3 comprising the amino acid sequence of SEQ ID NO:7, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3. In some aspects, the VHH1 comprises a CDR1 comprising the amino acid sequence of SEQ ID NO:5, a CDR2 comprising the amino acid sequence of SEQ ID NO:6, and a CDR3 comprising the amino acid sequence of SEQ ID NO:7, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4.

In some aspects, the VHH1 of the IL31 co-binder comprises a CDR1 comprising the amino acid sequence of SEQ ID NO:8, a CDR2 comprising the amino acid sequence of SEQ ID NO: 9, and a CDR3 comprising the amino acid sequence of SEQ ID NO: 10, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3. In some aspects, the VHH1 comprises a CDR1 comprising the amino acid sequence of SEQ ID NO:8, a CDR2 comprising the amino acid sequence of SEQ ID NO:9, and a CDR3 comprising the amino acid sequence of SEQ ID NO: 10, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4.

In some aspects, the VHH1 of the IL31 co-binder comprises a CDR1 comprising the amino acid sequence of SEQ ID NO:11, a CDR2 comprising the amino acid sequence of SEQ ID NO: 12, and a CDR3 comprising the amino acid sequence of SEQ ID NO:13, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3. In some aspects, the VHH1 comprises a CDR1 comprising the amino acid sequence of SEQ ID NO: 11, a CDR2 comprising the amino acid sequence of SEQ ID NO: 12, and a CDR3 comprising the amino acid sequence of SEQ ID NO: 13, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4.

In some aspects, the VHH2 of the IL31 co-binder comprises a CDR1 comprising the amino acid sequence of SEQ ID NO:16, a CDR2 comprising the amino acid sequence of SEQ ID NO: 17, and a CDR3 comprising the amino acid sequence of SEQ ID NO:18, wherein the VHH2 comprises an amino acid sequence at least 85%, at least 90%, at least 95%, at least 96%, at least 97%, at least 98%, or at least 99% identical to the amino acid sequence of SEQ ID NO: 14 or amino acid residues 2-119 of SEQ ID NO:14, optionally wherein residue 10 is valine according to SEQ ID NO: 14. In some aspects, the VHH2 comprises a CDR1 comprising the amino acid sequence of SEQ ID NO: 16, a CDR2 comprising the amino acid sequence of SEQ ID NO:17, and a CDR3 comprising the amino acid sequence of SEQ ID NO: 18, wherein the VHH2 comprises an amino acid sequence at least 85%, at least 90%, at least 95%, at least 96%, at least 97%, at least 98%, or at least 99% identical to the amino acid sequence of SEQ ID NO:15 or amino acid residues 2-119 of SEQ ID NO: 15, optionally wherein residue 10 is valine according to SEQ ID NO:15.

In some aspects, the VHH2 of the IL31 co-binder comprises a CDR1 comprising the amino acid sequence of SEQ ID NO: 19, a CDR2 comprising the amino acid sequence of SEQ ID NO: 20, and a CDR3 comprising the amino acid sequence of SEQ ID NO:21, wherein the VHH2 comprises an amino acid sequence at least 85%, at least 90%, at least 95%, at least 96%, at least 97%, at least 98%, or at least 99% identical to the amino acid sequence of SEQ ID NO: 14 or amino acid residues 2-119 of SEQ ID NO:14, optionally wherein residue 10 is valine according to SEQ ID NO:14. In some aspects, the VHH2 comprises a CDR1 comprising the amino acid sequence of SEQ ID NO: 19, a CDR2 comprising the amino acid sequence of SEQ ID NO:20, and a CDR3 comprising the amino acid sequence of SEQ ID NO:21, wherein the VHH2 comprises an amino acid sequence at least 85%, at least 90%, at least 95%, at least 96%, at least 97%, at least 98%, or at least 99% identical to the amino acid sequence of SEQ ID NO: 15 or amino acid residues 2-119 of SEQ ID NO:15, optionally wherein residue 10 is valine according to SEQ ID NO:15.

In some aspects, the VHH2 of the IL31 co-binder comprises a CDR1 comprising the amino acid sequence of SEQ ID NO:22, a CDR2 comprising the amino acid sequence of SEQ ID NO: 23, and a CDR3 comprising the amino acid sequence of SEQ ID NO:24, wherein the VHH2 comprises an amino acid sequence at least 85%, at least 90%, at least 95%, at least 96%, at least 97%, at least 98%, or at least 99% identical to the amino acid sequence of SEQ ID NO:14 or amino acid residues 2-119 of SEQ ID NO:14, optionally wherein residue 10 is valine according to SEQ ID NO:14. In some aspects, the VHH2 comprises a CDR1 comprising the amino acid sequence of SEQ ID NO:22, a CDR2 comprising the amino acid sequence of SEQ ID NO:23, and a CDR3 comprising the amino acid sequence of SEQ ID NO:24, wherein the VHH2 comprises an amino acid sequence at least 85%, at least 90%, at least 95%, at least 96%, at least 97%, at least 98%, or at least 99% identical to the amino acid sequence of SEQ ID NO:15 or amino acid residues 2-119 of SEQ ID NO:15, optionally wherein residue 10 is valine according to SEQ ID NO:15.

In some aspects, the VHH1 of the IL13 co-binder comprises the amino acid sequence of SEQ ID NO:29 or amino acid residues 2-115 of SEQ ID NO:29. In some aspects, the VHH1 of the IL 13 co-binder comprises the amino acid sequence of SEQ ID NO:30 or amino acid residues 2-115 of SEQ ID NO:30.

In some aspects, the VHH2 of the IL13 co-binder comprises the amino acid sequence of SEQ ID NO:40 or amino acid residues 2-127 of SEQ ID NO:40, optionally wherein residue 9 is valine according to SEQ ID NO:40. In some aspects, the VHH2 of the IL13 co-binder comprises the amino acid sequence of SEQ ID NO:41 or amino acid residues 2-127 of SEQ ID NO:41.

In some aspects, the VHH1 of the IL31 co-binder comprises the amino acid sequence of SEQ ID NO:3 or amino acid residues 2-118 of SEQ ID NO:3. In some aspects, the VHH1 of the IL31 co-binder comprises the amino acid sequence of SEQ ID NO:4 or amino acid residues 2-118 of SEQ ID NO:4.

In some aspects, the VHH2 of the IL31 co-binder comprises the amino acid sequence of SEQ ID NO: 14 or amino acid residues 2-119 of SEQ ID NO:14, optionally wherein residue 10 is valine according to SEQ ID NO:14. In some aspects, the VHH2 of the IL31 co-binder comprises the amino acid sequence of SEQ ID NO:15 or amino acid residues 2-119 of SEQ ID NO:15, optionally wherein residue 10 is valine according to SEQ ID NO:15.

In some aspects, the VHH1 of the IL13 co-binder comprises a CDR1 comprising the amino acid sequence of SEQ ID NO:31, a CDR2 comprising the amino acid sequence of SEQ ID NO: 32, and a CDR3 comprising the amino acid sequence of SEQ ID NO:33 or 60, wherein the VHH1 comprises an amino acid sequence at least 85%, at least 90%, at least 95%, at least 96%, at least 97%, at least 98%, or at least 99% identical to the amino acid sequence of SEQ ID NO:29 or amino acid residues 2-115 of SEQ ID NO:29; and the VHH2 of the IL 13 co-binder comprises a CDR1 comprising the amino acid sequence of SEQ ID NO:42, a CDR2 comprising the amino acid sequence of SEQ ID NO:43, and a CDR3 comprising the amino acid sequence of SEQ ID NO: 44 or 63, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40, optionally wherein residue 9 is valine according to SEQ ID NO:40.

In some aspects, the VHH1 of the IL13 co-binder comprises a CDR1 comprising the amino acid sequence of SEQ ID NO:34, a CDR2 comprising the amino acid sequence of SEQ ID NO: 35, and a CDR3 comprising the amino acid sequence of SEQ ID NO:36 or 61, wherein the VHH1 comprises an amino acid sequence at least 85%, at least 90%, at least 95%, at least 96%, at least 97%, at least 98%, or at least 99% identical to the amino acid sequence of SEQ ID NO:29 or amino acid residues 2-115 of SEQ ID NO:29; and the VHH2 of the IL 13 co-binder comprises a CDR1 comprising the amino acid sequence of SEQ ID NO:45, a CDR2 comprising the amino acid sequence of SEQ ID NO:46, and a CDR3 comprising the amino acid sequence of SEQ ID NO: 47 or 64, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40, optionally wherein residue 9 is valine according to SEQ ID NO:40.

In some aspects, the VHH1 of the IL13 co-binder comprises a CDR1 comprising the amino acid sequence of SEQ ID NO:37, a CDR2 comprising the amino acid sequence of SEQ ID NO: 38, and a CDR3 comprising the amino acid sequence of SEQ ID NO:39 or 62, wherein the VHH1 comprises an amino acid sequence at least 85%, at least 90%, at least 95%, at least 96%, at least 97%, at least 98%, or at least 99% identical to the amino acid sequence of SEQ ID NO:29 or amino acid residues 2-115 of SEQ ID NO:29; and the VHH2 of the IL13 co-binder comprises a CDR1 comprising the amino acid sequence of SEQ ID NO:48, a CDR2 comprising the amino acid sequence of SEQ ID NO:49, and a CDR3 comprising the amino acid sequence of SEQ ID NO: 50 or 65, wherein the VHH2 comprises an amino acid sequence at least 85%, at least 90%, at least 95%, at least 96%, at least 97%, at least 98%, or at least 99% identical to the amino acid sequence of SEQ ID NO:40 or amino acid residues 2-127 of SEQ ID NO:40.

In some aspects, the VHH1 of the IL13 co-binder comprises a CDR1 comprising the amino acid sequence of SEQ ID NO:31, a CDR2 comprising the amino acid sequence of SEQ ID NO: 32, and a CDR3 comprising the amino acid sequence of SEQ ID NO:33 or 60, wherein the VHH1 of the IL 13 co-binder comprises an amino acid sequence at least 85%, at least 90%, at least 95%, at least 96%, at least 97%, at least 98%, or at least 99% identical to the amino acid sequence of SEQ ID NO:30 or amino acid residues 2-115 of SEQ ID NO:30 and the VHH2 of the IL 13 co-binder comprises a CDR1 comprising the amino acid sequence of SEQ ID NO:42, a CDR2 comprising the amino acid sequence of SEQ ID NO:43, and a CDR3 comprising the amino acid sequence of SEQ ID NO:44 or 63, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, the VHH1 of the IL13 co-binder comprises a CDR1 comprising the amino acid sequence of SEQ ID NO:34, a CDR2 comprising the amino acid sequence of SEQ ID NO: 35, and a CDR3 comprising the amino acid sequence of SEQ ID NO:36 or 61, wherein the VHH1 comprises an amino acid sequence at least 85%, at least 90%, at least 95%, at least 96%, at least 97%, at least 98%, or at least 99% identical to the amino acid sequence of SEQ ID NO:30 or amino acid residues 2-115 of SEQ ID NO:30; and the VHH2 of the IL 13 co-binder comprises a CDR1 comprising the amino acid sequence of SEQ ID NO:45, a CDR2 comprising the amino acid sequence of SEQ ID NO:46, and a CDR3 comprising the amino acid sequence of SEQ ID NO: 47 or 64, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, the VHH1 of the IL13 co-binder comprises a CDR1 comprising the amino acid sequence of SEQ ID NO:37, a CDR2 comprising the amino acid sequence of SEQ ID NO: 38, and a CDR3 comprising the amino acid sequence of SEQ ID NO:39 or 62, wherein the VHH1 comprises an amino acid sequence at least 85%, at least 90%, at least 95%, at least 96%, at least 97%, at least 98%, or at least 99% identical to the amino acid sequence of SEQ ID NO:30 or amino acid residues 2-115 of SEQ ID NO:30; and the VHH2 of the IL 13 co-binder comprises a CDR1 comprising the amino acid sequence of SEQ ID NO:48, a CDR2 comprising the amino acid sequence of SEQ ID NO:49, and a CDR3 comprising the amino acid sequence of SEQ ID NO: 50 or 65, wherein the VHH2 comprises an amino acid sequence at least 85%, at least 90%, at least 95%, at least 96%, at least 97%, at least 98%, or at least 99% identical to the amino acid sequence of SEQ ID NO:41 or amino acid residues 2-127 of SEQ ID NO:41.

In some aspects, provided herein as a part of a bispecific polypeptide that binds IL13 and IL31 is a portion of this bispecific polypeptide that binds IL 13, wherein the VHH1, e.g., VHH, of the IL 13 co-binder comprises the amino acid sequence of SEQ ID NO:30 or amino acid residues 2-115 of SEQ ID NO:30 and the VHH2, e.g., VHH, of the IL 13 co-binder comprises the amino acid sequence of SEQ ID NO:41 or amino acid residues 2-127 of SEQ ID NO:41.

In some aspects, the VHH1 of the IL31 co-binder comprises a CDR1 comprising the amino acid sequence of SEQ ID NO:5, a CDR2 comprising the amino acid sequence of SEQ ID NO: 6, and a CDR3 comprising the amino acid sequence of SEQ ID NO:7, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3; and the VHH2 of the IL31 co-binder comprises a CDR 1 comprising the amino acid sequence of SEQ ID NO: 16, a CDR2 comprising the amino acid sequence of SEQ ID NO: 17, and a CDR3 comprising the amino acid sequence of SEQ ID NO: 18, wherein the VHH2 of the IL31 co-binder comprises an amino acid sequence at least 85%, at least 90%, at least 95%, at least 96%, at least 97%, at least 98%, or at least 99% identical to the amino acid sequence of SEQ ID NO: 14 or amino acid residues 2-119 of SEQ ID NO: 14, optionally wherein residue 10 is valine according to SEQ ID NO: 14.

In some aspects, the VHH1 of the IL31 co-binder comprises a CDR1 comprising the amino acid sequence of SEQ ID NO:8, a CDR2 comprising the amino acid sequence of SEQ ID NO: 9, and a CDR3 comprising the amino acid sequence of SEQ ID NO:10, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3; and the VHH2 of the IL31 co-binder comprises a CDR1 comprising the amino acid sequence of SEQ ID NO: 19, a CDR2 comprising the amino acid sequence of SEQ ID NO:20, and a CDR3 comprising the amino acid sequence of SEQ ID NO: 21, wherein the VHH2 comprises an amino acid sequence at least 85%, at least 90%, at least 95%, at least 96%, at least 97%, at least 98%, or at least 99% identical to the amino acid sequence of SEQ ID NO:14 or amino acid residues 2-119 of SEQ ID NO:14, optionally wherein residue 10 is valine according to SEQ ID NO: 14.

In some aspects, the VHH1 of the IL31 co-binder comprises a CDR1 comprising the amino acid sequence of SEQ ID NO:11, a CDR2 comprising the amino acid sequence of SEQ ID NO: 12, and a CDR3 comprising the amino acid sequence of SEQ ID NO: 13, wherein the VHH1 comprises an amino acid sequence at least 85%, at least 90%, at least 95%, at least 96%, at least 97%, at least 98%, or at least 99% identical to the amino acid sequence of SEQ ID NO:3 or amino acid residues 2-118 of SEQ ID NO:3; and the VHH2 of the IL31 co-binder comprises a CDR1 comprising the amino acid sequence of SEQ ID NO:22, a CDR2 comprising the amino acid sequence of SEQ ID NO:23, and a CDR3 comprising the amino acid sequence of SEQ ID NO: 24, wherein the VHH2 of the IL31 co-binder comprises an amino acid sequence at least 85%, at least 90%, at least 95%, at least 96%, at least 97%, at least 98%, or at least 99% identical to the amino acid sequence of SEQ ID NO: 14 or amino acid residues 2-119 of SEQ ID NO:14, optionally wherein residue 10 is valine according to SEQ ID NO: 14.

In some aspects, the VHH1 of the IL31 co-binder comprises a CDR1 comprising the amino acid sequence of SEQ ID NO:5, a CDR2 comprising the amino acid sequence of SEQ ID NO: 6, and a CDR3 comprising the amino acid sequence of SEQ ID NO:7, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4; and the VHH2 of the IL31 co-binder comprises a CDR1 comprising the amino acid sequence of SEQ ID NO:16, a CDR2 comprising the amino acid sequence of SEQ ID NO: 17, and a CDR3 comprising the amino acid sequence of SEQ ID NO: 18, wherein the VHH2 comprises an amino acid sequence at least 85%, at least 90%, at least 95%, at least 96%, at least 97%, at least 98%, or at least 99% identical to the amino acid sequence of SEQ ID NO: 15 or amino acid residues 2-119 of SEQ ID NO:15, optionally wherein residue 10 is valine according to SEQ ID NO:15.

In some aspects, the VHH1 of the IL31 co-binder comprises a CDR1 comprising the amino acid sequence of SEQ ID NO:8, a CDR2 comprising the amino acid sequence of SEQ ID NO: 9, and a CDR3 comprising the amino acid sequence of SEQ ID NO: 10, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4; and the VHH2 of the IL31 co-binder comprises a CDR 1 comprising the amino acid sequence of SEQ ID NO: 19, a CDR2 comprising the amino acid sequence of SEQ ID NO:20, and a CDR3 comprising the amino acid sequence of SEQ ID NO: 21, wherein the VHH2 comprises an amino acid sequence at least 85%, at least 90%, at least 95%, at least 96%, at least 97%, at least 98%, or at least 99% identical to the amino acid sequence of SEQ ID NO:15 or amino acid residues 2-119 of SEQ ID NO: 15, optionally wherein residue 10 is valine according to SEQ ID NO:15.

In some aspects, the VHH1 of the IL31 co-binder comprises a CDR1 comprising the amino acid sequence of SEQ ID NO: 11, a CDR2 comprising the amino acid sequence of SEQ ID NO: 12, and a CDR3 comprising the amino acid sequence of SEQ ID NO:13, wherein the VHH1 comprises an amino acid sequence at least 85%, at least 90%, at least 95%, at least 96%, at least 97%, at least 98%, or at least 99% identical to the amino acid sequence of SEQ ID NO:4 or amino acid residues 2-118 of SEQ ID NO:4; and the VHH2 of the IL31 co-binder comprises a CDR1 comprising the amino acid sequence of SEQ ID NO:22, a CDR2 comprising the amino acid sequence of SEQ ID NO:23, and a CDR3 comprising the amino acid sequence of SEQ ID NO: 24, wherein the VHH2 comprises an amino acid sequence at least 85%, at least 90%, at least 95%, at least 96%, at least 97%, at least 98%, or at least 99% identical to the amino acid sequence of SEQ ID NO: 15 or amino acid residues 2-119 of SEQ ID NO:15, optionally wherein residue 10 is valine according to SEQ ID NO:15.

In some aspects, provided herein as a part of a bispecific polypeptide that binds IL 13 and IL31 is a portion of this bispecific polypeptide that binds IL31, wherein the VHH1 of the IL31 co-binder comprises the amino acid sequence of SEQ ID NO:4 or amino acid residues 2-118 of SEQ ID NO:4 and the VHH2 of the IL31 co-binder comprises the amino acid sequence of SEQ ID NO: 15 or amino acid residues 2-119 of SEQ ID NO:15, optionally wherein residue 10 is valine according to SEQ ID NO:15.

In some aspects, the bispecific polypeptide that binds IL 13 and IL31 provided herein comprises one or more linker. In some aspects, the one or more linker is an amino acid linker. In some aspects, the one or more amino acid linker connects two or more single binders or VHHs. In some aspects, the VHH1 of the IL31 co-binder is connected to the VHH2 of the IL31 co-binder by a first linker. In some aspects, the VHH1, e.g., VHH3, of the IL 13 co-binder is connected to the VHH2, e.g., VHH4, of the IL 13 co-binder by a second linker. In some aspects, the first linker and the second linker are the same. In some aspects, the first linker and/or second linker comprise 33-43 amino acids in length. In some aspects, the first linker and second linker comprise 33-43 amino acids in length. In some aspects, the first linker and/or second linker comprise 37-39 amino acids in length. In some aspects, the first linker and second linker comprise 37-39 amino acids in length. In some aspects, the first linker and second linker comprise 38 amino acids in length. In some aspects, the VHH1, e.g., VHH1, and VHH2, e.g., VHH2, of the IL31 co-binder are joined by a first linker comprising the amino acid sequence of SEQ ID NO:66. In some aspects, the VHH1, e.g., VHH3, and VHH2, e.g., VHH4, of the IL 13 co-binderare joined by a second linker comprising the amino acid sequence of SEQ ID NO:67. In some aspects, the bispecific polypeptide binding IL31 and IL 13 may include a third linker, e.g., joining or connecting the C-terminus of an Fc region to the N-terminus of the second co-binder, e.g., the IL 13 co-binder. In some aspects, the third linker comprises an amino acid sequence of SEQ ID NO:68. In some aspects, the co-binder that binds IL31 has the structure: [first IL31 VHH]-first linker-[second IL31 VHH] or [VHH1]-first linker-[VHH2]. In some aspects, the co-binder that binds IL 13 has the structure: [first IL 13 VHH]-second linker-[second IL 13 VHH] or [VHH3]-second linker-[VHH4].

In some aspects, the one or more amino acid linker connects two or more polypeptides together. In some aspects, the co-binder that binds IL 13 is connected to the co-binder that binds IL31 by a third linker. In some aspects, the first linker, the second linker, and/or the third linker are the same. In some aspects, the first linker, the second linker, and/or the third linker are different. In some aspects, the bispecific polypeptide that binds IL13 and IL31 has a “Tandem Format” structure: [IL 13 co-binder]-linker-[IL31 co-binder]-Fc region, or [IL31 co-binder]-linker-[IL 13 co-binder]-Fc region. In some aspects, the bispecific polypeptide that binds IL 13 and IL31 has a “Morrison Format” structure: [IL13 co-binder]-Fc region-linker-[IL31 co-binder], or [IL31 co-binder]-Fc region-linker-[IL 13 co-binder]. In some aspects, for example, a bispecific polypeptide that binds IL31 and IL 13 has the following “Morrison Format”: [IL31 co-binder]-[Fc]-[linker]-[IL 13 co-binder]. In some aspects, a bispecific polypeptide that binds IL31 and IL 13 has the following “Morrison Format”: (VHH1-first linker-VHH2)-Fc-third linker-(VHH3-second linker-VHH4), wherein the IL31 co-binder is (VHH1-first linker-VHH2), and the IL13 co-binder is (VHH3-second linker-VHH4). If the binders or single binders are VHHs, then the bispecific Morrison Format in this example can have the following structure: (VHH1-first linker-VHH2)-Fc-third linker-(VHH3-second linker-VHH4), wherein the IL31 co-binder is (VHH1-first linker-VHH2), and the IL13 co-binder is (VHH3-second linker-VHH4). In some aspects, for example, a bispecific polypeptide that binds IL31 and IL 13 has the following “Morrison Format”: [IL13 co-binder]-[Fc]-[linker]-[IL31 co-binder]. In some aspects, a bispecific polypeptide that binds IL31 and IL13 has the following “Morrison Format”: (VHH1-first linker-VHH2)-Fc-third linker-(VHH3-second linker-VHH4), wherein the IL 13 binding polpeptide is (VHH1-first linker-VHH2), and the IL31 co-binder is (VHH3-second linker-VHH4). If the binders or single binders are VHHs, then the bispecific Morrison Format in this example can have the following structure: (VHH1-first linker-VHH2)-Fc-third linker-(VHH3-second linker-VHH4), wherein the IL13 co-binder is (VHH1-first linker-VHH2), and the IL31 co-binder is (VHH3-second linker-VHH4). In some aspects, for example, a bispecific polypeptide that binds IL31 and IL 13 has the following “Tandem Format”: [IL31 co-binder]-[linker]-[IL 13 co-binder]-Fc. In some aspects, a bispecific polypeptide that binds IL31 and IL13 has the following “Tandem Format”: (VHH1-first linker-VHH2)-third linker-(VHH3-second linker-VHH4)-Fc, wherein the IL31 co-binder is (VHH1-first linker-VHH2), and the IL13 co-binder is (VHH3-second linker-VHH4). If the binders or single binders are VHHs, then the bispecific Tandem Format in this example can have the following structure: (VHH1-first linker-VHH2)-third linker-(VHH3-second linker-VHH4)-Fc, wherein the IL31 co-binder is (VHH1-first linker-VHH2), and the IL 13 co-binder is (VHH3-second linker-VHH4). In some aspects, for example, a bispecific polypeptide that binds IL31 and IL 13 has the following “Tandem Format”: [IL 13 co-binder]-[linker]-[IL31 co-binder]-Fc. In some aspects, a bispecific polypeptide that binds IL31 and IL 13 has the following "Tandem Format": (VHH1-first linker-VHH2)-third linker-(VHH3-second linker-VHH4)-Fc, wherein the IL 13 co-binder is (VHH1-first linker-VHH2), and the IL31 co-binder is (VHH3-second linker-VHH4). If the binders or single binders are VHHs, then the bispecific Tandem Format in this example can have the following structure: (VHH1-first linker-VHH2)-third linker-(VHH3-second linker-VHH4)-Fc, wherein the IL 13 co-binder is (VHH1-first linker-VHH2), and the IL31 co-binder is (VHH3-second linker-VHH4).

In some aspects, any one of the linkers is from 5 to 50 amino acids long. In some aspects, any one of the linkers is between about 1-50, 8-40, 12-37, or 16-30 amino acids in length. In some aspects, any one of the linkers is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In some aspects, any one of the linkers is between about 8 to 40 amino acids in length. In some aspects, any one of the linkers is between about 12 to 38 amino acids in length. In some aspect, any one of the linkers is a flexible linker. In some aspects, any one of the linkers is a rigid linker. In some aspects, any one of the linkers is a charged linker. In some aspects, any one of the linkers comprises glycine and/or serine residues.

In some aspects, the co-binder that binds IL13 comprises the CDR1, CDR2, and CDR3 of the VHH1 of the IL13 co-binder and the CDR1, CDR2, and CDR3 of the VHH2 of the IL 13 co-binder as disclosed herein, and comprises an amino acid sequence at least 85% identical to the amino acid sequence of SEQ ID NO:51 or amino acid residues 2-280 of SEQ ID NO:51, optionally wherein residue 162 is valine according to SEQ ID NO:51. In some aspects, the co-binder that binds IL 13 comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 90% identical to the amino acid sequence of SEQ ID NO: 51 or amino acid residues 2-280 of SEQ ID NO:51, optionally wherein residue 162 is valine according to SEQ ID NO:51. In some aspects, the IL 13 co-binder comprises the CDR1, CDR2, and CDR3 of the VHH1 of the IL 13 co-binder and the CDR1, CDR2, and CDR3 of the VHH2 of the IL 13 co-binder as disclosed herein, and comprises an amino acid sequence at least 95% identical to the amino acid sequence of SEQ ID NO:51 or amino acid residues 2-280 of SEQ ID NO:51, optionally wherein residue 162 is valine according to SEQ ID NO:51. In some aspects, the IL13 co-binder comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 96% identical to the amino acid sequence of SEQ ID NO: 51 or amino acid residues 2-280 of SEQ ID NO:51, optionally wherein residue 162 is valine according to SEQ ID NO:51. In some aspects, the IL 13 co-binder comprises the CDR1, CDR2, and CDR3 of the VHH1 of the IL 13 co-binder and the CDR1, CDR2, and CDR3 of the VHH2 of the IL 13 co-binder as disclosed herein, and comprises an amino acid sequence at least 97% identical to the amino acid sequence of SEQ ID NO:51 or amino acid residues 2-280 of SEQ ID NO:51, optionally wherein residue 162 is valine according to SEQ ID NO:51. In some aspects, the co-binder that binds IL 13 comprises the CDR1, CDR2, and CDR3 of the VHH1 of the IL 13 co-binder and the CDR1, CDR2, and CDR3 of the VHH2 of the IL 13 co-binder as disclosed herein, and comprises an amino acid sequence at least 98% identical to the amino acid sequence of SEQ ID NO:51 or amino acid residues 2-280 of SEQ ID NO:51, optionally wherein residue 162 is valine according to SEQ ID NO:51. In some aspects, the polypeptide that binds IL13 comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 99% identical to the amino acid sequence of SEQ ID NO:51 or amino acid residues 2-280 of SEQ ID NO:51, optionally wherein residue 162 is valine according to SEQ ID NO:51.

In some aspects, the co-binder that binds IL13 comprises the CDR1, CDR2, and CDR3 of the VHH1 of the IL13 co-binder and the CDR1, CDR2, and CDR3 of the VHH2 of the IL13 co-binder as disclosed herein, and comprises an amino acid sequence at least 85% identical to the amino acid sequence of SEQ ID NO:52 or amino acid residues 2-280 of SEQ ID NO:52. In some aspects, the polypeptide that binds IL13 comprises the CDR1, CDR2, and CDR3 of the VHH1 of the IL 13 co-binder and the CDR1, CDR2, and CDR3 of the VHH2 of the IL 13 co-binder as disclosed herein, and comprises an amino acid sequence at least 90% identical to the amino acid sequence of SEQ ID NO:52 or amino acid residues 2-280 of SEQ ID NO:52. In some aspects, the polypeptide that binds IL13 comprises the CDR1, CDR2, and CDR3 of the VHH1 of the IL13 co-binder and the CDR1, CDR2, and CDR3 of the VHH2 of the IL13 co-binder as disclosed herein, and comprises an amino acid sequence at least 95% identical to the amino acid sequence of SEQ ID NO:52 or amino acid residues 2-280 of SEQ ID NO:52. In some aspects, the co-binder that binds IL 13 comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 96% identical to the amino acid sequence of SEQ ID NO: 52 or amino acid residues 2-280 of SEQ ID NO:52. In some aspects, the polypeptide that binds IL 13 comprises the CDR1, CDR2, and CDR3 of the VHH1 of the IL13 co-binder and the CDR1, CDR2, and CDR3 of the VHH2 of the IL13 co-binder as disclosed herein, and comprises an amino acid sequence at least 97% identical to the amino acid sequence of SEQ ID NO:52 or amino acid residues 2-280 of SEQ ID NO:52. In some aspects, the polypeptide that binds IL 13 comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 98% identical to the amino acid sequence of SEQ ID NO:52 or amino acid residues 2-280 of SEQ ID NO:52. In some aspects, the polypeptide that binds IL13 comprises the CDR1, CDR2, and CDR3 of the VHH1 of the IL 13 co-binder and the CDR1, CDR2, and CDR3 of the VHH2 of the IL13 co-binder as disclosed herein, and comprises an amino acid sequence at least 99% identical to the amino acid sequence of SEQ ID NO:52 or amino acid residues 2-280 of SEQ ID NO:52.

In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 85% identical to the amino acid sequence of SEQ ID NO:25 or amino acid residues 2-275 of SEQ ID NO:25, optionally wherein residue 166 is valine according to SEQ ID NO:25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 90% identical to the amino acid sequence of SEQ ID NO: 25 or amino acid residues 2-275 of SEQ ID NO:25, optionally wherein residue 166 is valine according to SEQ ID NO:25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 95% identical to the amino acid sequence of SEQ ID NO:25 or amino acid residues 2-275 of SEQ ID NO:25, optionally wherein residue 166 is valine according to SEQ ID NO:25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 96% identical to the amino acid sequence of SEQ ID NO:25 or amino acid residues 2-275 of SEQ ID NO:25, optionally wherein residue 166 is valine according to SEQ ID NO:25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder disclosed herein, and comprises an amino acid sequence at least 97% identical to the amino acid sequence of SEQ ID NO:25 or amino acid residues 2-275 of SEQ ID NO:25, optionally wherein residue 166 is valine according to SEQ ID NO: 25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 98% identical to the amino acid sequence of SEQ ID NO:25 or amino acid residues 2-275 of SEQ ID NO:25, optionally wherein residue 166 is valine according to SEQ ID NO:25. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 99% identical to the amino acid sequence of SEQ ID NO: 25 or amino acid residues 2-275 of SEQ ID NO:25, optionally wherein residue 166 is valine according to SEQ ID NO:25.

In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 85% identical to the amino acid sequence of SEQ ID NO:26 or amino acid residues 2-275 of SEQ ID NO:26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 90% identical to the amino acid sequence of SEQ ID NO: 26 or amino acid residues 2-275 of SEQ ID NO:26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 95% identical to the amino acid sequence of SEQ ID NO:26 or amino acid residues 2-275 of SEQ ID NO:26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 96% identical to the amino acid sequence of SEQ ID NO:26 or amino acid residues 2-275 of SEQ ID NO:26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 97% identical to the amino acid sequence of SEQ ID NO:26 or amino acid residues 2-275 of SEQ ID NO:26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 98% identical to the amino acid sequence of SEQ ID NO:26 or amino acid residues 2-275 of SEQ ID NO: 26, optionally wherein residue 166 is valine according to SEQ ID NO:26. In some aspects, the co-binder that binds IL31 comprises the CDR1, CDR2, and CDR3 of the VHH1 of the IL31 co-binder and the CDR1, CDR2, and CDR3 of the VHH2 of the IL31 co-binder as disclosed herein, and comprises an amino acid sequence at least 99% identical to the amino acid sequence of SEQ ID NO:26 or amino acid residues 2-275 of SEQ ID NO:26, optionally wherein residue 166 is valine according to SEQ ID NO:26.

In some aspects, the co-binder that binds IL13 comprises the amino acid sequence of SEQ ID NO:51 or 52 or amino acid residues 2-280 of SEQ ID NO:51 or 52, optionally wherein residue 162 is valine according to SEQ ID NO:51 or 52. In some aspects, the co-binder that binds IL13 comprises the amino acid sequence of SEQ ID NO:51 or amino acid residues 2-280 of SEQ ID NO: 51, optionally wherein residue 162 is valine according to SEQ ID NO:51. In some aspects, the co-binder that binds IL 13 comprises the amino acid sequence of SEQ ID NO:52 or amino acid residues 2-280 of SEQ ID NO:52.

In some aspects, the co-binder that binds IL31 comprises the amino acid sequence of SEQ ID NO:25 or 26, or amino acid residues 2-275 of SEQ ID NO:25 or 26, optionally wherein residue 166 is valine according to SEQ ID NO:25 or 26. In some aspects, the co-binder that binds IL31 comprises the amino acid sequence of SEQ ID NO:25 or amino acid residues 2-275 of SEQ ID NO: 25, optionally wherein residue 166 is valine according to SEQ ID NO:25. In some aspects, the co-binder that binds IL31 comprises the amino acid sequence of SEQ ID NO:26 or amino acid residues 2-275 of SEQ ID NO:26, optionally wherein residue 166 is valine according to SEQ ID NO:26.

In some aspects, provided herein is a bispecific polypeptide that binds IL13 and IL31 comprising a Fc region. In some aspects, the bispecific polypeptide that binds IL 13 and IL31 comprises an IgG1, IgG2, IgG3, or IgG4 Fc region. In some aspects, the Fc region is a human Fc region. In some aspects, the bispecific polypeptide that binds IL 13 and IL31 comprises a human IgG1, IgG2, IgG3, or IgG4 Fc region. In some aspects, the bispecific polypeptide that binds IL 13 and IL31 comprises an Fc region with a modified effector function. In some aspects, the bispecific polypeptide that binds IL13 and IL31 comprises an effector null Fc region. In some aspects, the Fc region comprises a full or partial hinge region. In some aspects, the Fc region comprises a partial hinge region. In some aspects, the partial hinge region comprises between about 1 to about 30, about 5 to about 25, about 10 to about 20, or about 12 to about 16 amino acid residues. In some aspects, the partial hinge region comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues. In some aspects, the partial hinge region comprises 15 amino acid residues. In some aspects, the hinge region is 15 amino acids in length. In some aspects, the partial hinge region comprises a cysteine (C) to serine(S) mutation at position 220 according to EU numbering (C220S). In some aspects, the Fc region includes one or more of the following CH2 region mutations: L234A, L235A, M252Y, S254T, T256E, L309Y, and Q311M as determined by EU numbering. In some aspects, the Fc region includes one or more of the following CH3 mutations: M428L and N434S as determined by EU numbering. In some aspects, the Fc region comprises one or more of the following mutations or substitutions (EU numbering): C220S, L234A, L235A, M252Y, S254T, T256E, L309Y, Q311M, M428L, N434S or any combination thereof. In some aspects, the Fc region comprises one or more of the following mutations or substitutions according to EU numbering: C220S, L234A, L235A, M252Y, S254T, and T256E. In some aspects, the Fc region comprises the following mutations or substitutions according to EU numbering: C220S, L234A, L235A, M252Y, S254T, and T256E. In some aspects, the one or more substitutions comprise C220S, L234A, L235A, M428L and N434S according to the EU numbering system. In some aspects, the one or more substitutions comprise C220S, L234A, L235A, L309Y, Q311M and M428L according to the EU numbering system. In some aspects, the Fc region comprises the amino acid sequence of SEQ ID NO:59 or the amino acid residues 1-231 of SEQ ID NO:59.

In some aspects, the bispecific polypeptide that binds IL 13 and IL31 comprises a Fc region, wherein the Fc region comprises an amino acid sequence at least 85%, at least 90%, at least 95%, at least 96%, at least 97%, at least 98%, or at least 99% identical to the amino acid sequence of SEQ ID NO:59 or the amino acid residues 1-231 of SEQ ID NO:59. In some aspects, the bispecific polypeptide that binds IL 13 and IL31 comprises a Fc region, wherein the Fc region comprises an amino acid sequence at least 85% identical to the amino acid sequence of SEQ ID NO: 59 or the amino acid residues 1-231 of SEQ ID NO:59. In some aspects, the bispecific polypeptide that binds IL13 and IL31 comprises a Fc region, wherein the Fc region comprises an amino acid sequence at least 90% identical to the amino acid sequence of SEQ ID NO:59 or the amino acid residues 1-231 of SEQ ID NO:59. In some aspects, the bispecific polypeptide that binds IL13 and IL31 comprises a Fc region, wherein the Fc region comprises an amino acid sequence at least 95% identical to the amino acid sequence of SEQ ID NO:59 or the amino acid residues 1-231 of SEQ ID NO:59. In some aspects, the bispecific polypeptide that binds IL13 and IL31 comprises a Fc region, wherein the Fc region comprises an amino acid sequence at least 96% identical to the amino acid sequence of SEQ ID NO:59 or the amino acid residues 1-231 of SEQ ID NO:59. In some aspects, the bispecific polypeptide that binds IL 13 and IL31 comprises a Fc region, wherein the Fc region comprises an amino acid sequence at least 97% identical to the amino acid sequence of SEQ ID NO:59 or the amino acid residues 1-231 of SEQ ID NO:59. In some aspects, the bispecific polypeptide that binds IL13 and IL31 comprises a Fc region, wherein the Fc region comprises an amino acid sequence at least 98% identical to the amino acid sequence of SEQ ID NO:59 or the amino acid residues 1-231 of SEQ ID NO:59. In some aspects, the bispecific polypeptide that binds IL 13 and IL31 comprises a Fc region, wherein the Fc region comprises an amino acid sequence at least 99% identical to the amino acid sequence of SEQ ID NO: 59 or the amino acid residues 1-231 of SEQ ID NO:59.

In some aspects, the Fc region comprises an amino acid sequence at least 85%, at least 90%, at least 95%, at least 96%, at least 97%, at least 98%, or at least 99% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 85% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 90% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 95% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 96% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 97% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO: 59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 98% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises an amino acid sequence at least 99% identical to the amino acid sequence of SEQ ID NO:59 or the amino acid residues 1-231 of SEQ ID NO:59, and wherein residue 5 is serine, residue 19 is alanine, residue 20 is alanine, residue 37 is tyrosine, residue 39 is threonine, and/or residue 41 is glutamate according to SEQ ID NO:59 or the amino acid residues 1-231 of SEQ ID NO:59, or wherein residue 220 is serine, residue 234 is alanine, residue 235 is alanine, residue 252 is tyrosine, residue 254 is threonine, and/or residue 256 is glutamate according to EU numbering. In some aspects, the Fc region comprises the amino acid sequence of SEQ ID NO:59 or the amino acid residues 1-231 of SEQ ID NO:59.

In some aspects, the bispecific polypeptide that binds IL 13 and IL31 comprises an Fc region comprising the amino acid sequence of SEQ ID NO:59 or the amino acid residues 1-231 of SEQ ID NO:59.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binderthat binds IL 13 comprises an amino acid sequence at least 85%, at least 90%, at least 95%, at least 96%, at least 97%, at least 98%, or at least 99% identical to the amino acid sequence of SEQ ID NO:53 or 54 or the amino acid residues 1-511 of SEQ ID NO:53 or 54.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 85%, at least 90%, at least 95%, at least 96%, at least 97%, at least 98%, or at least 99% identical to the amino acid sequence of SEQ ID NO:53 or the amino acid residues 1-511 of SEQ ID NO:53. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 85% identical to the amino acid sequence of SEQ ID NO:53 or the amino acid residues 1-511 of SEQ ID NO:53. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 90% identical to the amino acid sequence of SEQ ID NO:53 or the amino acid residues 1-511 of SEQ ID NO:53. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 95% identical to the amino acid sequence of SEQ ID NO: 53 or the amino acid residues 1-511 of SEQ ID NO:53. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 96% identical to the amino acid sequence of SEQ ID NO:53 or the amino acid residues 1-511 of SEQ ID NO:53.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 97% identical to the amino acid sequence of SEQ ID NO: 53 or the amino acid residues 1-511 of SEQ ID NO: 53. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 98% identical to the amino acid sequence of SEQ ID NO:53 or the amino acid residues 1-511 of SEQ ID NO: 53. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 99% identical to the amino acid sequence of SEQ ID NO:53 or the amino acid residues 1-511 of SEQ ID NO: 53.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 85%, at least 90%, at least 95%, at least 96%, at least 97%, at least 98%, or at least 99% identical to the amino acid sequence of SEQ ID NO:54 or the amino acid residues 1-511 of SEQ ID NO:54. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 85% identical to the amino acid sequence of SEQ ID NO:54 or the amino acid residues 1-511 of SEQ ID NO:54. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 90% identical to the amino acid sequence of SEQ ID NO:54 or the amino acid residues 1-511 of SEQ ID NO:54. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 95% identical to the amino acid sequence of SEQ ID NO: 54 or the amino acid residues 1-511 of SEQ ID NO:54. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL13 comprises an amino acid sequence at least 96% identical to the amino acid sequence of SEQ ID NO:54 or the amino acid residues 1-511 of SEQ ID NO:54.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 97% identical to the amino acid sequence of SEQ ID NO:54 or the amino acid residues 1-511 of SEQ ID NO: 54. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 98% identical to the amino acid sequence of SEQ ID NO:54 or the amino acid residues 1-511 of SEQ ID NO: 54. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and the co-binder that binds IL 13 comprises an amino acid sequence at least 99% identical to the amino acid sequence of SEQ ID NO:54 or the amino acid residues 1-511 of SEQ ID NO: 54.

In some aspects, the bispecific polypeptide that binds IL 13 and IL31 comprises the CDR1, CDR2, and CDR3 of the VHH1 of the IL31 co-binder and the CDR1, CDR2, and CDR3 of the VHH2 of the IL31 co-binder, as disclosed herein, and the co-binder that binds IL 13 comprises the amino acid sequence of SEQ ID NO:53 or 54 or the amino acid residues 1-511 of SEQ ID NO:53 or 54. In some aspects, the bispecific polypeptide that binds IL13 and IL31 comprises the CDR1, CDR2, and CDR3 of the VHH1 of the IL31 co-binder and the CDR1, CDR2, and CDR3 of the VHH2 of the IL31 co-binder, as disclosed herein, and the co-binder that binds IL13 comprises the amino acid sequence of SEQ ID NO:53 or the amino acid residues 1-511 of SEQ ID NO:53. In some aspects, the bispecific polypeptide that binds IL13 and IL31 comprises the CDR1, CDR2, and CDR3 of the VHH1 of the IL31 co-binder and the CDR1, CDR2, and CDR3 of the VHH2 of the IL31 co-binder, as disclosed herein, and the co-binder that binds IL13 comprises the amino acid sequence of SEQ ID NO:54 or the amino acid residues 1-511 of SEQ ID NO:54.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 85%, at least 90%, at least 95%, at least 96%, at least 97%, at least 98%, or at least 99% identical to the amino acid sequence of any one of SEQ ID NOs: 55-58 or the amino acid residues 1-797 of SEQ ID NO:56 or 58.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 85% identical to the amino acid sequence of SEQ ID NO:55. In some aspects, the bispecific polypeptide that binds IL 13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 90% identical to the amino acid sequence of SEQ ID NO:55. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 95% identical to the amino acid sequence of SEQ ID NO:55. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 96% identical to the amino acid sequence of SEQ ID NO:55. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 97% identical to the amino acid sequence of SEQ ID NO:55. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 98% identical to the amino acid sequence of SEQ ID NO:55. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 99% identical to the amino acid sequence of SEQ ID NO:55.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 85% identical to the amino acid sequence of SEQ ID NO:56 or the amino acid residues 1-797 of SEQ ID NO:56. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 90% identical to the amino acid sequence of SEQ ID NO:56 or the amino acid residues 1-797 of SEQ ID NO:56. In some aspects, the bispecific polypeptide that binds IL13 and IL31 comprises the CDR1, CDR2, and CDR3 of the VHH1 of the IL13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 95% identical to the amino acid sequence of SEQ ID NO:56 or the amino acid residues 1-797 of SEQ ID NO:56. In some aspects, the bispecific polypeptide that binds IL 13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 96% identical to the amino acid sequence of SEQ ID NO:56 or the amino acid residues 1-797 of SEQ ID NO:56. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 97% identical to the amino acid sequence of SEQ ID NO:56 or the amino acid residues 1-797 of SEQ ID NO: 56. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 98% identical to the amino acid sequence of SEQ ID NO:56 or the amino acid residues 1-797 of SEQ ID NO:56. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 99% identical to the amino acid sequence of SEQ ID NO:56 or the amino acid residues 1-797 of SEQ ID NO:56.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 85% identical to the amino acid sequence of SEQ ID NO:57. In some aspects, the bispecific polypeptide that binds IL 13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 90% identical to the amino acid sequence of SEQ ID NO:57. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 95% identical to the amino acid sequence of SEQ ID NO:57. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 96% identical to the amino acid sequence of SEQ ID NO:57. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 97% identical to the amino acid sequence of SEQ ID NO:57. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 98% identical to the amino acid sequence of SEQ ID NO:57. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 99% identical to the amino acid sequence of SEQ ID NO:57.

In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 85% identical to the amino acid sequence of SEQ ID NO:58 or the amino acid residues 1-797 of SEQ ID NO:58. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 90% identical to the amino acid sequence of SEQ ID NO:58 or the amino acid residues 1-797 of SEQ ID NO:58. In some aspects, the bispecific polypeptide that binds IL13 and IL31 comprises the CDR1, CDR2, and CDR3 of the VHH1 of the IL13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 95% identical to the amino acid sequence of SEQ ID NO:58 or the amino acid residues 1-797 of SEQ ID NO:58. In some aspects, the bispecific polypeptide that binds IL 13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 96% identical to the amino acid sequence of SEQ ID NO:58 or the amino acid residues 1-797 of SEQ ID NO:58. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 97% identical to the amino acid sequence of SEQ ID NO:58 or the amino acid residues 1-797 of SEQ ID NO: 58. In some aspects, the bispecific polypeptide that binds IL 13 and IL31 comprises the CDR1, CDR2, and CDR3 of the VHH1 of the IL13 co-binder, the CDR1, CDR2, and CDR3 of the VHH2 of the IL 13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 98% identical to the amino acid sequence of SEQ ID NO:58 or the amino acid residues 1-797 of SEQ ID NO:58. In some aspects, the bispecific polypeptide that binds IL13 and IL31 comprises the CDR1, CDR2, and CDR3 of the VHH1 of the IL 13 co-binder, the CDR1, CDR2, and CDR3 of the VHH2 of the IL13 co-binder, the CDR1, CDR2, and CDR3 of the VHH1 of the IL31 co-binder, and the CDR1, CDR2, and CDR3 of the VHH2 of the IL31 co-binder, as disclosed herein, and comprises an amino acid sequence at least 99% identical to the amino acid sequence of SEQ ID NO:58 or the amino acid residues 1-797 of SEQ ID NO:58.

In some aspects, the bispecific polypeptide that binds IL 13 and IL31 comprises the amino acid sequence of any one of SEQ ID NOs: 55-58 or the amino acid residues 1-797 of SEQ ID NO: 56 or 58. In some aspects, the bispecific polypeptide that binds IL13 and IL31 comprises the amino acid sequence of SEQ ID NO:55. In some aspects, the bispecific polypeptide that binds IL13 and IL31 comprises the amino acid sequence of SEQ ID NO:56 or the amino acid residues 1-797 of SEQ ID NO:56. In some aspects, the bispecific polypeptide that binds IL13 and IL31 comprises the amino acid sequence of SEQ ID NO:57. In some aspects, the bispecific polypeptide that binds IL13 and IL31 comprises the amino acid sequence of SEQ ID NO:58 or the amino acid residues 1-797 of SEQ ID NO:58.

In some aspects, the bispecific polypeptide that binds IL 13 and IL31 binds to human IL13. In some aspects, human IL13 comprises a signal sequence. In some aspects, human IL13 does not comprise a signal sequence. In some aspects, human IL 13 comprises an amino acid sequence at least 95%, at least 96%, at least 97%, at least 98%, or at least 99% identical to the amino acid sequence of the amino acid sequence of SEQ ID NO:27 or SEQ ID NO:28. In some aspects, the human IL 13 comprises the amino acid sequence of SEQ ID NO:27, amino acid residues 21-132 of SEQ ID NO:27, the amino acid sequence of SEQ ID NO:28, or amino acid residues 21-132 of SEQ ID NO:28.

In some aspects, the bispecific polypeptide that binds IL 13 and IL31 binds to human IL31. In some aspects, human IL31 comprises a signal sequence. In some aspects, human IL31 does not comprise a signal sequence. In some aspects, human IL31 comprises an amino acid sequence at least 95%, at least 96%, at least 97%, at least 98%, or at least 99% identical to the amino acid sequence of the amino acid sequence of SEQ ID NO:1, amino acid residues 24-164 of SEQ ID NO:1, or SEQ ID NO:2. In some aspects, the human IL31 comprises the amino acid sequence of SEQ ID NO:1 or SEQ ID NO:2.

The binding affinity for the bispecific polypeptide that binds IL13 and IL31 can be determined by means of surface plasmon resonance. In some aspects, an equilibrium dissociation constant of an antigen-binding molecule and antigen interaction is determined, wherein the antigen is human IL13 and/or IL31. In some aspects, the bispecific polypeptide that binds IL13 and IL31 binds to human IL13 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the bispecific polypeptide that binds IL13 and IL31 binds to human IL 13 at a kD of no more than or equal to $1\times10^{-9}$ M, no more than or equal to $5\times10^{-10}$ M, no more than or equal to $1\times10^{-10}$ M, no more than or equal to $5\times10^{-11}$ M, no more than or equal to $1\times10^{-11}$ M, no more than or equal to $5\times10^{-12}$ M, or no more than or equal to $1\times10^{-12}$ M, as measured by surface plasmon resonance. In some aspects, the bispecific polypeptide that binds IL 13 and IL31 binds to human IL 13 with a kD between about $1\times10^{-9}$ M and about $1\times10^{-12}$ M, about $5\times10^{-10}$ M and about $5\times10^{-11}$ M, or about $1\times10^{-10}$ M and about $1\times10^{-11}$ M, or about $5\times10^{-11}$ M, as measured by surface plasmon resonance. In some aspects, the bispecific polypeptide that binds IL13 and IL31 binds to human IL 13 at a kD of about $1\times10^{-9}$ M, about $9\times10^{-10}$ M, about $8\times10^{-10}$ M, about $7\times10^{-10}$ M, about $6\times10^{-10}$ M, about $5\times10^{-10}$ M, about $4\times10^{-10}$ M, about $3\times10^{-10}$ M, about $2\times10^{-10}$ M, about $1\times10^{-10}$ M, about $9\times10^{-11}$ M, about $8\times10^{-11}$ M, about $7\times10^{-11}$ M, about $6\times10^{-11}$ M, about $5\times10^{-11}$ M, about $4\times10^{-11}$ M, about $3\times10^{-11}$ M, about $2\times10^{-11}$ M, about $1\times10^{-11}$ M, about $9\times10^{-12}$ M, about $8\times12^{-10}$ M, about $7\times10^{-12}$ M, about $6\times10^{-12}$ M, about $5\times10^{-12}$ M, about $4\times10^{-12}$ M, about $3\times10^{-12}$ M, about $2\times10^{-12}$ M, or about $1\times10^{-12}$ M, as measured by surface plasmon resonance. In some aspects, the bispecific polypeptide that binds IL13 and IL31 binds to human IL31 at a kD of less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, or less than or equal to $1\times10^{-12}$ M, as measured by surface plasmon resonance. In some aspects, the bispecific polypeptide that binds IL13 and IL31 binds to human IL31 at a kD of no more than or equal to $1\times10^{-9}$ M, no more than or equal to $5\times10^{-10}$ M, no more than or equal to $1\times10^{-10}$ M, no more than or equal to $5\times10^{-11}$ M, no more than or equal to $1\times10^{-11}$ M, no more than or equal to $5\times10^{-12}$ M, or no more than or equal to $1\times10^{-12}$ M, as measured by surface plasmon resonance. In some aspects, the bispecific polypeptide that binds IL13 and IL31 binds to human IL31 with a kD between about $1\times10^{-9}$ M and about $1\times10^{-12}$ M, about $5\times10^{-10}$ M and about $5\times10^{-11}$ M, or about $1\times10^{-10}$ M and about $1\times10^{-11}$ M, or about $5\times10^{-11}$ M, as measured by surface plasmon resonance. In some aspects, the bispecific polypeptide that binds IL13 and IL31 binds to human IL31 at a kD of about $1\times10^{-9}$ M, about $9\times10^{-10}$ M, about $8\times10^{-10}$ M, about $7\times10^{-10}$ M, about $6\times10^{-10}$ M, about $5\times10^{-10}$ M, about $4\times10^{-10}$ M, about $3\times10^{-10}$ M, about $2\times10^{-10}$ M, about $1\times10^{-10}$ M, about $9\times10^{-11}$ M, about $8\times10^{-11}$ M, about $7\times10^{-11}$ M, about $6\times10^{-11}$ M, about $5\times10^{-11}$ M, about $4\times10^{-11}$ M, about $3\times10^{-11}$ M, about $2\times10^{-11}$ M, about $1\times10^{-11}$ M, about $9\times10^{-12}$ M, about $8\times12^{-10}$ M, about $7\times10^{-12}$ M, about $6\times10^{-12}$ M, about $5\times10^{-12}$ M, about $4\times10^{-12}$ M, about $3\times10^{-12}$ M, about $2\times10^{-12}$ M, or about $1\times10^{-12}$ M, as measured by surface plasmon resonance.

In some aspects, the bispecific polypeptide that binds IL 13 and IL31 binds to human IL13 at a kD of about $1\times10^{-9}$ M, about $5\times10^{-10}$ M, about $1\times10^{-10}$ M, about $5\times10^{-11}$ M, about $1\times10^{-11}$ M, about $5\times10^{-12}$ M, or about $1\times10^{-12}$ M, as measured by surface plasmon resonance. In some aspects, the bispecific polypeptide that binds IL13 and IL31 binds to human IL13 at a kD of about $1\times10^{-9}$ M. In some aspects, the bispecific polypeptide that binds IL13 and IL31 binds to human IL 13 at a kD of about $5\times10^{-10}$ M. In some aspects, the bispecific polypeptide that binds IL13 and IL31 binds to human IL 13 at a kD of about $1\times10^{-10}$ M. In some aspects, the bispecific polypeptide that binds IL 13 and IL31 binds to human IL 13 at a kD of about $5\times10^{-11}$ M. In some aspects, the bispecific polypeptide that binds IL 13 and IL31 binds to human IL 13 at a kD of about $1\times10^{-11}$ M. In some aspects, the bispecific polypeptide that binds IL 13 and IL31 binds to human IL 13 at a kD of about $5\times10^{-12}$ M. In some aspects, the bispecific polypeptide that binds IL13 and IL31 binds to human IL 13 at a kD of about $1\times10^{-12}$ M. In some aspects, the bispecific polypeptide that binds IL13 and IL31 binds to human IL31 at a kD of about $1\times10^{-9}$ M, about $5\times10^{-10}$ M, about $1\times10^{-10}$ M, about $5\times10^{-11}$ M, about $1\times10^{-11}$ M, about $5\times10^{-12}$ M, or about $1\times10^{-12}$ M, as measured by surface plasmon resonance. In some aspects, the bispecific polypeptide that binds IL13 and IL31 binds to human IL31 at a kD of about $1\times10^{-9}$ M. In some aspects, the bispecific polypeptide that binds IL13 and IL31 binds to human IL31 at a kD of about $5\times10^{-10}$ M. In some aspects, the bispecific polypeptide that binds IL13 and IL31 binds to human IL31 at a kD of about $1\times10^{-10}$ M. In some aspects, the bispecific polypeptide that binds IL13 and IL31 binds to human IL31 at a kD of about $5\times10^{-11}$ M. In some aspects, the bispecific polypeptide that binds IL13 and IL31 binds to human IL31 at a kD of about $1\times10^{-11}$ M. In some aspects, the bispecific polypeptide that binds IL 13 and IL31 binds to human IL31 at a kD of about $5\times10^{-12}$ M. In some aspects, the bispecific polypeptide that binds IL13 and IL31 binds to human IL31 at a kD of about $1\times10^{-12}$ M.

In some aspects, the bispecific polypeptide that binds IL 13 and IL31 binds to human IL 13 at a kD of $1\times10^{-9}$ M, $5\times10^{-10}$ M, $1\times10^{-10}$ M, $5\times10^{-11}$ M, $1\times10^{-11}$ M, $5\times10^{-12}$ M, or $1\times10^{-12}$ M, as measured by surface plasmon resonance. In some aspects, the bispecific polypeptide that binds IL13 and IL31 binds to human IL13 at a kD of $1\times10^{-9}$ M. In some aspects, the bispecific polypeptide that binds IL13 and IL31 binds to human IL 13 at a kD of $5\times10^{-10}$ M. In some aspects, the bispecific polypeptide that binds IL13 and IL31 binds to human IL 13 at a kD of $1\times10^{-10}$ M. In some aspects, the bispecific polypeptide that binds IL 13 and IL31 binds to human IL 13 at a kD of $5\times10^{-11}$ M. In some aspects, the bispecific polypeptide that binds IL13 and IL31 binds to human IL 13 at a kD of $1\times10^{-11}$ M. In some aspects, the bispecific polypeptide that binds IL13 and IL31 binds to human IL13 at a kD of $5\times10^{-12}$ M. In some aspects, the bispecific polypeptide that binds IL 13 and IL31 binds to human IL 13 at a kD of $1\times10^{-12}$ M. In some aspects, the bispecific polypeptide that binds IL13 and IL31 binds to human IL31 at a kD of $1\times10^{-9}$ M, $5\times10^{-10}$ M, $1\times10^{-10}$ M, $5\times10^{-11}$ M, $1\times10^{-11}$ M, $5\times10^{-12}$ M, or $1\times10^{-12}$ M, as measured by surface plasmon resonance. In some aspects, the bispecific polypeptide that binds IL13 and IL31 binds to human IL31 at a kD of $1\times10^{-9}$ M. In some aspects, the bispecific polypeptide that binds IL13 and IL31 binds to human IL31 at a kD of $5\times10^{-10}$ M. In some aspects, the bispecific polypeptide that binds IL 13 and IL31 binds to human IL31 at a kD of $1\times10^{-10}$ M. In some aspects, the bispecific polypeptide that binds IL 13 and IL31 binds to human IL31 at a kD of $5\times10^{-11}$ M. In some aspects, the bispecific polypeptide that binds IL13 and IL31 binds to human IL31 at a kD of $1\times10^{-11}$ M. In some aspects, the bispecific polypeptide that binds IL13 and IL31 binds to human IL31 at a kD of $5\times10^{-12}$ M. In some aspects, the bispecific polypeptide that binds IL13 and IL31 binds to human IL31 at a kD of $1\times10^{-12}$ M.

In some aspects, the bispecific polypeptide that binds IL 13 and IL31 has a slow off-rate, wherein the off-rate ($k_{off}$) is the rate of dissociation between polypeptide and human IL31.

In some aspects, the bispecific polypeptide that binds IL 13 and IL31 binds to human IL13 with a $k_{off}$ rate of less than or equal to $5\times10^{-4}$ M per second, less than or equal to $1\times1^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance. In some aspects, the bispecific polypeptide that binds IL13 and IL31 binds to human IL 13 with a $k_{off}$ rate of no more than or equal to $5\times10^{-4}$ M per second, no more than or equal to $1\times1^{-4}$ M per second, no more than or equal to $5\times10^{-5}$ M per second, no more than or equal to $1\times10^{-5}$ M per second, no more than or equal to $5\times10^{-6}$ M per second, or no more than or equal to $1\times10^{-6}$ M per second, as measured by surface plasmon resonance. In some aspects, the bispecific polypeptide that binds IL 13 and IL31 binds to human IL13 with a kor rate of between about 5x10-+M per second and $1\times10^{-6}$ M per second, between about $1\times1^{-4}$ M per second and $5\times10^{-6}$ M per second, or between about $5\times10^{-5}$ M per second and $1\times10^{-5}$ M per second, as measured by surface plasmon resonance. In some aspects, the bispecific polypeptide that binds IL 13 and IL31 binds to human IL 13 with a $k_{off}$ rate of about $9\times10^{-4}$ M per second, about $8\times10^{-4}$ M per second, about $7\times10^{-4}$ M per second, about $6\times10^{-4}$ M per second, about $5\times10^{-4}$ M per second, about $4\times10^{-4}$ M per second, about $3\times10^{-4}$ M per second, about $2\times10^{-4}$ M per second, about $1\times1^{-4}$ M per second, about $9\times10^{-5}$ M per second, about $8\times10^{-5}$ M per second, about $7\times10^{-5}$ M per second, about $6\times10^{-5}$ M per second, about $5\times10^{-5}$ M per second, about $4\times10^{-5}$ M per second, about $3\times10^{-5}$ M per second, about $2\times10^{-5}$ M per second, about $1\times10^{-5}$ M per second, about $9\times10^{-6}$ M per second, about $8\times10^{-6}$ M per second, about $7\times10^{-6}$ M per second, about $6\times10^{-6}$ M per second, about $5\times10^{-6}$ M per second, about $4\times10^{-6}$ M per second, about $3\times10^{-6}$ M per second, about $2\times10^{-6}$ M per second, or about $1\times10^{-6}$ M per second, as measured by surface plasmon resonance. In some aspects, the bispecific polypeptide that binds IL 13 and IL31 binds to human IL31 with a $k_{off}$ rate of less than or equal to $5\times10^{-4}$ M per second, less than or equal to $1\times1^{-4}$ M per second, less than or equal to $5\times10^{-5}$ M per second, less than or equal to $1\times10^{-5}$ M per second, less than or equal to $5\times10^{-6}$ M per second, or less than or equal to $1\times10^{-6}$ M per second, as measured by surface plasmon resonance. In some aspects, the bispecific polypeptide that binds IL 13 and IL31 binds to human IL31 with a $k_{off}$ rate of no more than or equal to $5\times10^{-4}$ M per second, no more than or equal to $1\times1^{-4}$ M per second, no more than or equal to $5\times10^{-5}$ M per second, no more than or equal to $1\times10^{-5}$ M per second, no more than or equal to $5\times10^{-6}$ M per second, or no more than or equal to $1\times10^{-6}$ M per second, as measured by surface plasmon resonance. In some aspects, the bispecific polypeptide that binds IL 13 and IL31 binds to human IL31 with a $k_{off}$ rate of between about $5\times10^{-4}$ M per second and $1\times10^{-6}$ M per second, between about $1\times1^{-4}$ M per second and $5\times10^{-6}$ M per second, or between about $5\times10^{-5}$ M per second and $1\times10^{-5}$ M per second, as measured by surface plasmon resonance. In some aspects, the bispecific polypeptide that binds IL13 and IL31 binds to human IL31 with a $k_{off}$ rate of about $9\times10^{-4}$ M per second, about $8\times10^{-4}$ M per second, about $7\times10^{-4}$ M per second, about $6\times10^{-4}$ M per second, about $5\times10^{-4}$ M per second, about $4\times10^{-4}$ M per second, about $3\times10^{-4}$ M per second, about $2\times10^{-4}$ M per second, about $1\times1^{-4}$ M per second, about $9\times10^{-5}$ M per second, about $8\times10^{-5}$ M per second, about $7\times10^{-5}$ M per second, about $6\times10^{-5}$ M per second, about $5\times10^{-5}$ M per second, about $4\times10^{-5}$ M per second, about $3\times10^{-5}$ M per second, about $2\times10^{-5}$ M per second, about $1\times10^{-5}$ M per second, about $9\times10^{-6}$ M per second, about $8\times10^{-6}$ M per second, about $7\times10^{-6}$ M per second, about $6\times10^{-6}$ M per second, about $5\times10^{-6}$ M per second, about $4\times10^{-6}$ M per second, about $3\times10^{-6}$ M per second, about $2\times10^{-6}$ M per second, or about $1\times10^{-6}$ M per second, as measured by surface plasmon resonance.

In some aspects, the bispecific polypeptide that binds IL13 and IL31 binds to human IL13 with a kor rate of about $5\times10^{-4}$ M per second, about $1\times1^{-4}$ M per second, about $5\times10^{-5}$ M per second, about $1\times10^{-5}$ M per second, about $5\times10^{-6}$ M per second, or about $1\times10^{-6}$ M per second, as measured by surface plasmon resonance. In some aspects, the bispecific polypeptide that binds IL13 and IL31 binds to human IL 13 with a $k_{off}$ rate of about $5\times10^{-4}$ M per second, as measured by surface plasmon resonance. In some aspects, the bispecific polypeptide that binds IL13 and IL31 binds to human IL 13 with a kor rate of about $1\times10^{-4}$ M per second, as measured by surface plasmon resonance. In some aspects, the bispecific polypeptide that binds IL13 and IL31 binds to human IL 13 with a $k_{off}$ rate of about $5\times10^{-5}$ M per second, as measured by surface plasmon resonance. In some aspects, the bispecific polypeptide that binds IL13 and IL31 binds to human IL 13 with a $k_{off}$ rate of about $1\times10^{-5}$ M per second, as measured by surface plasmon resonance. In some aspects, the bispecific polypeptide that binds IL 13 and IL31 binds to human IL13 with a $k_{off}$ rate of about $5\times10^{-6}$ M per second, as measured by surface plasmon resonance. In some aspects, the bispecific polypeptide that binds IL13 and IL31 binds to human IL 13 with a $k_{off}$ rate of about $1\times10^{-6}$ M per second, as measured by surface plasmon resonance. In some aspects, the bispecific polypeptide that binds IL13 and IL31 binds to human IL31 with a $k_{off}$ rate of about $5\times10^{-4}$ M per second, about $1\times1^{-4}$ M per second, about $5\times10^{-5}$ M per second, about $1\times10^{-5}$ M per second, about $5\times10^{-6}$ M per second, or about $1\times10^{-6}$ M per second, as measured by surface plasmon resonance. In some aspects, the bispecific polypeptide that binds IL13 and IL31 binds to human IL31 with a $k_{off}$ rate of about $5\times10^{-4}$ M per second, as measured by surface plasmon resonance. In some aspects, the bispecific polypeptide that binds IL13 and IL31 binds to human IL31 with a $k_{off}$ rate of about $1\times10^{-4}$ M per second, as measured by surface plasmon resonance. In some aspects, the bispecific polypeptide that binds IL 13 and IL31 binds to human IL31 with a $k_{off}$ rate of about $5\times10^{-5}$ M per second, as measured by surface plasmon resonance. In some aspects, the bispecific polypeptide that binds IL13 and IL31 binds to human IL31 with a $k_{off}$ rate of about $1\times10^{-5}$ M per second, as measured by surface plasmon resonance. In some aspects, the bispecific polypeptide that binds IL13 and IL31 binds to human IL31 with a kor rate of about $5\times10^{-6}$ M per second, as measured by surface plasmon resonance. In some aspects, the bispecific polypeptide that binds IL 13 and IL31 binds to human IL31 with a $k_{off}$ rate of about $1\times10^{-6}$ M per second, as measured by surface plasmon resonance.

In some aspects, the bispecific polypeptide that binds IL 13 and IL31 binds to human IL13 with a $k_{off}$ rate of $5\times10^{-4}$ M per second, $1\times1^{-4}$ M per second, $5\times10^{-5}$ M per second, $1\times10^{-5}$ M per second, $5\times10^{-6}$ M per second, or $1\times10^{-6}$ M per second, as measured by surface plasmon resonance. In some aspects, the bispecific polypeptide that binds IL13 and IL31 binds to human IL 13 with a $k_{off}$ rate of $5\times10^{-4}$ M per second, as measured by surface plasmon resonance. In some aspects, the bispecific polypeptide that binds IL13 and IL31 binds to human IL 13 with a $k_{off}$ rate of $1\times10^{-4}$ M per second, as measured by surface plasmon resonance. In some aspects, the bispecific polypeptide that binds IL 13 and IL31 binds to human IL13 with a $k_{off}$ rate of $5\times10^{-5}$ M per second, as measured by surface plasmon resonance. In some aspects, the bispecific polypeptide that binds IL13 and IL31 binds to human IL13 with a $k_{off}$ rate of $1\times10^{-5}$ M per second, as measured by surface plasmon resonance. In some aspects, the bispecific polypeptide that binds IL13 and IL31 binds to human IL 13 with a $k_{off}$ rate of $5\times10^{-6}$ M per second, as measured by surface plasmon resonance. In some aspects, the bispecific polypeptide that binds IL13 and IL31 binds to human IL 13 with a $k_{off}$ rate of $1\times10^{-6}$ M per second, as measured by surface plasmon resonance. In some aspects, the bispecific polypeptide that binds IL 13 and IL31 binds to human IL31 with a $k_{off}$ rate of $5\times10^{-4}$ M per second, $1\times1^{-4}$ M per second, $5\times10^{-5}$ M per second, $1\times10^{-5}$ M per second, $5\times10^{-6}$ M per second, or $1\times10^{-6}$ M per second, as measured by surface plasmon resonance. In some aspects, the bispecific polypeptide that binds IL13 and IL31 binds to human IL31 with a $k_{off}$ rate of $5\times10^{-4}$ M per second, as measured by surface plasmon resonance. In some aspects, the bispecific polypeptide that binds IL13 and IL31 binds to human IL31 with a $k_{off}$ rate of $1\times10^{-4}$ M per second, as measured by surface plasmon resonance. In some aspects, the bispecific polypeptide that binds IL13 and IL31 binds to human IL31 with a $k_{off}$ rate of $5\times10^{-5}$ M per second, as measured by surface plasmon resonance. In some aspects, the bispecific polypeptide that binds IL 13 and IL31 binds to human IL31 with a $k_{off}$ rate of $1\times10^{-5}$ M per second, as measured by surface plasmon resonance. In some aspects, the bispecific polypeptide that binds IL13 and IL31 binds to human IL31 with a $k_{off}$ rate of $5\times10^{-6}$ M per second, as measured by surface plasmon resonance. In some aspects, the bispecific polypeptide that binds IL13 and IL31 binds to human IL31 with a $k_{off}$ rate of $1\times10^{-6}$ M per second, as measured by surface plasmon resonance.

Also provided herein are multimeric polypeptides, each comprising two of the any one of the polypeptides that bind IL 13 and IL31 provided herein. Also provided herein are multimeric polypeptides, each comprising two polypeptides that bind IL13 and IL31, wherein each of the polypeptides that bind IL13 and IL31 comprises the amino acid sequence of SEQ ID NO: 55. Also provided herein are multimeric polypeptides, each comprising two polypeptides that bind IL 13 and IL31, wherein each of the polypeptides that bind IL13 and IL31 comprises the amino acid sequence of SEQ ID NO:56 or the amino acid residues 1-797 of SEQ ID NO:56. Also provided herein are multimeric polypeptides, each comprising two polypeptides that bind IL 13 and IL31, wherein each of the polypeptides that bind IL13 and IL31 comprises the amino acid sequence of SEQ ID NO:57. Also provided herein are multimeric polypeptides, each comprising two polypeptides that bind IL13 and IL31, wherein each of the polypeptides that bind IL13 and IL31 comprises the amino acid sequence of SEQ ID NO:58 or the amino acid residues 1-797 of SEQ ID NO:58.

III. Exemplary Polypeptide Expression and Production

Nucleic acid molecules comprising polynucleotides that encode a bispecific polypeptide that binds IL13 and IL31 as described herein (e.g., Section II and the Examples) are provided. In some aspects, an isolated nucleic acid that encodes the polypeptide is provided. In some aspects, the nucleic acid molecule may also encode a leader sequence that directs secretion of the bispecific polypeptide that binds IL13 and IL31, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some aspects, a nucleic acid molecule is an expression vector that is suitable for expression in a selected host cell. In some aspects, a vector comprising the nucleic acid is provided.

Vectors comprising nucleic acids that encode the bispecific polypeptide that binds IL 13 and IL31 described herein are provided. Such vectors include, but are not limited to, DNA vectors, phage vectors, viral vectors, retroviral vectors, etc. In some aspects, a vector is selected that is optimized for expression of polypeptides in a desired cell type, such as CHO or CHO-derived cells, or in NSO cells. Exemplary such vectors are described, for example, in Running Deer et al., Biotechnol. Prog. 20:880-889 (2004).

In some aspects, a host cell comprising the described nucleic acid is provided herein. In some aspects, a host cell that expresses the polypeptide is provided herein. In some aspects, a bispecific polypeptide that binds IL13 and IL31 may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44 or 63. Lec13 CHO cells, and FUT8 CHO cells; PER.C6® cells (Crucell); and NSO cells. In some aspects, the polypeptide that binds IL31 may be expressed in yeast. See, e.g., U.S. Publication No. US 2006/0270045 A1. In some aspects, a particular eukaryotic host cell is selected based on its ability to make desired post-translational modifications to the polypeptide. For example, in some aspects, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Host cells comprising any of the nucleic acids or vectors described herein are also provided. In some aspects, a host cell that expresses a bispecific polypeptide that binds IL 13 and IL31 described herein (e.g., Section II and the Examples) is provided. The IL13-co-binders and IL31-co-binders expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify the co-binder that binds IL31 that comprises an Fc region. Hydrophobic interactive chromatography, for example, a butyl or phenyl column, may also be suitable for purifying some polypeptides such as antibodies. Ion exchange chromatography (for example anion exchange chromatography and/or cation exchange chromatography) may also be suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also be suitable for purifying some polypeptides such as antibodies. Many methods of purifying polypeptides are known in the art.

Also provided is a host cell comprising a nucleic acid encoding any of the polypeptides described herein. Suitable host cells for cloning or expression of polypeptide-encoding vectors include prokaryotic or eukaryotic cells described herein. For example, the bispecific polypeptide that binds IL13 and IL31 may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B.K.C. Lo, ed., Humana Press, Totowa, NJ, 2003), pp. 245-254, describing expression of antibody fragments in *E. coli*.) After expression, the polypeptide may be isolated from the bacterial cell paste in a soluble fraction and can be further purified.

In some aspects, provided herein is a host cell comprising a vector comprising a nucleic acid(s) encoding a polypeptide of the present disclosure.

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al, J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al, Annals N Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al, Proc. Natl. Acad. Sci. USA 77:4216 (1980)); and myeloma cell lines such as YO, NSO and Sp2/0. For a review of certain mammalian host cell lines suitable for polypeptide production, see, e.g., Yazaki and Wu, Methods in Molecular Biology, Vol. 248 (B.K.C. Lo, ed., Humana Press, Totowa, NJ), pp. 255-268 (2003).

In some aspects, the bispecific polypeptide that binds IL 13 and IL31 is produced in a cell-free system. Nonlimiting exemplary cell-free systems are described, for example, in Sitaraman et al., Methods Mol. Biol. 498:229-44 (2009); Spirin, Trends Biotechnol. 22:538-45 (2004); Endo et al., Biotechnol. Adv. 21:695-713 (2003).

In some aspects, a method of producing the bispecific polypeptide that binds IL13 and IL31 described herein (e.g., Section II and the Examples) is provided. In some aspects, the method comprises culturing a host cell under conditions suitable for expression of the polypeptide. In some aspects, the method further comprises isolating the polypeptide.

In some aspects, a bispecific polypeptide that binds IL 13 and IL31 is prepared by the methods described above. In some aspects, the bispecific polypeptide that binds IL 13 and IL31 is prepared in a host cell. In some aspects, the bispecific polypeptide that binds IL 13 and IL31 is prepared in a cell-free system. In some aspects, the bispecific polypeptide that binds IL 13 and IL31 is purified.

IV. Exemplary Pharmaceutical Compositions

Pharmaceutical compositions comprising a bispecific polypeptide that binds IL 13 and IL31 are provided. In some aspects, the bispecific polypeptide that binds IL13 and IL31 is any one of the polypeptides described herein (e.g., Section II and the Examples). The pharmaceutical compositions can additionally contain other therapeutic agents that are suitable for treating or preventing a given skin disease or disorder (e.g., see Section V). In some aspects, the pharmaceutical composition further comprises a pharmaceutically acceptable carrier.

Accordingly, described herein are pharmaceutical compositions comprising a bispecific polypeptide that binds IL13 and IL31. In some aspects, the bispecific polypeptide that binds IL 13 and IL31 comprises one or more IL 13 co-binders (e.g., a first IL 13 VHH, and a second IL13 VHH, optionally joined by a linker, for a IL13 co-binder) and one or more IL31 co-binders (e.g., a first IL31 VHH and a second IL31 VHH, optionally joined by a linker, for a IL31 co-binder). The two IL 13 VHHs can bind IL13 biparatopically, which allows both single binders to bind the same IL13 target antigen simultaneously. The two IL31 VHHs can bind IL31 biparatopically, which allows both single binders to bind the same IL31 target antigen simultaneously.

In some aspects, the bispecific polypeptide comprises (a) an IL13 co-binder comprising (ai) a VHH1 comprising a CDR1 comprising the amino acid sequence of SEQ ID NO:31; a CDR2 comprising the amino acid sequence of SEQ ID NO:32; and a CDR3 comprising the amino acid sequence of SEQ ID NO:33 or 60 and (aii) a VHH2 comprising a CDR1 comprising the amino acid sequence of SEQ ID NO:42; a CDR2 comprising the amino acid sequence of SEQ ID NO: 43; and a CDR3 comprising the amino acid sequence of SEQ ID NO:44 or 63 and (b) an IL31 co-binder comprising (bi) a VHH1 comprising a CDR1 comprising the amino acid sequence of SEQ ID NO:5; a CDR2 comprising the amino acid sequence of SEQ ID NO:6; and a CDR3 comprising the amino acid sequence of SEQ ID NO:7; and (bii) a VHH2 comprising a CDR 1 comprising the amino acid sequence of SEQ ID NO: 16; a CDR2 comprising the amino acid sequence of SEQ ID NO: 17; and a CDR3 comprising the amino acid sequence of SEQ ID NO: 18.

In some aspects, the bispecific polypeptide comprises (a) an IL13 co-binder comprising (ai) a VHH1 comprising a CDR1 comprising the amino acid sequence of SEQ ID NO:31; a CDR2 comprising the amino acid sequence of SEQ ID NO:32; and a CDR3 comprising the amino acid sequence of SEQ ID NO:60 and (aii) a VHH2 comprising a CDR1 comprising the amino acid sequence of SEQ ID NO:42; a CDR2 comprising the amino acid sequence of SEQ ID NO: 43; and a CDR3 comprising the amino acid sequence of SEQ ID NO:63 and (b) an IL31 co-binder comprising (bi) a VHH1 comprising a CDR1 comprising the amino acid sequence of SEQ ID NO: 5; a CDR2 comprising the amino acid sequence of SEQ ID NO:6; and a CDR3 comprising the amino acid sequence of SEQ ID NO:7; and (bii) a VHH2 comprising a CDR1 comprising the amino acid sequence of SEQ ID NO: 16; a CDR2 comprising the amino acid sequence of SEQ ID NO:17; and a CDR3 comprising the amino acid sequence of SEQ ID NO: 18.

In some aspects, the bispecific polypeptide comprises (a) an IL13 co-binder comprising (ai) a VHH1 comprising a CDR1 comprising the amino acid sequence of SEQ ID NO:34; a CDR2 comprising the amino acid sequence of SEQ ID NO:35; and a CDR3 comprising the amino acid sequence of SEQ ID NO:36 or 61 and (aii) a VHH2 comprising a CDR1 comprising the amino acid sequence of SEQ ID NO:45; a CDR2 comprising the amino acid sequence of SEQ ID NO: 46; and a CDR3 comprising the amino acid sequence of SEQ ID NO:47 or 64 and (b) an IL31 co-binder comprising (bi) a VHH1 comprising a CDR1 comprising the amino acid sequence of SEQ ID NO:8; a CDR2 comprising the amino acid sequence of SEQ ID NO:9; and a CDR3 comprising the amino acid sequence of SEQ ID NO:10; and (bii) a VHH2 comprising a CDR1 comprising the amino acid sequence of SEQ ID NO: 19; a CDR2 comprising the amino acid sequence of SEQ ID NO:20; and a CDR3 comprising the amino acid sequence of SEQ ID NO: 21.

In some aspects, the bispecific polypeptide comprises (a) an IL13 co-binder comprising (ai) a VHH1 comprising a CDR1 comprising the amino acid sequence of SEQ ID NO:34; a CDR2 comprising the amino acid sequence of SEQ ID NO:35; and a CDR3 comprising the amino acid sequence of SEQ ID NO:61 and (aii) a VHH2 comprising a CDR1 comprising the amino acid sequence of SEQ ID NO:45; a CDR2 comprising the amino acid sequence of SEQ ID NO: 46; and a CDR3 comprising the amino acid sequence of SEQ ID NO:64 and (b) an IL31 co-binder comprising (bi) a VHH1 comprising a CDR1 comprising the amino acid sequence of SEQ ID NO: 8; a CDR2 comprising the amino acid sequence of SEQ ID NO:9; and a CDR3 comprising the amino acid sequence of SEQ ID NO: 10; and (bii) a VHH2 comprising a CDR1 comprising the amino acid sequence of SEQ ID NO: 19; a CDR2 comprising the amino acid sequence of SEQ ID NO:20; and a CDR3 comprising the amino acid sequence of SEQ ID NO: 21.

In some aspects, the bispecific polypeptide comprises (a) an IL13 co-binder comprising (ai) a VHH1 comprising a CDR1 comprising the amino acid sequence of SEQ ID NO:37; a CDR2 comprising the amino acid sequence of SEQ ID NO:38; and a CDR3 comprising the amino acid sequence of SEQ ID NO:39 or 62 and (aii) a VHH2 comprising a CDR1 comprising the amino acid sequence of SEQ ID NO:48; a CDR2 comprising the amino acid sequence of SEQ ID NO: 49; and a CDR3 comprising the amino acid sequence of SEQ ID NO:50 or 65 and (b) an IL31 co-binder comprising (bi) a VHH1 comprising a CDR1 comprising the amino acid sequence of SEQ ID NO:11; a CDR2 comprising the amino acid sequence of SEQ ID NO: 12; and a CDR3 comprising the amino acid sequence of SEQ ID NO: 13; and (bii) a VHH2 comprising a CDR1 comprising the amino acid sequence of SEQ ID NO:22; a CDR2 comprising the amino acid sequence of SEQ ID NO:23; and a CDR3 comprising the amino acid sequence of SEQ ID NO:24.

In some aspects, the bispecific polypeptide comprises (a) an IL13 co-binder comprising (ai) a VHH1 comprising a CDR1 comprising the amino acid sequence of SEQ ID NO:37; a CDR2 comprising the amino acid sequence of SEQ ID NO:38; and a CDR3 comprising the amino acid sequence of SEQ ID NO:62; and (aii) a VHH2 comprising a CDR1 comprising the amino acid sequence of SEQ ID NO:48; a CDR2 comprising the amino acid sequence of SEQ ID NO: 49; and a CDR3 comprising the amino acid sequence of SEQ ID NO:65; and (b) an IL31 co-binder comprising (bi) a VHH1 comprising a CDR1 comprising the amino acid sequence of SEQ ID NO: 11; a CDR2 comprising the amino acid sequence of SEQ ID NO:12; and a CDR3 comprising the amino acid sequence of SEQ ID NO:13; and (bii) a VHH2 comprising a CDR1 comprising the amino acid sequence of SEQ ID NO:22; a CDR2 comprising the amino acid sequence of SEQ ID NO:23; and a CDR3 comprising the amino acid sequence of SEQ ID NO: 24.

In some aspects, the pharmaceutical composition comprises a bispecific polypeptide that binds IL13 and IL31, comprising an IL13 co-binder comprising a VHH1 and a VHH2 and an IL31 co-binder comprising a VHH1 and a VHH2. In some aspects, the IL13 co-binder comprises a VHH1 and a VHH2, the IL31 co-binder comprises a VHH1 and a VHH2, wherein the VHH1 of the IL 13 co-binder comprises an amino acid sequence at least 85%, at least 90%, at least 95%, at least 96%, at least 97%, at least 98%, or at least 99% identical to the amino acid residues 1-115 or 2-115 of SEQ ID NO:51 or 52. In some aspects, the VHH1 of the IL 13 co-binder comprises the amino acid residues 1-115 or 2-115 of SEQ ID NO:51 or 52.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:51 or 52, optionally wherein residue 162 is valine according to SEQ ID NO:51 or 52. In some aspects, the VHH2 of the IL 13 co-binder comprises amino acid residues 154-280 of SEQ ID NO:51 or 52, optionally wherein residue 162 is valine according to SEQ ID NO:51 or 52.

In some aspects, the VHH1 of the IL13 co-binder comprises amino acid residues 1-115 or 2-115 of SEQ ID NO:51 or 52, and the VHH2 of the IL13 co-binder comprises amino acid residues 154-280 of SEQ ID NO:51 or 52, optionally wherein residue 162 is valine according to SEQ ID NO:51 or 52.

In some aspects, the VHH1 of the IL31 co-binder comprises an amino acid sequence at least 85%, at least 90%, at least 95%, at least 96%, at least 97%, at least 98%, or at least 99% identical to the amino acid residues 1-118 or 2-118 of SEQ ID NO:25 or 26. In some aspects, the VHH1 of the IL31 co-binder comprises amino acid residues 1-118 or 2-118 of SEQ ID NO:25 or 26.

In some aspects, the VHH2 of the IL31 co-binder comprises an amino acid sequence at least 85%, at least 90%, at least 95%, at least 96%, at least 97%, at least 98%, or at least 99% identical to the amino acid residues 157-275 of SEQ ID NO:25 or 26, optionally wherein residue 166 is valine according to SEQ ID NO:25 or 26. In some aspects, the VHH2 of the IL31 co-binder comprises amino acid residues 157-275 of SEQ ID NO:25 or 26, optionally wherein residue 166 is valine according to SEQ ID NO:25 or 26.

In some aspects, the VHH1 of the IL31 co-binder comprises amino acid residues 1-118 or 2-118 of SEQ ID NO:25 or 26, and the VHH2 of the IL31 co-binder comprises amino acid residues 157-275 of SEQ ID NO:25 or 26, optionally wherein residue 166 is valine according to SEQ ID NO:25 or 26.

In some aspects, the pharmaceutical composition comprises a bispecific polypeptide that binds IL 13 and IL31, comprising an IL13 co-binder comprising a VHH1 and a VHH2 and an IL31 co-binder comprising a VHH1 and a VHH2. In some aspects, the IL 13 co-binder comprises a VHH1 and a VHH2, the IL31 co-binder comprises a VHH1, and a VHH2, wherein the IL13 co-binder comprises an amino acid sequence at least 85%, at least 90%, at least 95%, at least 96%, at least 97%, at least 98%, or at least 99% identical to the amino acid sequence of SEQ ID NO:51 or 52 or to amino acid residues 2-280 of SEQ ID NO:51 or 52, optionally wherein residue 162 is valine according to SEQ ID NO:51 or 52. In some aspects, the IL 13 co-binder comprises the amino acid sequence of SEQ ID NO:51 or 52, or amino acid residues 2-280 of SEQ ID NO:51 or 52, optionally wherein residue 162 is valine according to SEQ ID NO:51 or 52.

In some aspects, the IL31 co-binder comprises an amino acid sequence at least 85%, at least 90%, at least 95%, at least 96%, at least 97%, at least 98%, or at least 99% identical to the amino acid sequence of SEQ ID NO:26 or to amino acid residues 2-275 of SEQ ID NO:26, optionally wherein residue 166 is valine according to SEQ ID NO:26. In some aspects, the IL31 co-binder comprises the amino acid sequence of SEQ ID NO:26 or amino acid residues 2-275 of SEQ ID NO:26, optionally wherein residue 166 is valine according to SEQ ID NO:26.

In some aspects, the bispecific polypeptide that binds IL 13 and IL31 comprises the amino acid sequence of any one of SEQ ID NOs: 55-58 or the amino acid residues 1-797 of SEQ ID NO: 56 or 58. In some aspects, the bispecific polypeptide that binds IL13 and IL31 comprises the amino acid sequence of SEQ ID NO:55. In some aspects, the bispecific polypeptide that binds IL13 and IL31 comprises the amino acid sequence of SEQ ID NO:56 or amino acid residues 1-797 of SEQ ID NO:56. In some aspects, the bispecific polypeptide that binds IL13 and IL31 comprises the amino acid sequence of SEQ ID NO:57. In some aspects, the bispecific polypeptide that binds IL13 and IL31 comprises the amino acid sequence of SEQ ID NO:58 or amino acid residues 1-797 of SEQ ID NO:58.

In some aspects, the pharmaceutical composition comprises a multimeric polypeptide, comprising two of the any one of the bispecific polypeptides that bind IL 13 and IL31 provided herein. In some aspects, the pharmaceutical composition comprises a multimeric polypeptide, comprising two bispecific polypeptides that bind IL 13 and IL31, wherein each of the bispecific polypeptides that bind IL13 and IL31 comprises the amino acid sequence of SEQ ID NO:55.

A pharmaceutical composition of the present disclosure can be administered by a variety of methods known in the art. The route and/or mode of administration vary depending upon the desired results. It is preferred that administration be parenterally, intramuscular, intraperitoneal, intravenous, or subcutaneous, or administered proximal to the site of the target. The pharmaceutically acceptable carrier should be suitable for parenterally, intramuscular, intraperitoneal, intravenous, subcutaneous, parenteral, spinal, or epidermal administration (e.g., by injection or infusion). Depending on the route of administration, the active compound may be coated in a material to protect the compound from the action of acids and other natural conditions that may inactivate the compound. In some aspects, parenteral administration is preferred. In some aspects, intramuscular administration is preferred. In some aspects, intraperitoneal administration is preferred.

Pharmaceutical compositions of the disclosure can be prepared in accordance with methods well known and routinely practiced in the art. Pharmaceutical compositions are preferably manufactured under GMP conditions. Typically, a therapeutically effective dose or efficacious dose of the bispecific polypeptide that binds IL 13 and IL31 is employed in the pharmaceutical compositions of the disclosure. The bispecific polypeptide that binds IL13 and IL31 is formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the polypeptides of the disclosure employed in the pharmaceutical composition at levels lower than that required to achieve the desired therapeutic effect and gradually increase the dosage until the desired effect is achieved. In general, effective doses of the compositions of the present disclosure, for the treatment of an inflammatory skin disorder or skin disease described herein vary depending upon many different factors, including means of administration, target site, physiological state of the patient, other medications administered, and whether treatment is prophylactic or therapeutic. Treatment dosages need to be titrated to optimize safety and efficacy.

V. Exemplary Methods of Using IL31 Polypeptides

A. Exemplary Uses and Methods of Treatment

Provided herein are bispecific polypeptides that bind IL13 and IL31 (e.g., VHH) that may have therapeutic effects against chronic inflammatory skin diseases such as atopic dermatitis (AD) and prurigo nodularis (PN), which lead to intensely pruritic skin lesions resulting in severe scratching and can be extremely disabling (e.g., major psychological problems, significant sleep loss, and impaired quality of life (QOL) that lead to a high socioeconomic cost). In some instances, the bispecific polypeptides that bind IL 13 and IL31 may be used to treat a subject having an IL13-associated condition and/or an IL31-associated condition, such as a disease or disorder (e.g., inflammatory skin disease). In some instances, the methods or uses provided herein are for treating a subject having an IL13-associated condition and/or an IL31-associated condition comprising administering to the subject a pharmaceutically effective amount of any one the bispecific polypeptides or multimeric polypeptides described herein (e.g., Section II and the Examples) or the pharmaceutical composition thereof (e.g., Section IV). Uses of the bispecific polypeptide that binds IL13 and IL31, multimeric polypeptides, or pharmaceutical compositions thereof for the manufacture of a medicament, wherein the medicament is for treating a subject having an IL 13-associated condition and/or an IL31-associated condition, such as an inflammatory skin disease (e.g., a pruritic condition) are provided herein. Also provided herein are bispecific polypeptides that bind IL 13 and IL31, multimeric polypeptides, or pharmaceutical compositions thereof for use in treating a subject having an IL 13-associated condition and/or an IL31-associated condition, such as an inflammatory skin disease (e.g., a In some aspects, provided herein is a method for treating a subject having an IL13-associated condition and/or an IL31-associated condition, comprising administering to the subject a pharmaceutically effective amount of any of the bispecific polypeptides that binds IL 13 and IL31, multimeric polypeptides, or pharmaceutical compositions thereof disclosed herein. In some aspects, the bispecific polypeptide that binds IL13 and IL31 comprises one or more IL13 co-binder (e.g., a VHH1 and a VHH2) and one or more IL31 co-binder (e.g., a VHH1 and a VHH2). In some aspects, the one or more IL13 co-binder and/or the one or more IL31 co-binder comprises a VHH1. In some aspects, the one or more IL13 co-binder and/or the one or more IL31 co-binder comprises a VHH1 and a VHH2, optionally joined by a peptide linker.

In some aspects, the bispecific polypeptide comprises (a) an IL13 co-binder comprising (ai) a VHH1 comprising a CDR1 comprising the amino acid sequence of SEQ ID NO:31; a CDR2 comprising the amino acid sequence of SEQ ID NO:32; and a CDR3 comprising the amino acid sequence of SEQ ID NO:33 and 60 and (aii) a VHH2 comprising a CDR1 comprising the amino acid sequence of SEQ ID NO:42; a CDR2 comprising the amino acid sequence of SEQ ID NO: 43; and a CDR3 comprising the amino acid sequence of SEQ ID NO:44 or 63 and (b) an IL31 co-binder comprising (bi) a VHH1 comprising a CDR1 comprising the amino acid sequence of SEQ ID NO:5; a CDR2 comprising the amino acid sequence of SEQ ID NO:6; and a CDR3 comprising the amino acid sequence of SEQ ID NO:7; and (bii) a VHH2 comprising a CDR 1 comprising the amino acid sequence of SEQ ID NO: 16; a CDR2 comprising the amino acid sequence of SEQ ID NO: 17; and a CDR3 comprising the amino acid sequence of SEQ ID NO: 18.

In some aspects, the bispecific polypeptide comprises (a) an IL13 co-binder comprising (ai) a VHH1 comprising a CDR1 comprising the amino acid sequence of SEQ ID NO:31; a CDR2 comprising the amino acid sequence of SEQ ID NO:32; and a CDR3 comprising the amino acid sequence of SEQ ID NO:60 and (aii) a VHH2 comprising a CDR1 comprising the amino acid sequence of SEQ ID NO:42; a CDR2 comprising the amino acid sequence of SEQ ID NO: 43; and a CDR3 comprising the amino acid sequence of SEQ ID NO:63 and (b) an IL31 co-binder comprising (bi) a VHH1 comprising a CDR1 comprising the amino acid sequence of SEQ ID NO: 5; a CDR2 comprising the amino acid sequence of SEQ ID NO:6; and a CDR3 comprising the amino acid sequence of SEQ ID NO:7; and (bii) a VHH2 comprising a CDR1 comprising the amino acid sequence of SEQ ID NO:16; a CDR2 comprising the amino acid sequence of SEQ ID NO: 17; and a CDR3 comprising the amino acid sequence of SEQ ID NO: 18.

In some aspects, the bispecific polypeptide comprises (a) an IL13 co-binder comprising (ai) a VHH1 comprising a CDR1 comprising the amino acid sequence of SEQ ID NO:34; a CDR2 comprising the amino acid sequence of SEQ ID NO:35; and a CDR3 comprising the amino acid sequence of SEQ ID NO:36 or 61 and (aii) VHH2 comprising a CDR1 comprising the amino acid sequence of SEQ ID NO:45; a CDR2 comprising the amino acid sequence of SEQ ID NO: 46; and a CDR3 comprising the amino acid sequence of SEQ ID NO:47 or 64 and (b) an IL31 co-binder comprising (bi) a VHH1 comprising a CDR1 comprising the amino acid sequence of SEQ ID NO:8; a CDR2 comprising the amino acid sequence of SEQ ID NO:9; and a CDR3 comprising the amino acid sequence of SEQ ID NO: 10; and (bii) a VHH2 comprising a CDR 1 comprising the amino acid sequence of SEQ ID NO: 19; a CDR2 comprising the amino acid sequence of SEQ ID NO:20; and a CDR3 comprising the amino acid sequence of SEQ ID NO: 21.

In some aspects, the bispecific polypeptide comprises (a) an IL13 co-binder comprising (ai) a VHH1 comprising a CDR1 comprising the amino acid sequence of SEQ ID NO:34; a CDR2 comprising the amino acid sequence of SEQ ID NO:35; and a CDR3 comprising the amino acid sequence of SEQ ID NO:61 and (aii) a VHH2 comprising a CDR1 comprising the amino acid sequence of SEQ ID NO:45; a CDR2 comprising the amino acid sequence of SEQ ID NO: 46; and a CDR3 comprising the amino acid sequence of SEQ ID NO:64; and (b) an IL31 co-binder comprising (bi) a VHH1 comprising a CDR1 comprising the amino acid sequence of SEQ ID NO: 8; a CDR2 comprising the amino acid sequence of SEQ ID NO:9; and a CDR3 comprising the amino acid sequence of SEQ ID NO: 10; and (bii) a VHH2 comprising a CDR1 comprising the amino acid sequence of SEQ ID NO:19; a CDR2 comprising the amino acid sequence of SEQ ID NO:20; and a CDR3 comprising the amino acid sequence of SEQ ID NO: 21.

In some aspects, the bispecific polypeptide comprises (a) an IL13 co-binder comprising (ai) a VHH1 comprising a CDR1 comprising the amino acid sequence of SEQ ID NO:37; a CDR2 comprising the amino acid sequence of SEQ ID NO:38; and a CDR3 comprising the amino acid sequence of SEQ ID NO:39 or 62; and (aii) a VHH2 comprising a CDR1 comprising the amino acid sequence of SEQ ID NO:48; a CDR2 comprising the amino acid sequence of SEQ ID NO: 49; and a CDR3 comprising the amino acid sequence of SEQ ID NO:50 or 65; and (b) an IL31 co-binder comprising (bi) a VHH1 comprising a CDR1 comprising the amino acid sequence of SEQ ID NO: 11; a CDR2 comprising the amino acid sequence of SEQ ID NO:12; and a CDR3 comprising the amino acid sequence of SEQ ID NO:13; and (bii) a VHH2 comprising a CDR1 comprising the amino acid sequence of SEQ ID NO:22; a CDR2 comprising the amino acid sequence of SEQ ID NO:23; and a CDR3 comprising the amino acid sequence of SEQ ID NO:24.

In some aspects, the bispecific polypeptide comprises (a) an IL13 co-binder comprising (ai) a VHH1 comprising a CDR1 comprising the amino acid sequence of SEQ ID NO:37; a CDR2 comprising the amino acid sequence of SEQ ID NO:38; and a CDR3 comprising the amino acid sequence of SEQ ID NO:62; and (aii) a VHH2 comprising a CDR1 comprising the amino acid sequence of SEQ ID NO:48; a CDR2 comprising the amino acid sequence of SEQ ID NO: 49; and a CDR3 comprising the amino acid sequence of SEQ ID NO:65; and (b) an IL31 co-binder comprising (bi) a VHH1 comprising a CDR1 comprising the amino acid sequence of SEQ ID NO: 11; a CDR2 comprising the amino acid sequence of SEQ ID NO:12; and a CDR3 comprising the amino acid sequence of SEQ ID NO: 13; and (bii) a VHH2 comprising a CDR1 comprising the amino acid sequence of SEQ ID NO:22; a CDR2 comprising the amino acid sequence of SEQ ID NO:23; and a CDR3 comprising the amino acid sequence of SEQ ID NO: 24.

In some aspects, the method comprises uses of a bispecific polypeptide that binds IL13 and IL31, comprising an IL13 co-binder comprising a VHH1 and a VHH2 and an IL31 co-binder comprising a VHH1 and a VHH2. In some aspects, the IL13 co-binder comprises a VHH1, the IL13 co-binder comprises a VHH2, the IL31 co-binder comprises a VHH1, and the IL31 co-binder comprises a VHH2, wherein the VHH1 of the IL 13 co-binder comprises an amino acid sequence at least 85%, at least 90%, at least 95%, at least 96%, at least 97%, at least 98%, or at least 99% identical to the amino acid residues 1-115 or 2-115 of SEQ ID NO:51 or 52. In some aspects, the VHH1 of the IL 13 co-binder comprises amino acid residues 1-115 or 2-115 of SEQ ID NO: 51 or 52.

In some aspects, the VHH2 of the IL13 co-binder comprises an amino acid sequence at least 85%, at least 90%, at least 95%, at least 96%, at least 97%, at least 98%, or at least 99% identical to the amino acid residues 154-280 of SEQ ID NO:51 or 52, optionally wherein residue 162 is valine according to SEQ ID NO:51 or 52. In some aspects, the VHH2 of the IL 13 co-binder comprises amino acid residues 154-280 of SEQ ID NO:51 or 52, optionally wherein residue 162 is valine according to SEQ ID NO:51 or 52.

In some aspects, the VHH1 of the IL13 co-binder comprises amino acid residues 1-115 or 2-115 of SEQ ID NO:51 or 52, and the VHH2 of the IL 13 co-binder comprises amino acid residues 154-280 of SEQ ID NO:51 or 52, optionally wherein residue 162 is valine according to SEQ ID NO:51 or 52.

In some aspects, the VHH1 of the IL31 co-binder comprises an amino acid sequence at least 85%, at least 90%, at least 95%, at least 96%, at least 97%, at least 98%, or at least 99% identical to amino acid residues 1-118 or 2-118 of SEQ ID NO:25 or 26. In some aspects, the VHH1 of the IL31 co-binder comprises amino acid residues 1-118 or 2-118 of SEQ ID NO:25 or 26.

In some aspects, the VHH2 of the IL31 co-binder comprises an amino acid sequence at least 85%, at least 90%, at least 95%, at least 96%, at least 97%, at least 98%, or at least 99% identical to the amino acid residues 157-275 of SEQ ID NO:25 or 26, optionally wherein residue 166 is valine according to SEQ ID NO:25 or 26. In some aspects, the VHH2 of the IL31 co-binder comprises amino acid residues 157-275 of SEQ ID NO:25 or 26, optionally wherein residue 166 is valine according to SEQ ID NO:25 or 26.

In some aspects, the VHH1 of the IL31 co-binder comprises amino acid residues 1-118 or 2-118 of SEQ ID NO:25 or 26 and the VHH2 of the IL31 co-binder comprises amino acid residues 157-275 of SEQ ID NO:25 or 26, optionally wherein residue 166 is valine according to SEQ ID NO:25 or 26.

In some aspects, the IL 13 co-binder comprises an amino acid sequence at least 85%, at least 90%, at least 95%, at least 96%, at least 97%, at least 98%, or at least 99% identical to the amino acid sequence of SEQ ID NO:51 or 52 or to amino acid residues 2-280 of SEQ ID NO:51 or 52, optionally wherein residue 162 is valine according to SEQ ID NO:51 or 52. In some aspects, the IL13 co-binder comprises the amino acid sequence of SEQ ID NO:51 or 52 or amino acid residues 2-280 of SEQ ID NO:51 or 52, optionally wherein residue 162 is valine according to SEQ ID NO:51 or 52.

In some aspects, the IL31 co-binder comprises an amino acid sequence at least 85%, at least 90%, at least 95%, at least 96%, at least 97%, at least 98%, or at least 99% identical to the amino acid sequence of SEQ ID NO:26 or to amino acid residues 2-275 of SEQ ID NO:26, optionally wherein residue 166 is valine according to SEQ ID NO:26. In some aspects, the IL31 co-binder comprises the amino acid sequence of SEQ ID NO:26 or amino acid residues 2-275 of SEQ ID NO:26, optionally wherein residue 166 is valine according to SEQ ID NO:26.

In some aspects, the bispecific polypeptide that binds IL 13 and IL31 comprises the amino acid sequence of any one of SEQ ID NOs: 55-58, or amino acid residues 1-797 of SEQ ID NO: 56 or 58. In some aspects, the bispecific polypeptide that binds IL 13 and IL31 comprises the amino acid sequence of SEQ ID NO:55. In some aspects, the bispecific polypeptide that binds IL13 and IL31 comprises the amino acid sequence of SEQ ID NO:56 or the amino acid residues 1-797 of SEQ ID NO:56. In some aspects, the bispecific polypeptide that binds IL 13 and IL31 comprises the amino acid sequence of SEQ ID NO:57. In some aspects, the bispecific polypeptide that binds IL13 and IL31 comprises the amino acid sequence of SEQ ID NO:58 or amino acid residues 1-797 of SEQ ID NO:58.

In some aspects, the method comprises uses of a multimeric polypeptide, comprising two of the any one of the bispecific polypeptides that bind IL13 and IL31 provided herein. In some aspects, the method comprises uses of a multimeric polypeptide, comprising two bispecific polypeptides that bind IL13 and IL31, wherein each of the bispecific polypeptides that bind IL13 and IL31 comprises the amino acid sequence of SEQ ID NO:55.

Exemplary IL13-associated conditions include, but are not limited to, airway hyperresponsiveness, allergic asthma, allergic conjunctivitis, allergic contact dermatitis, allergic lung disease, allergic rhinitis, alopecia areata, Alzheimer's disease, aspirin-exacerbated respiratory disease, asthma, atopic dermatitis, atopic keratoconjunctivitis, bronchial asthma, bullous pemphigoid, chronic hand eczema, chronic inducible urticaria, chronic obstructive pulmonary disease, chronic pruritus of unknown origin, chronic Rhinosinusitis with nasal polyposis, chronic spontaneous urticaria, colitis, dermatitis, eczema, eosinophilic COPD, eosinophilic esophagitis, eosinophilic gastritis, eosinophilic duodenitis, epidermolysis bullosa, food allergy, goblet cell metaplasia, hepatic fibrosis, Hodgkin's disease, idiopathic pulmonary fibrosis, Netherton syndrome, progressive systemic sclerosis, prurigo nodularis, rheumatoid arthritis, sinusitis, Sjogren's syndrome, systemic lupus erythematosus, systemic sclerosis, type 1 diabetes, and ulcerative colitis.

Exemplary IL31-associated conditions include, but are not limited to, acne rosacea, acne vulgaris, allergic asthma, allergic contact dermatitis, allergic rhinitis, alopecia areata, arthritis, atopic dermatitis, bile acid induced urticaria, bullous pemphigoid, checkpoint inhibitor induced pruritus, cholestatic pruritus, chronic hand eczema, chronic inducible urticaria, chronic kidney disease associated pruritus, chronic pruritus of unknown origin, chronic spontaneous urticaria, chronic urticaria, contact dermatitis, contact hypersensitivity, Crohn's disease, cutaneous (lichen) amyloidosis, cutaneous T cell lymphoma, dermatomyositis, a drug-induced allergic reaction, eczema, epidermolysis bullosa, folliculitis, inflammatory bowel disease, intrahepatic cholestasis of pregnancy, itch associated with wound healing, lichen planus, metabolic dysfunction-associated (non-alcoholic) steatohepatitis, neurodermatitis, osteoarthritis, osteoporosis, pemphigus, pemphigus herpetiformis, porokeratosis, primary biliary cholangitis, primary sclerosing cholangitis, prurigo nodularis, pruritus, pruritus associated with cutaneous T-cell lymphoma, psoriasis, psoriatic arthritis, rheumatoid arthritis, scleroderma, skin-tropic viruses and viral associated pruritus, spondyloarthritis, stasis dermatitis, systemic lupus erythematosus, systemic sclerosis, toxic epidermal necrolysis, ulcerative colitis, uremic pruritus, and wound healing pruritus.

Exemplary inflammatory skin diseases include, but are not limited to, IL31-associated skin diseases, such as atopic dermatitis, prurigo nodularis, chronic spontaneous urticaria, chronic pruritus of unknown origin, psoriasis, and eczema. Rare skin disorders having similar features include, for example, epidermolysis bullosa, toxic epidermal necrolysis, and folliculitis. In other instances, skin diseases involving inflammation and/or immune system dysregulation can result in mobility issues, partial disability, and even death if left untreated. For example, psoriatic arthritis, diabetic skin ulcers, and melanoma are skin diseases requiring medical attention. In some instances, the polypeptide that binds IL13 and IL31, multimeric polypeptide, or pharmaceutical composition thereof as described herein is used for treatment of atopic dermatitis, prurigo nodularis, chronic spontaneous urticaria, chronic pruritus of unknown origin, psoriasis, and eczema. In some instances, the polypeptide that binds IL13 and IL31, multimeric polypeptide, or pharmaceutical composition thereof is used for treating any of the inflammatory skin diseases described herein.

In some aspects, the IL 13-associated condition and/or IL31-associated condition is a pruritic condition. Uses of a bispecific polypeptide that binds IL13 and IL31, multimeric polypeptide, or pharmaceutical composition thereof to inhibit, reduce, prevent, or minimize the effects of a pruritic condition are described herein. In some aspects, the IL13-associated condition and/or IL31-associated condition is atopic dermatitis (AD). In some aspects, the IL13-associated condition and/or IL31-associated condition is prurigo nodularis (PN). In some aspects, the IL 13-associated condition and/or IL31-associated condition is chronic spontaneous urticaria. In some aspects, the IL13-associated condition and/or IL31-associated condition is chronic pruritus of unknown origin. In some aspects, the IL 13-associated condition and/or IL31-associated condition is eczema. In some aspects, the IL31-associated condition is psoriasis. In some aspects, the IL31-associated condition is uremic pruritus (chronic kidney disease-associated pruritus). In some aspects, the IL31-associated condition is bile acid induced urticaria.

The bispecific polypeptide that binds IL13 and IL31, multimeric polypeptide, or pharmaceutical composition thereof can be administered as needed to subjects in need thereof. Determination of the frequency of administration can be made by persons skilled in the art, such as an attending physician based on considerations of the condition being treated, age of the subject being treated, severity of the condition being treated, general state of health of the subject being treated and the like. In some aspects, the method comprises administering to a subject having an IL13-associated condition and/or IL31-associated condition a single dose of the polypeptide that binds IL13 and IL31, multimeric polypeptide, or pharmaceutical composition thereof. In some aspects, the method comprises administering to a subject having an IL13-associated condition and/or IL31-associated condition multiple doses of the bispecific polypeptide that binds IL13 and IL31, multimeric polypeptide, or pharmaceutical composition thereof.

In some aspects, the bispecific polypeptide that binds IL13 and IL31, multimeric polypeptide, or pharmaceutical composition thereof is administered in a pharmaceutically effective amount for treating an inflammatory skin disease (e.g., a pruritic condition). In some aspects, the bispecific polypeptide that binds IL13 and IL31, multimeric polypeptide, or pharmaceutical composition thereof is administered in a pharmaceutically effective amount for prophylactic treatment of an inflammatory skin disease (e.g., a pruritic condition). In some aspects, use of the bispecific polypeptide that binds IL13 and IL31, multimeric polypeptide, or pharmaceutical compositions thereof for treating an inflammatory skin disease (e.g., a pruritic condition), including prophylactic treatment is described, wherein the polypeptide that binds IL13 and IL31, multimeric polypeptide, or pharmaceutical compositions thereof is administered in a pharmaceutically effective amount.

In some aspects, the method and uses provided herein comprises administering the bispecific polypeptide that binds IL13 and IL31, multimeric polypeptide, or the pharmaceutical composition in combination with one or more therapeutic agent. In some aspects, the one or more therapeutic agent is a drug substance useful in treating an inflammatory skin disease (e.g., a Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some aspects, the one or more therapeutic agent comprises, for example, an antibody, a topical steroid, a small molecule inhibitor, and/or a systemic immunosuppressant agent.

In some aspects, the methods and uses comprise administering a bispecific polypeptide that binds IL13 and IL31, multimeric protein, or a pharmaceutical composition thereof in combination with, for example, a topical corticosteroid, a calcineurin inhibitor, an anti-IL4RA antibody, an anti-IL13RA antibody, an anti-OSMR antibody, an anti-Ox40 antibody, an anti-Ox40L antibody, an anti-TSLP antibody an anti-IL 17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, anti-IL23p19 antibody, an anti-IL31RA antibody, an anti-IgE antibody, an anti-CD11α antibody, anti-IL6R antibody, anti-α4-Intergrin antibody, an anti-IL12 antibody, an anti-IL1β antibody, an anti-BlyS antibody, an anti-CKIT antibody, an anti-MRGPRX2 antibody, an anti-Fc epsilon receptor (FcεRI) antibody, an anti-SIGLEC-6 antibody, or an anti-SIGLEC-8 antibody. In some aspects, the methods and uses comprise administering a bispecific polypeptide that binds IL13 and IL31, multimeric protein, or a pharmaceutical composition thereof in combination with, for example, a small molecule inhibitor of calcineurin, IL4RA, IL13RA, IL13, IL31RA, OSMR, Ox40, Ox40L, TSLP, IL17, TNFα, CD20, CD19, CD25, IL4, IL23, IgE, CD11α, IL6R, α4-Intergrin, IL12, ILIB, BlyS, CKIT, MRGPRX2, Fc epsilon receptor (FcεRI), SIGLEC-6, and/or SIGLEC-8. In some aspects, the methods and uses provided herein comprise administering a bispecific polypeptide that binds IL 13 and IL31, multimeric protein, or a pharmaceutical composition thereof in combination with, for example, a calcineurin inhibitor, a STAT inhibitor, a JAK inhibitor, a PI3K inhibitor, an AKT inhibitor, a MAPK inhibitor, a MRGPRX2 inhibitor, and/or a fusion protein comprising a portion of CTLA-4 and an Fc region of an immunoglobulin, optionally wherein the fusion protein is abatacept or belatacept. In some aspects, the methods and uses comprise administering a bispecific polypeptide that binds IL13 and IL31, multimeric protein, or a pharmaceutical composition thereof in combination with, for example, a topical steroid or a calcineurin inhibitor. In some aspects, the methods and uses comprise administering a bispecific polypeptide that binds IL13 and IL31, multimeric protein, or a pharmaceutical composition thereof in combination with systemic immunosuppressant, for example, cyclosporine A, methotrexate, mycophenolate mofetil, azathioprine, an oral corticosteroid, and interferon-gamma.

A therapeutic agent of the disclosure may be mixed with the other drug substance in a fixed pharmaceutical composition, or it may be administered separately, before, simultaneously with or after the other drug substance. Accordingly, the disclosure includes a combination of an agent as described herein with one or more therapeutic agent in the same or different pharmaceutical composition.

In some aspects, the methods, uses, or pharmaceutical compositions for use described herein are for treating an IL 13-associated and/or IL31-associated skin disease such as atopic dermatitis, prurigo nodularis, chronic spontaneous urticaria, chronic pruritus of unknown origin, psoriasis, eczema, epidermolysis bullosa, epidermolysis bullosa simplex, seborrheic dermatitis, rosacea, toxic epidermal necrolysis, Stevens Johnson syndrome, Lyell syndrome, erythema multiforme, necrobiosis lipoidica, peeling skin syndrome, ichthyosis, neurodermatitis, pemphigus, folliculitis, uremic pruritus (chronic kidney disease-associated pruritus), bile acid induced urticaria, psoriatic arthritis, diabetic skin ulcers, and/or melanoma.

In some aspects, the bispecific polypeptide that binds IL13 and IL31, multimeric polypeptide, or pharmaceutical composition thereof can be administered in vivo by various routes, including, but not limited to, parenteral, intramuscular, intraperitoneal, intravenous, intra-arterial, or subcutaneous. The appropriate route of administration may be selected according to the intended application. In some aspects, the bispecific polypeptide that binds IL 13 and IL31, multimeric polypeptide, or the pharmaceutical composition is administered parenterally. In some aspects, the bispecific polypeptide that binds IL13 and IL31, multimeric polypeptide, or the pharmaceutical composition is administered by a subcutaneous route. In some aspects, the bispecific polypeptide that binds IL13 and IL31, multimeric polypeptide, or the pharmaceutical composition is administered by an intravenous route. In some aspects, the bispecific polypeptide that binds IL 13 and IL31, multimeric polypeptide, or the pharmaceutical composition is administered by an intramuscular route. In some aspects, the bispecific polypeptide that binds IL13 and IL31, multimeric polypeptide, or the pharmaceutical composition is administered by an intraperitoneal route.

In some aspects, treatment according to the methods, uses, and pharmaceutical compositions for use provided herein results in improved skin health comprising reduced skin redness, smaller skin lesions, and reduced skin itching.

In some instances, the subject is a mammal. In some instances, the subject is a human. Subjects treated by methods described herein may be infants, adults, or children.

B. Exemplary Indications and Patient Populations

Disclosed methods, uses, or pharmaceutical compositions for use herein comprise treating an IL 13-associated and/or IL31-associated condition in a subject in need thereof. The subject may have one or more indication that may benefit from the application of any one of the bispecific polypeptides described herein or pharmaceutical compositions thereof.

In some aspects, the subject receiving treatment has one or more of an inflammatory skin disease, a pruritic condition, atopic dermatitis, prurigo nodularis, chronic spontaneous urticaria, chronic pruritus of unknown origin, psoriasis, eczema, epidermolysis bullosa, epidermolysis bullosa simplex, seborrheic dermatitis, rosacea, toxic epidermal necrolysis, Stevens Johnson syndrome, Lyell syndrome, erythema multiforme, necrobiosis lipoidica, peeling skin syndrome, ichthyosis, neurodermatitis, pemphigus, folliculitis, uremic pruritus (chronic kidney disease-associated pruritus), bile acid induced urticaria, psoriatic arthritis, diabetic skin ulcers, and/or melanoma.

In some aspects, the subject receiving treatment has an inflammatory skin disease. In some aspects, the subject receiving treatment has a pruritic condition. In some aspects, the subject receiving treatment has atopic dermatitis. In some aspects, the subject receiving treatment has prurigo nodularis. In some aspects, the subject receiving treatment has chronic spontaneous urticaria. In some aspects, the subject receiving treatment has chronic pruritus of unknown origin. In some aspects, the subject receiving treatment has psoriasis. In some aspects, the subject receiving treatment has eczema. In some aspects, the subject receiving treatment has epidermolysis bullosa. In some aspects, the subject receiving treatment has epidermolysis bullosa simplex. In some aspects, the subject receiving treatment has seborrheic dermatitis. In some aspects, the subject receiving treatment has rosacea. In some aspects, the subject receiving treatment has toxic epidermal necrolysis. In some aspects, the subject receiving treatment has Stevens Johnson syndrome. In some aspects, the subject receiving treatment has Lyell syndrome. In some aspects, the subject receiving treatment has erythema multiforme. In some aspects, the subject receiving treatment has Necrobiosis lipoidica. In some aspects, the subject receiving treatment has peeling skin syndrome. In some aspects, the subject receiving treatment has ichthyosis. In some aspects, the subject receiving treatment has neurodermatitis. In some aspects, the subject receiving treatment has pemphigus. In some aspects, the subject receiving treatment has folliculitis. In some aspects, the subject receiving treatment has uremic pruritus (chronic kidney disease-associated pruritus). In some aspects, the subject receiving treatment has bile acid induced urticaria. In some aspects, the subject receiving treatment has psoriatic arthritis. In some aspects, the subject receiving treatment has diabetic skin ulcers. In some aspects, the subject receiving treatment has melanoma. In some aspects, the subject receiving treatment has airway hyperresponsiveness. In some aspects, the subject receiving treatment has allergic asthma. In some aspects, the subject receiving treatment has allergic conjunctivitis. In some aspects, the subject receiving treatment has allergic contact dermatitis. In some aspects, the subject receiving treatment has allergic lung disease. In some aspects, the subject receiving treatment has allergic rhinitis. In some aspects, the subject receiving treatment has alopecia areata. In some aspects, the subject receiving treatment has Alzheimer's disease. In some aspects, the subject receiving treatment has aspirin-exacerbated respiratory disease. In some aspects, the subject receiving treatment has asthma. In some aspects, the subject receiving treatment has atopic keratoconjunctivitis. In some aspects, the subject receiving treatment has bronchial asthma. In some aspects, the subject receiving treatment has bullous pemphigoid. In some aspects, the subject receiving treatment has chronic hand eczema. In some aspects, the subject receiving treatment has chronic inducible urticaria. In some aspects, the subject receiving treatment has chronic obstructive pulmonary disease. In some aspects, the subject receiving treatment has chronic Rhinosinusitis with nasal polyposis. In some aspects, the subject receiving treatment has colitis. In some aspects, the subject receiving treatment has dermatitis. In some aspects, the subject receiving treatment has eosinophilic COPD. In some aspects, the subject receiving treatment has eosinophilic esophagitis. In some aspects, the subject receiving treatment has eosinophilic gastritis. In some aspects, the subject receiving treatment has eosinophilic duodenitis. In some aspects, the subject receiving treatment has a food allergy. In some aspects, the subject receiving treatment has goblet cell metaplasia. In some aspects, the subject receiving treatment has hepatic fibrosis. In some aspects, the subject receiving treatment has Hodgkin's disease. In some aspects, the subject receiving treatment has idiopathic pulmonary fibrosis. In some aspects, the subject receiving treatment has Netherton syndrome. In some aspects, the subject receiving treatment has progressive systemic sclerosis. In some aspects, the subject receiving treatment has rheumatoid arthritis. In some aspects, the subject receiving treatment has sinusitis. In some aspects, the subject receiving treatment has Sjogren's syndrome. In some aspects, the subject receiving treatment has systemic lupus erythematosus. In some aspects, the subject receiving treatment has systemic sclerosis. In some aspects, the subject receiving treatment has type 1 diabetes. In some aspects, the subject receiving treatment has ulcerative colitis. In some aspects, the subject receiving treatment has acne rosacea. In some aspects, the subject receiving treatment has acne vulgaris. In some aspects, the subject receiving treatment has allergic asthma. In some aspects, the subject receiving treatment has allergic contact dermatitis. In some aspects, the subject receiving treatment has allergic rhinitis. In some aspects, the subject receiving treatment has alopecia areata. In some aspects, the subject receiving treatment has arthritis. In some aspects, the subject receiving treatment has bullous pemphigoid. In some aspects, the subject receiving treatment has checkpoint inhibitor induced pruritus. In some aspects, the subject receiving treatment has cholestatic pruritus. In some aspects, the subject receiving treatment has chronic hand chronic inducible urticaria. In some aspects, the subject receiving treatment has chronic urticaria. In some aspects, the subject receiving treatment has contact dermatitis. In some aspects, the subject receiving treatment has contact hypersensitivity. In some aspects, the subject receiving treatment has Crohn's disease. In some aspects, the subject receiving treatment has cutaneous (lichen) amyloidosis. In some aspects, the subject receiving treatment has cutaneous T cell lymphoma. In some aspects, the subject receiving treatment has dermatomyositis. In some aspects, the subject receiving treatment has a drug-induced allergic reaction. In some aspects, the subject receiving treatment has. In some aspects, the subject receiving treatment has inflammatory bowel disease. In some aspects, the subject receiving treatment has intrahepatic cholestasis of pregnancy. In some aspects, the subject receiving treatment has itch associated with wound healing. In some aspects, the subject receiving treatment has lichen planus. In some aspects, the subject receiving treatment has metabolic dysfunction-associated (non-alcoholic) steatohepatitis. In some aspects, the subject receiving treatment has osteoarthritis. In some aspects, the subject receiving treatment has osteoporosis. In some aspects, the subject receiving treatment has pemphigus herpetiformis. In some aspects, the subject receiving treatment has porokeratosis. In some aspects, the subject receiving treatment has primary biliary cholangitis. In some aspects, the subject receiving treatment has primary sclerosing cholangitis. In some aspects, the subject receiving treatment has pruritus. In some aspects, the subject receiving treatment has pruritus associated with cutaneous T-cell lymphoma. In some aspects, the subject receiving treatment has rheumatoid arthritis. In some aspects, the subject receiving treatment has scleroderma. In some aspects, the subject receiving treatment has skin-tropic viruses and viral associated pruritus. In some aspects, the subject receiving treatment has spondyloarthritis. In some aspects, the subject receiving treatment has stasis dermatitis. In some aspects, the subject receiving treatment has systemic lupus erythematosus. In some aspects, the subject receiving treatment has systemic sclerosis. In some aspects, the subject receiving treatment has ulcerative colitis. In some aspects, the subject receiving treatment has wound healing pruritus.

In some aspects, the subject receiving treatment is an adult. In some aspects, the subject receiving treatment is a child. In some aspects, the subject has an inflammatory skin condition but is otherwise healthy. In some aspects, the subject has one or more comorbidities.

VI. Exemplary Kits

Also provided are articles of manufacture and kits that include any of the bispecific polypeptides that bind to IL13 and IL31 provided herein (e.g., Section II and the Examples) and suitable packaging. In some aspects, the disclosure includes a kit with (i) a bispecific polypeptide that binds IL13 and IL31, and (ii) instructions for using the kit to administer the bispecific polypeptide to an individual. In some aspects, the disclosure includes a kit with (i) a pharmaceutical composition comprising a bispecific polypeptide that binds IL 13 and IL31 (e.g., Section IV and the Examples), and (ii) instructions for using the kit to administer the pharmaceutical composition to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The kit may further comprise a description of selecting an individual suitable or treatment.

The following examples illustrate particular aspects of the disclosure and are not intended in any way to limit the disclosure.

EXAMPLES

Example 1. Anti-IL13 Single Binder Library Construction

To identify IL 13-specific single binders, His-tagged human IL13 was injected into 4 llamas. Following repeated injections, plasma samples were collected from the llamas and analyzed for the presence of anti-IL13 single binders via ELISA. Specifically, MaxiSorp 96-well plates were coated with human IL13 protein followed by incubation with plasma, anti-camelid single binder cocktail, and HRP-conjugated secondary antibody.

From the whole blood of animals demonstrating the presence of anti-IL13 single binders, red blood cells were lysed, whole RNA was extracted from the white blood cells using Qiagen® RNeasy, and cDNA was synthesized by RevertAid H Minus First Strand cDNA Synthesis Kit (Thermo Fisher Scientific). The anti-IL 13 single binder library was generated from cDNA by PCR using Q5® Hot Start DNA polymerase (New England Biolabs). Additionally, 5'-HR arm and 3'-HR arm, which are from upstream and downstream sequences of gene insertion site of yeast surface display vector respectively, were constructed by PCR using Q5® Hot Start DNA polymerase. The anti-IL13 single binder library was extended at 5' and 3' ends with 5'-HR arm and 3'-HR arm by overlap extension PCR using Q5® Hot Start DNA polymerase, and its product was further amplified in a PCR using OneTaq® DNA polymerase (New England Biolabs) (WO2022147463). The final PCR product was electroporated into EBY100 strain *Saccharomyces cerevisiae* together with the linearized yeast surface display plasmid for homologous recombination (Benatuil et al., Protein Eng Des Sel. 2010 April; 23 (4): 155-9; Wang, Protein Eng Des Sel. 2005 July; 18 (7): 337-43). The anti-IL 13 single binder transformed cells were cultured in SDCAA (Synthetic Dextrose medium supplemented with Casamino Acids) medium.

Example 2. Anti-IL13 Single Binder Library Selection

Figure 1A:
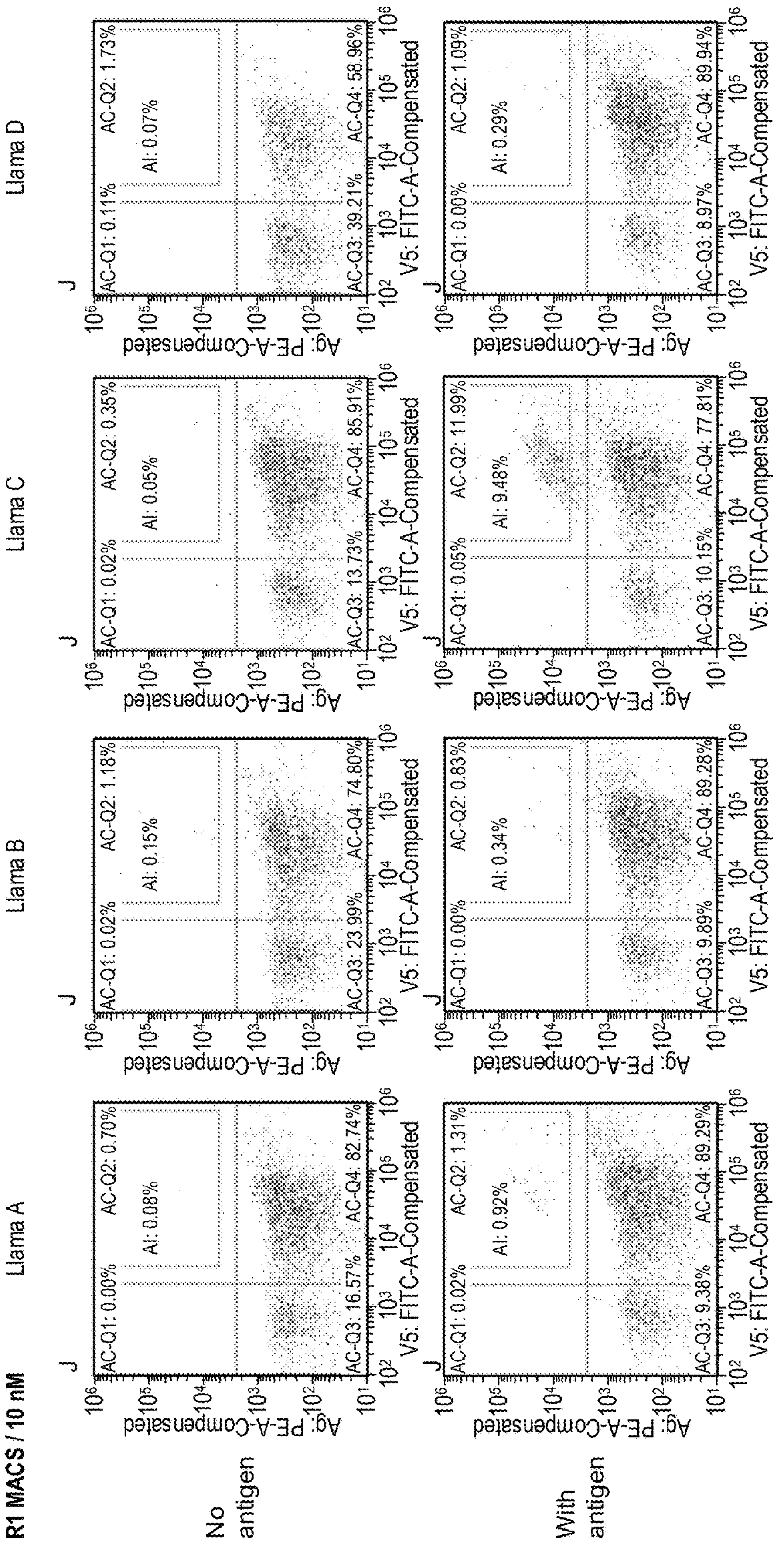
FIGS. 1A-1C show anti-IL13 single binder selection flow cytometry plots with each panel pair representing the results from a single immunized animal.
Figure 1B:
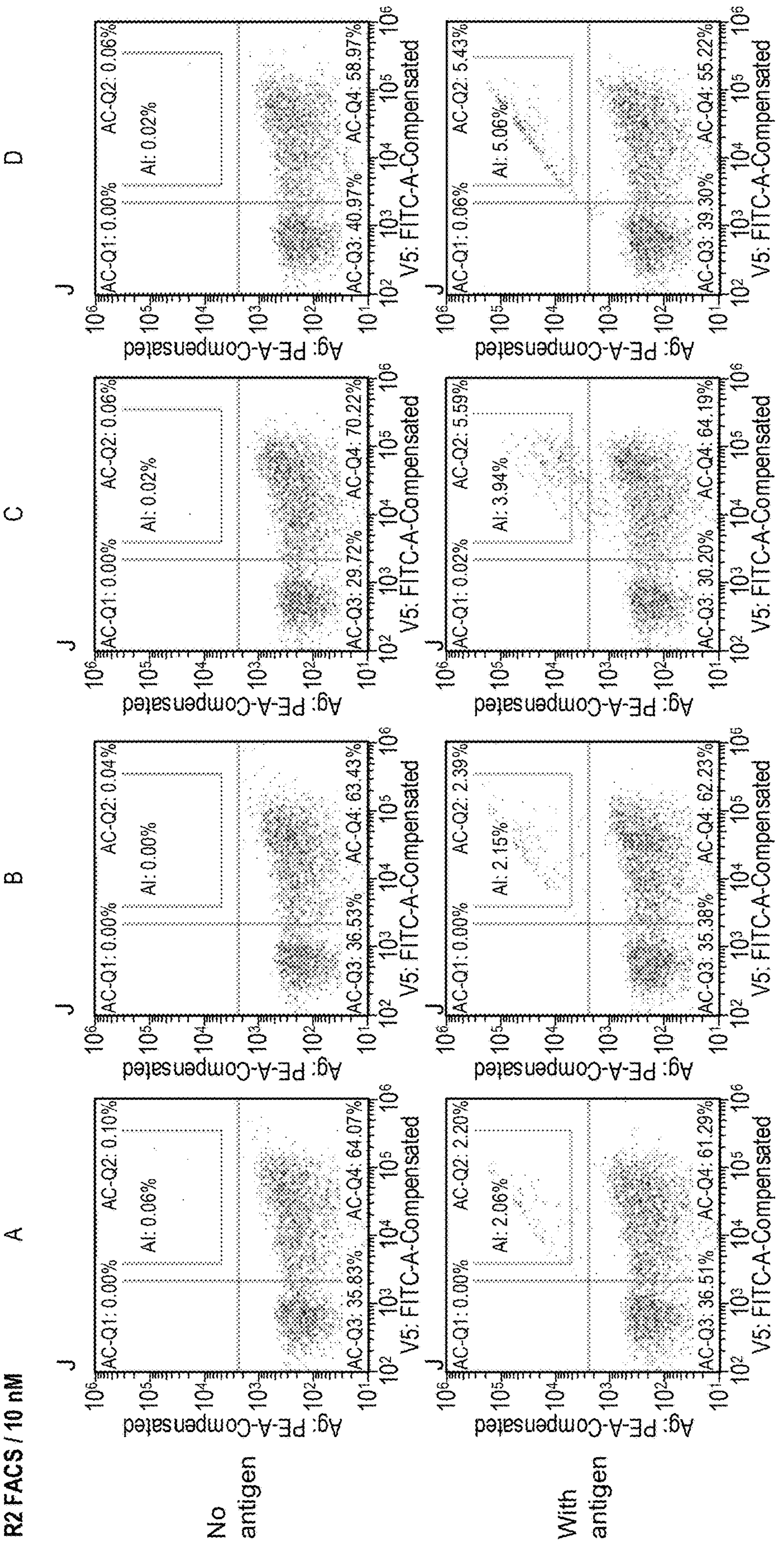
Figure 1C:
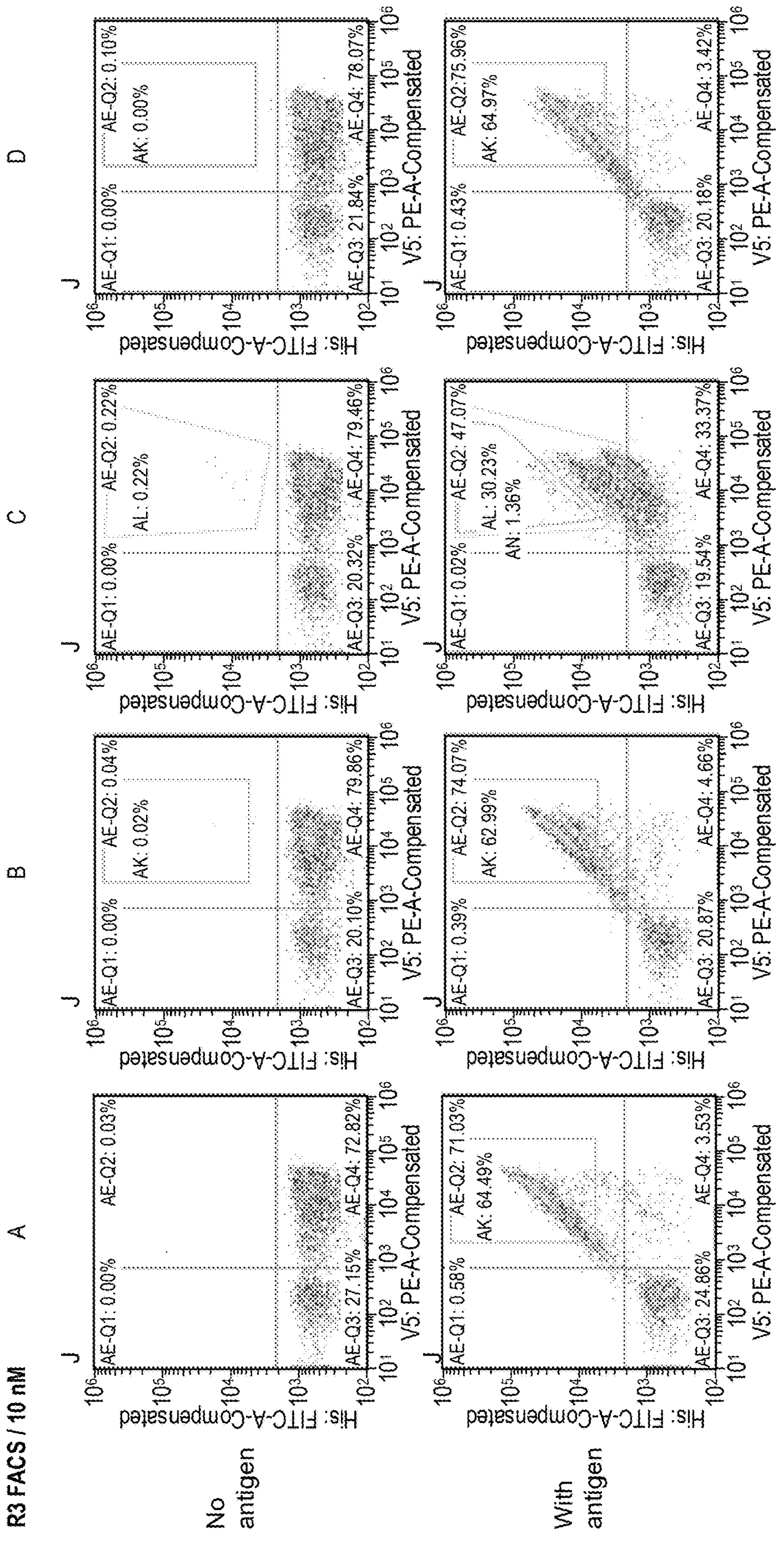

The anti-IL 13 single binder yeast library was induced with 2% galactose (SGCAA, Synthetic Galactose medium supplemented with Casamino Acids) overnight. Library transformed cells were blocked in a blocking buffer (PBS containing 0.5% BSA). Blocked library cells were enriched through a round of MACS using 10 nM Avi-tagged human IL 13 and mix of anti-biotin microbeads and streptavidin microbeads (FIG. 1A). Enrichment was confirmed via FACS (FIGS. 1B-1C). MACS-enriched cells were subsequently sorted through two rounds of positive selection (AI gates for round 2 (R2) and AK gates and an AL gate for round 3 (R3)) via FACS with Avi-tagged human IL13 at 10 nM. Streptavidin and V5 antibody were used for FACS with PE and FITC fluorophores alternating. Sorted cells were cultured in SDCAA medium for plasmid isolation.

Example 3. Anti-IL13 Co-binder Library Construction and Selection

For plasmid isolation, cultured cells were treated with Zymolyase, and plasmids were isolated using QIAGEN® Spin Miniprep Kits. Approximately 350 base segments on the plasmid library covering anti-IL13 single binder and about 400 base segments upstream of the anti-IL13 single binder were PCR amplified using Q5 Hot Start DNA polymerase with the first half of linker library sequences within reverse primer. Another 350 base segments on the plasmid library covering anti-IL 13 single binder and about 400 base segments downstream of anti-IL13 single binder were PCR amplified using Q5® Hot Start DNA polymerase with the second half of linker library sequences within forward primer to generate binder 2. A linear co-binder library was constructed by GIBSON ASSEMBLY® between binder 1 and binder 2 (WO2022147463). The assembled co-binder library was purified on a 1% agarose E-gel. The purified library was further amplified via PCR using ONETAQ® DNA polymerase. The amplified library was purified and electroporated into EBY100 *S. cerevisiae* cells together with linearized yeast surface display plasmid, which has about 400 bases overlap at 5' and 3' ends with co-binder library DNA, for homologous recombination. Anti-IL13 co-binder-transformed cells were cultured in SDCAA medium.

Anti-IL13 co-binder library cells were enriched in 3 rounds of MACS and FACS. In round 1 (R1) MACS, 0.3 nM Avi-tagged human IL13 was used in blocking buffer (FIG. 2). In round 2 (R2) MACS, 30 PM Avi-tagged human IL13 was used in blocking buffer. Enrichment from both rounds of MACS were confirmed on FACS. In round 3 (R3), previously enriched cells were further enriched via FACS with 0.1 nM Avi-tagged human IL13, PE conjugated streptavidin, and FITC conjugated V5 antibody in blocking buffer. Single cells (G, H, I gates) were sorted into 96-well plates. Colony PCR was performed with sorted cells and PCR products were used for sequencing.

Example 4. Preliminary Assessments for Selection of Anti-IL13 Co-Binder Candidates A total of 305 anti-IL 13 co-binders from the co-binder campaign library were sequenced and subjected to initial binding affinity testing. Fc fusions were prepared and subjected to one or more further assessments to determine affinity, potency, and developability, including polyspecificity, melting temperature, hydrophobicity, and thermal stability. As shown in Table 3, 3G12_YTE-Fc showed strong binding affinity and potency and desirable developability characteristics.

TABLE 3

3G12 Co-Binder Selection Characteristics

| Characteristic | Value |
|---|---|
| kon (1/Ms) | $8.2 \times 10^4$ |
| koff (1/s) | $5.5 \times 10^{-6}$ |
| Affinity (KD, pM) | 67.0 ± 26.9 |
| Activity (IC50, nM) | 0.00336 |
| SEC purity % | 97.70 |
| Heparin column retention time (min) | 8.28 |
| HIC column retention time (min) | 17.5 |
| Tm (° C.) | 59.5 |
| Thermal stability (40° C. x2d) | stable |
| BVP binding (Relative to background) | 3.867 |

SEC: size exclusion chromatography
HIC: hydrophobic interaction chromatography
BVP: Baculovirus particle
Stable: no discernible aggregation after incubation at 40° C. x2d Binding affinity was measured on a Carterra LSA SAD200M or CMD200M chip using the Carterra LSA system. For SAD200M chip, single cycle kinetics was used. Co-binder was biotinylated using oYo-Link Single Biotin (AlphaThera) and immobilized to the streptavidin on the SAD200M chip. For 3G12_YTE-Fc, 10 nM, 30 nM, and 90 nM concentrations of His-tagged human IL13 were sequentially flowed as analytes for 900 seconds association and running buffer was flowed for 3000 seconds dissociation. For single mutation variants of IL 13_3G12 Fc-YTE, 3.3 nM, 10 nM, and 30 nM His-tagged human IL13 were used as analytes. For CMD200M chip, multi cycle kinetics was used. Co-binder was immobilized via 1-Ethyl-3-(3-dimethylaminopropyl) carbodiimide hydrochloride (EDC) and N-hydroxysuccinimide (NHS) reaction on CMD200M chip. 3.3 nM, 10 nM, and 30 nM concentrations of His-tagged human IL13, His-tagged human IL 13_R130Q variant, or 10 nM, 30 nM, and 90 nM human IL31 were sequentially flowed as analytes for 900 seconds association and running buffer was flowed for 3000 seconds dissociation. pH 2.0 10 mM Glycine was used for regeneration of the chip. HBS-EP+(0.15 M Sodium Chloride, 10 mM HEPES Free Acid, 3 mM EDTA, 0.05% Tween-20) with 0.05% BSA was used as running buffer.

Binding affinity was measured on a RGD200M chip (XanTec bioanalytics GmbH) or Series S CM5 chip (Cytiva) using the Biacore T200 system. Single cycle kinetics method was used. For the RGD200M chip, initially, co-binder was oYo-Link Single Biotin labeled. Oligo-modified streptavidin (RG-SA) was flowed followed by biotinylated co-binder to immobilize on the chip. 3.3 nM, 10 nM, and 30 nM His-tagged human IL13 were sequentially flowed as analyte for 300 seconds association and running buffer was flowed for 3000 seconds dissociation. The chip was regenerated by 6M guanidine hydrochloride and 0.25 M sodium hydroxide. For the Series S CM5 chip, anti-IL31 and anti-IL13 bispecific polypeptide (SEQ ID NO:55) was coupled to the chip via EDC and NHS reaction. 3.3 nM, 10 nM, and 30 nM His-tagged human IL 13, His-tagged human IL 13_R130Q variant, or 10 nM, 30 nM, and 90 nM human IL31 were sequentially flowed for 300 seconds association and running buffer was flowed for 3000 seconds dissociation. HBS-EP+ was used as running buffer for both chips.

The ability of anti-IL13 co-binder 3G12_YTE-Fc to block the IL 13 binding to and dimerization of the IL13 receptor was assessed. An IL13 dimerization assay was performed using IL13 dimerization kits from Eurofins Scientific (Fremont, CA) according to the manufacturer's instructions. Briefly, U2OS OSMRb/IL31R or U2OS IL4R/IL13RA1 dimerization cells were seeded at 0.1 million/well in 80 μl ASSAYCOMPLETE™ Cell Plating 0 Reagent (Eurofins DiscoverX) into a 96-well clear flat-bottom white plate and incubated at 37° C., 5% $CO_2$ for overnight. Anti-IL13 co-binder were diluted from 30 μg/ml with 3×dilution for 12 points and incubated with equal volume of 10 ng/ml IL-13 in ASSAYCOMPLETE™ Cell Plating 0 Reagent for 1 hour at room temperature. 20 μl of IL13 and anti-IL 13 co-binder complex was added to each well of the cell culture plate and incubated for 16 hours. Plates and detection reagent were equilibrated to room temperature. 100 μl of detection reagent mix was added to each well of the plates and incubated at room temperature for 1 hour in the dark. RLU was read using VICTOR® NIVO™ Multimode Plate Reader and normalized to IL 13 activity without co-binders and presented as a percentage.

Melting temperature was analyzed by differential scanning fluorimetry (DSF) according to the manufacturer's instructions using a CFX90 RT-PCR instrument (Bio-Rad). In triplicate, co-binder samples (2.5 μg to 10 μg) were added to 5×final dye (INVITROGEN™ SYPRO™ Orange; Thermo Fisher Scientific) solution in 30 μL final volume. The hydrophobic dye binds to proteins as they unfold due to an increase in temperature. Temperature was increased from 10° C. to 95° C. in increments of 0.5° C. per second to develop a melting curve. Data was analyzed using CFX Maestro Software (Bio-Rad) to find the first derivative, or Tm, of the melting curve. At Tm, 50% of co-binder is in native state and 50% is in denatured state. Tm ≥55° C. was used as a minimal cutoff point to screen drug candidates.

To assess polyspecificity of co-binder candidates, baculovirus particle (BVP) binding was assessed by ELISA according to the manufacturer's protocol (MEDNA Scientific, Irving, TX). MaxiSorp 96-well plates were coated with baculovirus particle in sodium carbonate buffer (pH 9.6). Coated plates were blocked in blocking buffer (PBS with 0.5% BSA) and incubated with 1 μM samples. Horseradish peroxidase conjugated anti-human Fc was used for detection. Hits within ≤5× of the negative control (blank) were given a pass in the assay which is within the range of commercially viable mAb for polyspecificity.

Hydrophobicity was measured by hydrophobic interaction chromatography (HIC) using a published protocol (Jain et al., 2017 Proc Natl Acad Sci, 114 (5): 944-949.). This assay measures relative protein surface hydrophobicity which in turn can indicate protein tendency to self-associate under salt stress conditions. Co-binder samples (5 μg to 10 μg) were re-buffered to Buffer B (0.1 M sodium phosphate pH 6.5)+1M Ammonium Sulfate (AS) and then loaded on a 1.67 mL HPLC Proteomix HIC Butyl-NP5 column (4.6×100 mm) at 0.75 mL/min. The column was equilibrated with Buffer A (0.1 M Sodium Phosphate pH 6.5+2 M AS). A linear gradient to 100% Buffer B was developed over 20 minutes. Buffer B concentration was held for 5 minutes at 100% before the column was re-equilibrated with buffer A. Detection was performed with a UV detector set at 280 nm. HIC retention time was measured for one minute.

Thermal stability was assessed via HPLC Size Exclusion Chromatography (SEC) of co-binders following incubation for two days at 40° C. Co-binder samples (10 μg) were loaded onto a ZENIX®-C SEC-300 gel filtration column (7.8×150 mm) (SEPAX Technologies). An isocratic gradient was performed with 150 mM Sodium Phosphate pH 7.0 according to the manufacturer's instructions (SEPAX Technologies) at 1 mL/min. Additionally, percent aggregates and percent monomer were measured (data not shown).

Heparin Chromatography was performed as an in vitro predictor for antibody clearance rate through pinocytosis and was based on previous methods (Kraft et al., 2020, MAbs; 12 (1): 1683432-949). Co-binder protein samples (5 μg to 10 μg) were diluted at least 10-fold in 15 mM MES pH 5.5 and then loaded on a 1.7 mL HPLC POROS™ Heparin column (4.6×100 mm) (Thermo Fisher Scientific) at 1 mL/min. Buffer A is 50 mM Tris buffer pH 7.4 and Buffer B is Buffer A+1 M NaCl. After 4-minute post injection, a 55% B linear gradient was developed over 23 min. Buffer B concentration was increased to 100% and held for 2 minutes before the column was re-equilibrated with buffer A. Detection of co-binder protein level was performed with a UV detector set at 280 nm.

Example 5. Comparative Potency Assay of Anti-IL13 Co-Binder

To determine relative potency of IL13 co-binder 3G12, IL13 inhibition activity of 3G12_YTE-Fc was compared to other approved IL13 binding agents, including lebrikizumab and tralokinumab (FIG. 3). An IL13 dimerization assay was performed for 3G12_YTE-Fc, as described in Example 4. Lebrikizumab and tralokinumab were used for comparison of IL13 inhibitory activity. All IL13 binders showed a dose-response inhibition of IL 13 dimerization with 3G12_YTE-Fc demonstrating the greatest potency (FIG. 3).

Example 6. Sequencing of Anti-IL13 Co-Binder Candidates

High affinity anti-IL13 co-binder clones were sequenced and decomposed into VHH1 and VHH2. VHH1 and VHH2 single binders exhibited low affinity in IL13 binding with Kds in the double digits to single digit nM range (data not shown). In contrast, co-binder candidates were 100-1000-fold more potent. The bi-paratropic format of the co-binders led to significant synergy in binding.

Example 7. Designs of Fc Format and Humanization of Anti-IL13 Co-Binders and CDR Sequence Liability Removal Fc format of 3G12 was designed using huIgG1Fc_YTE_LALA_C→S (SEQ ID NO: 59), which includes (1) the YTE mutations (residue 252 being tyrosine, residue 254 being threonine, and residue 256 being glutamate according to EU numbering) to increase the binding affinity to the MHC Class I neonatal FcR (FcRn), to enhance retention in the serum, (2) L to A substitutions at amino acids 234 and 235 (IGHG1 EU numbering) (3) extra sequence at the N-terminus for spacing starting at amino acid 216 (IGHG1 EU numbering), and (4) a C to S substitution at amino acid 220 (IGHG1 EU numbering).

VHH1 and VHH2 sequences of 3G12 were subjected to humanization. Framework regions 1, 2, 3, and 4 were converted to human VH framework regions by searching human VH germline sequences. The selected human frames were grafted into the VHH sequences. In certain cases, a part of VHH frame 2 from llama was solvent exposed as opposed to being in the interface between VH/VL in IgG format. Thus, back mutations were introduced. For the humanization analysis, the three CDRs were left intact from the original sequences.

During the 13G12 VHH1 humanization process, the frame 1, 2 and 3 were grafted with human germline IGHV3-74*01 frames, except that frame 2 was maintained from the original sequence (with 3 back mutations). VHH2 frames 1, 2 and 3 were grafted from IGHV3-23*04 where frame 1 has one back mutation and frame 2 was maintained from the original 3 amino acids. Properties of the humanized 3G12 candidates are provided in Table 4 below. 3G12 M1m0m1m0-m1m0m1m0) exhibited strong potency and desirable developability characteristics and was selected for further characterization.

TABLE 4

Properties of humanized anti-IL13 co-binder candidates

| Sample name | Activity (IC50, nM) | SEC purity % | Heparin RT (min) | HIC RT (min) | Tm (° C.) |
|---|---|---|---|---|---|
| SEQ_10 IL13_3G12 M1m0m0m0-m0m0m0m0 | 0.01996 | 91.93 | 8.83 | 16.96 | 61.2 |
| SEQ_11 IL13_3G12 M0m1m0m0-m0m0m0m0 | 0.02184 | 98.55 | 7.9 | 17.76 | 59.8 |
| SEQ_12 IL13_3G12 M0m0m1m0-m0m0m0m0 | 0.0182 | 98.81 | 8 | 17.62 | 61.3 |
| SEQ_14 IL13_3G12 M0m0m0m0-m0m1m0m0 | 0.02038 | 98.41 | 7.84 | 17.56 | 61.1 |
| SEQ_16 IL13_3G12 M1m0m1m0-m1m0m1m0 | 0.01512 | 93.46 | 8.2 | 17.03 | 58.3 |
| SEQ_18 IL13_3G12 M1m0m1m0-m1m1m1m0 | 0.01916 | 92.83 | 9.04 | 16.92 | 58.5 |
| SEQ_19 IL13_3G12 M1m1m1m0-m1m1m1m0 | 0.1363 | 92.5 | 8.61 | 17.26 | 58 |
| SEQ_10 IL 13 3G12 M1m0m0m0-m0m0m0m0 | 0.01996 | 91.93 | 8.83 | 16.96 | 61.2 |

SEC: size exclusion chromatography;
RT: column retention time;
HIC: hydrophobic interaction chromatography;
Tm: melting temperature To avoid potential preexisting antidrug antibodies (ADA) against nascent c-terminal epitope in the Morrison bispecific format, VHH2 frame 1 was modified with a different germline. Specifically, the C-terminal VHH2 of 3G12 frame 1 was humanized using germline IGHV3-42*02 for use in the Morrison bispecific format.

3G12 VHH1 CDR3 contains an RGD motif, which may involve integrin binding. The RGD motif in VHH1 CDR3 of 3G12_YTE-Fc was modified by changing D to A, D to N, and R to E or A and the IC50 and other properties of the resulting variant co-binders were determined. RGA and ADG variants had a significant reduction in activity (data not shown). EGD variant of 3G12_YTE-Fc with an R to E modification demonstrated the lowest IC50 value and was comparable to the RGD wildtype 3G12_YTE-Fc (Table 5).

3G12 VHH2 CDR3 has a fast deamination site "NG". The NG site in VHH2 CDR3 of 3G12 YTE-Fc was modified by changing N to E or A and the IC50 and other properties of the resulting variant co-binders were determined. The AG variant has significant reduction in activity (data not shown). While mutation N to Q negatively impacts IC50 bioactivity, mutation N to E maintains IC50 potency (Table 5). As a result, both RGD to EGD and NG to NE mutations were incorporated into the humanized form (SEQ ID NO:52 (without huIgG1Fc_YTE_LALA_C→S); SEQ ID NO:54 (with huIgG1Fc_YTE_LALA_C→S)).

TABLE 5

Properties of variant anti-IL13 co-binder candidates versus wildtype

| Sample name | Activity (IC50, nM) | SEC purity % | Heparin RT (min) | HIC RT (min) | Tm (° C.) |
|---|---|---|---|---|---|
| SEQ_1 IL13_3G12 D to N | 0.3746 | 97.96 | 8.3 | 17.76 | 61.2 |
| SEQ_3 IL13_3G12 R to E | 0.01806 | 97.89 | 7.9 | 18.01 | 61 |
| SEQ_5 IL13_3G12 N to E | 0.0171 | 99.14 | 7.8 | 18.1 | 61.3 |
| SEQ_6 IL13_3G12 N to Q | 0.02507 | 98.29 | 8.2 | 17.5 | 60.8 |

SEC: size exclusion chromatography;
RT: column retention time;
HIC: hydrophobic interaction chromatography;
Tm: melting temperature

Example 8. Anti-IL31 Single Binder Library Construction

To identify IL31-specific single binders (VHHs), two immunization campaigns were carried out. In campaign 1, 4 llamas were immunized with His-tagged human IL31. In campaign 2, His-tagged human IL31 was crosslinked to itself or to keyhole limpet hemocyanin (KLH) or bovine serum albumin (BSA). Self-crosslinked IL31, non-crosslinked IL31, and KLH/BSA-crosslinked IL31 were immunized to two animals each. Following repeated injections, plasma samples were collected from the llamas and analyzed for the presence of anti-IL31 single binders via ELISA. Specifically, MaxiSorp 96-well plates were coated with human IL31 protein followed by incubation with plasma, anti-camelid VHH cocktail, and HRP-conjugated secondary antibody.

From the whole blood of animals demonstrating the presence of anti-IL31 single binders, red blood cells were lysed, whole RNA was extracted from the white blood cell using QIAGEN® RNeasy, and cDNA was synthesized by RevertAid H Minus First Strand cDNA Synthesis Kit (Thermo Fisher Scientific). The anti-IL31 single binder library was generated from cDNA by PCR using Q5® Hot Start DNA polymerase (New England Biolabs). Additionally, 5'-HR arm and 3'-HR arm, which are from upstream and downstream sequences of gene insertion site of yeast surface display vector respectively, were constructed by PCR using Q5® Hot Start DNA polymerase. The anti-IL31 single binder library was extended at 5' and 3' ends with 5'-HR arm and 3'-HR arm by overlap extension PCR using Q5® Hot Start DNA polymerase, and its product was further amplified in a PCR using ONETAQR DNA polymerase (New England Biolabs) (WO2022147463). The final PCR product was electroporated into EBY100 strain *Saccharomyces cerevisiae* together with the linearized yeast surface display plasmid for homologous recombination (Benatuil et al., Protein Eng Des Sel. 2010 April; 23 (4): 155-9; Wang, Protein Eng Des Sel. 2005 July; 18 (7): 337-43). The anti-IL31 single binder transformed cells were cultured in SDCAA (Synthetic Dextrose medium supplemented with Casamino Acids) medium.

Example 9. Campaign 1 Anti-IL31 Single Binder Library Selection

The anti-IL31 single binder yeast library was induced with 2% galactose (SGCAA, Synthetic Galactose medium supplemented with Casamino Acids) overnight. Library transformed cells were blocked in a blocking buffer (PBS containing 0.5% BSA). 100 nM His-tagged recombinant human IL31 was mixed with 2× mols (relative to His-tagged human IL31) of TrisNTA-Biotin and was used for binding the blocked cells. Cells were subsequently incubated with a mix of anti-biotin microbeads and streptavidin microbeads, and anti-IL31 displaying cells were enriched using magnetic activated cell sorting (MACS). Enrichment was confirmed via staining with phycoerythrin (PE) conjugated His antibody (Miltenyi Biotec, Inc. Auburn, CA) and fluorescein isothiocyanate (FITC) conjugated V5 antibody, followed by flow cytometric analysis (FIG. 4). Following MACS, anti-IL31 single binder displaying cells (second quadrant) were sorted via two consecutive rounds of FACS using 100 nM and 30 nM biotinylated human IL31, respectively. V5 tag is encoded downstream of single binder gene in the yeast surface display vector, and it is used to assess single binder expression. PE and FITC fluorophores were alternated between streptavidin and V5 antibody. Sorted cells were cultured in SDCAA medium for plasmid isolation.

For plasmid isolation, cultured cells were treated with Zymolyase, and plasmids were isolated using QIAGEN Spin Miniprep Kits. Approximately 750 bases segment on the plasmid library covering anti-IL31 single binder (VHH1) and about 400 bases upstream segment of the anti-IL31 single binder was PCR amplified using Q5® Hot Start DNA polymerase with the first half of linker library sequences within reverse primer. Another 750 bases segment on the plasmid library covering anti-IL31 single binder and about 400 bases segment downstream of anti-IL31 single binder was PCR amplified using Q5® Hot Start DNA polymerase with the second half of linker library sequences within forward primer to generate a second IL31 single binder (VHH2). A linear co-binder library was constructed by GIBSON ASSEMBLY® between VHH1 and VHH2 (e.g., see WO2022147463A2, WO2022147463A3). The assembled co-binder library was purified on a 1% agarose E-gel. The purified library was further amplified via PCR using ONETAQR DNA polymerase. The amplified library was electroporated into EBY100 *S. cerevisiae* cells together with linearized yeast surface display plasmid, which has about 400 bases overlap at 5' and 3' ends with co-binder library DNA, for homologous recombination. Anti-IL31 co-binder transformed cells were cultured in SDCAA medium.

Anti-IL31 co-binder library-transformed yeast cells were induced with 2% galactose overnight. Induced yeast cells were blocked with blocking buffer (PBS containing 0.5% BSA). His-tagged human IL31 was mixed with 2× concentration (relative to His-tagged human IL31) of Tris-NTA Biotin trifluoroacetate salt (Sigma-Aldrich, St. Louis, MO) and was used for incubating the blocked cells at final His-tagged human IL31 concentration of 10 nM in blocking buffer. After further incubation with mix of anti-biotin microbeads and streptavidin microbeads, anti-IL31 co-binder-displaying cells were enriched using MACS in round 1. Enrichment was confirmed via staining with PE conjugated His antibody (Miltenyi Biotec, Inc. Auburn, CA) and FITC conjugated V5 antibody, followed by flow cytometric analysis (FIG. 5). MACS-enriched cells were further sorted (AH gate in round 2 and M gate in round 3) via three consecutive rounds of FACS using 10 nM, 3 nM, and 1 nM his-tagged human IL31. In the fourth round of FACS, AI, a higher affinity gate, and AJ, a lower affinity gate, were separately sorted into 96-well plates with single cell each well. PE, FITC, and allophycocyanin (APC) were rotated as fluorophore for His antibody and V5 antibody. Colony PCR was performed with sorted cells and PCR products were used for sequencing.

Example 10. Campaign 2 Anti-IL31 Single Binder Library Selection

Campaign 2 derived yeast surface display IL31 single binder library was enriched through a single round (R1) of MACS using 30 nM His-tagged human IL31 following the method described above (FIGS. 6A-6B). MACS-enriched cells were subsequently sorted through two rounds of positive selection (M and I gates for round 2 (R2) and round 3 (R3), respectively) via FACS with human IL31 at 30 nM and 10 nM. Round 3 sorted cells were negatively selected (AL gate) in round 4 (R4) after staining with PE conjugated streptavidin and FITC conjugated V5 antibody without human IL31 via FACS to reduce potential off-target binders. Finally, cells were sorted (I gate) in round 5 (R5) via FACS for binding to 10 nM human IL31, and sorted cells were cultured in SDCAA medium for plasmid isolation.

Plasmids from campaign 1 and campaign 2 were mixed and the anti-IL31 co-binder library was constructed following the method described above. Anti-IL31 co-binder-displaying yeast cells were MACS enriched with human IL31 at 0.3 nM in blocking buffer in round 1 (R1) (FIGS. 7A-7B). Cells were subsequently enriched further using FACS with 3 nM human IL31 in round 2 (R2). To reduce potential off-target binders, cells were then incubated with biotinylated polyspecificity reagent prepared from CHO-K1 cell lysate (Xu et al., Protein Eng Des Sel. 2013 October; 26 (10): 663-70), PE conjugated streptavidin, APC conjugated His antibody, and FITC conjugated V5 antibody in blocking buffer. PE negative, APC negative, and FITC positive populations (K gate) were sorted in round 3 (R3), and anti-IL31 VHH-containing yeast cells were further enriched through two more rounds of FACS using 1 nM (round 4 (R4)) and 0.1 nM (round 5 (R5)) human IL31. Single cells with the higher affinity (K) and lower affinity (L) for IL31 were sorted into 96-well plates and colony PCR was performed with sorted cells and PCR products were used for sequencing.

Example 11. Preliminary Assessments for Selection of Anti-IL31 Co-Binder Candidates A total of 2006 anti-IL31 co-binders from the two co-binder campaign libraries were sequenced and subjected to initial binding affinity testing. Fc fusions were prepared and subjected to one or more further assessments to determine affinity, potency, and developability, including polyspecificity, melting temperature, hydrophobicity, and thermal stability. As shown in Table 6, four co-binder candidates, 1C10, 1D1, 1H5, and 21H7 showed strong binding affinity and potency and desirable developability characteristics.

TABLE 6

Anti-Il31 Co-Binder Selection Characteristics

| Clone | Affinity (KD, pM) | Activity (IC50, nM) | Tm (° C.) | BVP binding | HIC retention time (min) | Thermal Stability (% Aggregation, 2d) |
|---|---|---|---|---|---|---|
| 1C10 | 58.7 ± 50.5 | 8.5 ± 1.3 | 66.5 | No | 16.36 | −0.3 |
| 1D1 | 24 ± 29 | 6.7 ± 0.9 | 60.7 | No | 15.93 | 0.2 |
| 1H5 | 3.2 ± 1.3 | 6.1 ± 0.7 | 58.7 | No | 15.24 | 0.9 |
| 21H7 | 14.8 | 8.4 | 61 | No | 15.76 | 0 |

Tm: melting temperature;
BVP: baculovirus protein;
HIC: hydrophobic interaction chromatography Binding affinity was measured using Biotin CAPture Kit (Cytiva Life Sciences) and the BIACORE™ T200 SPR system (Cytiva Life Sciences). Initially, Biotin CAPture Reagent (Cytiva Life Sciences) was flowed to immobilize 3 nM biotinylated IL31 (ligand). 3 nM, 9 nM, and 27 nM anti-IL31 co-binders were flowed as analyte with 180 seconds association and running buffer was flowed with 3000 seconds dissociation. The sensor chip was regenerated by guanidine hydrochloride and sodium hydroxide.

Candidate co-binders were screened by a cell-based potency assay that measured direct response of IL31 co-binders in A549 cells expressing IL31Ra. After binding to IL31Ra, IL31 activates JAK1/2 signaling molecules, which, in turn, activate phosphorylation of STAT3. A decrease in IL31 signaling is evidenced by a reduction in STAT3 phosphorylation as the concentration of IL31 co-binders exposed to the cells is increased. A549 cells were cultured in Ham's F12K+2 mM Glutamine+10% FBS at 37° C. with 5% $CO_2$. 24 hours before the experiment, A549 cells were detached and plated into 96-well plates at $2\times10e^4$ cells/well in Ham's F12K+2 mM Glutamine+10% FBS and incubated overnight. The next day, the cell culture supernatant was removed from the plate and the cells were washed with 100 μl serum free medium followed by 1 hr serum starvation at 37° C. with 50 μl of serum free medium. Co-binders were diluted from 80 μg/ml with 2× dilution for 12 points and incubated with equal volume of 1 μg/ml IL-31 in serum free medium for 1 hour at room temperature. 50 μl of IL31 and co-binder complex were added to each well of the cell culture plate and incubated for 10 minutes at 37° C. The supernatant was then removed and the cells were lysed in 110 μl of lysis buffer. A pSTAT3 ELISA was performed using PathScan® Phospho-Stat3 (Tyr705) Sandwich ELISA Kit #7300 (Cell signaling technologies, Danvers, MA).

Thermostability was also analyzed by differential scanning fluorimetry (DSF) according to the manufacturer's instructions using a CFX90 RT-PCR instrument (Bio-Rad). In triplicate, co-binder samples (2.5 μg to 10 μg) were added to 5× final dye (INVITROGEN™ SYPRO™ Orange; Thermo Fisher Scientific) solution in 30 μL final volume. The hydrophobic dye binds to proteins as they unfold due to an increase in temperature. Temperature was increased from 10° C. to 95° C. in increments of 0.5° C. per second to develop a melting curve. Data was analyzed using CFX Maestro Software (Bio-Rad) to find the first derivative, or Tm, of the melting curve. At Tm, 50% of co-binder is in native state and 50% is in denatured state. Tm ≥55° C. was used as a minimal cutoff point to screen drug candidates.

To assess polyspecificity of co-binder candidates, baculovirus particle (BVP) binding was assessed by ELISA according to the manufacturer's protocol (MEDNA Scientific, Irving, TX). MaxiSorp 96-well plates were coated with baculovirus particle in sodium carbonate buffer (pH 9.6). Coated plates were blocked in blocking buffer (PBS with 0.5% BSA) and incubated with 1 μM samples. Horseradish peroxidase conjugated anti-human Fc was used for detection. Hits within ≤5× of the negative control (blank) were given a pass in the assay which is within the range of commercially viable mAb for polyspecificity.

Hydrophobicity was measured by hydrophobic interaction chromatography (HIC) using a published protocol (Jain et al., 2017 Proc Natl Acad Sci, 114 (5): 944-949.). This assay measures relative protein surface hydrophobicity which in turn can indicate protein tendency to self-associate under salt stress conditions. Co-binder samples (5 μg to 10 μg) were re-buffered to Buffer B (0.1 M sodium phosphate pH 6.5)+1M Ammonium Sulfate (AS) and then loaded on a 1.67 mL HPLC Proteomix HIC Butyl-NP5 column (4.6×100 mm) at 0.75 mL/min. The column was equilibrated with Buffer A (0.1 M Sodium Phosphate pH 6.5+2 M AS). A linear gradient to 100% Buffer B was developed over 20 minutes. Buffer B concentration was held for 5 minutes at 100% before the column was re-equilibrated with buffer A. Detection was performed with a UV detector set at 280 nm. HIC retention time was measured for one minute.

HPLC Size Exclusion Chromatography (SEC) was used to assess thermal stability of co-binders as measured by percent aggregation after storage for two days at 40° C. Co-binder samples (10 μg) were loaded onto a ZENIX®-C SEC-300 gel filtration column (7.8×150 mm) (SEPAX Technologies). An isocratic gradient was performed with 150 mM Sodium Phosphate pH 7.0 according to the manufacturer's instructions (SEPAX Technologies) at 1 mL/min. Additionally, percent aggregates and percent monomer were measured (data not shown).

Only the unique anti-IL31 co-binders 1C10, 1D1, 1H5, and 21H7 displayed desirable binding affinity, potency, and developability characteristics (Table 7) and were carried forward for further characterization and development.

TABLE 7

Anti-IL31 Co-Binder Selection Characteristics

| Clone | Affinity (KD, pM) | Activity (IC50, nM) | Tm (° C.) | BVP binding | HIC retention time (min) | Thermal Stability (% Aggregation, 2d) |
|---|---|---|---|---|---|---|
| 1H5 | 3.2 ± 1.3 | 6.1 ± 0.7 | 58.7 | No | 15.24 | 0.9 |
| 1D1 | 24 ± 29 | 6.7 ± 0.9 | 60.7 | No | 15.93 | 0.2 |
| 1C10 | 58.7 ± 50.5 | 8.5 ± 1.3 | 66.5 | No | 16.36 | −0.3 |
| 21H7 | 14.8 | 8.4 | 61 | No | 15.76 | 0 |
| 20C7 | 27.1 | 9.8 | 58.5 | No | 18 | 0 |
| 1H4 | 10.8 ± 9 | 9.1 ± 1.6 | 53.5 | No | 16.15 | 49 |
| 1C2 | 109.9 ± 45.2## | 10.5 ± 0.8 | 66.5 | No | 17.9^ | 0 |
| 1E3 | 8.6 ± 4 | 12.1 ± 0.9 | 58 | No | 15.32 | 0 |
| 1D12 | 152.3 ± 42.6## | 14.6 ± 0.2 | 60.5 | No | 18.09^ | 0 |
| 2H2 | 97.7 ± 51.5 | 24.3 ± 0.2# | 57.8 | No | 17.49 | 0 |
| 1H2 | 3145 ± 3772.9## | 34.9 ± 1.7# | 60.5 | No | No peak | 5.6 |
| 1C7 | 202.3 ± 24.2## | 7.9 ± 1.0 | 62 | Yes* | 15.91 | 0 |
| 1B10 | 140.3 ± 12.9## | 12.6 ± 0.9 | 63.5 | Yes* | 18.06^ | 1.8 |
| 1G6 | 419.3 ± 9.3## | 13.4 ± 0.8 | 46.8** | Yes* | 17^ | 41.7 |
| 1E2 | 94.3 ± 12.4 | 18.1 ± 0.8 | 64.3 | Yes* | 15.86 | 0 |
| 1B 12 | 158.7 ± 8.3## | 19.8 ± 2.6 | 59 | Yes* | 16.18 | 5 |
| 1C3 | 466.5 ± 285## | 55.9 ± 1.6# | 57.5 | Yes* | 18.42^ | 6.7 |

Tm: melting temperature;
BVP: baculovirus protein;
HIC: hydrophobic interaction chromatography
#In vitro potency below the desired threshold;
Binding affinity below the desired threshold;
*Polyspecificity score above the desired threshold;
**Melting temperature below the desired threshold;
^HIC retention time above the desired threshold

Example 12. Further Characterization of Anti-IL31 Co-Binders

Large-scale expression of 1H5, 1D1, 1C10, and 21H7 showed co-binders exhibited strong affinity and cell potency (data not shown), similar to data described in Example 11. These four candidates were also assessed for several manufacturability criteria. 1H5, 1D1, 1C10, and 21H7 demonstrated good stability in a freeze-thaw assay in optimized buffer formulation (data not shown).

As shown in Table 8, below, 1H5, 1D1, 1C10, and 21H7 retained strong affinity after repeated freeze-thaw.

TABLE 8

Anti-IL31 Co-binder Freeze-thaw Analysis

| Co-binder clone | Sample | ka (1/s*M) | kd (1/s) | KD (M) |
|---|---|---|---|---|
| 1H5 | Baseline | 1.01E+06 | 1.38E−04 | 1.36E−10 |
| | 3x F/T | 8.90E+05 | 5.51E−04 | 6.19E−10 |
| 1D1 | Baseline | 2.09E+05 | 4.05E−04 | 1.94E−09 |
| | 3x F/T | 1.95E+05 | 6.28E−04 | 3.22E−09 |
| 1C10 | Baseline | 2.20E+05 | 3.30E−04 | 1.50E−09 |
| | 3x F/T | 1.96E+05 | 6.75E−04 | 3.45E−09 |
| 21H7 | Baseline | 2.28E+05 | 4.23E−03 | 1.86E−08 |
| | 3x F/T | 2.24E+05 | 4.35E−03 | 1.94E−08 |

When expressed at large-scale, 1H5, 1D1, 1C10, and 21H7 retained good thermostability (Tm ≥55° C.) as measured by DSF assay and showed good hydrophobicity properties (data not shown). Among the four anti-IL31 co-binders, 1H5 showed stronger non-specific binding to BVP, insulin, and DNA versus the other three co-binders (data not shown) and was deprioritized. Overall, however, 1H5, 1D1, 1C10, and 21H7 demonstrated good overall developability.

Example 13. Anti-Pruritic Activity in Non-Human Primates

Male cynomolgus monkeys (3 to 5 years old) were selected from available stock animals at SNBL (Kagoshima, Japan). After two weeks of acclimation, all animals were administered recombinant cynomolgus IL-31 (1 μg/kg, Sino Biological, Beijing, China) via intravenous injection and observed for pruritic response for 3 hours. Animals that demonstrated a pruritic response to cyIL31 injection were allocated into 3 treatment groups of 3 monkeys each. Anti-IL31 co-binder 1C10 (SEQ ID NO:69) was administered on Study Day 0 at 1 or 5 mg/kg. Approximately 24 hours after co-binder administration, serum was collected from all co-binder treated animals. Serum was also collected on Study Days 8, 15, 22, and 29. Recombinant cyIL31 was injected intravenously (1 μg/kg) on Study Days 1, 8, 15, and 29, and scratching activity was recorded to assess frequency and total duration over 3 hours.

Pruritic activity for all animals was normalized to activity assessed upon cyIL31 treatment prior to study initiation. Clear incidence of pruritic activity was observed in all treatment groups prior to study initiation. As shown in FIG. 8A, when anti-IL31 1C10 co-binder was administered at 1 or 5 mg/kg a clear reduction in relative duration of pruritic activity was observed. The reduction in relative duration of pruritic activity persisted to Day 8. After Day 8, animals in the 1 mg/kg treatment group began demonstrating increased pruritic activity over time, increasing to pre-study levels by Day 29. In contrast, animals treated with 5 mg/kg of test article failed to show a clear resumption of cyIL31-induced pruritic activity throughout the course of the study.

Serum collected from all animals was assessed for anti-IL31 1C10 co-binder concentration by ELISA. All animals possessed quantifiable levels of 1C10 co-binder at all time points tested with a clear reduction in serum drug concentration over time. These data suggest time and drug concentration effects of 1C10 co-binder on suppressing IL31-induced pruritus. This is further supported when comparing the relative duration of pruritic activity to calculated serum drug concentration (FIG. 8B). Specifically, animals with the highest serum drug concentration had the lowest relative pruritic activity upon cyIL31 treatment, in contrast with the notably higher pruritic activity in animals demonstrating the lowest serum drug concentrations.

Example 14. Preparation and Characterization of Anti-IL13/Anti-IL31 Bi-Specifics Bispecifics were expressed in four different tandem or Morrison formats using huIgG1Fc_YTE_LALA_C→S (SEQ ID NOs: 55-58). For the Morrison format, the C-terminal VHH2 of 1C10 was humanized using germline IGHV3-43*02. All activities for IL 13 and IL31 were preserved with no position effect among the four bispecific formats and each of the four proteins expressed very well and similar to 3G12-YTE-Fc. The bispecific format shown in FIG. 9 (SEQ ID NO:55) was further characterized.

The ability of the anti-IL 13/anti-IL31 bispecific to block IL13/IL31 binding to and dimeration of the IL 13/IL31 receptor was assessed. An IL13/IL31 dimerization assay was performed using IL 13/IL31 dimerization kits from Eurofins Scientific (Fremont, CA) according to the manufacturer's instructions. U2OS OSMRb/IL31R or U2OS IL4R/IL 13RA1 dimerization cells were seeded at 0.1 million/well in 80 μl AssayComplete™ Cell Plating 0 Reagent (Eurofins DiscoverX) into a 96-well clear flat-bottom white plate and incubated at 37° C., 5% $CO_2$ for overnight. The anti-IL13/anti-IL31 bispecific was diluted from 30 μg/ml with 3×dilution for 12 points and incubated with equal volume of 10 ng/ml IL13/IL31 in AssayComplete™ Cell Plating 0 Reagent for 1 hour at room temperature. 20 μl of IL 13/IL31 and the anti-IL13/anti-IL31 bispecific was added to each well of the cell culture plate and incubated for 16 hours. Plates and detection reagent were equilibrated to room temperature. 100 μl of detection reagent mix was added to each well of the plates and incubated at room temperature for 1 hour in the dark. RLU was read using VICTOR® Nivo™ Multimode Plate Reader and normalized to IL13/IL31 activity without the anti-IL 13/anti-IL31 bispecific and presented as a percentage. For comparison, lebrikizumab (anti-IL13 hIgG4 monoclonal) or an IL31 co-binder 1C10-Fc (SEQ ID NO:69) were diluted and incubated with IL13/IL31 and assessed for IL13 and IL31 receptor dimerization, respectively.

Anti-IL31 and anti-IL13 bispecific polypeptide (SEQ ID NO:55) exhibited dose-dependent inhibition of IL13 activity (FIG. 10A) and IL31 activity (FIG. 10B).

As shown in Table 9, the anti-IL31 and anti-IL13 bispecific polypeptide (SEQ ID NO: 55) was further characterized by binding affinity, melting temperature, hydrophobicity, thermal stability, and heparin retention time (see methods listed in Examples 4 and 11). Stability at pH 3.0 (0.1M sodium acetate, pH 3) was assessed via HPLC Size Exclusion Chromatography (SEC) of the bispecific polypeptide (SEQ ID NO:55) following incubation for 90 minutes at room temperature. Samples were neutralized to pH 7.2 with 1 M Tris-base, and 10 μg was loaded onto a Zenix®-C SEC-300 gel filtration column (7.8×150 mm) (SEPAX Technologies). An isocratic gradient was performed with 150 mM Sodium Phosphate pH 7.0 according to the manufacturer's instructions (SEPAX Technologies) at 1 mL/min. Additionally, percent aggregates and percent monomer were measured (data not shown).

TABLE 9

Anti-IL31 and Anti-IL13_Bispecific Polypeptide (SEQ_ID NO: 55) Characteristics

| Characteristic | Value |
|---|---|
| Transient expression titer | 2.2 g/L |
| SEC purity % | 95.23 |
| IL13 activity (IC50, nM) | 0.023 |
| IL31 activity (IC50, nM) | 0.182 |
| Heparin RT (min) | 9.8 |
| HIC RT (min) | 17.2, 17.8 |
| Tm (° C.) | 60.5 |
| Thermal stability (40° C. x2d) | stable |
| pH stability (pH3.0 x90 min) | stable |
| Concentratability | >200 mg/ml |
| IL13RA2 blocking | No |

SEC: size exclusion chromatography
RT: retention time
HIC: hydrophobic interaction chromatography
Tm: melting temperature
Stable: no discernible aggregation after incubation

Example 15. Binding Affinity Assessment of Anti-IL31 and Anti-IL13 Bispecific Polypeptide The anti-IL31 and anti-IL 13 bispecific polypeptide (SEQ ID NO:55), as shown in FIG. 4 and comprising the anti-IL13 co-binder 3G12 and the anti-IL31 co-binder, 1C10, was assessed for binding affinity to target antigens IL13 and IL31.

Binding affinity was measured on a KinExA 3200 biosensor (Sapidyne Instruments, Boise, ID) using a Kinetic Exclusion Assay (KINEXA) at 25° C., which measured the equilibrium binding affinity and kinetics between molecules in solution. The bispecific polypeptide (2.28 mg/mL in 1× PBS+1 mg/mL BSA, pH 7.4) was mixed with either IL13 (0.6 mg/mL) or IL31 (0.4 mg/mL) until an equilibrated sample was achieved. Each Interleukin molecule was used as a concentration reference to calculate the activity of the bispecific polypeptide, allowing for direct comparison of the anti-IL 13 co-binder and anti-IL31 co-binder of the bispecific polypeptide to the respective Interleukin molecule. Glass beads coated with either biotinylated IL 13 or biotinylated IL31 (30 μg/mL) were then added to each equilibrated sample to capture a portion of free bispecific polypeptide. Captured bispecific polypeptide was then detected by adding 0.5 μg/mL fluorescently labeled anti-Human IgG (ALEXAFLUOR® 647 goat, anti-human IgG (H+L), Jackson ImmunoResearch, West Grove, PA). The detected fluorescent signal was converted to a voltage signal that was directly proportional to the amount of free bispecific polypeptide in the equilibrated sample, which was used to determine binding affinity and kinetic properties.

The affinity parameter values listed in Table 10 (below) are from replicates in one run. The equilibrium constant ($K_d$), percent activity, on rate ($k_{on}$), and off rate ($k_{off}$) for bispecific polypeptide and IL13 or IL31 were determined. The 95% confidence interval for $K_d$, $k_{on}$, and $k_{off}$ was also determined.

TABLE 10

| Binding Affinity of Bispecific Polypeptide (SEQ ID NO: 55) to IL13 and IL31 | | |
|---|---|---|
| | IL13 | IL31 |
| $K_d$ | 307 fM | 135 PM |
| 95% Confidence Interval | 82.5 fM to 665 fM | 112 pM to 161 pM |
| % Activity | 66.5% | 110% |
| 95% Confidence Interval | 54.7% to 76.1% | 94.9% to 126% |
| On Rate ($M^{-1}s^{-1}$) | $7.16 \times 10^5$ | $4.94 \times 10^4$ |
| 95% Confidence Interval | $6.09 \times 10^5$ to $8.48 \times 10^5$ | $4.59 \times 10^4$ to $5.29 \times 10^4$ |
| Off Rate ($s^{-1}$) | $2.20 \times 10^{-7}$ | $6.66 \times 10^{-6}$ |

As shown in Table 10, the bispecific polypeptide (SEQ ID NO:55) bound tighter to IL13 than IL31. In particular, the bispecific polypeptide bound to IL13 with an extremely low, "glue-like" off rate ($k_{off}$). Compared to the assays described in Examples 4 and 11, the assay in this example allowed for detection of lower off rates. Also, non-standard binding was observed for the bispecific polypeptide to IL 13 (data not shown). The good fit of the remaining measurement curves to the raw data ensured confidence in the final results provided in Table 10.

Example 16. Comparative Potency Assay of Anti-IL31 and Anti-IL13 Bispecific Polypeptide To determine relative potency for IL13 and IL31 inhibition, bispecific polypeptide (SEQ ID NO:55) inhibition activity was compared to other approved IL 13 and IL31 binders, including lebrikizumab, tralokinumab, APG777, and NM26-2198 (FIGS. 11A-11B). An IL13/IL31 dimerization assay was performed for bispecific polypeptide (SEQ ID NO:55), as described in Example 14. Lebrikizumab, tralokinumab, and APG777 were used for comparison of IL13 inhibitory activity, and the IC50 for each was normalized to lebrikizumab (FIG. 11A). For IL31 inhibitory activity, bispecific polypeptide (SEQ ID NO:55) was compared to NM26-2198 and the IC50 (nM) for each is shown (FIG. 11B). Bispecific polypeptide (SEQ ID NO:55) is more potent than lebrikizumab, tralokinumab, and APG777 in inhibiting IL13 (FIG. 11A), and the bispecific polypeptide has similar potency to NM26-2198 in inhibiting IL31 (FIG. 11B). Moreover, potency is retained when both IL13 and IL31 antigen-binding sites are occupied.

EQUIVALENTS

The foregoing written specification is considered to be sufficient to enable one skilled in the art to practice the aspects. The foregoing description and Examples detail certain aspects and describe the best mode contemplated by the inventors. It will be appreciated, however, that no matter how detailed the foregoing may appear in text, the aspect may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all the values or ranges provided in the list. In some instances, the term about may include numerical values that are rounded to the nearest significant figure.

What is claimed is:

1. A bispecific polypeptide that binds IL31 and IL13, wherein the polypeptide comprises:

i) a first co-binder that specifically binds IL31 comprising a first Variable Heavy domain of Heavy chain 1 (VHH1) and a second VHH (VHH2), and ii) a second co-binder that specifically binds IL 13 comprising a third VHH (VHH3) and a fourth VHH (VHH4), wherein:

a) the VHH1 comprises a CDR1 comprising the amino acid sequence of SEQ ID NO:5; a CDR2 comprising the amino acid sequence of SEQ ID NO:6; and a CDR3 comprising the amino acid sequence of SEQ ID NO:7; the VHH2 comprises a CDR1 comprising the amino acid sequence of SEQ ID NO:16; a CDR2 comprising the amino acid sequence of SEQ ID NO:17; and a CDR3 comprising the amino acid sequence of SEQ ID NO: 18; the VHH3 comprises a CDR1 comprising the amino acid sequence of SEQ ID NO:31; a CDR2 comprising the amino acid sequence of SEQ ID NO: 32; and a CDR3 comprising the amino acid sequence of SEQ ID NO:33 or 60; and the VHH4 comprises a CDR1 comprising the amino acid sequence of SEQ ID NO:42; a CDR2 comprising the amino acid sequence of SEQ ID NO:43; and a CDR3 comprising the amino acid sequence of SEQ ID NO:44 or 63; or b) the VHH1 comprises a CDR1 comprising the amino acid sequence of SEQ ID NO:5; a CDR2 comprising the amino acid sequence of SEQ ID NO:6; and a CDR3 comprising the amino acid sequence of SEQ ID NO:7; the VHH2 comprises a CDR1 comprising the amino acid sequence of SEQ ID NO: 16; a CDR2 comprising the amino acid sequence of SEQ ID NO:17; and a CDR3 comprising the amino acid sequence of SEQ ID NO: 18; the VHH3 comprises a CDR1 comprising the amino acid sequence of SEQ ID NO:31; a CDR2 comprising the amino acid sequence of SEQ ID NO: 32; and a CDR3 comprising the amino acid sequence of SEQ ID NO:60; and the VHH4 comprises a CDR1 comprising the amino acid sequence of SEQ ID NO:42; a CDR2 comprising the amino acid sequence of SEQ ID NO:43; and a CDR3 comprising the amino acid sequence of SEQ ID NO: 63; or c) the VHH1 comprises a CDR1 comprising the amino acid sequence of SEQ ID NO:8; a CDR2 comprising the amino acid sequence of SEQ ID NO:9; and a CDR3 comprising the amino acid sequence of SEQ ID NO:10; the VHH2 comprises a CDR1 comprising the amino acid sequence of SEQ ID NO:19; a CDR2 comprising the amino acid sequence of SEQ ID NO:20; and a CDR3 comprising the amino acid sequence of SEQ ID NO:21; the VHH3 comprises a CDR1 comprising the amino acid sequence of SEQ ID NO:34; a CDR2 comprising the amino acid sequence of SEQ ID NO:35; and a CDR3 comprising the amino acid sequence of SEQ ID NO:36 or 61; and the VHH4 comprises a CDR1 comprising the amino acid sequence of SEQ ID NO:45; a CDR2 comprising the amino acid sequence of SEQ ID NO:46; and a CDR3 comprising the amino acid sequence of SEQ ID NO:47 or 64; or d) the VHH1 comprises a CDR1 comprising the amino acid sequence of SEQ ID NO:8; a CDR2 comprising the amino acid sequence of SEQ ID NO:9; and a CDR3 comprising the amino acid sequence of SEQ ID NO: 10; the VHH2 comprises a CDR1 comprising the amino acid sequence of SEQ ID NO:19; a CDR2 comprising the amino acid sequence of SEQ ID NO:20; and a CDR3 comprising the amino acid sequence of SEQ ID NO:21; the VHH3 comprises a CDR1 comprising the amino acid sequence of SEQ ID NO:34; a CDR2 comprising the amino acid sequence of SEQ ID NO:35; and a CDR3 comprising the amino acid sequence of SEQ ID NO:61; and the VHH4 comprises a CDR1 comprising the amino acid sequence of SEQ ID NO:45; a CDR2 comprising the amino acid sequence of SEQ ID NO:46; and a CDR3 comprising the amino acid sequence of SEQ ID NO:64; or e) the VHH1 comprises a CDR1 comprising the amino acid sequence of SEQ ID NO: 11; a CDR2 comprising the amino acid sequence of SEQ ID NO:12; and a CDR3 comprising the amino acid sequence of SEQ ID NO:13; the VHH2 comprises a CDR1 comprising the amino acid sequence of SEQ ID NO:22; a CDR2 comprising the amino acid sequence of SEQ ID NO:23; and a CDR3 comprising the amino acid sequence of SEQ ID NO:24; the VHH3 comprises a CDR1 comprising the amino acid sequence of SEQ ID NO:37; a CDR2 comprising the amino acid sequence of SEQ ID NO:38; and a CDR3 comprising the amino acid sequence of SEQ ID NO:39 or 62; and the VHH4 comprises a CDR1 comprising the amino acid sequence of SEQ ID NO:48; a CDR2 comprising the amino acid sequence of SEQ ID NO:49; and a CDR3 comprising the amino acid sequence of SEQ ID NO:50 or 65; or f) the VHH1 comprises a CDR1 comprising the amino acid sequence of SEQ ID NO: 11; a CDR2 comprising the amino acid sequence of SEQ ID NO:12; and a CDR3 comprising the amino acid sequence of SEQ ID NO:13; the VHH2 comprises a CDR1 comprising the amino acid sequence of SEQ ID NO:22; a CDR2 comprising the amino acid sequence of SEQ ID NO:23; and a CDR3 comprising the amino acid sequence of SEQ ID NO:24; the VHH3 comprises a CDR1 comprising the amino acid sequence of SEQ ID NO:37; a CDR2 comprising the amino acid sequence of SEQ ID NO:38; and a CDR3 comprising the amino acid sequence of SEQ ID NO:62; and the VHH4 comprises a CDR1 comprising the amino acid sequence of SEQ ID NO:48; a CDR2 comprising the amino acid sequence of SEQ ID NO:49; and a CDR3 comprising the amino acid sequence of SEQ ID NO:65.

2. The bispecific polypeptide of claim 1, wherein the VHH1 of the first co-binder comprises the amino acid sequence of SEQ ID NO:3 or 4, or amino acid residues 2-118 of SEQ ID NO:3 or 4, and the VHH2 of the first co-binder comprises the amino acid sequence of SEQ ID NO: 14 or 15, or amino acid residues 2-119 of SEQ ID NO: 14 or 15.

3. The bispecific polypeptide of claim 1, wherein the VHH1 of the first co-binder comprises the amino acid sequence of SEQ ID NO:4, or amino acid residues 2-118 of SEQ ID NO:4, and the VHH2 of the first co-binder comprises the amino acid sequence of SEQ ID NO: 15, or amino acid residues 2-119 of SEQ ID NO: 15.

4. The bispecific polypeptide of claim 1, wherein the VHH3 of the second co-binder comprises the amino acid sequence of SEQ ID NO: 29 or 30, or amino acid residues 2-115 of SEQ ID NO:29 or 30; and the VHH4 of the second co-binder comprises the amino acid sequence of SEQ ID NO:40 or 41, or amino acid residues 2-127 of SEQ ID NO: 40 or 41.

5. The bispecific polypeptide of claim 1, wherein the VHH3 of the second co-binder comprises the amino acid sequence of SEQ ID NO: 30, or amino acid residues 2-115 of SEQ ID NO:30; and the VHH4 of the second co-binder comprises the amino acid sequence of SEQ ID NO:41, or amino acid residues 2-127 of SEQ ID NO: 41.

6. The bispecific polypeptide of claim 1, wherein the VHH1 of the first co-binder comprises the amino acid sequence of SEQ ID NO:4, or amino acid residues 2-118 of SEQ ID NO:4, wherein the VHH2 of the first co-binder comprises the amino acid sequence of SEQ ID NO: 15, or amino acid residues 2-119 of SEQ ID NO:15, wherein the VHH3 of the second co-binder comprises the amino acid sequence of SEQ ID NO:30, or amino acid residues 2-115 of SEQ ID NO:30; and wherein the VHH4 of the second co-binder comprises the amino acid sequence of SEQ ID NO:41, or amino acid residues 2-127 of SEQ ID NO:41.

7. The bispecific polypeptide of claim 6, wherein the VHH1 of the first co-binder is connected to the VHH2 of the first co-binder by a first linker; wherein the VHH3 of the second co-binder is connected to the VHH4 of the second co-binder by a second linker, wherein the first co-binder has the structure: [VHH1]-first linker-[VHH2]; and wherein the second co-binder has the structure: [VHH3]-second linker-[VHH4].

8. The bispecific polypeptide of claim 1, wherein the first co-binder comprises the amino acid sequence of SEQ ID NO:25 or 26 or the amino acid residues 2-275 of SEQ ID NO:25 or 26.

9. The bispecific polypeptide of claim 1, wherein the first co-binder comprises the amino acid sequence of SEQ ID NO:26 or the amino acid residues 2-275 of SEQ ID NO: 26.

10. The bispecific polypeptide of claim 1, wherein the second co-binder comprises the amino acid sequence of SEQ ID NO:51 or 52, or the amino acid residues 2-280 of SEQ ID NO:51 or 52.

11. The bispecific polypeptide of claim 1, wherein the second co-binder comprises the amino acid sequence of SEQ ID NO:52, or the amino acid residues 2-280 of SEQ ID NO:52.

12. The bispecific polypeptide of claim 7, wherein the bispecific polypeptide comprises a third linker, and wherein the bispecific polypeptide has a structure of [first co-binder]-Fc region-third linker-[second co-binder].

13. The bispecific polypeptide of claim 12, wherein the first linker comprises the amino acid sequence of SEQ ID NO:66, wherein the second linker comprises the amino acid sequence of SEQ ID NO:67, and wherein the third linker comprises the amino acid sequence of SEQ ID NO:68.

14. The bispecific polypeptide of claim 12, wherein the Fc region comprises a human IgG1 Fc region.

15. The bispecific polypeptide of claim 14, wherein the Fc region comprises the amino acid sequence of SEQ ID NO:59 or amino acid residues 1-231 of SEQ ID NO:59.

16. The bispecific polypeptide of claim 1, wherein the bispecific polypeptide comprises the amino acid sequence of any one of SEQ ID NOs: 55-58 or amino acid residues 1-797 of SEQ ID NO:56 or 58.

17. A bispecific polypeptide that binds IL31 and IL13 comprising the amino acid sequence of SEQ ID NO:55.

18. The bispecific polypeptide of claim 1, wherein the bispecific polypeptide binds to human IL 13 at a kD of less than or equal to $1\times10^{-9}$ M, as measured by surface plasmon resonance; and/or wherein the bispecific polypeptide binds to human IL31 at a kD of less than or equal to $1\times10^{-9}$ M, as measured by surface plasmon resonance.

19. A multimeric polypeptide, comprising two of the bispecific polypeptides of claim 17.

20. A pharmaceutical composition comprising the bispecific polypeptide of claim 17 and a pharmaceutically acceptable carrier.

21. An isolated nucleic acid that encodes the bispecific polypeptide of claim 1.

22. A method of producing a bispecific polypeptide that binds IL31 and IL13, comprising transfecting the isolated nucleic acid of claim 21 into host cell under conditions suitable for expression of the bispecific polypeptide.

23. A method for treating a subject having an IL13-associated condition and/or an IL31-associated condition comprising administering to the subject a therapeutically effective amount of the bispecific polypeptide of claim 17.

24. A bispecific polypeptide that binds IL31 and IL13 comprising a first co-binder that specifically binds IL31 and a second co-binder that specifically binds IL13, wherein the first co-binder comprises the amino acid sequence of SEQ ID NO:26 or the amino acid residues 2-275 of SEQ ID NO:26, and wherein the second co-binder comprises the amino acid sequence of SEQ ID NO:52, or the amino acid residues 2-280 of SEQ ID NO:52.

25. The bispecific polypeptide of claim 24, wherein the bispecific polypeptide comprises a third linker, and wherein the bispecific polypeptide has a structure of [first co-binder]-Fc region-third linker-[second co-binder].

26. The bispecific polypeptide of claim 25, wherein the Fc region comprises a human IgG1 Fc region.

27. A pharmaceutical composition comprising the bispecific polypeptide of claim 24 and a pharmaceutically acceptable carrier.

28. A pharmaceutical composition comprising the multimeric polypeptide of claim 19 and a pharmaceutically acceptable carrier.

29. A method for treating a subject having an IL13-associated condition and/or an IL31-associated condition comprising administering to the subject a therapeutically effective amount of the bispecific polypeptide of claim 24.

30. A method for treating a subject having an IL13-associated condition and/or an IL31-associated condition comprising administering to the subject a therapeutically effective amount of the multimeric polypeptide of claim 19.

* * * * *